United States Patent
Kim et al.

(10) Patent No.: US 10,903,429 B2
(45) Date of Patent: Jan. 26, 2021

(54) CONDENSED CYCLIC COMPOUND AND ORGANIC LIGHT-EMITTING DEVICE INCLUDING THE SAME

(71) Applicants: Samsung Electronics Co., Ltd., Suwon-si (KR); Samsung SDI Co., Ltd., Yongin-si (KR)

(72) Inventors: Sangmo Kim, Hwaseong-si (KR); Ohyun Kwon, Yongin-si (KR); Byoungki Choi, Hwaseong-si (KR); Kyuyoung Hwang, Ansan-si (KR)

(73) Assignees: SAMSUNG ELECTRONICS CO., LTD., Gyeonggi-do (KR); SAMSUNG SDI CO., LTD., Gyeonggi-do (KR)

( * ) Notice: Subject to any disclaimer, the term of this patent is extended or adjusted under 35 U.S.C. 154(b) by 560 days.

(21) Appl. No.: 14/619,778

(22) Filed: Feb. 11, 2015

(65) Prior Publication Data

US 2015/0228909 A1 Aug. 13, 2015

(30) Foreign Application Priority Data

Feb. 12, 2014 (KR) .................. 10-2014-0016282
Jan. 26, 2015 (KR) .................. 10-2015-0011855

(51) Int. Cl.
*H01L 51/00* (2006.01)
*C07D 491/153* (2006.01)
(Continued)

(52) U.S. Cl.
CPC ........ *H01L 51/0067* (2013.01); *C07D 209/82* (2013.01); *C07D 401/04* (2013.01); *C07D 487/14* (2013.01); *C07D 491/04* (2013.01); *C07D 491/14* (2013.01); *C07D 491/153* (2013.01); *C07D 495/04* (2013.01);
(Continued)

(58) Field of Classification Search
CPC ............ H01L 51/0067; H01L 51/0071; H01L 2251/5384; H01L 51/5016; H01L 51/5056; C09B 69/008; C09B 57/00; C07D 495/14; C07D 487/14; C07D 401/04; C07D 491/04; C07D 491/14; C07D 495/04; C07D 209/82; C07D 491/153; C07D 491/048; C07D 491/147; C09K 11/06; C09K 2211/1066; C09K 2211/1062;
(Continued)

(56) References Cited

U.S. PATENT DOCUMENTS 6,687,266 B1 2/2004 Ma et al.
7,154,144 B2 12/2006 Kim et al.
(Continued)

FOREIGN PATENT DOCUMENTS

CN 102754238 A 10/2012
CN 103030585 A 4/2013
(Continued)

OTHER PUBLICATIONS

English language translation of KR 1020110016288, pp. 1-9, May 2017.*
(Continued)

*Primary Examiner* — Alexander C Kollias
(74) *Attorney, Agent, or Firm* — Cantor Colburn LLP

(57) ABSTRACT

A condensed cyclic compound represented by one of Formulae 1-1 to 1-12 is described in the specification.

20 Claims, 1 Drawing Sheet

(51) Int. Cl.
| | | |
|---|---|---|
| | *C07D 495/14* | (2006.01) |
| | *C07D 491/14* | (2006.01) |
| | *C07D 487/14* | (2006.01) |
| | *C07D 209/82* | (2006.01) |
| | *C07D 401/04* | (2006.01) |
| | *C07D 495/04* | (2006.01) |
| | *C07D 491/04* | (2006.01) |
| | *C09B 57/00* | (2006.01) |
| | *C09B 69/00* | (2006.01) |
| | *H01L 51/50* | (2006.01) |

(52) U.S. Cl.
CPC ............ *C07D 495/14* (2013.01); *C09B 57/00* (2013.01); *C09B 69/008* (2013.01); *H01L 51/0071* (2013.01); *H01L 51/5016* (2013.01); *H01L 51/5056* (2013.01); *H01L 2251/5384* (2013.01)

(58) Field of Classification Search
CPC .... C09K 2211/1051; C09K 2211/1048; C09K 2211/1037; C09K 2211/1033
See application file for complete search history.

(56) References Cited

U.S. PATENT DOCUMENTS

| | | | |
|---|---|---|---|
| 7,429,426 B2 | 9/2008 | Brown et al. | |
| 7,585,573 B2 | 9/2009 | Lee et al. | |
| 7,671,272 B2 | 3/2010 | Sohn et al. | |
| 8,062,769 B2 | 11/2011 | Kai et al. | |
| 9,324,954 B2 | 4/2016 | Parham et al. | |
| 9,385,335 B2 | 7/2016 | Pflumm et al. | |
| 9,627,629 B2 | 4/2017 | Hwang et al. | |
| 2007/0001166 A1 | 1/2007 | Tao et al. | |
| 2010/0181900 A1* | 7/2010 | Lyu | C07D 209/86 313/504 |
| 2011/0136755 A1 | 6/2011 | Rieger et al. | |
| 2011/0278555 A1 | 11/2011 | Inoue et al. | |
| 2012/0068170 A1* | 3/2012 | Pflumm | C07D 209/82 257/40 |
| 2012/0138911 A1 | 6/2012 | Inoue et al. | |
| 2012/0305904 A1* | 12/2012 | Kai | C07D 519/00 257/40 |
| 2013/0240796 A1* | 9/2013 | Parham | C07D 403/10 252/500 |
| 2014/0197386 A1 | 7/2014 | Kim et al. | |
| 2014/0225046 A1* | 8/2014 | Jatsch | C07D 405/14 252/519.3 |
| 2015/0228909 A1 | 8/2015 | Kim et al. | |
| 2016/0308142 A1 | 10/2016 | Kim et al. | |
| 2016/0351826 A1 | 12/2016 | Kim et al. | |
| 2017/0012216 A1 | 1/2017 | Kim et al. | |

FOREIGN PATENT DOCUMENTS

| | | | |
|---|---|---|---|
| CN | 103554131 A | 10/2013 | |
| CN | 103842339 A | 6/2014 | |
| EP | 2535958 A1 | 12/2012 | |
| EP | 2581365 A1 | 4/2013 | |
| JP | 2011198900 A | 10/2011 | |
| JP | 2012-175025 A | 9/2012 | |
| JP | 2012175025 A | 9/2012 | |
| JP | 2012531383 A | 12/2012 | |
| KR | 101108512 B1 | 2/2011 | |
| KR | 1020110102055 A | 9/2011 | |
| KR | 1020120081539 A | 7/2012 | |
| KR | 101380335 B1 | 3/2014 | |
| KR | 10-2014-0096203 A | 8/2014 | |
| KR | 10-2014-0101699 A | 8/2014 | |
| KR | 10-2015-0083786 A | 7/2015 | |
| WO | 2008008419 A2 | 1/2008 | |
| WO | 2008056746 A1 | 5/2008 | |
| WO | 2008084109 A1 | 7/2008 | |
| WO | 2011019173 A2 | 2/2011 | |
| WO | 2011099451 A1 | 8/2011 | |
| WO | 2012-069121 A1 | 5/2012 | |
| WO | 2012076886 A2 | 6/2012 | |
| WO | 2012076886 A3 | 6/2012 | |
| WO | 2012136295 A1 | 10/2012 | |
| WO | 2012159213 A1 | 11/2012 | |
| WO | 2013-041176 A1 | 3/2013 | |
| WO | WO-2013041176 * | 3/2013 | .......... C07D 209/86 |
| WO | 2014-010910 A1 | 1/2014 | |
| WO | 2014010910 A1 | 1/2014 | |

OTHER PUBLICATIONS

Michel Belletete et al. "A first principles calculations and experimental study of the ground- and excited-state properties of ladder oligo(p-aniline)s" The Journal of Chemical Physics 122, 104303 (2005).

Partial European Search Report issued by the European Patent Office dated Jun. 5, 2015.

Potjaman Poolmee et al. "Photophysical properties and vibrational structure of ladder-type penta p-phenylene and carbazole derivatives based on SAC-CI calculations" Theor Chem Acc (2011) 130:161-173.

Extended Search Report for EP 15154505 dated Oct. 23, 2015, issued by the European Patent Office.

Jimmy Bouchard et al. "Synthesis of Diindolocarbazoles by Cadogan Reaction: Route to Ladder Olido(p-aniline)s" J. Org. Chem. 2004, 69, 5705-5711.

Salem Wakim et al. "Synthesis of Diindolocarbazoles by Ullmann Reaction: A Rapid Route to Ladder Olido(p-aniline)s" Organic Letters, 2004, vol. 6, No. 19, 3413-3416.

Office Action issued by the Chinese Patent Office for Patent Application No. 2015100765031 dated Dec. 1, 2018, with the English Translation.

Salem Wakim et al. "Synthesis of Diindolocarbazoles by Ullmann Reaction: A Rapid Route to Ladder Oligo(p-aniline)s", Organic Letters, 2004, vol. 6, No. 19, 3413-3416.

Jimmy Bouchard et al. "Synthesis of Diindolocarbazoles by Cadogan Reaction: Route to Ladder Oligo(p-aniline)s", J. Org. Chem. 2004, 69, 5705-5711.

Michel Belletête et al. "A first principles calculations and experimental study of the ground-and excited-state properties of ladder oligo(p-aniline)s", The Journal of Chemical Physics 2005, 122, pp. 104303-1 to 104303-9.

Nicolas Blouin et al. "Optical, Electrochemical, Magnetic, and Conductive Properties of New Polyindolocarbazoles and Polydiindolocarbazoles", Macromol. Chem. Phys. 2006, 207, 166-174.

Potjaman Poolmee et al. "Photophysical properties and vibrational structure of ladder-type penta p-phenylene and carbazoles derivatives based on SAC-CI calculations", Theor Chem Acc 2011, 130, 161-173.

Office Action issued by the Japanese Patent Office dated Sep. 18, 2018, in the examination of the Japanese Patent Application No. 2015-025710.

Chinese Office Action issued by the Chinese Patent Office dated Jan. 21, 2019, in the examination of the Chinese Patent Application No. 201510076503.1 with English Translation.

Decision of Final Rejection issued by the Chinese Patent Office dated Aug. 27, 2019 in the examination of the Chinese Patent Application No. 201510076503.1, which corresponds to the U.S. Application above.

English Translation of Office Action issued by the Japanese Patent Office dated Nov. 26, 2019 in the examination of the Japanese Patent Application No. 2018-236743.

Office Action issued by the Japanese Patent Office dated Nov. 26, 2019 in the examination of the Japanese Patent Application No. 2018-236743, which corresponds to the U.S. Application above.

* cited by examiner

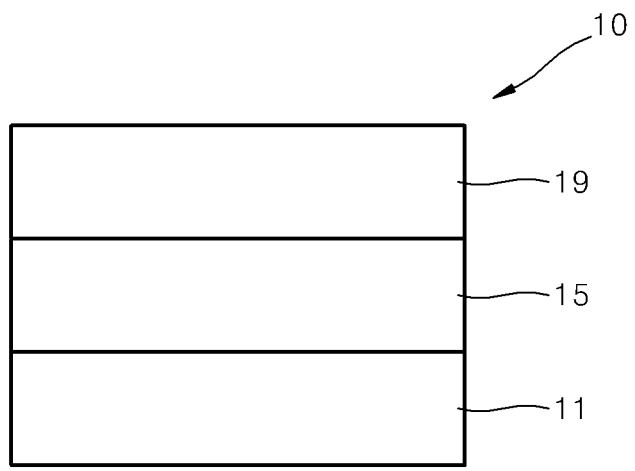

CONDENSED CYCLIC COMPOUND AND ORGANIC LIGHT-EMITTING DEVICE INCLUDING THE SAME

CROSS-REFERENCE TO RELATED APPLICATIONS

This application claims priority to Korean Patent Application No. 10-2014-0016282, filed on Feb. 12, 2014, and Korean Patent Application No. 10-2015-0011855, filed on Jan. 26, 2015, and all the benefits accruing therefrom under 35 U.S.C. § 119, the contents of which are incorporated herein in their entirety by reference.

BACKGROUND

1. Field

The present disclosure relates to a condensed cyclic compound and an organic light-emitting device including the same.

2. Description of the Related Art

Organic light emitting devices (OLEDs) are self-emission devices that have wide viewing angles, high contrast ratios, and short response times. In addition, the OLEDs exhibit excellent brightness, driving voltage, and response speed characteristics. They also produce full-color images.

A typical organic light-emitting device includes an anode, a cathode, and an organic layer including an emission layer that is disposed between the anode and the cathode. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carrier, such as the holes and the electrons, are recombined in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

Provided are a novel condensed cyclic compound and an organic light-emitting device including the same.

Additional aspects will be set forth in part in the description which follows and, in part, will be apparent from the description, or may be learned by practice of the presented embodiments.

According to an aspect, a condensed cyclic compound is represented by Formula 1:

Formula 1 wherein, in Formula 1, $X_{11}$ is $N\text{-}[(L_{11})_{a11}\text{-}(R_{11})_{b11}]$, S, O, S(=O), S(=O)$_2$, C(=O), $C(R_{12})(R_{13})$, $Si(R_{12})(R_{13})$, $P(R_{12})$, or P(=O)$(R_{12})$, f1 and f2 are each independently 0 or 1, and f1+f2 is 1;

$X_{21}$ is $N\text{-}[(L_{21})_{a21}\text{-}(R_{21})_{b21}]$, S, O, S(=O), S(=O)$_2$, C(=O), $C(R_{22})(R_{23})$, $Si(R_{22})(R_{23})$, $P(R_{22})$, or P(=O)$(R_{22})$, f3 and f4 are each independently 0 or 1, and f3+f4 is 1;

$X_{31}$ to $X_{34}$ are each independently N or $C\text{-}[(L_2)_{a2}\text{-}(R_2)_{b2}]$;

g1 and g2 are each independently 0, 1 or 2, and g1+g2 is 2; provided that conditions i) to viii) are met:

i) in Formula 1, when f1 is 1, f2 is 0, f3 is 1, f4 is 0, g1 is 1, g2 is 1, and $X_{11}$ is $C(R_{12})(R_{13})$, $X_{21}$ is not $N\text{-}[(L_{21})_{a21}\text{-}(R_{21})_{b21}]$, ii) in Formula 1, when f1 is 1, f2 is 0, f3 is 1, f4 is 0, g1 is 1, g2 is 1, and $X_{11}$ is $N\text{-}[(L_{11})_{a11}\text{-}(R_{11})_{b11}]$, $X_{21}$ is not $N\text{-}[(L_{21})_{a21}\text{-}(R_{21})_{b21}]$ or $C(R_{22})(R_{23})$, iii) in Formula 1, when f1 is 1, f2 is 0, f3 is 0, f4 is 1, g1 is 0, g2 is 2, and $X_{11}$ is $C(R_{12})(R_{13})$, $X_{21}$ is not $N\text{-}[(L_{21})_{a21}\text{-}(R_{21})_{b21}]$, iv) in Formula 1, when f1 is 0, f2 is 1, f3 is 1, f4 is 0, g1 is 1, g2 is 1, and $X_{11}$ is $C(R_{12})(R_{13})$, $X_{21}$ is not $N\text{-}[(L_{21})_{a21}\text{-}(R_{21})_{b21}]$ or $C(R_{22})(R_{23})$, v) in Formula 1, when f1 is 0, f2 is 1, f3 is 1, f4 is 0, g1 is 1, g2 is 1, and $X_{11}$ is $N\text{-}[(L_{11})_{a11}\text{-}(R_{11})_{b11}]$, $X_{21}$ is not $C(R_{22})(R_{23})$, vi) in Formula 1, when f1 is 0, f2 is 1, f3 is 1, f4 is 0, g1 is 1, g2 is 1, and $X_{11}$ is S, $X_{21}$ is not $N\text{-}[(L_{21})_{a21}\text{-}(R_{21})_{b21}]$, vii) in Formula 1, when f1 is 0, f2 is 1, f3 is 1, f4 is 0, g1 is 1, g2 is 1, and $X_{11}$ is $Si(R_{12})(R_{13})$, $X_{21}$ is not $N\text{-}[(L_{21})_{a21}\text{-}(R_{21})_{b21}]$, viii) in Formula 1, when f1 is 0, f2 is 1, f3 is 0, f4 is 1, g1 is 1, g2 is 1, and $X_{11}$ is $N\text{-}[(L_{11})_{a11}\text{-}(R_{11})_{b11}]$, $X_{21}$ is not $C(R_{22})(R_{23})$;

$L_1$ to $L_3$, $L_{11}$, and $L_{21}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a3, a11, and a21 are each independently an integer selected from 0 to 5;

$R_1$ to $R_7$, $R_{11}$ to $R_{13}$, and $R_{21}$ to $R_{23}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

b1 to b3, b11, and b21 are each independently an integer selected from 1 to 5;

c1 is an integer selected from 1 to 4;

at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_1$-$C_{60}$ heteroaryloxy group, substituted $C_1$-$C_{60}$ heteroarylthio group, substituted $C_2$-$C_{60}$ heteroarylalkyl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$); wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group.

According to another aspect, an organic light-emitting device includes a first electrode;

a second electrode; and an organic layer disposed between the first electrode and the second electrode, wherein the organic layer includes an emission layer and at least one of the condensed cyclic compounds represented by Formula 1.

The condensed cyclic compound may be included in the emission layer, and the condensed cyclic compound may be included in the hole transport region.

BRIEF DESCRIPTION OF THE DRAWINGS

These and/or other aspects will become apparent and more readily appreciated from the following description of the embodiments, taken in conjunction with the accompanying drawings of which:

FIG. 1 is a cross-section view schematically illustrating an organic light-emitting device according to an embodiment.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

A condensed cyclic compound is represented by Formula 1.

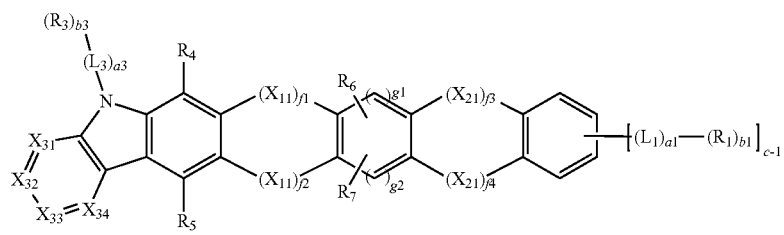

Formula 1 wherein, in Formula 1, $X_{11}$ is N-[$(L_{11})_{a11}$-$(R_{11})_{b11}$], S, O, S(=O), S(=O)$_2$, C(=O), C($R_{12}$)($R_{13}$), Si($R_{12}$)($R_{13}$), P($R_{12}$), or P(=O)($R_{12}$), f1 and f2 are each independently 0 or 1, and f1+f2 is 1;

$X_{21}$ is N-[$(L_{21})_{a21}$-$(R_{21})_{b21}$], S, O, S(=O), S(=O)$_2$, C(=O), C($R_{22}$)($R_{23}$), Si($R_{22}$)($R_{23}$), P($R_{22}$), or P(=O)($R_{22}$), f3 and f4 are each independently 0 or 1, and f3+f4 is 1;

$X_{31}$ to $X_{34}$ are each independently N or C-[$(L_2)_{a2}$-$(R_2)_{b2}$];

g1 and g2 are each independently 0, 1 or 2, and g1+g2 is 2;

provided that conditions i) to viii) are met:

i) in Formula 1, when f1 is 1, f2 is 0, f3 is 1, f4 is 0, g1 is 1, g2 is 1, and $X_{11}$ is C($R_{12}$)($R_{13}$), $X_{21}$ is not N-[$(L_{21})_{a21}$-$(R_{21})_{b21}$], ii) in Formula 1, when f1 is 1, f2 is 0, f3 is 1, f4 is 0, g1 is 1, g2 is 1, and $X_{11}$ is N-[$(L_{11})_{a11}$-$(R_{11})_{b11}$], $X_{21}$ is not N-[$(L_{21})_{a21}$-$(R_{21})_{b21}$] or C($R_{22}$)($R_{23}$), iii) in Formula 1, when f1 is 1, f2 is 0, f3 is 0, f4 is 1, g1 is 0, g2 is 2, and $X_{11}$ is C($R_{12}$)($R_{13}$), $X_{21}$ is not N-[$(L_{21})_{a21}$-$(R_{21})_{b21}$], iv) in Formula 1, when f1 is 0, f2 is 1, f3 is 1, f4 is 0, g1 is 1, g2 is 1, and $X_{11}$ is C($R_{12}$)($R_{13}$), $X_{21}$ is not N-[$(L_{21})_{a21}$-$(R_{21})_{b21}$] or C($R_{22}$)($R_{23}$), v) in Formula 1, when f1 is 0, f2 is 1, f3 is 1, f4 is 0, g1 is 1, g2 is 1, and $X_{11}$ is N-[$(L_{11})_{a11}$-$(R_{11})_{b11}$], $X_{21}$ is not C($R_{22}$)($R_{23}$), vi) in Formula 1, when f1 is 0, f2 is 1, f3 is 1, f4 is 0, g1 is 1, g2 is 1, and $X_{11}$ is S, $X_{21}$ is not N-[$(L_{21})_{a21}$-$(R_{21})_{b21}$], vii) in Formula 1, when f1 is 0, f2 is 1, f3 is 1, f4 is 0, g1 is 1, g2 is 1, and $X_{11}$ is Si($R_{12}$)($R_{13}$), $X_{21}$ is not N-[$(L_{21})_{a21}$-$(R_{21})_{b21}$], viii) in Formula 1, when f1 is 0, f2 is 1, f3 is 0, f4 is 1, g1 is 1, g2 is 1, and $X_{11}$ is N-[$(L_{11})_{a11}$-$(R_{11})_{b11}$], $X_{21}$ is not C($R_{22}$)($R_{23}$);

$L_1$ to $L_3$, $L_{11}$, and $L_{21}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a3, a11, and a21 are each independently an integer selected from 0 to 5;

$R_1$ to $R_7$, $R_{11}$ to $R_{13}$, and $R_{21}$ to $R_{23}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

b1 to b3, b11, and b21 are each independently an integer selected from 1 to 5;

c1 is an integer selected from 1 to 4;

at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_1$-$C_{60}$ heteroaryloxy group, substituted $C_1$-$C_{60}$ heteroarylthio group, substituted $C_2$-$C_{60}$ heteroarylalkyl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$); wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group.

For example, the condensed cyclic compound may be represented by one of Formulae 1-1 to 1-12.
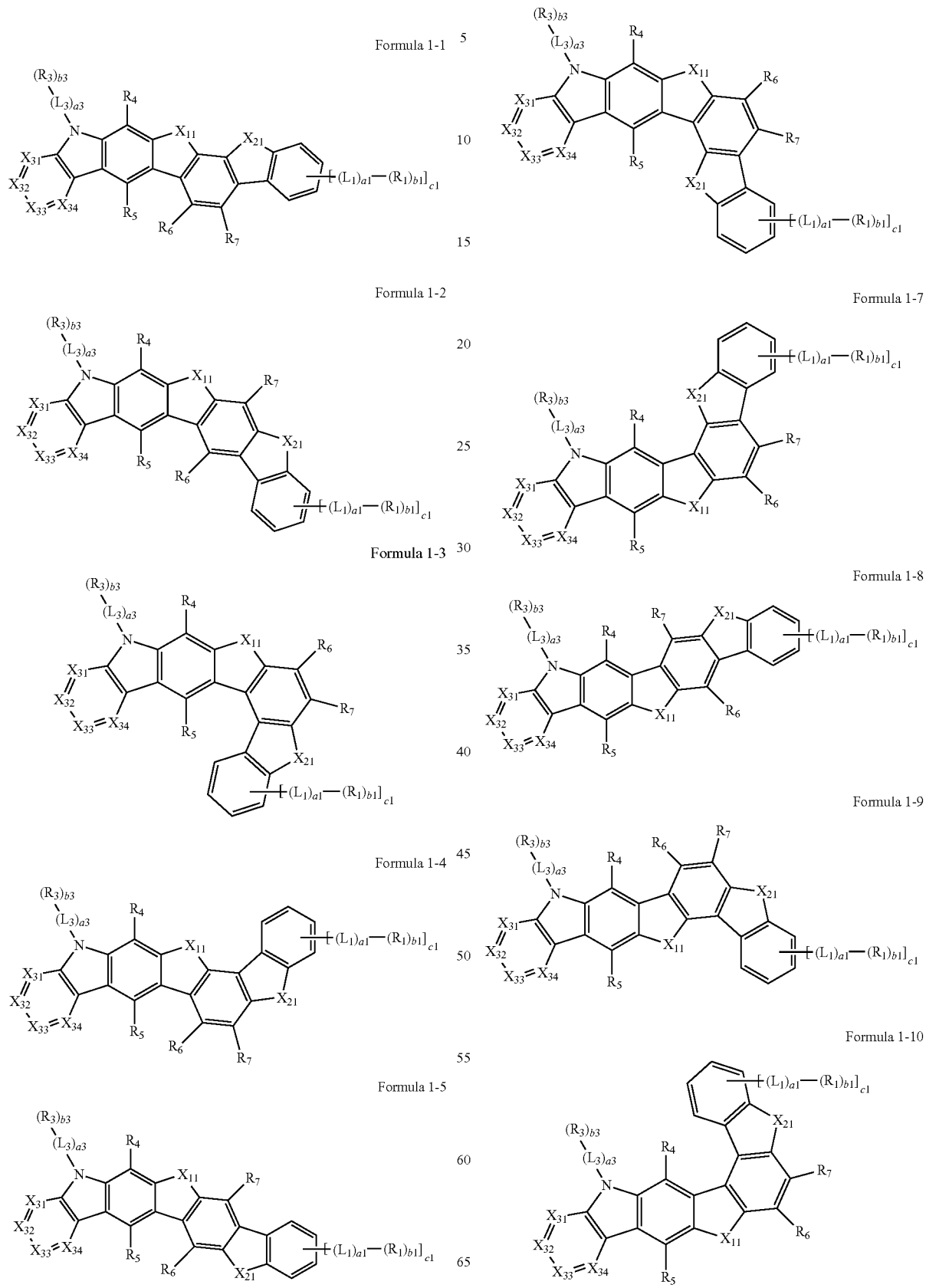

Formula 1-11

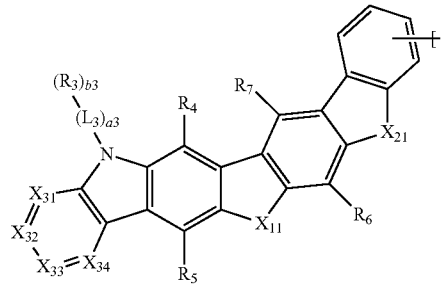

Formula 1-12

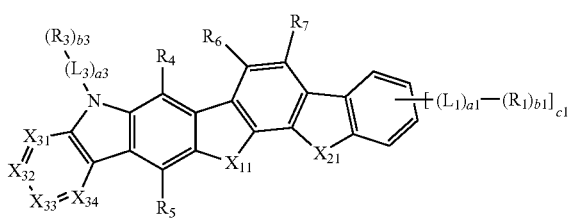

In Formulae 1 and 1-1 to 1-12, $X_{11}$ is N-$[(L_{11})_{a11}$-$(R_{11})_{b11}]$, S, O, S(=O), S(=O)$_2$, C(=O), C($R_{12}$)($R_{13}$), Si($R_{12}$)($R_{13}$), P($R_{12}$), or P(=O)($R_{12}$); and $X_{21}$ is N-$[(L_{21})_{a21}$-$(R_{21})_{b21}]$, S, O, S(=O), S(=O)$_2$, C(=O), C($R_{22}$)($R_{23}$), Si($R_{22}$)($R_{23}$), P($R_{22}$), or P(=O)($R_{22}$).

In some embodiments, in Formulae 1 and 1-1 to 1-12, $X_{11}$ is N-$[(L_{11})_{a11}$-$(R_{11})_{b11}]$, S, O, C($R_{12}$)($R_{13}$), or Si($R_{12}$)($R_{13}$); and $X_{21}$ is N-$[(L_{21})_{a21}$-$(R_{21})_{b21}]$, S, O, C($R_{22}$)($R_{23}$), or Si($R_{22}$)($R_{23}$), but $X_{11}$ and $X_{12}$ are not limited thereto.

In Formulae 1 and 1-1 to 1-12, $X_{31}$ to $X_{34}$ are each independently N or C-$[(L_2)_{a2}$-$(R_2)_{b2}]$.

When at least two of $X_{31}$ to $X_{34}$ are C-$[(L_2)_{a2}$-$(R_2)_{b2}]$, the at least two of $X_{31}$ to $X_{34}$ may be identical or different from each other.

In some embodiments, in Formulae 1 and 1-1 to 1-12, all of $X_{31}$ to $X_{34}$ may be C-$[(L_2)_{a2}$-$(R_2)_{b2}]$.

Thus, the condensed cyclic compound may be represented by one of Formulae 1A-1 to 1A-12:

Formula 1A-1

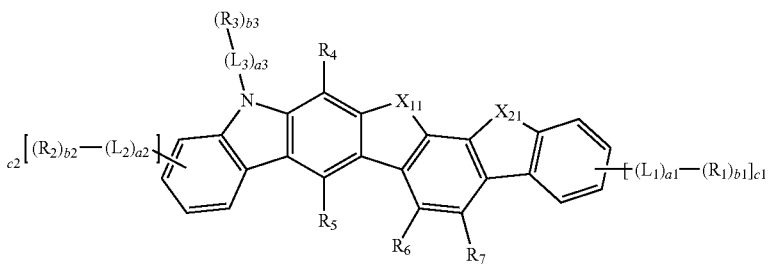

Formula 1A-2

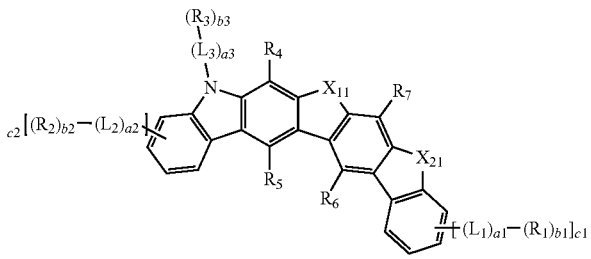

Formula 1A-3

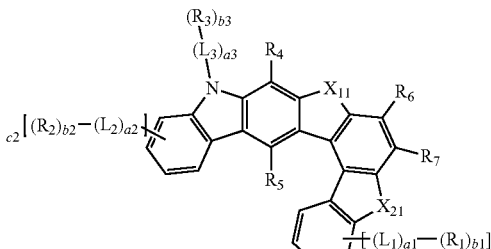

Formula 1A-4

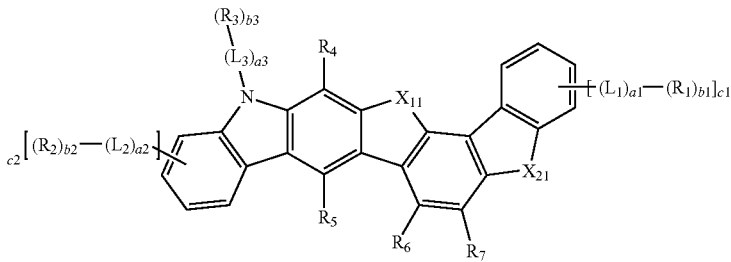

-continued
Formula 1A-5
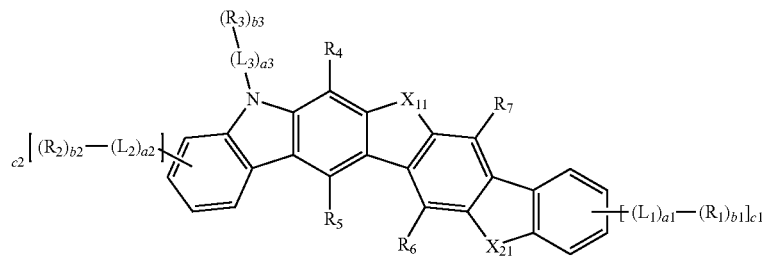
Formula 1A-6
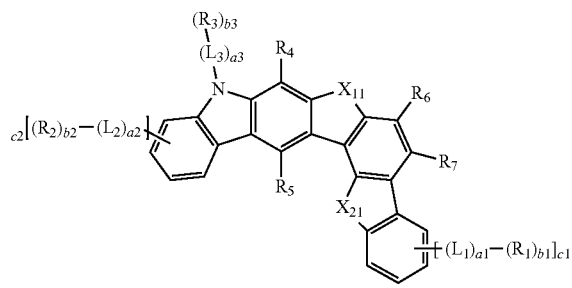
Formula 1A-7
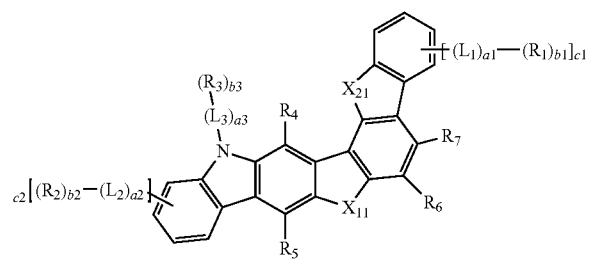
Formula 1A-8
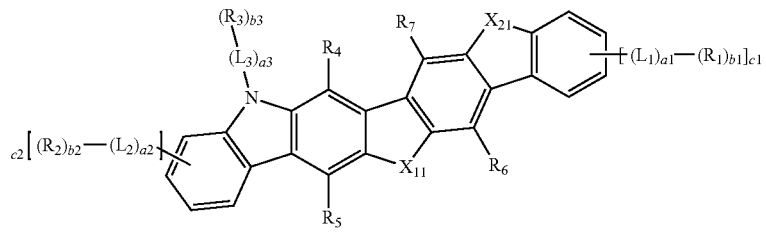
Formula 1A-9
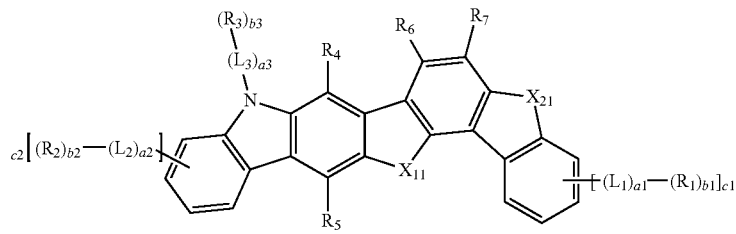
Formula 1A-10
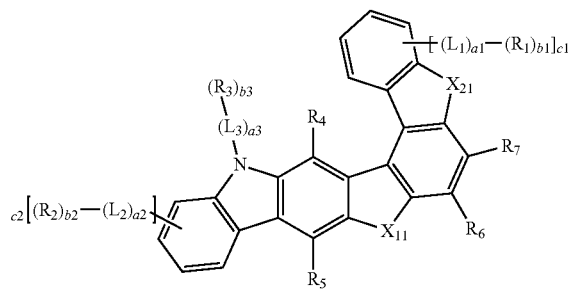

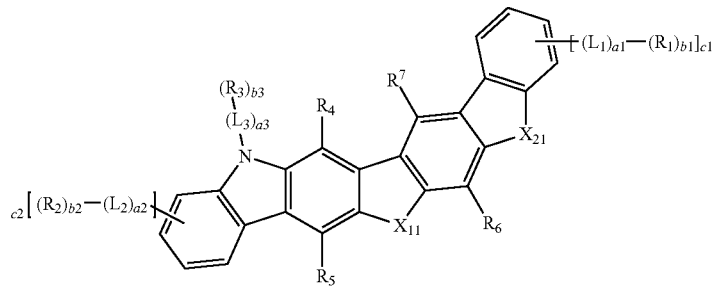

Formula 1A-11

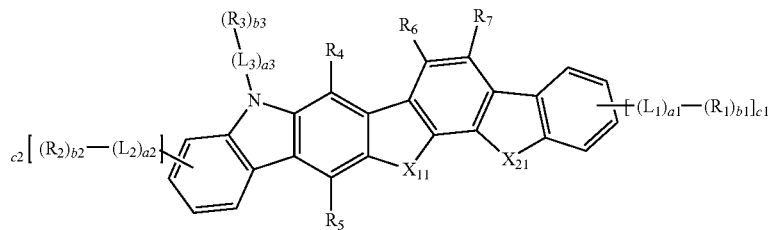

Formula 1A-12

In Formulae 1A-1 to 1A-12, the descriptions of $X_{11}$, $X_{21}$, $L_1$ to $L_3$, a1 to a3, $R_1$ to $R_7$, and c1 are as defined in the present specification, and c2 is an integer selected from 1 to 4.

Regarding the condensed cyclic compound, i) in Formula 1-2, when $X_{11}$ is $C(R_{12})(R_{13})$, $X_{21}$ is not $N-[(L_{21})_{a21}-(R_{21})_{b21}]$, ii) in Formula 1-2, when $X_{11}$ is $N-[(L_{11})_{a11}-(R_{11})_{b11}]$, $X_{21}$ is not $N-[(L_{21})_{a21}-(R_{21})_{b21}]$ or $C(R_{22})(R_{23})$, iii) in Formula 1-4, when $X_{11}$ is $C(R_{12})(R_{13})$, $X_{21}$ is not $N-[(L_{21})_{a21}-(R_{21})_{b21}]$, iv) in Formula 1-8, when $X_{11}$ is $C(R_{12})(R_{13})$, $X_{21}$ is not $N-[(L_{21})_{a21}-(R_{21})_{b21}]$ or $C(R_{22})(R_{23})$, v) in Formula 1-8, when $X_{11}$ is $N-[(L_{11})_{a11}-(R_{11})_{b11}]$, $X_{21}$ is not $C(R_{22})(R_{23})$, vi) in Formula 1-8, when $X_{11}$ is S, $X_{21}$ is not $N-[(L_{21})_{a21}-(R_{21})_{b21}]$, vii) in Formula 1-8, when $X_{11}$ is $Si(R_{12})(R_{13})$, $X_{21}$ is not $N-[(L_{21})_{a21}-(R_{21})_{b21}]$, and viii) in Formula 1-11, when $X_{11}$ is $N-[(L_{11})_{a11}-(R_{11})_{b11}]$, $X_{21}$ is not $C(R_{22})(R_{23})$.

Thus, when the condensed cyclic compound is represented by Formula 1-2, the condensed cyclic compound may be represented by one of Formulae 1A-2-1 to 1A-2-22, when the condensed cyclic compound is represented by Formula 1-4, the condensed cyclic compound may be represented by one of Formulae 1A-4-1 to 1A-4-24, when the condensed cyclic compound is represented by Formula 1-8, the condensed cyclic compound may be represented by one of Formulae 1A-8-1 to 1A-8-20, and when the condensed cyclic compound is represented by Formula 1-11, the condensed cyclic compound may be represented by one of Formulae 1A-11-1 to 1A-11-24, but the condensed cyclic compound is not limited thereto:

TABLE 1

| Formula No. | Backbone of corresponding Formula | $X_{11}$ from backbone of corresponding Formula | $X_{12}$ from backbone of corresponding Formula |
|---|---|---|---|
| 1A-2-1 | 1A-2 | $C(R_{12})(R_{13})$ | $C(R_{22})(R_{23})$ |
| 1A-2-2 | 1A-2 | $C(R_{12})(R_{13})$ | O |
| 1A-2-3 | 1A-2 | $C(R_{12})(R_{13})$ | S |
| 1A-2-4 | 1A-2 | $C(R_{12})(R_{13})$ | $Si(R_{22})(R_{23})$ |
| 1A-2-5 | 1A-2 | $N-[(L_{11})_{a11}-(R_{11})_{b11}]$ | O |
| 1A-2-6 | 1A-2 | $N-[(L_{11})_{a11}-(R_{11})_{b11}]$ | S |
| 1A-2-7 | 1A-2 | $N-[(L_{11})_{a11}-(R_{11})_{b11}]$ | $Si(R_{22})(R_{23})$ |
| 1A-2-8 | 1A-2 | O | $C(R_{22})(R_{23})$ |
| 1A-2-9 | 1A-2 | O | $N-[(L_{21})_{a21}-(R_{21})_{b21}]$ |
| 1A-2-10 | 1A-2 | O | O |
| 1A-2-11 | 1A-2 | O | S |
| 1A-2-12 | 1A-2 | O | $Si(R_{22})(R_{23})$ |
| 1A-2-13 | 1A-2 | S | $C(R_{22})(R_{23})$ |
| 1A-2-14 | 1A-2 | S | $N-[(L_{21})_{a21}-(R_{21})_{b21}]$ |
| 1A-2-15 | 1A-2 | S | O |
| 1A-2-16 | 1A-2 | S | S |
| 1A-2-17 | 1A-2 | S | $Si(R_{22})(R_{23})$ |
| 1A-2-18 | 1A-2 | $Si(R_{12})(R_{13})$ | $C(R_{22})(R_{23})$ |
| 1A-2-19 | 1A-2 | $Si(R_{12})(R_{13})$ | $N-[(L_{21})_{a21}-(R_{21})_{b21}]$ |
| 1A-2-20 | 1A-2 | $Si(R_{12})(R_{13})$ | O |
| 1A-2-21 | 1A-2 | $Si(R_{12})(R_{13})$ | S |
| 1A-2-22 | 1A-2 | $Si(R_{12})(R_{13})$ | $Si(R_{22})(R_{23})$ |
| 1A-4-1 | 1A-4 | $C(R_{12})(R_{13})$ | $C(R_{22})(R_{23})$ |
| 1A-4-2 | 1A-4 | $C(R_{12})(R_{13})$ | O |
| 1A-4-3 | 1A-4 | $C(R_{12})(R_{13})$ | S |
| 1A-4-4 | 1A-4 | $C(R_{12})(R_{13})$ | $Si(R_{22})(R_{23})$ |
| 1A-4-5 | 1A-4 | $N-[(L_{11})_{a11}-(R_{11})_{b11}]$ | $C(R_{22})(R_{23})$ |
| 1A-4-6 | 1A-4 | $N-[(L_{11})_{a11}-(R_{11})_{b11}]$ | $N-[(L_{21})_{a21}-(R_{21})_{b21}]$ |
| 1A-4-7 | 1A-4 | $N-[(L_{11})_{a11}-(R_{11})_{b11}]$ | O |
| 1A-4-8 | 1A-4 | $N-[(L_{11})_{a11}-(R_{11})_{b11}]$ | S |
| 1A-4-9 | 1A-4 | $N-[(L_{11})_{a11}-(R_{11})_{b11}]$ | $Si(R_{22})(R_{23})$ |
| 1A-4-10 | 1A-4 | O | $C(R_{22})(R_{23})$ |
| 1A-4-11 | 1A-4 | O | $N-[(L_{21})_{a21}-(R_{21})_{b21}]$ |
| 1A-4-12 | 1A-4 | O | O |
| 1A-4-13 | 1A-4 | O | S |
| 1A-4-14 | 1A-4 | O | $Si(R_{22})(R_{23})$ |
| 1A-4-15 | 1A-4 | S | $C(R_{22})(R_{23})$ |
| 1A-4-16 | 1A-4 | S | $N-[(L_{21})_{a21}-(R_{21})_{b21}]$ |
| 1A-4-17 | 1A-4 | S | O |
| 1A-4-18 | 1A-4 | S | S |

TABLE 1-continued

| Formula No. | Backbone of corresponding Formula | $X_{11}$ from backbone of corresponding Formula | $X_{12}$ from backbone of corresponding Formula |
|---|---|---|---|
| 1A-4-19 | 1A-4 | S | $Si(R_{22})(R_{23})$ |
| 1A-4-20 | 1A-4 | $Si(R_{12})(R_{13})$ | $C(R_{22})(R_{23})$ |
| 1A-4-21 | 1A-4 | $Si(R_{12})(R_{13})$ | $N-[(L_{21})_{a21}-(R_{21})_{b21}]$ |
| 1A-4-22 | 1A-4 | $Si(R_{12})(R_{13})$ | O |
| 1A-4-23 | 1A-4 | $Si(R_{12})(R_{13})$ | S |
| 1A-4-24 | 1A-4 | $Si(R_{12})(R_{13})$ | $Si(R_{22})(R_{23})$ |
| 1A-8-1 | 1A-8 | $C(R_{12})(R_{13})$ | O |
| 1A-8-2 | 1A-8 | $C(R_{12})(R_{13})$ | S |
| 1A-8-3 | 1A-8 | $C(R_{12})(R_{13})$ | $Si(R_{22})(R_{23})$ |
| 1A-8-4 | 1A-8 | $N-[(L_{11})_{a11}-(R_{11})_{b11}]$ | $N-[(L_{21})_{a21}-(R_{21})_{b21}]$ |
| 1A-8-5 | 1A-8 | $N-[(L_{11})_{a11}-(R_{11})_{b11}]$ | O |
| 1A-8-6 | 1A-8 | $N-[(L_{11})_{a11}-(R_{11})_{b11}]$ | S |
| 1A-8-7 | 1A-8 | $N-[(L_{11})_{a11}-(R_{11})_{b11}]$ | $Si(R_{22})(R_{23})$ |
| 1A-8-8 | 1A-8 | O | $C(R_{22})(R_{23})$ |
| 1A-8-9 | 1A-8 | O | $N-[(L_{21})_{a21}-(R_{21})_{b21}]$ |
| 1A-8-10 | 1A-8 | O | O |
| 1A-8-11 | 1A-8 | O | S |
| 1A-8-12 | 1A-8 | O | $Si(R_{22})(R_{23})$ |
| 1A-8-13 | 1A-8 | S | $C(R_{22})(R_{23})$ |
| 1A-8-14 | 1A-8 | S | O |
| 1A-8-15 | 1A-8 | S | S |
| 1A-8-16 | 1A-8 | S | $Si(R_{22})(R_{23})$ |
| 1A-8-17 | 1A-8 | $Si(R_{12})(R_{13})$ | $C(R_{22})(R_{23})$ |
| 1A-8-18 | 1A-8 | $Si(R_{12})(R_{13})$ | O |
| 1A-8-19 | 1A-8 | $Si(R_{12})(R_{13})$ | S |
| 1A-8-20 | 1A-8 | $Si(R_{12})(R_{13})$ | $Si(R_{22})(R_{23})$ |
| 1A-11-1 | 1A-11 | $C(R_{12})(R_{13})$ | $C(R_{22})(R_{23})$ |
| 1A-11-2 | 1A-11 | $C(R_{12})(R_{13})$ | $N-[(L_{21})_{a21}-(R_{21})_{b21}]$ |
| 1A-11-3 | 1A-11 | $C(R_{12})(R_{13})$ | O |
| 1A-11-4 | 1A-11 | $C(R_{12})(R_{13})$ | S |
| 1A-11-5 | 1A-11 | $C(R_{12})(R_{13})$ | $Si(R_{22})(R_{23})$ |
| 1A-11-6 | 1A-11 | $N-[(L_{11})_{a11}-(R_{11})_{b11}]$ | $N-[(L_{21})_{a21}-(R_{21})_{b21}]$ |
| 1A-11-7 | 1A-11 | $N-[(L_{11})_{a11}-(R_{11})_{b11}]$ | O |
| 1A-11-8 | 1A-11 | $N-[(L_{11})_{a11}-(R_{11})_{b11}]$ | S |
| 1A-11-9 | 1A-11 | $N-[(L_{11})_{a11}-(R_{11})_{b11}]$ | $Si(R_{22})(R_{23})$ |
| 1A-11-10 | 1A-11 | O | $C(R_{22})(R_{23})$ |
| 1A-11-11 | 1A-11 | O | $N-[(L_{21})_{a21}-(R_{21})_{b21}]$ |
| 1A-11-12 | 1A-11 | O | O |
| 1A-11-13 | 1A-11 | O | S |
| 1A-11-14 | 1A-11 | O | $Si(R_{22})(R_{23})$ |
| 1A-11-15 | 1A-11 | S | $C(R_{22})(R_{23})$ |
| 1A-11-16 | 1A-11 | S | $N-[(L_{21})_{a21}-(R_{21})_{b21}]$ |
| 1A-11-17 | 1A-11 | S | O |
| 1A-11-18 | 1A-11 | S | S |
| 1A-11-19 | 1A-11 | S | $Si(R_{22})(R_{23})$ |
| 1A-11-20 | 1A-11 | $Si(R_{12})(R_{13})$ | $C(R_{22})(R_{23})$ |
| 1A-11-21 | 1A-11 | $Si(R_{12})(R_{13})$ | $N-[(L_{21})_{a21}-(R_{21})_{b21}]$ |
| 1A-11-22 | 1A-11 | $Si(R_{12})(R_{13})$ | O |
| 1A-11-23 | 1A-11 | $Si(R_{12})(R_{13})$ | S |
| 1A-11-24 | 1A-11 | $Si(R_{12})(R_{13})$ | $Si(R_{22})(R_{23})$ |

For example, Formula 1A-2-10 has a backbone of Formula 1A-2, where $X_{11}$ is O, and $X_{12}$ is O. Also, Formula 1A-2-14 has a backbone of Formula 1A-2, where $X_{11}$ is S, and $X_{12}$ is $N-[(L_{21})_{a21}-(R_{21})_{b21}]$:

Formula 1A-2-10

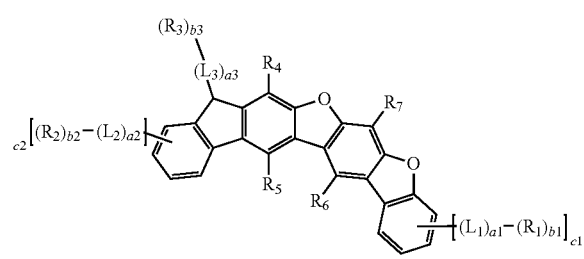

Formula 1A-2-14

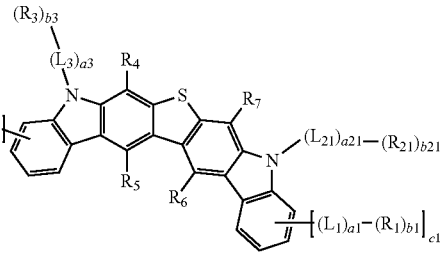

Structures of Formulae 1A-2-1 to 1A-2-22, 1A-4-1 to 1A-4-24, 1A-8-1 to 1A-8-20, and 1A-11-1 to 1A-11-24 may be understood from the descriptions of the substituents and variables defined above.

In some embodiments, the condensed cyclic compound is represented by one of Formulae 1-1 to 1-7 and 1-9 to 1-12, wherein in Formulae 1-1 to 1-7 and 1-9 to 1-12, $X_{11}$ and $X_{12}$ are each independently O or S;

$X_{11}$ is O or S, and $X_{12}$ is $N-[(L_{21})_{a21}-(R_{21})_{b21}]$ or $C(R_{22})(R_{23})$;

$X_{11}$ is $N-[(L_{11})_{a11}-(R_{11})_{b11}]$ or $C(R_{12})(R_{13})$, and $X_{12}$ is O or S; or $X_{11}$ is $C(R_{12})(R_{13})$, and $X_{12}$ is $C(R_{22})(R_{23})$.

In some embodiments, the condensed cyclic compound may be represented by one of Formulae 1A-1 to 1A-7 and 1A-9 to 1A-12, wherein in Formulae 1A-1 to 1A-7 and 1A-9 to 1A-12, $X_{11}$ and $X_{12}$ are each independently O or S;

$X_{11}$ is O or S, and $X_{12}$ is $N-[(L_{21})_{a21}-(R_{21})_{b21}]$ or $C(R_{22})(R_{23})$;

$X_{11}$ is $N-[(L_{11})_{a11}-(R_{11})_{b11}]$ or $C(R_{12})(R_{13})$, and $X_{12}$ is O or S; or $X_{11}$ is $C(R_{12})(R_{13})$, and $X_{12}$ is $C(R_{22})(R_{23})$.

In some embodiments, the condensed cyclic compound is represented by one of Formulae 1-1, 1-3 to 1-7 and 1-9 to 1-11, wherein $X_{11}$ may be $N-[(L_{11})_{a11}-(R_{11})_{b11}]$ and $X_{12}$ may be $N-[(L_{21})_{a21}-(R_{21})_{b21}]$.

In some embodiments, the condensed cyclic compound is represented by one of Formulae 1A-1, 1A-3 to 1A-7, and 1A-9 to 1A-11, wherein $X_{11}$ may be $N-[(L_{11})_{a11}-(R_{11})_{b11}]$ and $X_{12}$ may be $N-[(L_{21})_{a21}-(R_{21})_{b21}]$.

In some embodiments, the condensed cyclic compound is represented by Formula 1-2, wherein $X_{11}$ may be O or S and $X_{12}$ may be O, S, or $N-[(L_{21})_{a21}-(R_{21})_{b21}]$.

In some embodiments, the condensed cyclic compound is represented by Formula 1A-2, wherein $X_{11}$ may be O or S and $X_{12}$ may be O, S, or $N-[(L_{21})_{a21}-(R_{21})_{b21}]$.

In some embodiments, the condensed cyclic compound is represented by one of Formulae 1-1 to 1-7 and 1-9 to 1-12, wherein $X_{11}$ may be O or S. When $X_{11}$ is O or S, the condensed cyclic compound may have an improved planarization property and may have excellent charge mobility due to an electron lone pair of O or S.

In Formulae 1, 1-1 to 1-12 and 1A-1 to 1A-12 and the formulae in Table 1, $L_1$ to $L_3$, $L_{11}$, and $L_{21}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In some embodiments, in Formulae 1, 1-1 to 1-12 and 1A-1 to 1A-12 and the formulae in Table 1, $L_1$ to $L_3$, $L_{11}$, and $L_{21}$ are each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group an imidazopyrimidinylene group, and an imidazopyridinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{20}$ aryl group, a $C_1$-$C_{20}$ heteroaryl group, a monovalent non-aromatic condensed polycyclic group, a monovalent non-aromatic condensed heteropolycyclic group, and —Si($Q_{33}$)($Q_{34}$)($Q_{35}$);

wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

In some embodiments, in Formulae 1, 1-1 to 1-12 and 1A-1 to 1A-12 and the formulae in Table 1, $L_1$ to $L_3$, $L_{11}$, and $L_{21}$ may be each independently selected from a phenylene group, a naphthylene group, and a triphenylene group; and a phenylene group, a naphthylene group, and a triphenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, and a chrysenyl group, but are not limited thereto.

In some embodiments, in Formulae 1, 1-1 to 1-12 and 1A-1 to 1A-12 and the formulae in Table 1, $L_1$ to $L_3$, $L_{11}$, and $L_{21}$ may be each independently represented by one of Formulae 2-1 to 2-34:

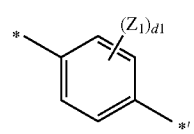

Formula 2-1

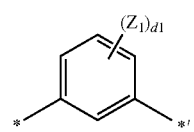

Formula 2-2

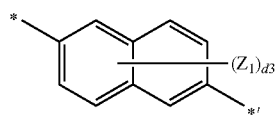

Formula 2-3

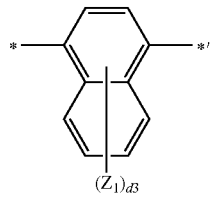

Formula 2-4

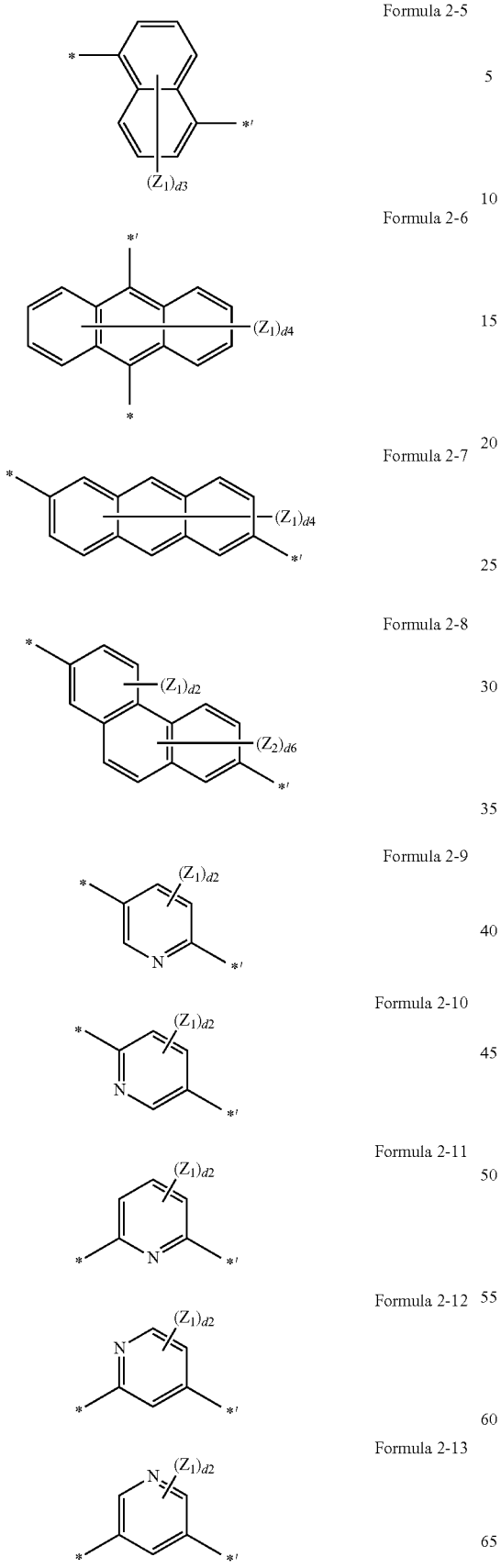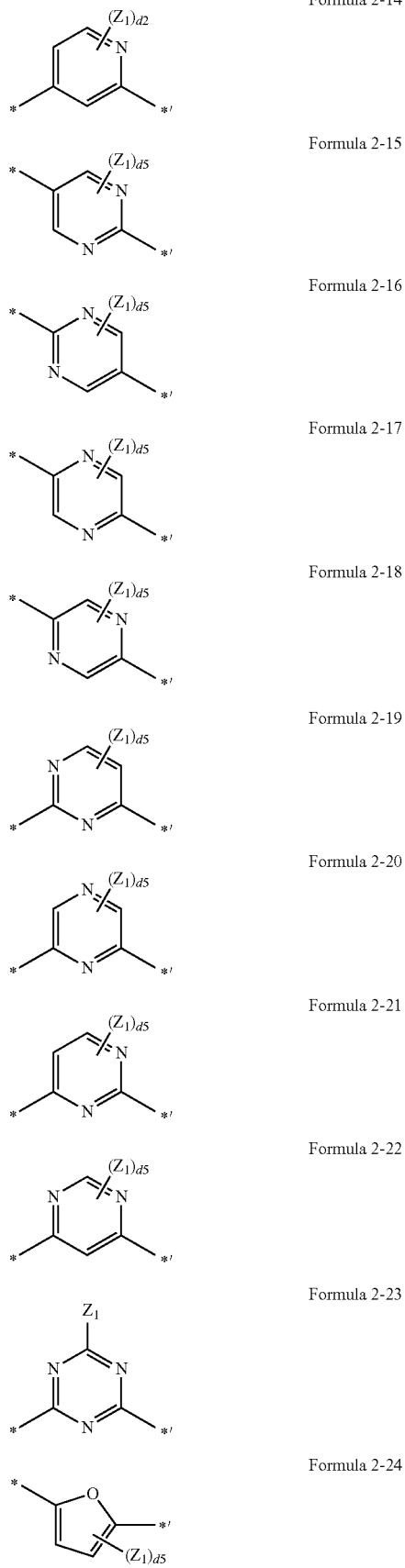

Formula 2-25
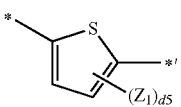

Formula 2-26
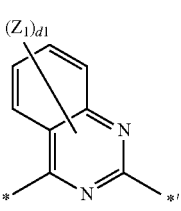

Formula 2-27
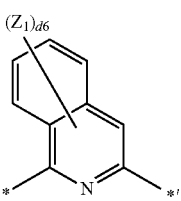

Formula 2-28
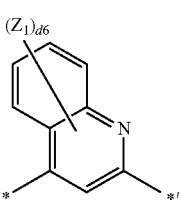

Formula 2-29
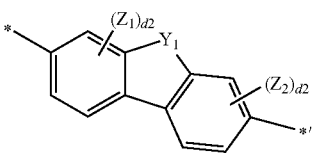

Formula 2-30
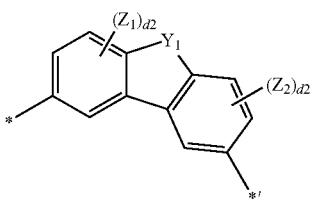

Formula 2-31
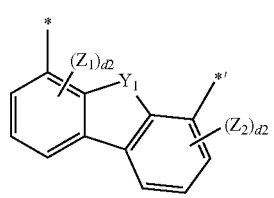

Formula 2-32
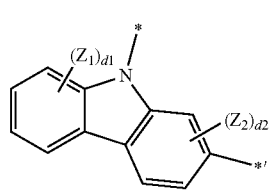

Formula 2-33
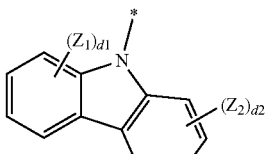

Formula 2-34
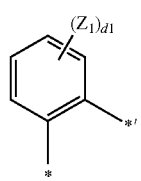

In Formulae 2-1 to 2-34, $Y_1$ is O, S, S(=O), S(=O)$_2$, C($Z_3$)($Z_4$), N($Z_5$), or Si($Z_6$)($Z_7$);

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —Si($Q_{33}$)($Q_{34}$)($Q_{35}$); wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

d1 is an integer selected from 1 to 4,
d2 is an integer selected from 1 to 3,
d3 is an integer selected from 1 to 6,
d4 is an integer selected from 1 to 8,
d5 is an integer of 1 or 2, and
d6 is an integer selected from 1 to 5; and
* and *' each indicates a binding site with a neighboring atom.

In some embodiments, in Formulae 1, 1-1 to 1-12 and 1A-1 to 1A-12 and the formulae in Table 1, $L_1$ to $L_3$, $L_{11}$, and $L_{21}$ may be each independently one of Formulae 3-1 to 3-21, but are not limited thereto:

Formula 3-1
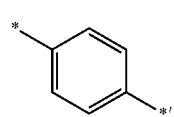

-continued

Formula 3-2

Formula 3-3

Formula 3-4

Formula 3-5

Formula 3-6

Formula 3-7

Formula 3-8

Formula 3-9

Formula 3-10

Formula 3-11

Formula 3-12

Formula 3-13

Formula 3-14

Formula 3-15

Formula 3-16

Formula 3-17

Formula 3-18

Formula 3-19

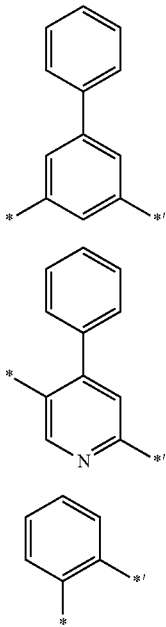

Formula 3-20

Formula 3-21

* and *' each indicates a binding site with a neighboring atom.

In some embodiments, $L_1$ to $L_3$, $L_{11}$, and $L_{21}$ in Formulae 1, 1-1 to 1-12 and 1A-1 to 1A-12 and the formulae in Table 1, may be each independently, but not limited to, selected from a phenylene group, a naphthylene group, a pyridinylene group, a pyrimidinylene group, and a triazinylene group; and a phenylene group, a naphthylene group, a pyridinylene group, a pyrimidinylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group.

In Formulae 1, 1-1 to 1-12 and 1A-1 to 1A-12 and the formulae in Table 1, a1 denotes the number of groups $L_1$, and a1 may be 0, 1, 2, 3, 4 or 5, for example, 0, 1, or 2, for example, 0 or 1. When a1 is 0, *-$(L_1)_{a1}$-*' is a single bond. When a1 is 2 or higher, groups $L_1$ may be identical to or different from each other. The descriptions of a2, a3, a11, and a21 may be understood from the descriptions of a1 and Formulae 1, 1-1 to 1-12 and 1A-1 to 1A-12 and the formulae in Table 1.

In Formulae 1, 1-1 to 1-12 and 1A-1 to 1A-12 and the formulae in Table 1, $R_1$ to $R_7$, $R_{11}$ to $R_{13}$, and $R_{21}$ to $R_{23}$ are each independently selected from, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$).

In some embodiments, in Formulae 1, 1-1 to 1-12 and 1A-1 to 1A-12 and the formulae in Table 1, $R_1$ to $R_7$, $R_{11}$ to $R_{13}$, and $R_{21}$ to $R_{23}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, a substituted or unsubstituted monovalent non-aromatic condensed heteropolycyclic group, and —Si($Q_3$)($Q_4$)($Q_5$).

In some embodiments, in Formulae 1, 1-1 to 1-12 and 1A-1 to 1A-12 and the formulae in Table 1, i) when $X_{11}$ is N-[$(L_{11})_{a11}$-$(R_{11})_{b11}$], at least one of $R_3$ and $R_{11}$, ii) when $X_{12}$ is N-[$(L_{21})_{a11}$-$(R_{21})_{b11}$], at least one of $R_3$ and $R_{21}$, and iii) when $X_{11}$ is N-[$(L_{11})_{a11}$-$(R_{11})_{b11}$] and $X_{12}$ is N-[$(L_{21})_{a11}$-$(R_{21})_{b11}$], at least one of $R_3$, $R_{11}$, and $R_{21}$ may be each independently selected from a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 1, 1-1 to 1-12 and 1A-1 to 1A-12 and the formulae in Table 1, $R_3$ may be, but not limited to, selected from a substituted or unsubstituted $C_1$-$C_{30}$ heteroaryl group and a substituted or unsubstituted monovalent non-aromatic condensed heteropolycyclic group, including at least one nitrogen atom as a ring forming atom.

In some embodiments, in Formulae 1, 1-1 to 1-12 and 1A-1 to 1A-12 and the formulae in Table 1, $R_1$ to $R_7$, $R_{11}$ to $R_{13}$, and $R_{21}$ to $R_{23}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, and —Si($Q_{33}$)($Q_{34}$)($Q_{35}$); and —Si($Q_3$)($Q_4$)($Q_5$); wherein $Q_3$ to $Q_5$ and $Q_{33}$ to $Q_{35}$ may be, each independently, selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but are not limited thereto.

In some embodiments, in Formulae 1, 1-1 to 1-12 and 1A-1 to 1A-12 and the formulae in Table 1, $R_1$ to $R_7$, $R_{11}$ to $R_{13}$, and $R_{21}$ to $R_{23}$ may be, each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, one of Formulae 4-1 to 4-31, and —Si($Q_3$)($Q_4$)($Q_5$); wherein $Q_3$ to $Q_5$ may be, each independently, selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but are not limited thereto:

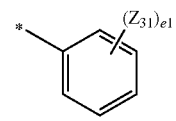

Formula 4-1

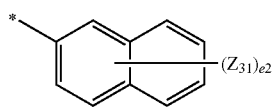

Formula 4-2

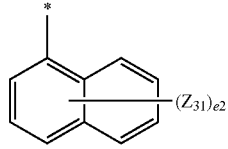

Formula 4-3

-continued
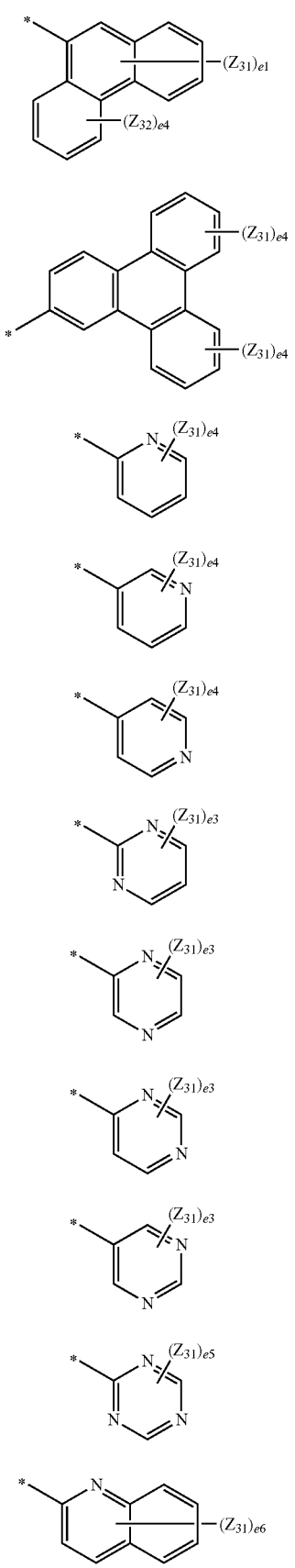
Formula 4-4
Formula 4-5
Formula 4-6
Formula 4-7
Formula 4-8
Formula 4-9
Formula 4-10
Formula 4-11
Formula 4-12
Formula 4-13
Formula 4-14
-continued
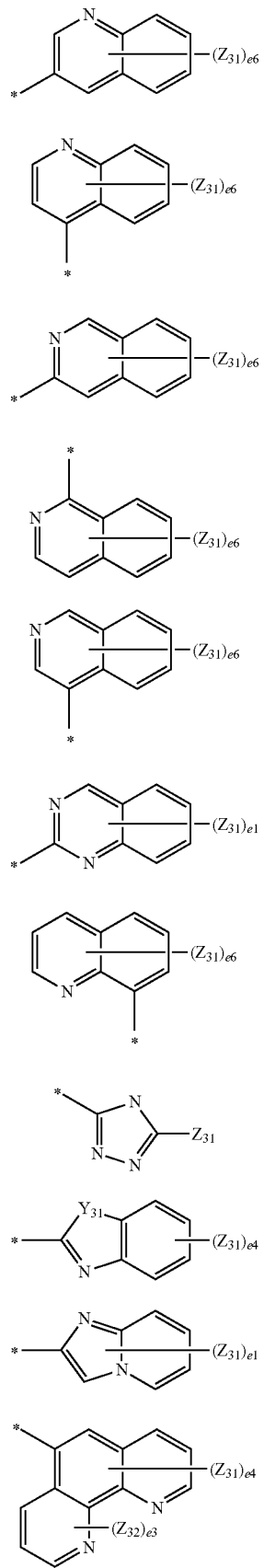
Formula 4-15
Formula 4-16
Formula 4-17
Formula 4-18
Formula 4-19
Formula 4-20
Formula 4-21
Formula 4-22
Formula 4-23
Formula 4-24
Formula 4-25

-continued

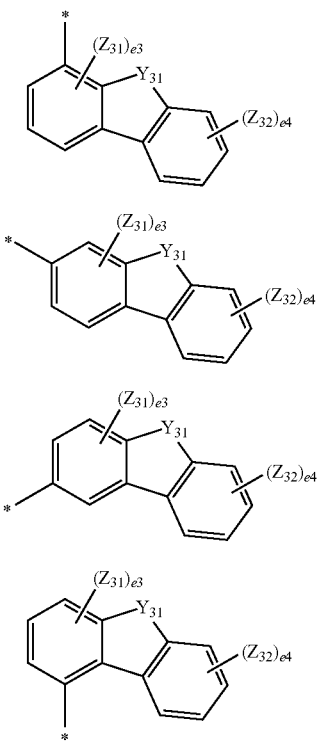

Formula 4-26

Formula 4-27

Formula 4-28

Formula 4-29

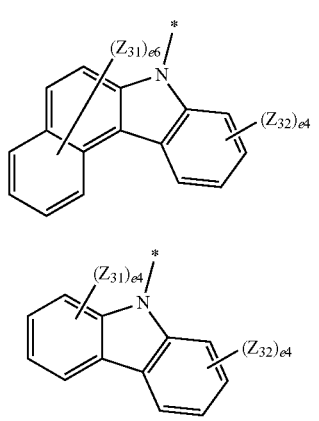

Formula 4-30

Formula 4-31

In Formulae 4-1 to 4-31, $Y_{31}$ is O, S, $C(Z_{33})(Z_{34})$, $N(Z_{35})$, or $Si(Z_{36})(Z_{37})$; wherein $Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —$Si(Q_{33})(Q_{34})(Q_{35})$; wherein $Q_{33}$ to $Q_{35}$ are each independently, selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, or a quinoxalinyl group.

e1 is an integer selected from 1 to 5,
e2 is an integer selected from 1 to 7,
e3 is an integer selected from 1 to 3,
e4 is an integer selected from 1 to 4,
e5 is an integer of 1 or 2,
e6 is an integer selected from 1 to 6, and
* indicates a binding site with a neighboring atom.

In some embodiments, in Formulae 1, 1-1 to 1-12 and 1A-1 to 1A-12 and the formulae in Table 1, $R_1$ to $R_7$, $R_{11}$ to $R_{13}$, and $R_{21}$ to $R_{23}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, one of Formulae 5-1 to 5-55, and —$Si(Q_3)(Q_4)(Q_5)$; wherein $Q_3$ to $Q_5$ are, each independently, selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but are not limited thereto:

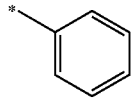

Formula 5-1

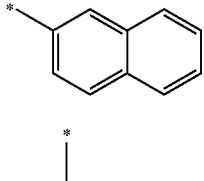

Formula 5-2

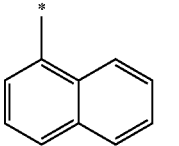

Formula 5-3

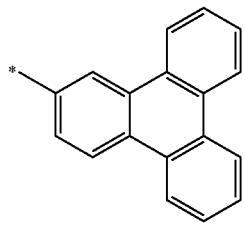

Formula 5-4

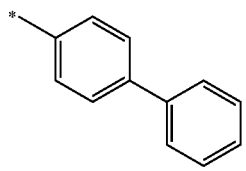

Formula 5-5

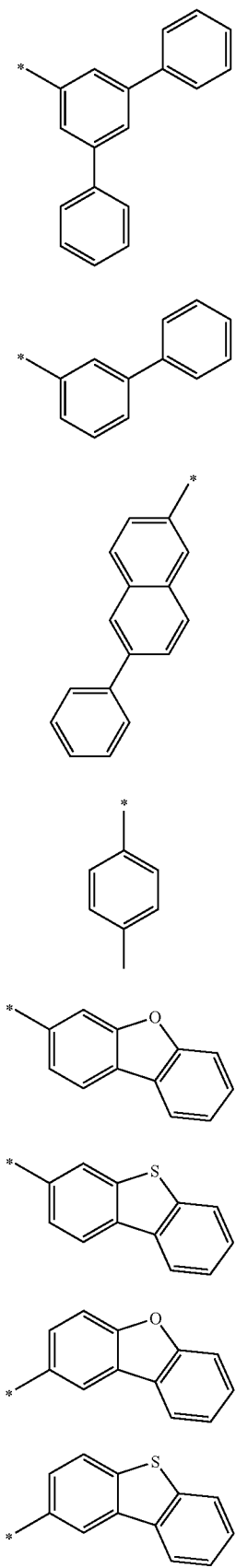
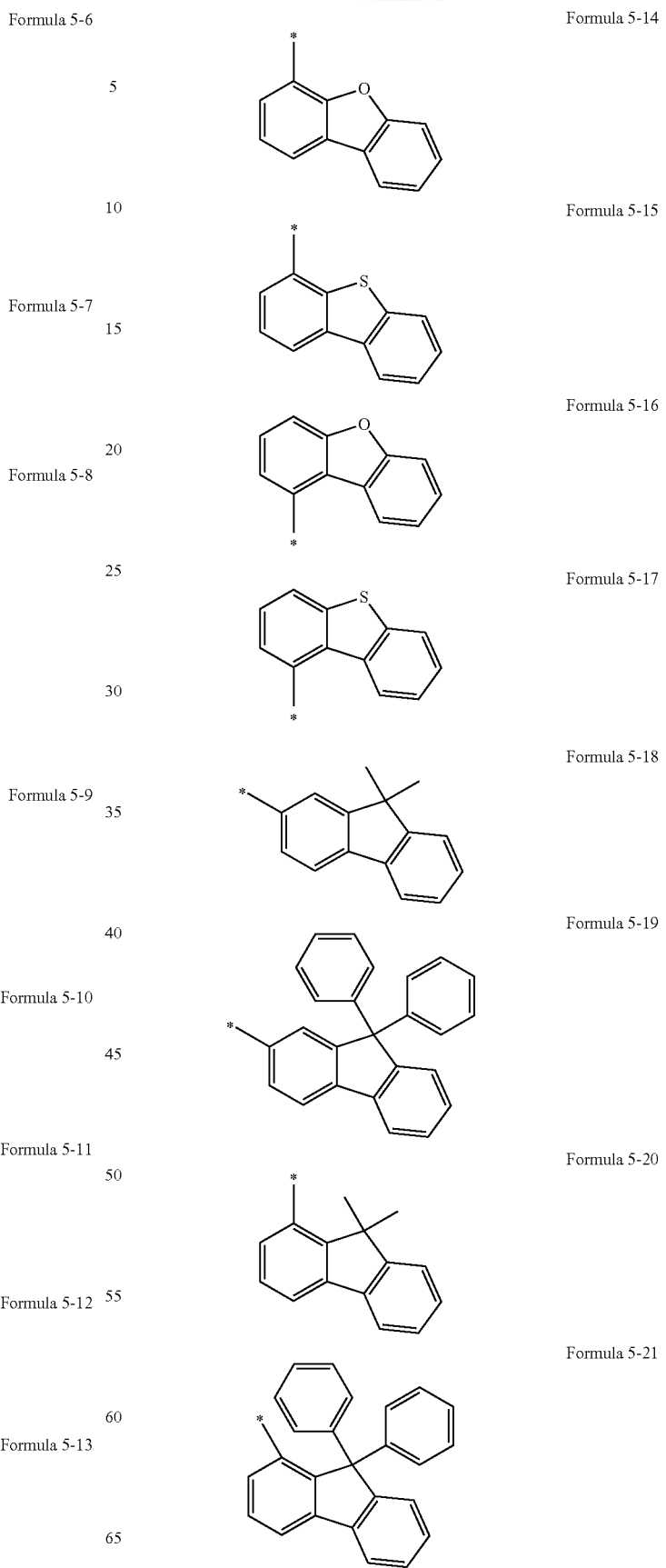

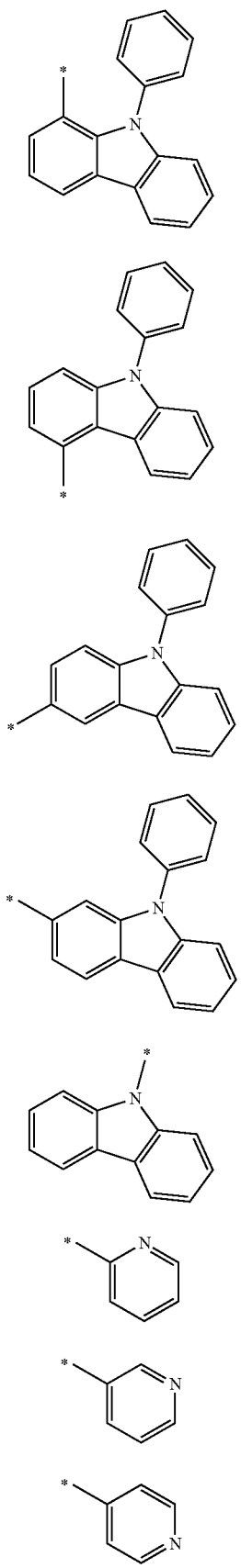
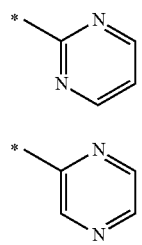
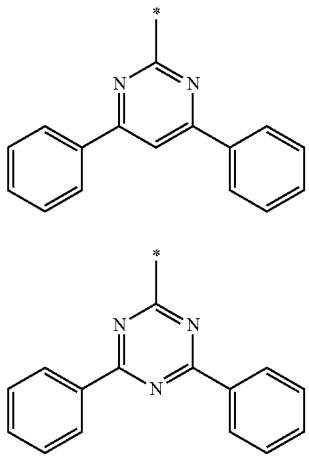
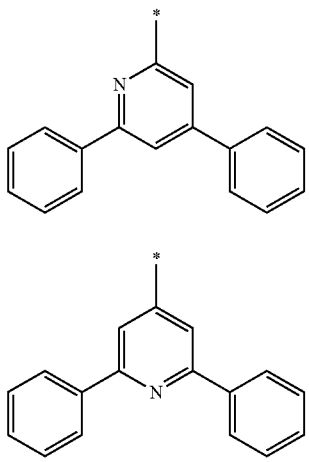
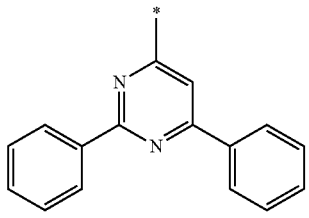
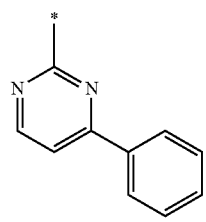
Formula 5-22
Formula 5-23
Formula 5-24
Formula 5-25
Formula 5-26
Formula 5-27
Formula 5-28
Formula 5-29
Formula 5-30
Formula 5-31
Formula 5-32
Formula 5-33
Formula 5-34
Formula 5-35
Formula 5-36
Formula 5-37

Formula 5-38
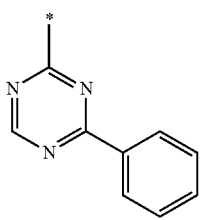
Formula 5-39
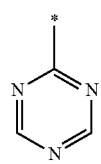
Formula 5-40
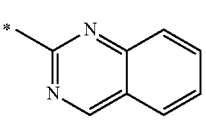
Formula 5-41
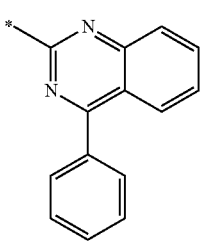
Formula 5-42
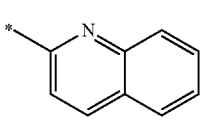
Formula 5-43
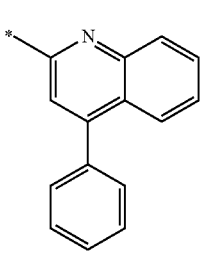
Formula 5-44
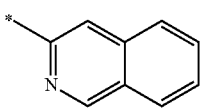
Formula 5-45
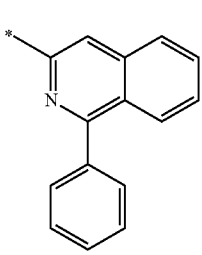
Formula 5-46
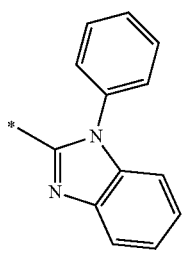
Formula 5-47
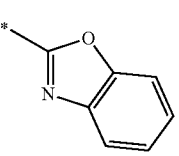
Formula 5-48
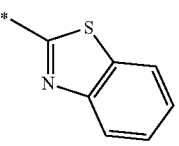
Formula 5-49
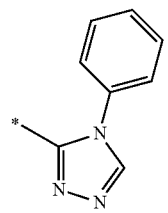
Formula 5-50
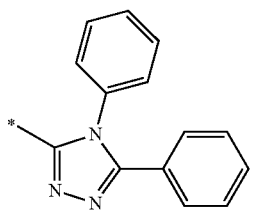
Formula 5-51
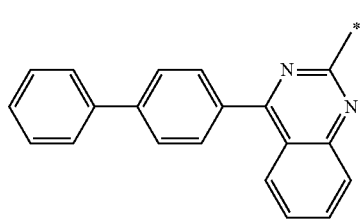
Formula 5-52
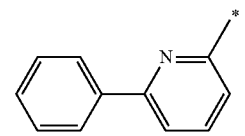

-continued

Formula 5-53

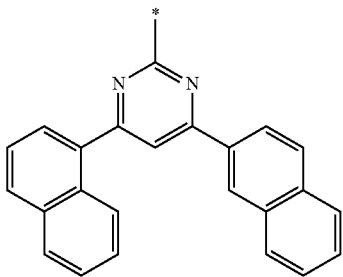

Formula 5-54

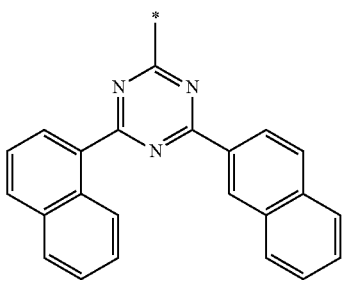

Formula 5-55

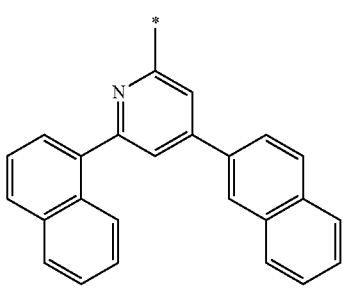

In Formulae 5-1 to 5-53, * indicates a binding site to a neighboring atom.

In some embodiments, in Formulae 1, 1-1 to 1-12 and 1A-1 to 1A-12 and the formulae in Table 1, $R_1$, $R_2$, and $R_4$ to $R_7$ may be a hydrogen but are not limited thereto.

In Formulae 1, 1-1 to 1-12 and 1A-1 to 1A-12 and the formulae in Table 1, b1 denotes the number of groups $R_1$, and thus b1 may be selected from 1 to 5. For example, b1 may be an integer of 1 or 2. For example, b1 may be 1. When b1 is 2 or higher, groups $R_1$ may be identical to or different from each other. The descriptions of b2 to b3, b11, and b12 are the same as defined in the descriptions of b1 and Formulae 1, 1-1 to 1-12 and 1A-1 to 1A-12 and the formulae in Table 1.

In Formulae 1, 1-1 to 1-12 and 1A-1 to 1A-12 and the formulae in Table 1, c1 denotes the number of groups -[$(L_1)_{a1}$-$(R_1)_{b1}$], and thus c1 may be an integer selected from 1 to 4. For example, c1 is 1 or 2. When c1 is 2 or higher, groups -[$(L_1)_{a1}$-$(R_1)_{b1}$] may be identical to or different from each other.

In Formulae 1, 1-1 to 1-12 and 1A-1 to 1A-12 and the formulae in Table 1, when $X_{11}$ is $C(R_{12})(R_{13})$ or $Si(R_{12})(R_{13})$, $R_{12}$ and $R_{13}$ may be identical to or different from each other. For example, when $X_{11}$ is $C(R_{12})(R_{13})$, $R_{12}$ may be a methyl group, and $R_{13}$ may be a phenyl group.

In Formulae 1, 1-1 to 1-12 and 1A-1 to 1A-12 and the formulae in Table 1, when $X_{21}$ is $C(R_{22})(R_{23})$ or $Si(R_{22})(R_{23})$, $R_{22}$ and $R_{23}$ may be identical to or different from each other. For example, when $X_{21}$ is $C(R_{22})(R_{23})$, $R_{22}$ may be a methyl group, and $R_{23}$ may be a phenyl group.

In Formulae 1, 1-1 to 1-12 and 1A-1 to 1A-12 and the formulae in Table 1, $L_3$ may be selected from a substituted or unsubstituted $C_6$-$C_{60}$ arylene group and a substituted or unsubstituted divalent non-aromatic condensed polycyclic group, and $R_3$ may be selected from a substituted or unsubstituted $C_6$-$C_{60}$ aryl group and a substituted or unsubstituted monovalent non-aromatic condensed polycyclic group.

For example, in Formulae 1, 1-1 to 1-12 and 1A-1 to 1A-12 and the formulae in Table 1, $L_3$ may be selected from a phenylene group, a naphthylene group, and a triphenylene group; and a phenylene group, a naphthylene group, and a triphenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, and a chrysenyl group, and $R_3$ may be selected from Formulae 4-1 to 4-5.

In some embodiments, a condensed cyclic compound represented by Formula 1 in which $L_3$ is selected from a substituted or unsubstituted $C_6$-$C_{60}$ arylene group and a substituted or unsubstituted divalent non-aromatic condensed polycyclic group and $R_3$ is selected from a substituted or unsubstituted a $C_6$-$C_{60}$ aryl group and a substituted or unsubstituted monovalent non-aromatic condensed polycyclic group may be included in a hole transport region of an organic light-emitting device, which will be described later in the present specification.

In some embodiments, $R_3$ in Formulae 1, 1-1 to 1-12 and 1A-1 to 1A-12 and the formulae in Table 1 may be an electron transport moiety. For example, in Formulae 1, 1-1 to 1-12 and 1A-1 to 1A-12 and the formulae in Table 1, $R_3$ may be a substituted or unsubstituted $C_1$-$C_{60}$ heteroaryl group or a substituted or unsubstituted monovalent non-aromatic condensed heteropolycyclic group.

For example, in Formulae 1, 1-1 to 1-12 and 1A-1 to 1A-12 and the formulae in Table 1, $R_3$ may be represented by one of Formulae 4-6 to 4-25, but is not limited thereto.

In some embodiments, the condensed cyclic compound represented by one of Formulae 1-1 to 1-12 in which $R_3$ is a substituted or unsubstituted $C_1$-$C_{60}$ heteroaryl group or a substituted or unsubstituted monovalent non-aromatic condensed heteropolycyclic group may be included in an emission layer of an organic light-emitting device.

The condensed cyclic compound may be one of Compounds 1 to 167, but is not limited thereto:

1

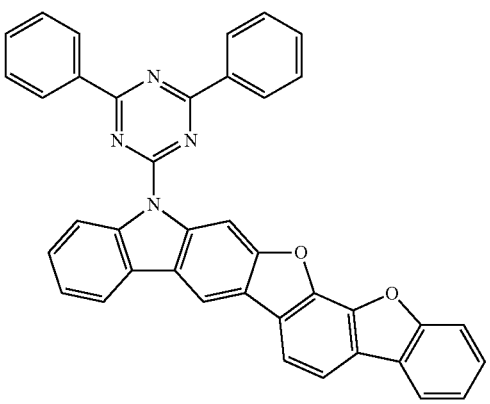

2
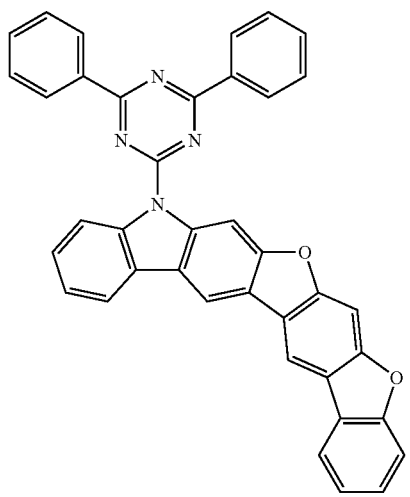
3
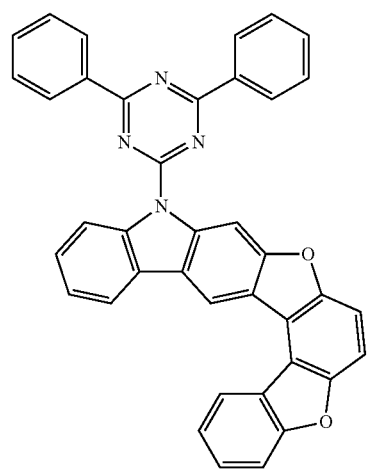
4
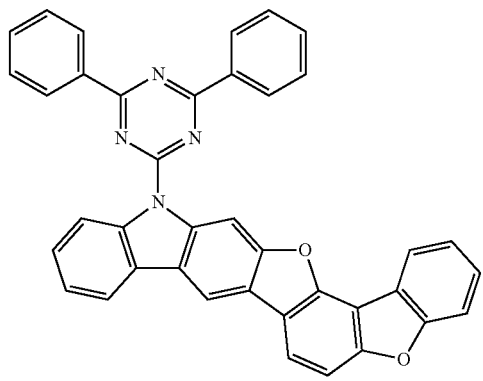
5
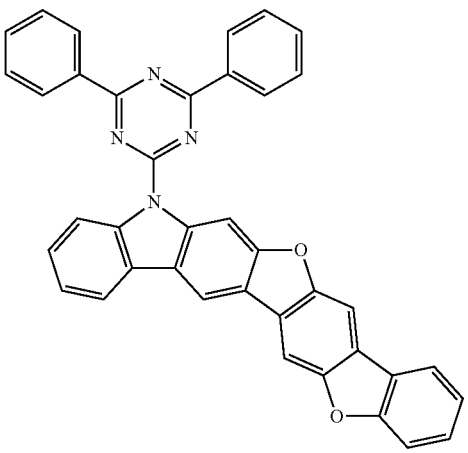
6
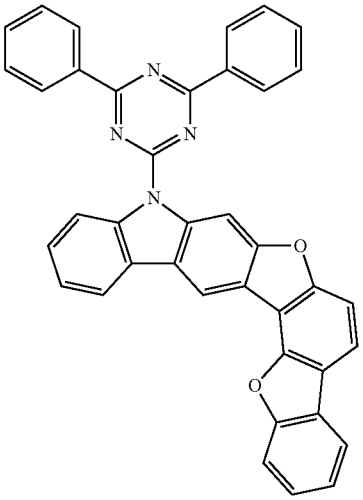
7
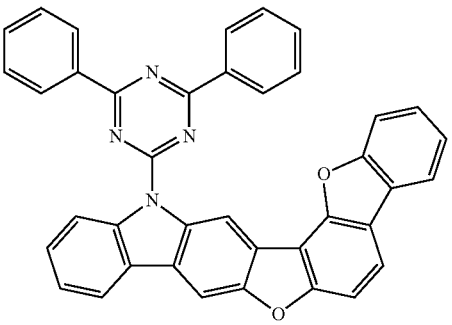

8
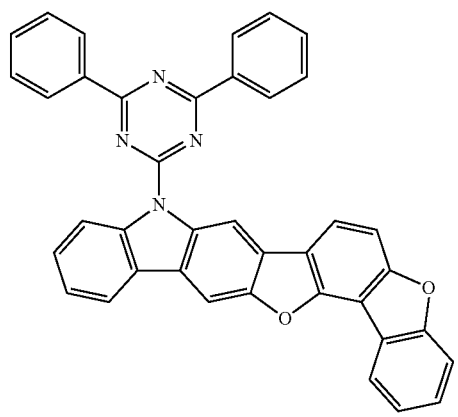
9
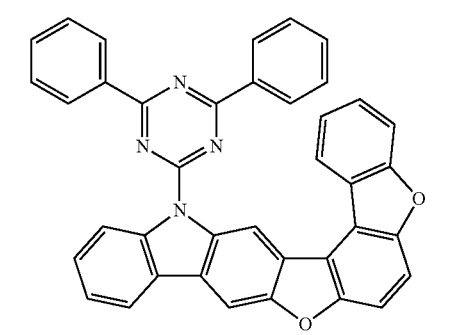
10
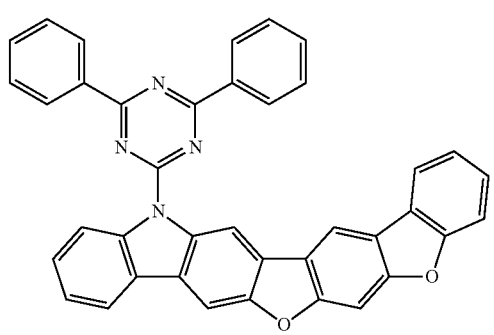
11
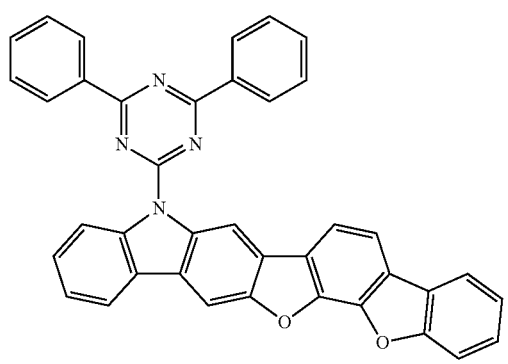
12
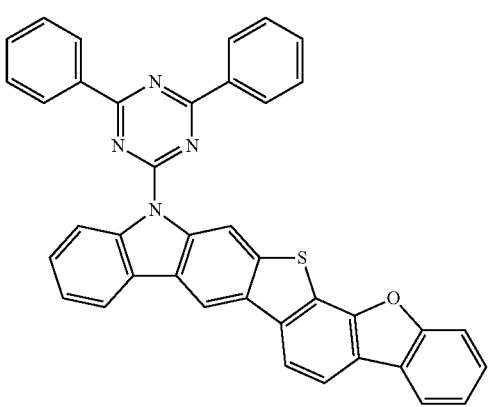
13
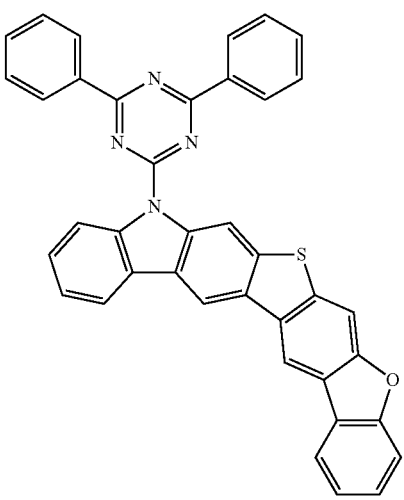
14
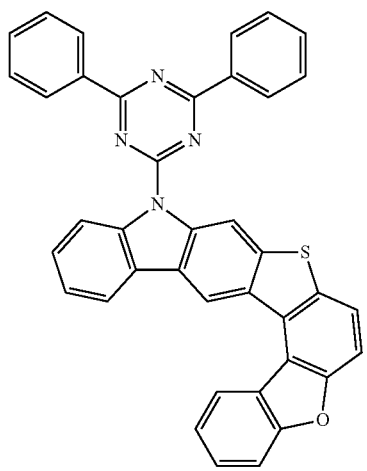

15
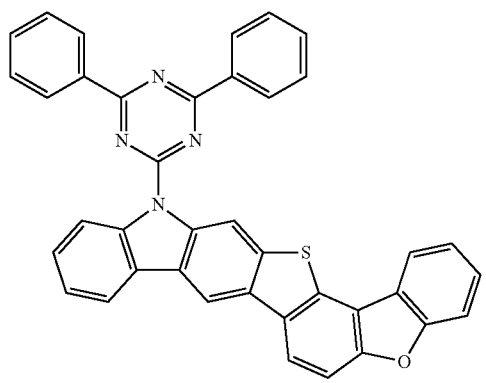
16
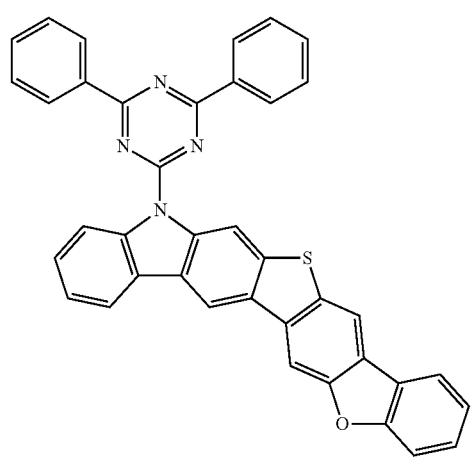
17
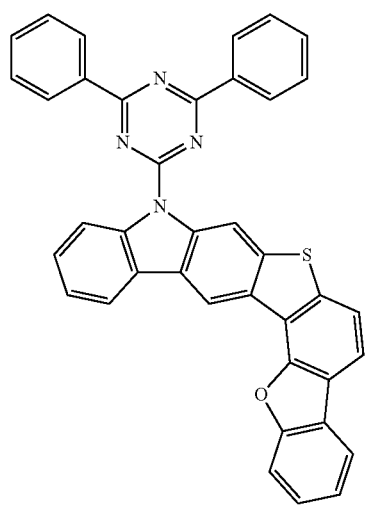
18
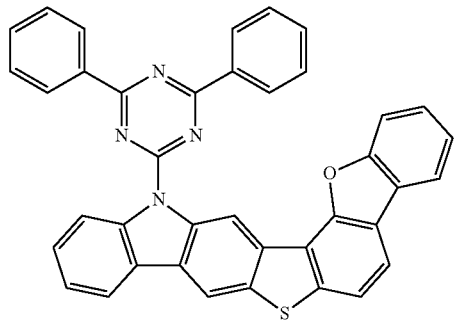
19
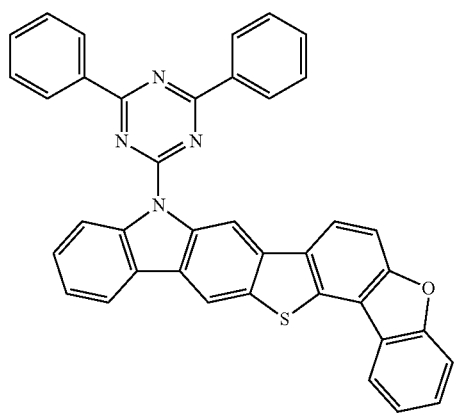
20
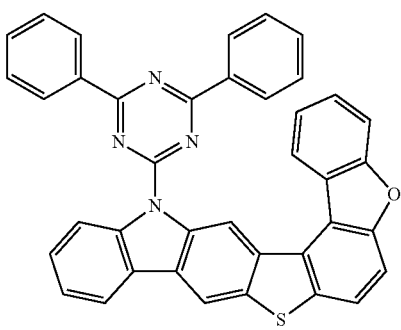
21
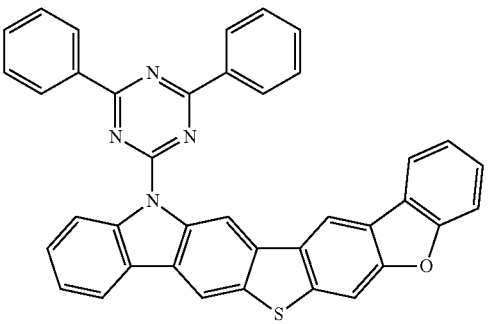

22
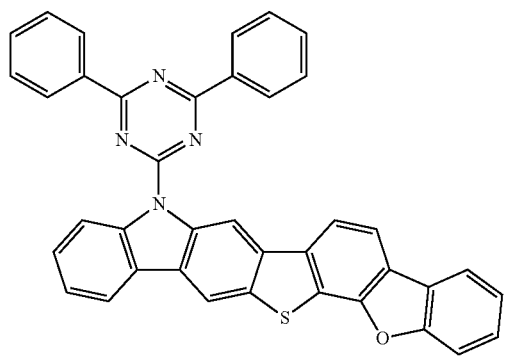
23
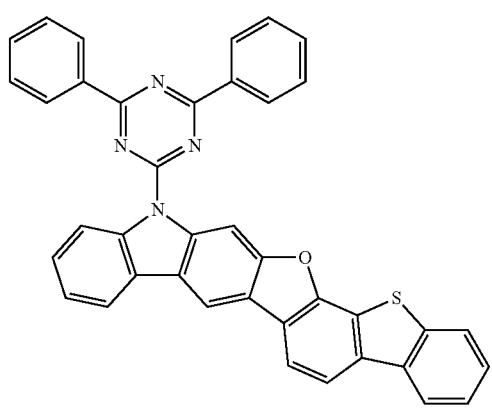
24
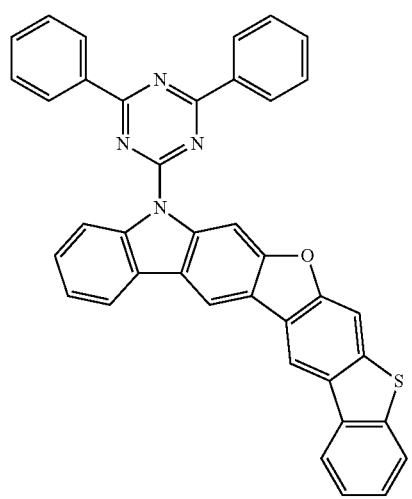
25
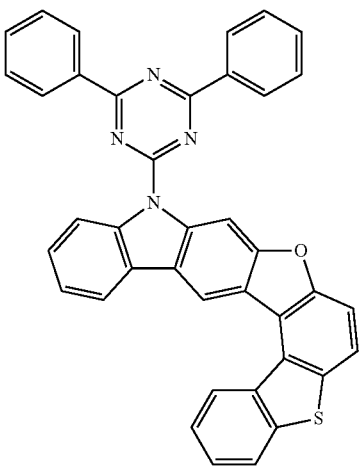
26
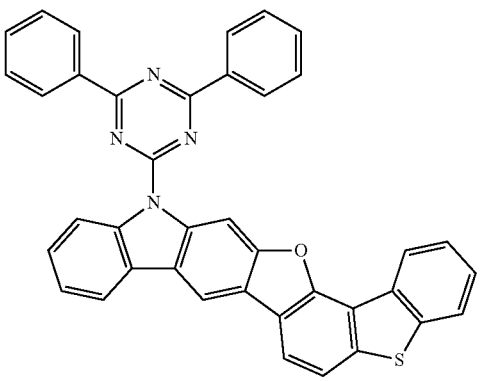
27
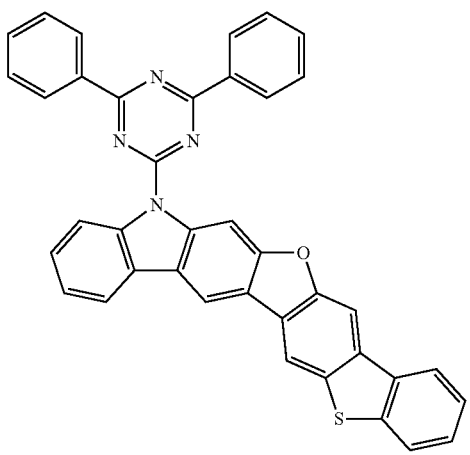

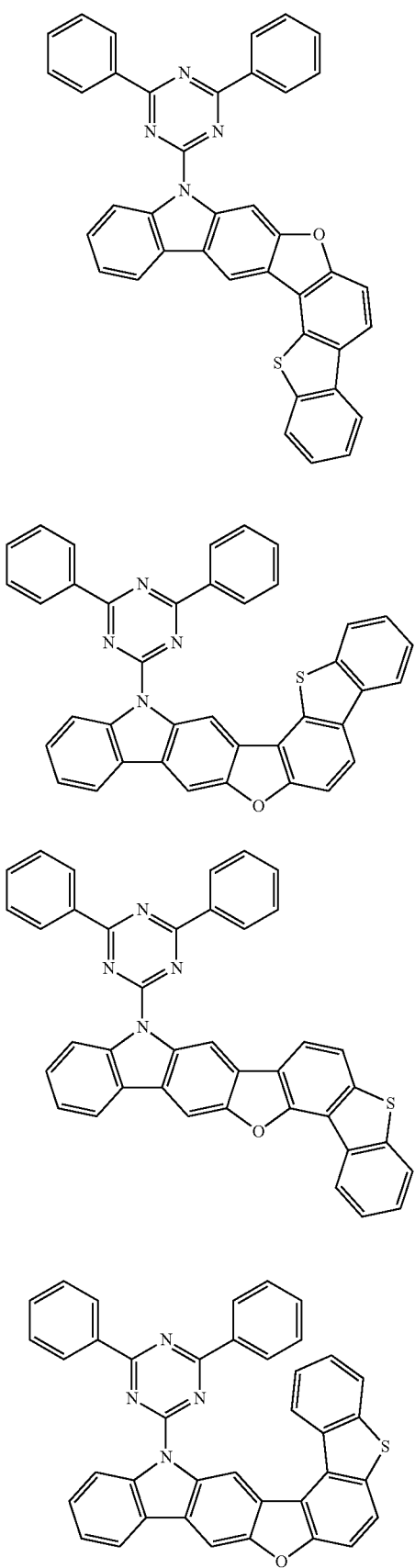
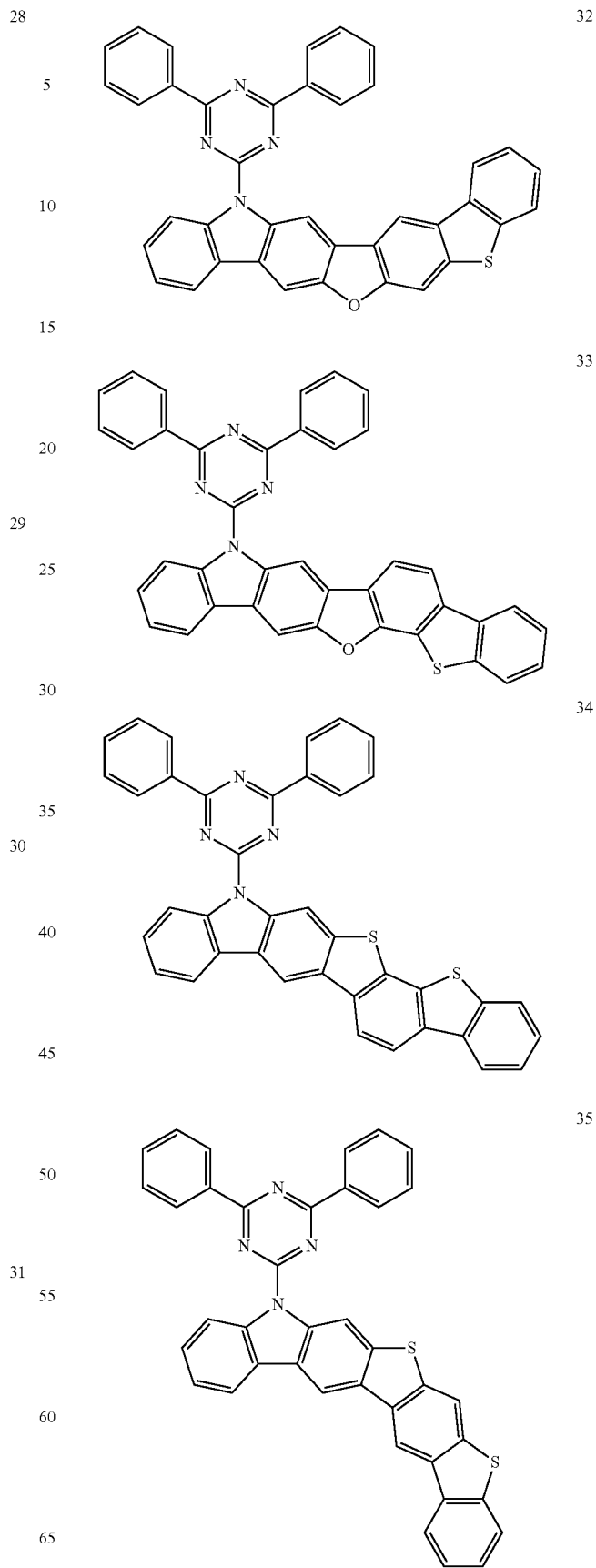

36
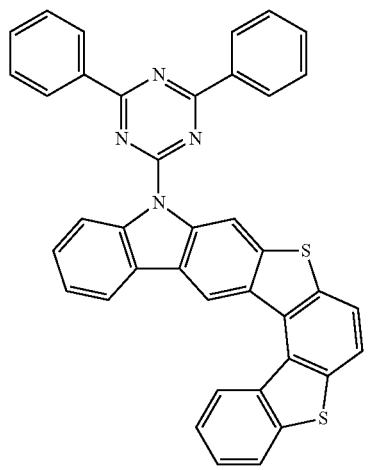
37
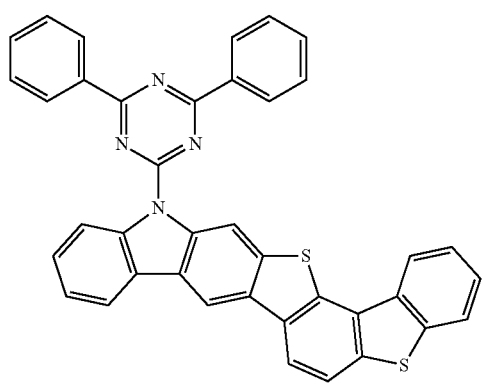
38
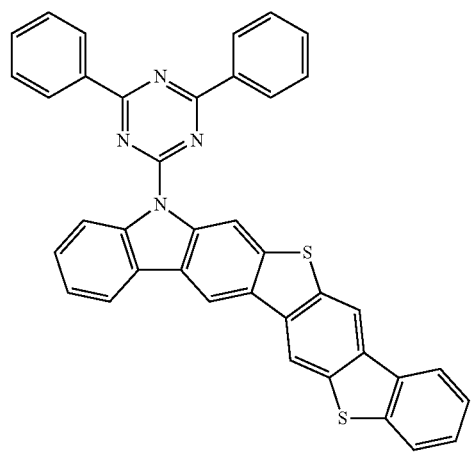
39
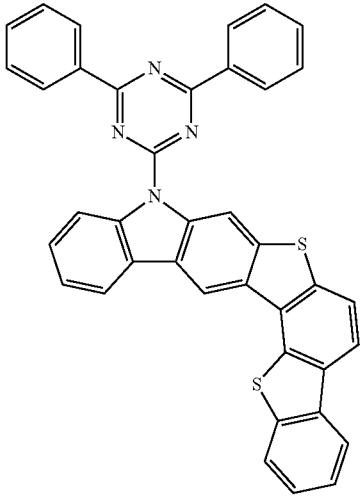
40
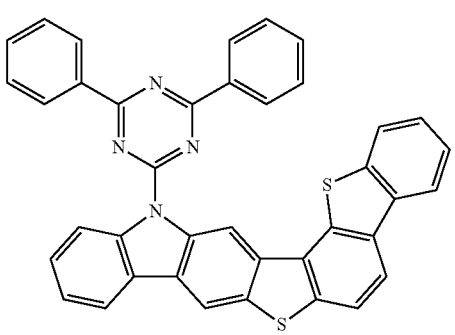
41
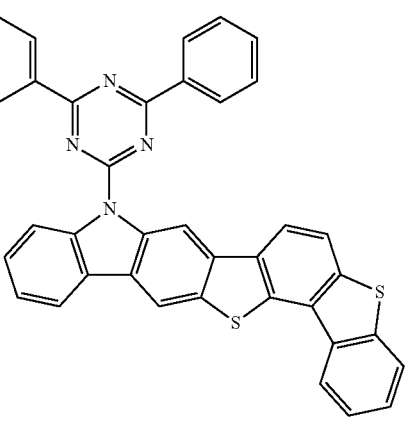
42
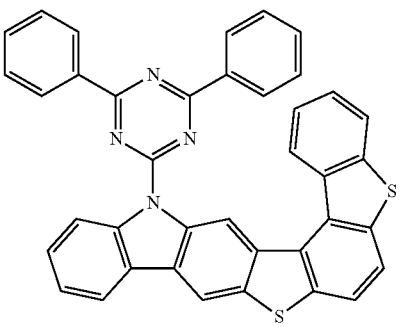

43
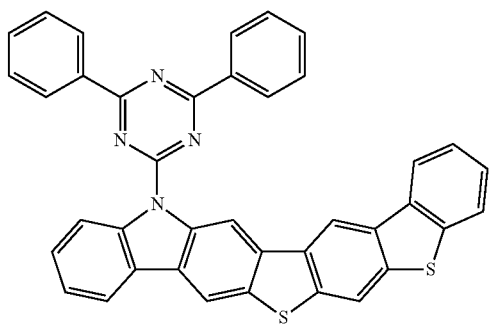
44
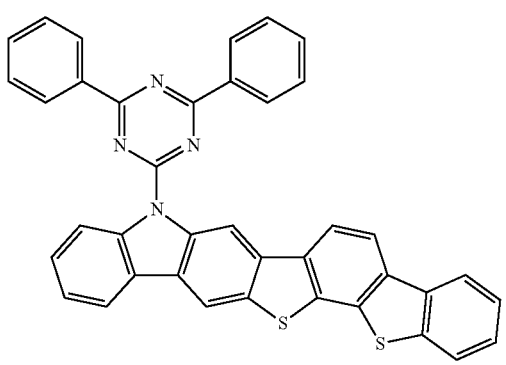
45
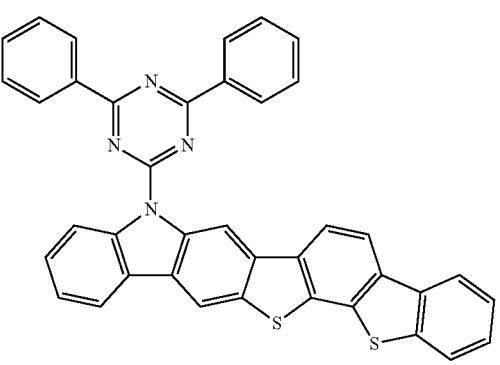
46
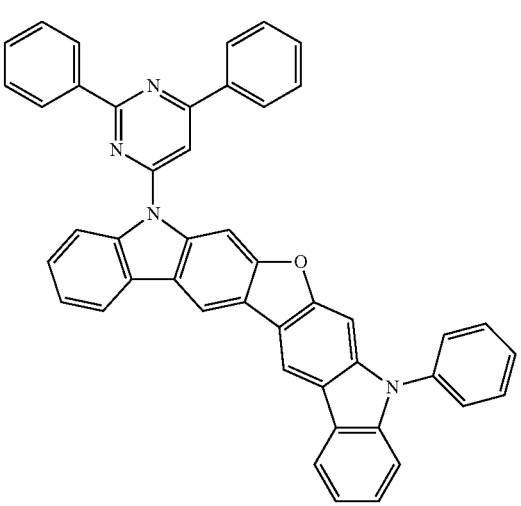
47
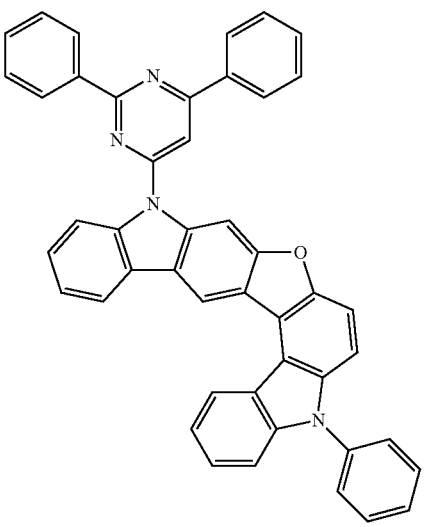
48
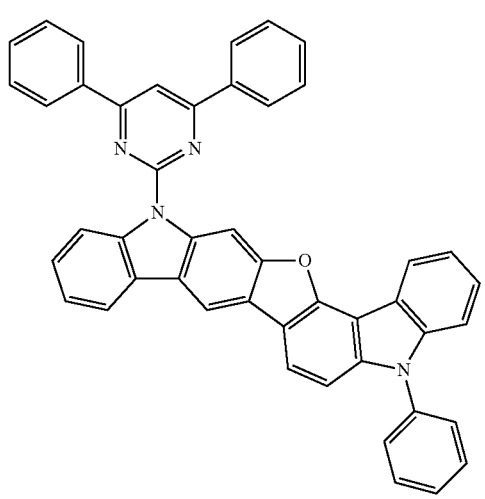
49
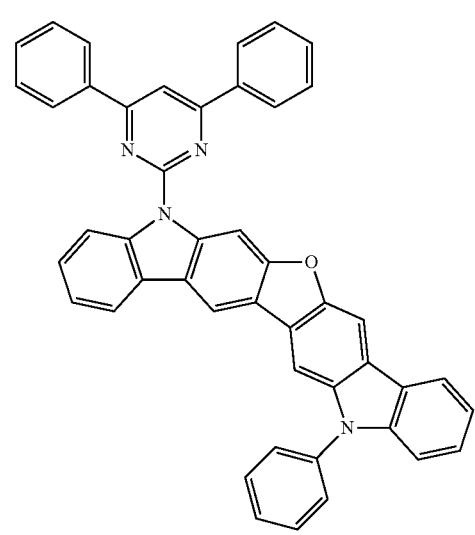

57
-continued
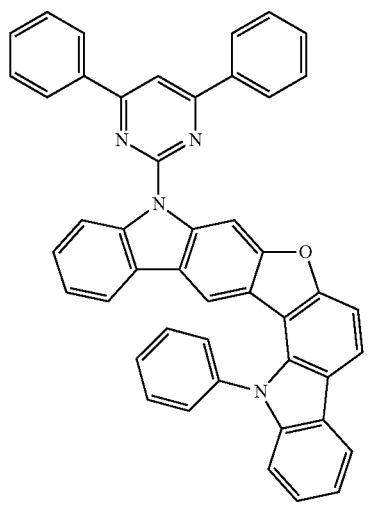
50
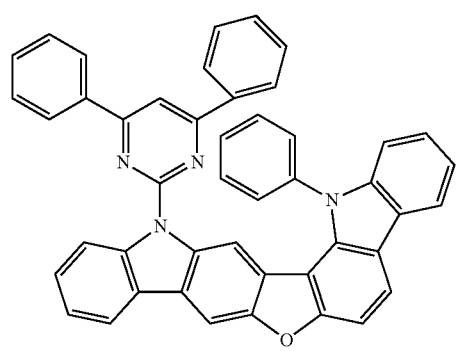
51
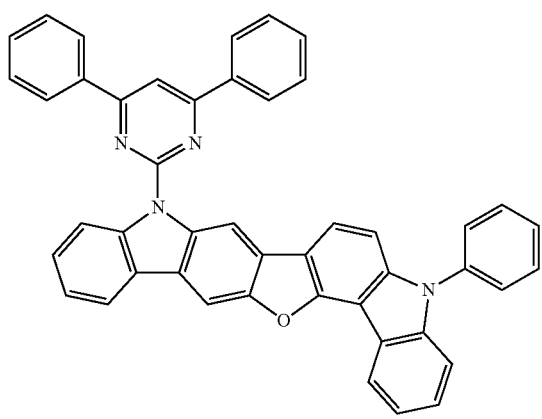
52
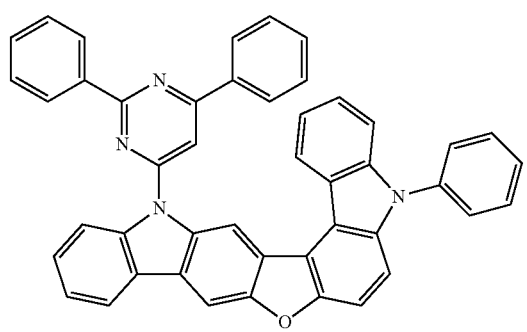
53
58
-continued
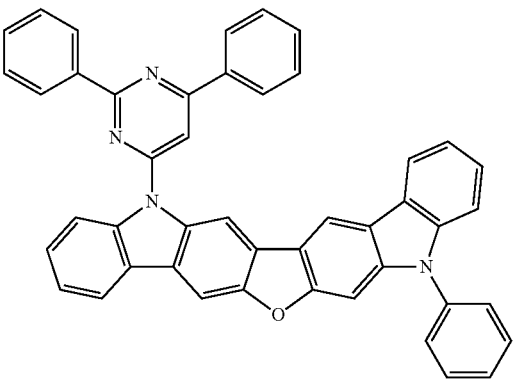
54
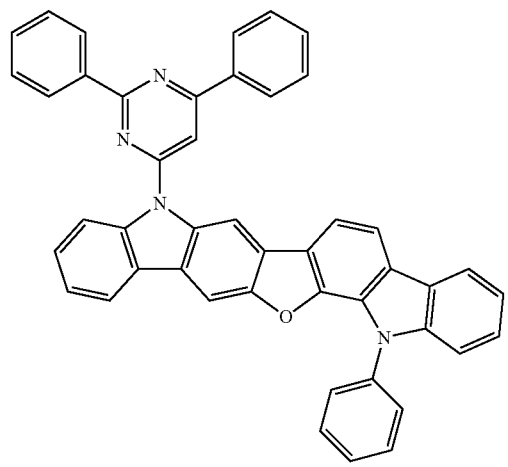
55
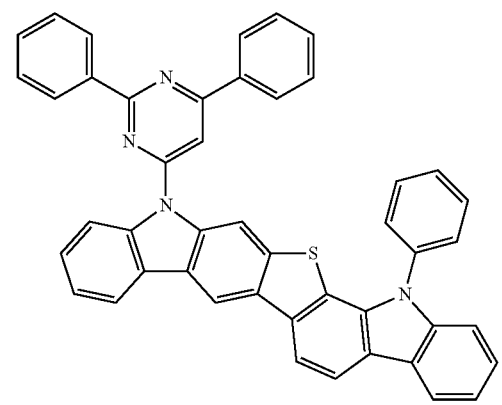
56

-continued
57
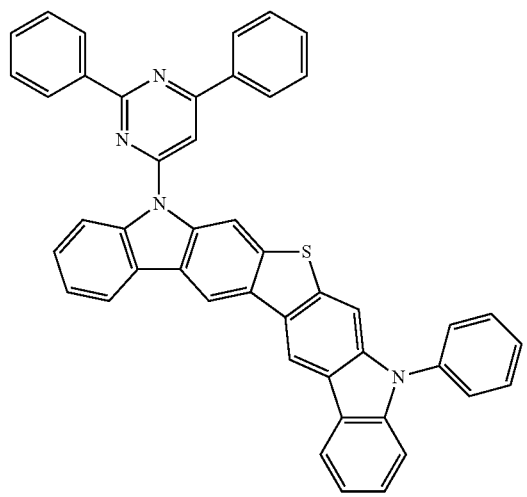
58
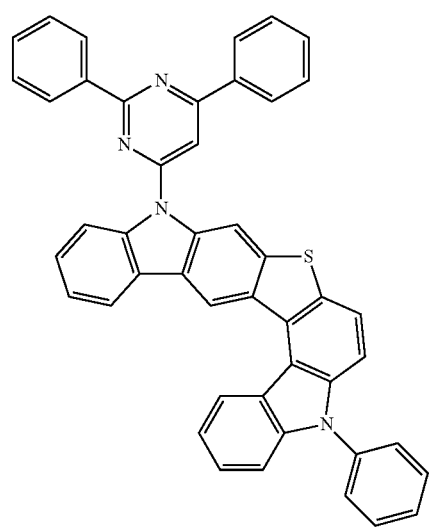
59
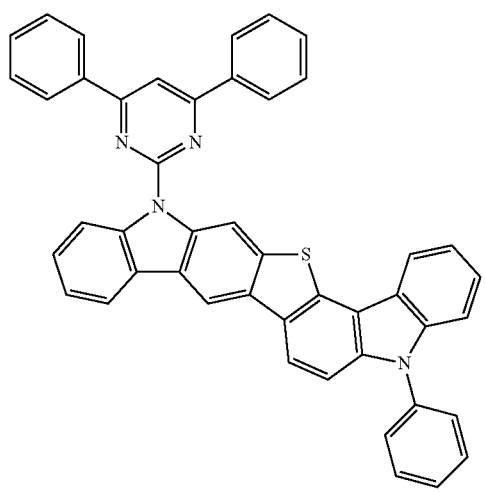
-continued
60
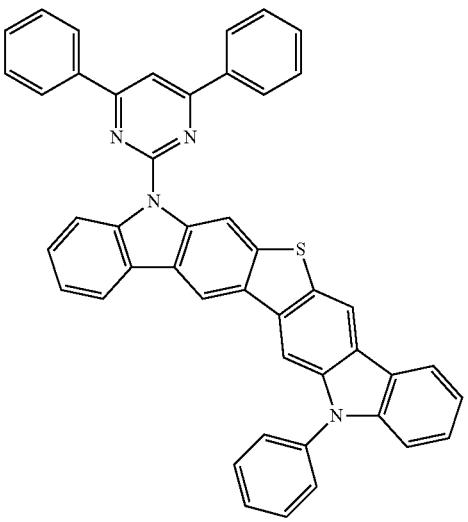
61
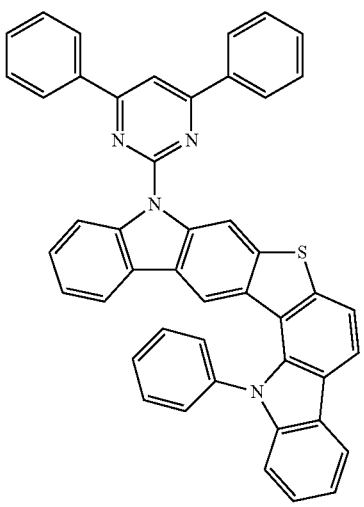
62
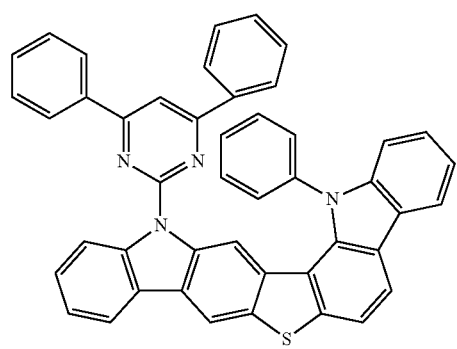

63
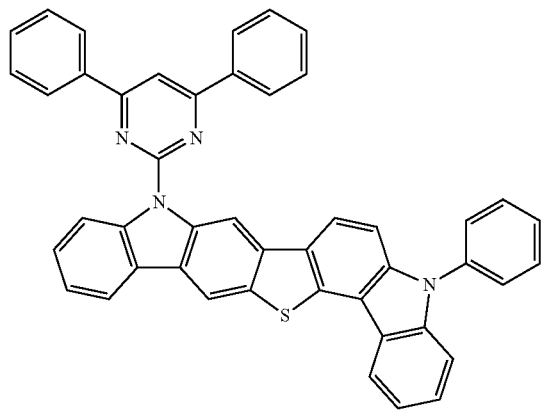
64
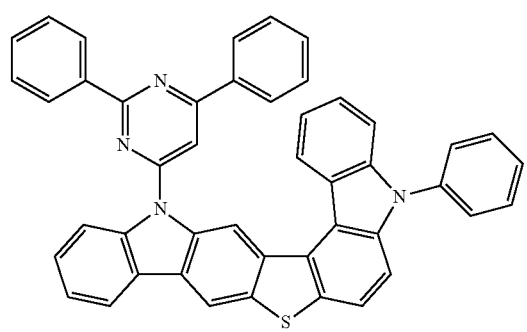
65
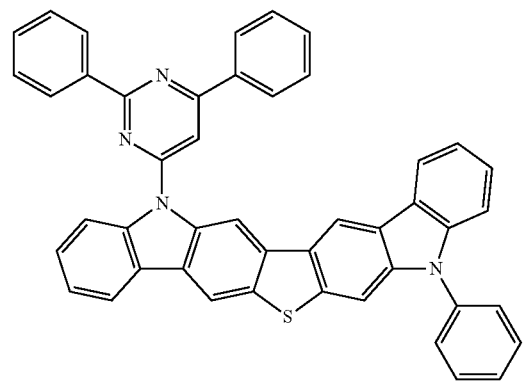
66
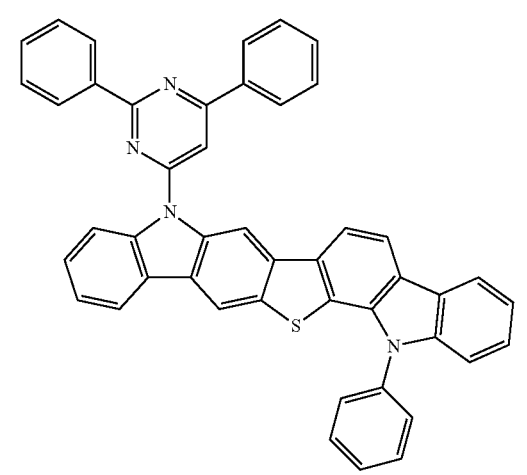
67
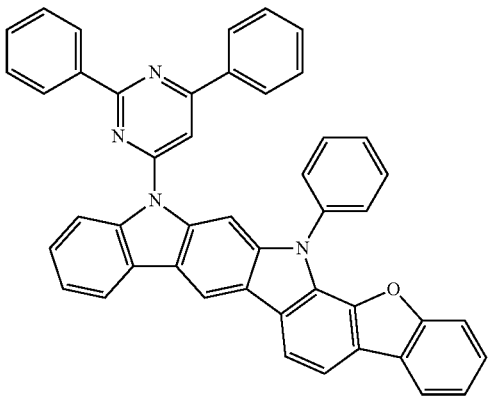
68
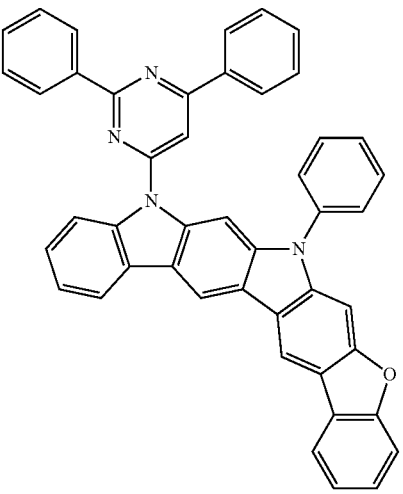
69
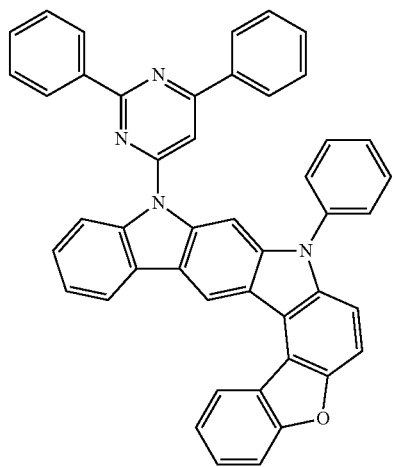

70
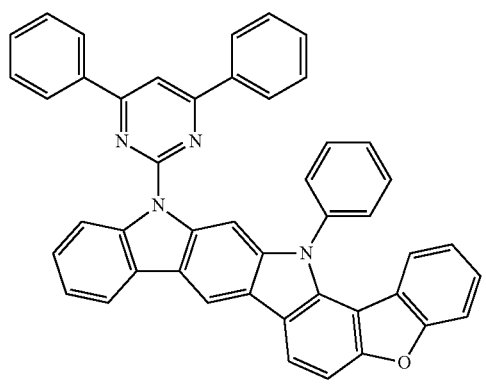
71
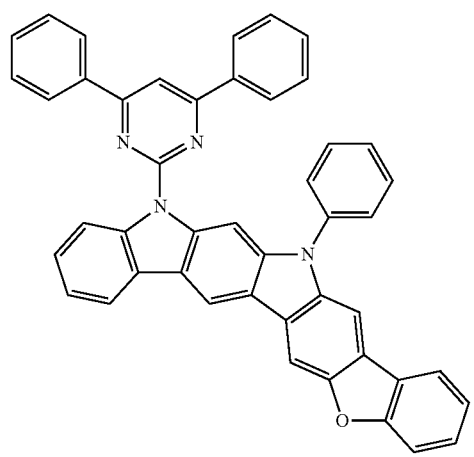
72
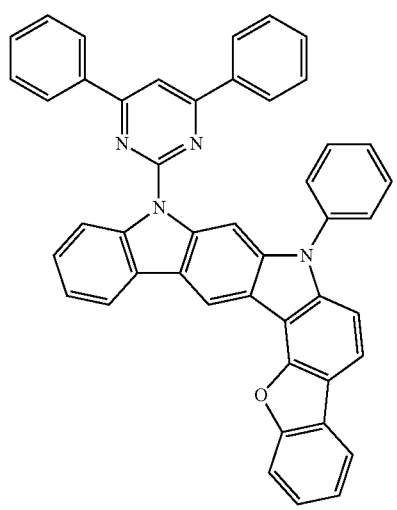
73
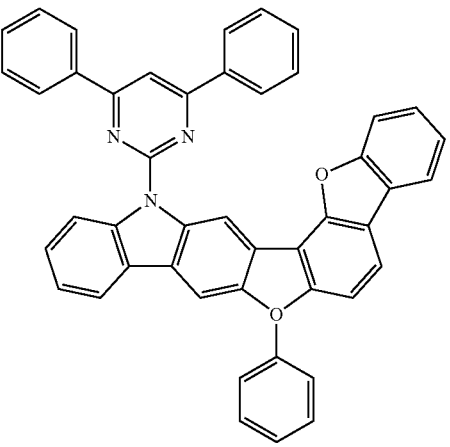
74
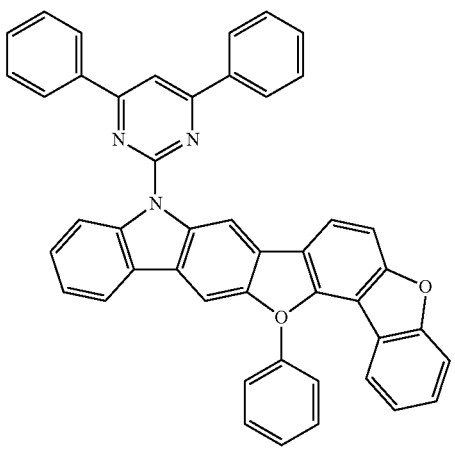
75
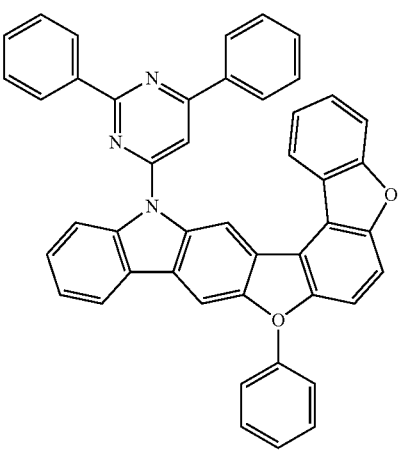

76
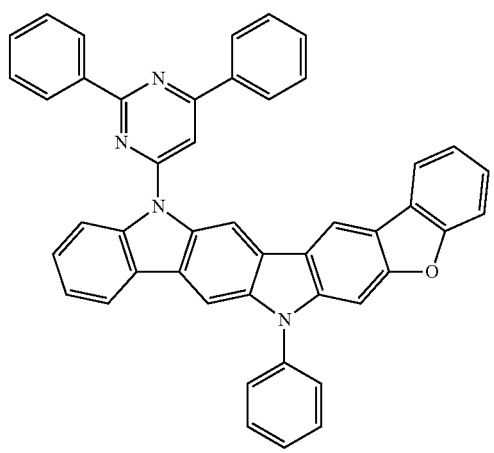
77
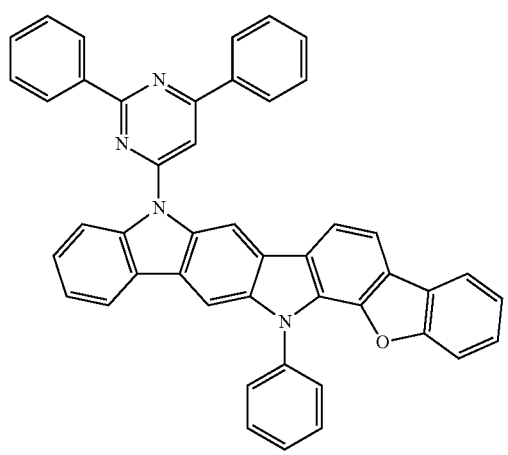
78
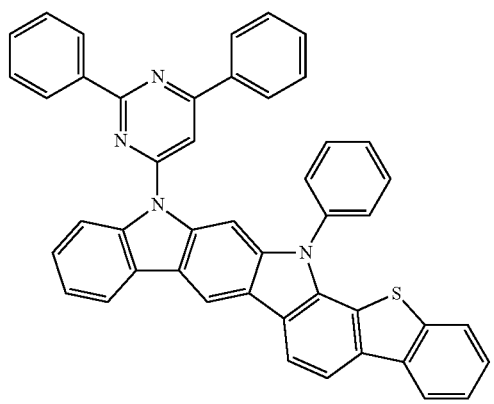
79
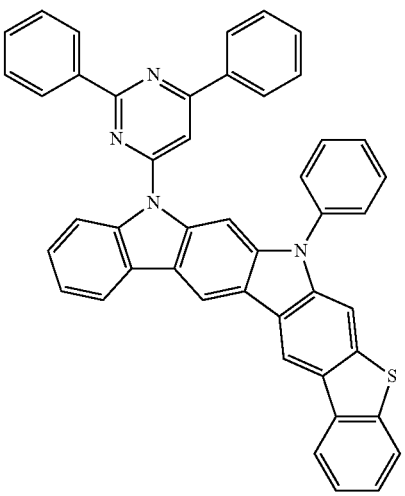
80
80
81
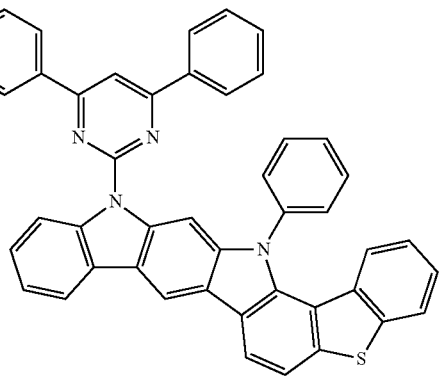

82
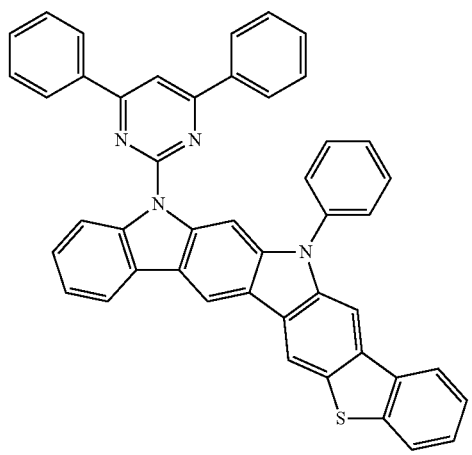
85
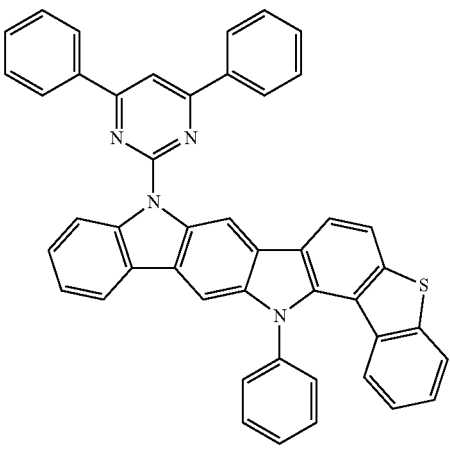
83
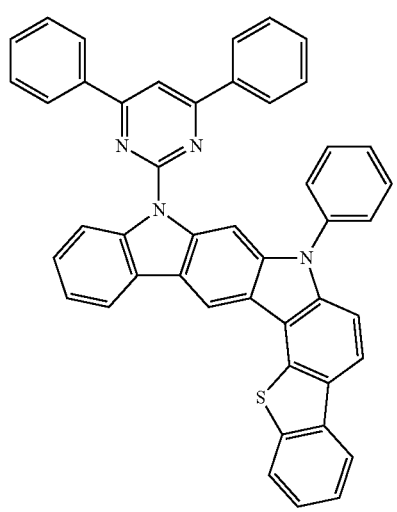
86
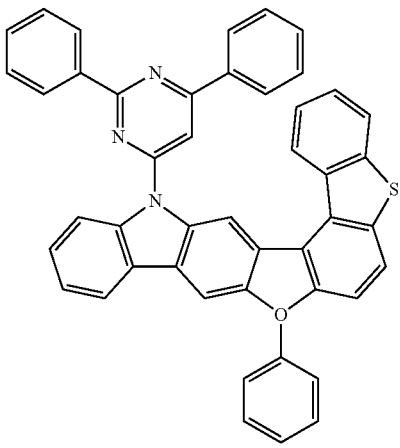
84
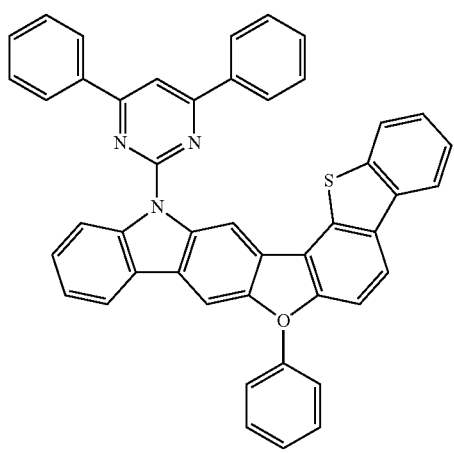
87
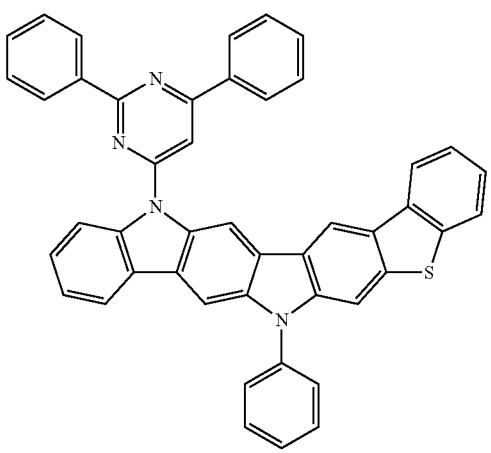

88
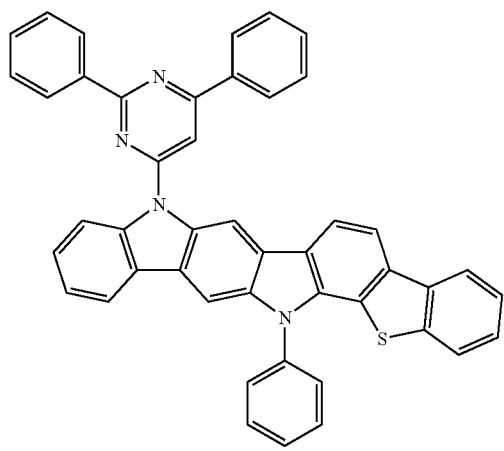
89
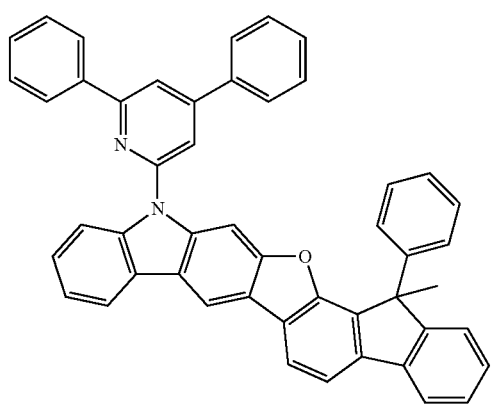
90
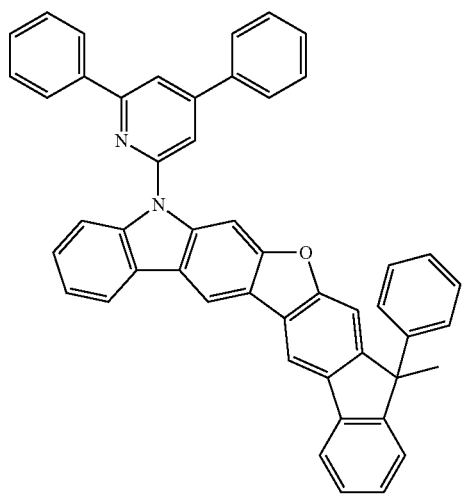
91
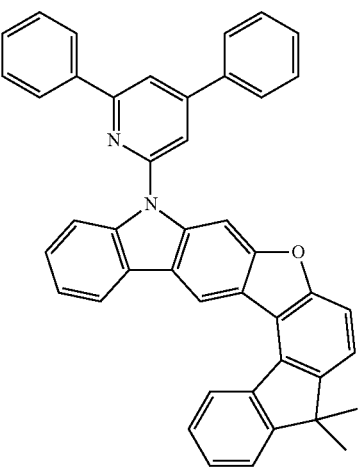
92
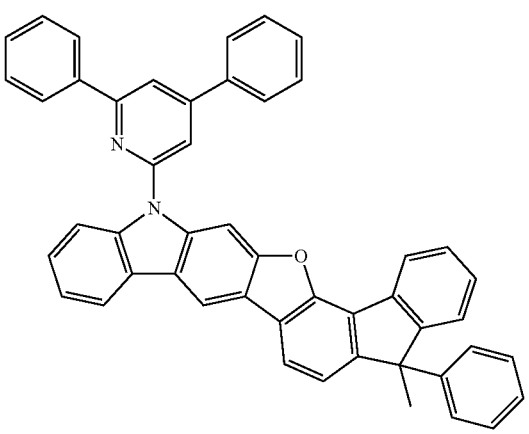
93
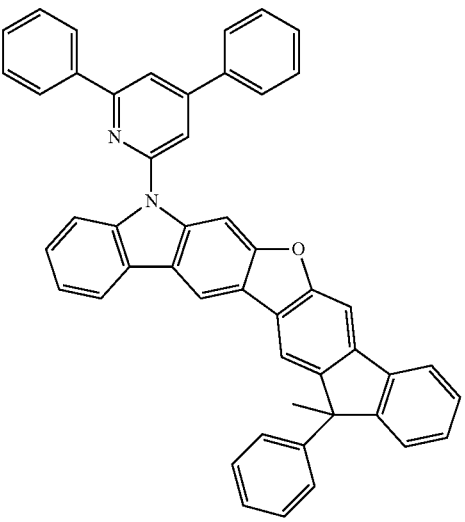

71
-continued
94
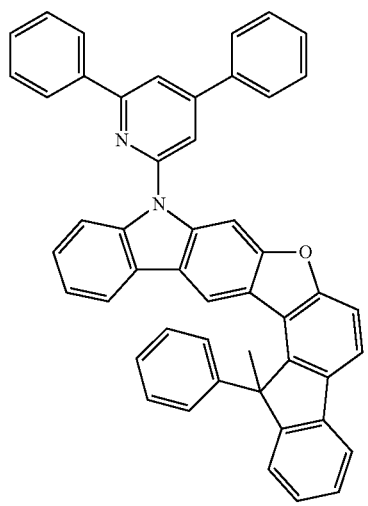
95
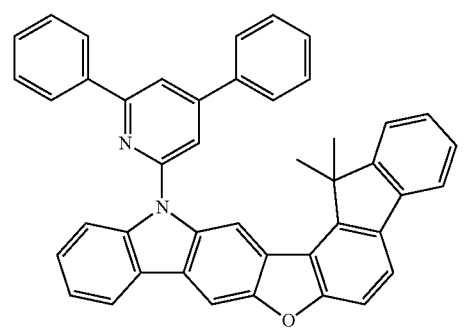
96
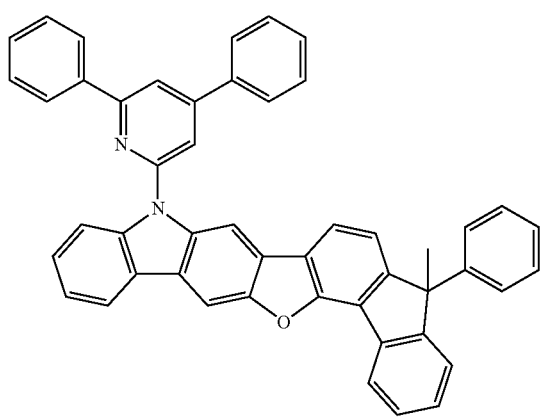
97
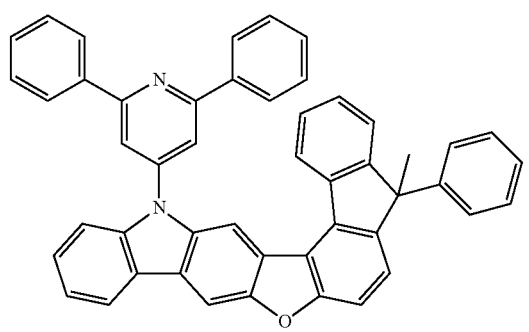
72
-continued
98
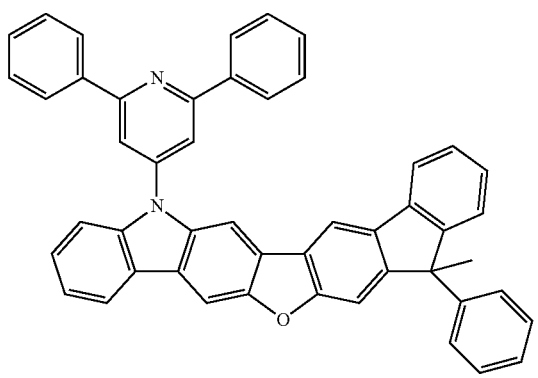
99
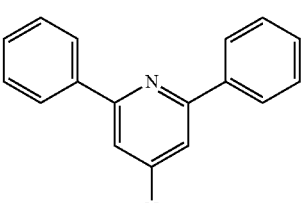
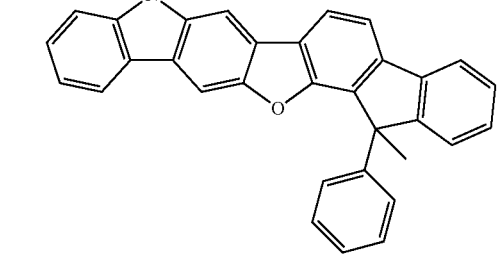
100
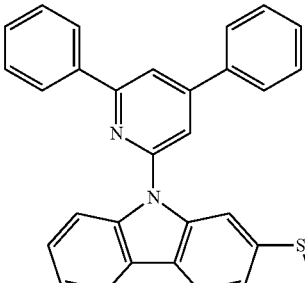

73
-continued
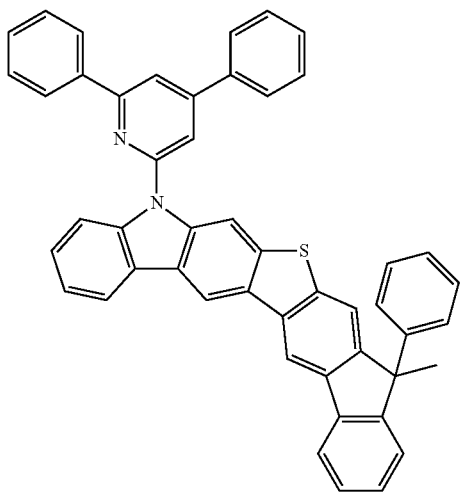
101
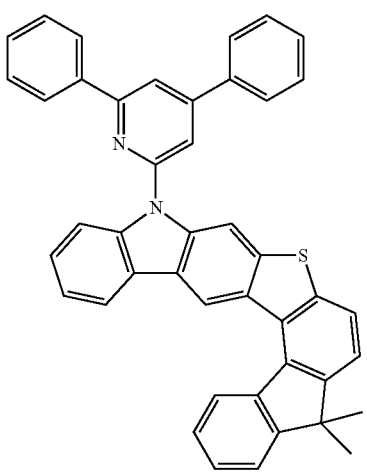
102
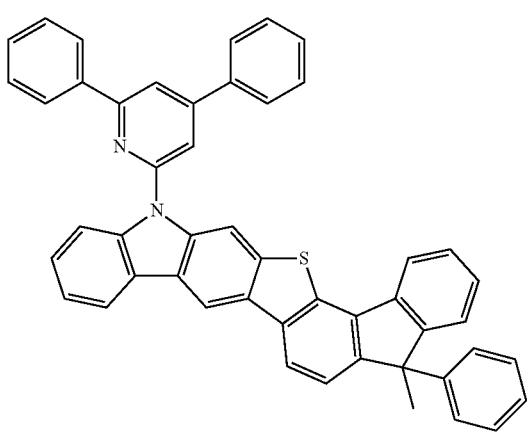
103
74
-continued
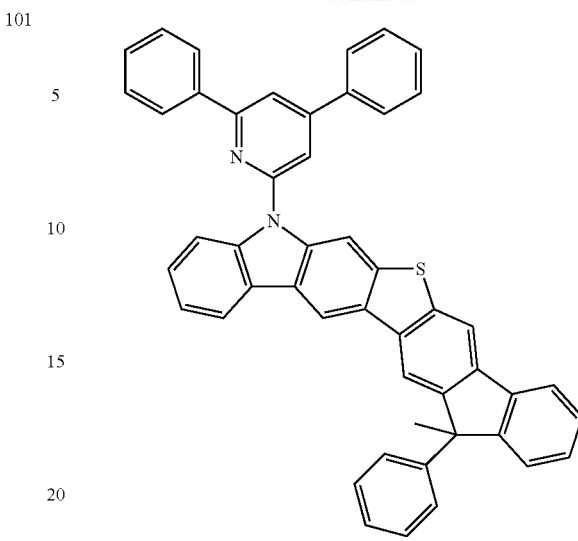
104
105
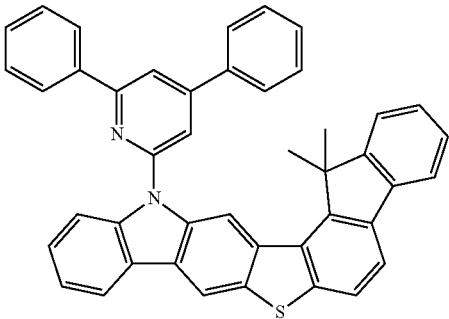
106

107
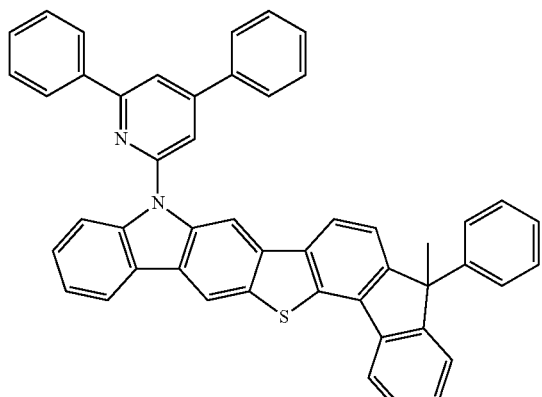
108
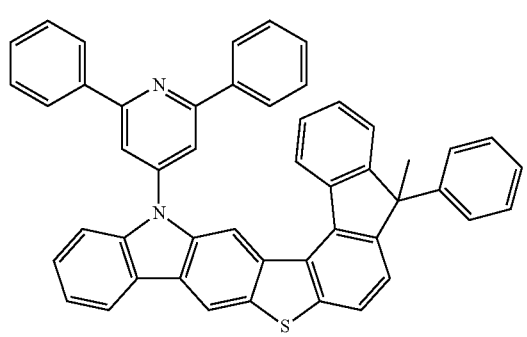
109
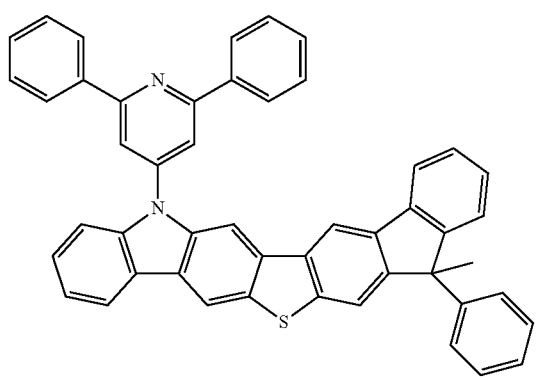
110
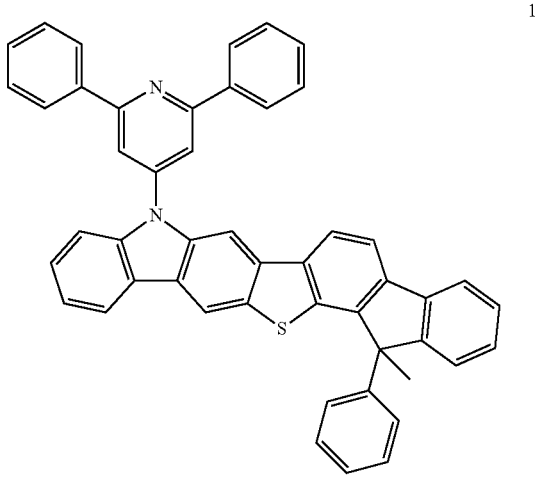
111
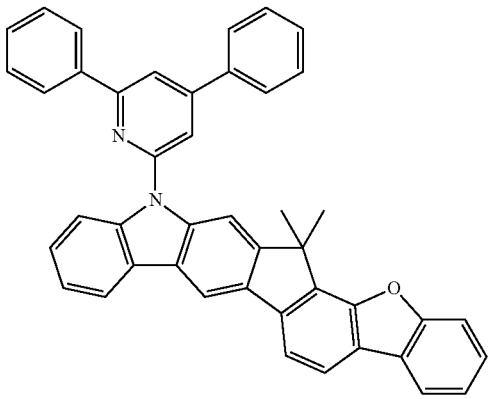
112
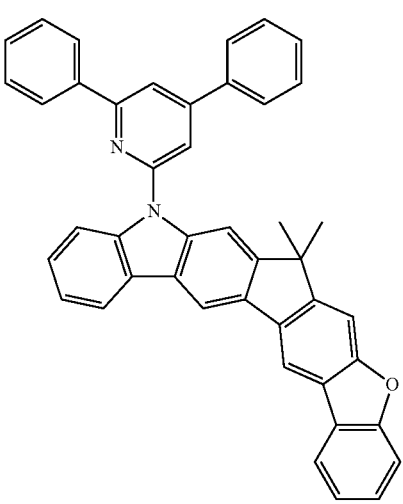
113
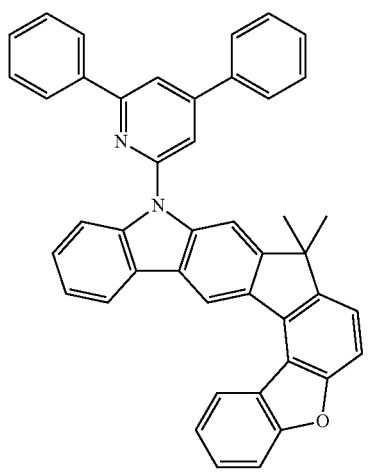

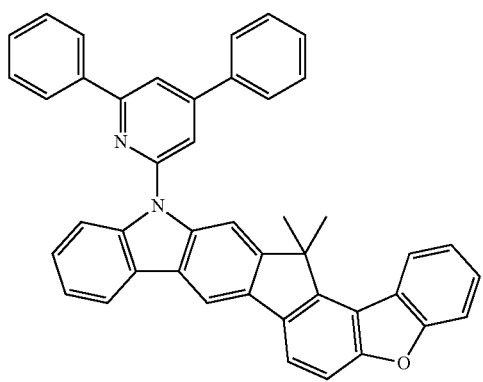
114
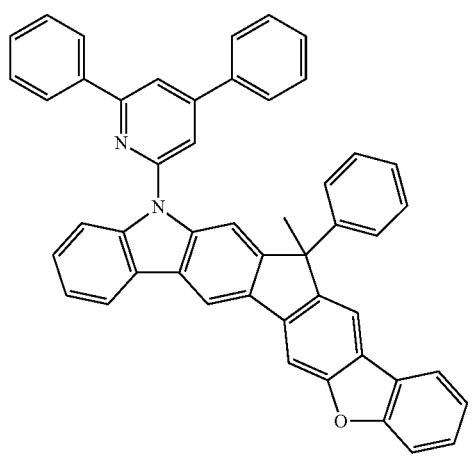
115
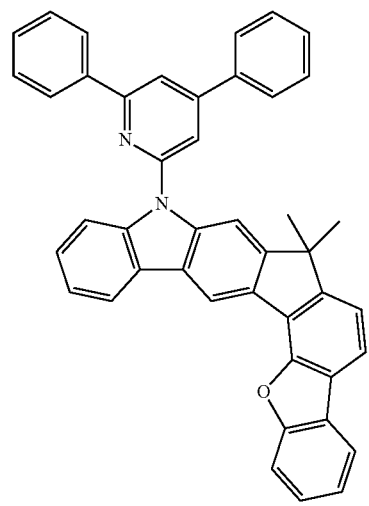
116
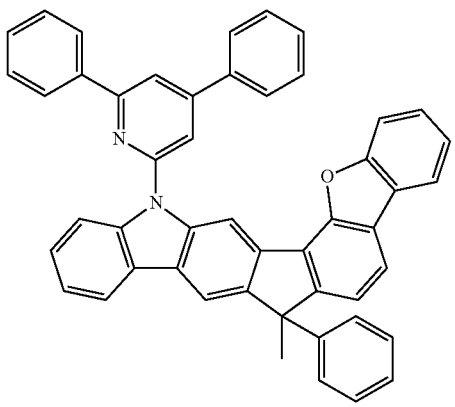
117
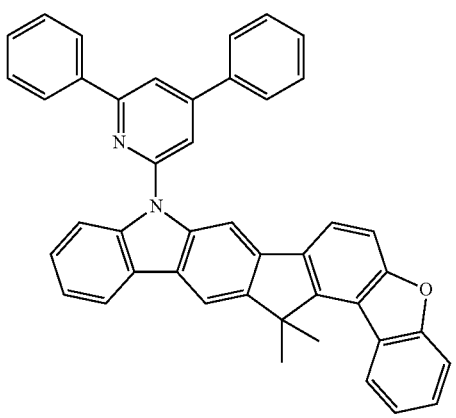
118
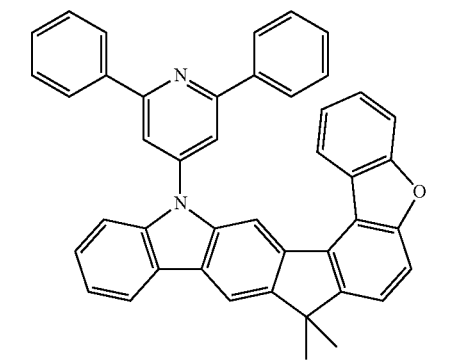
119
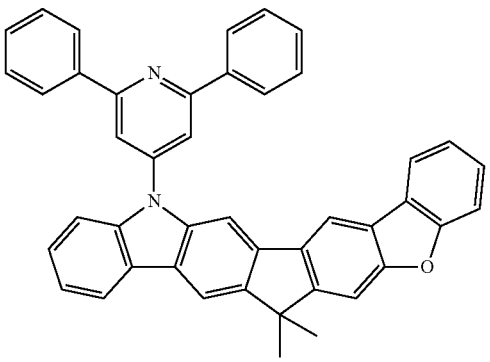
120

121
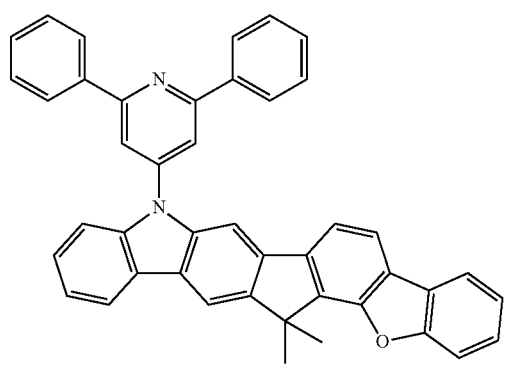
124
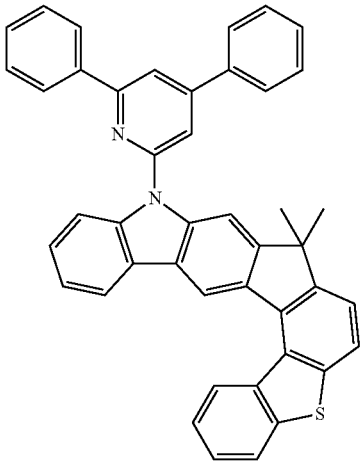
122
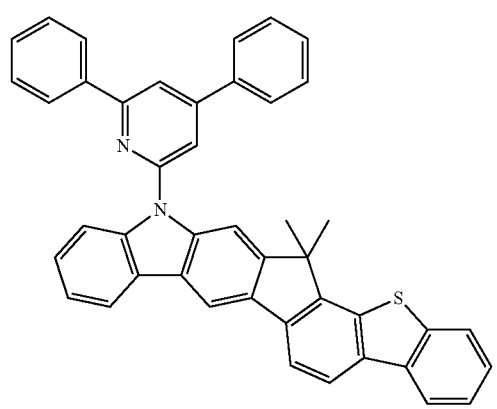
125
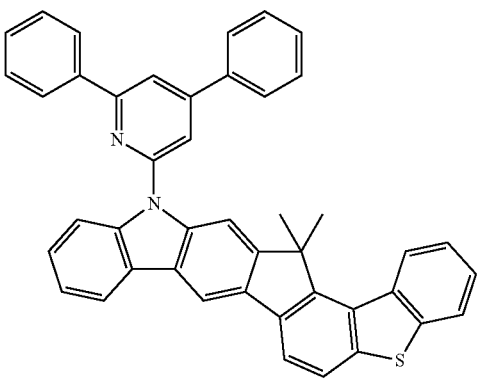
123
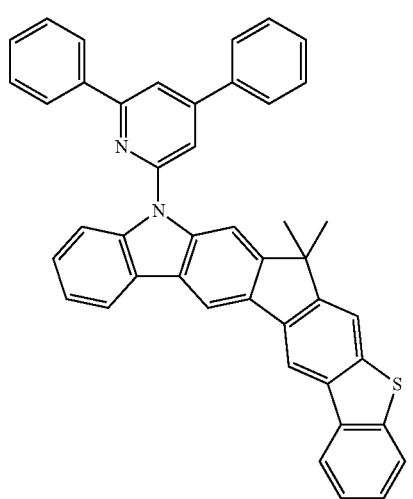
126
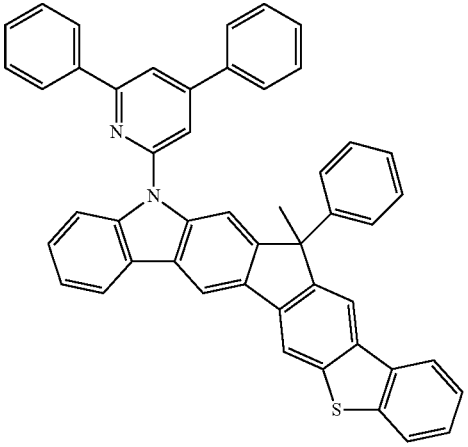

127
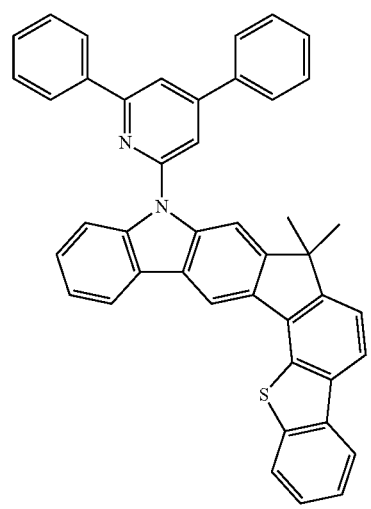
128
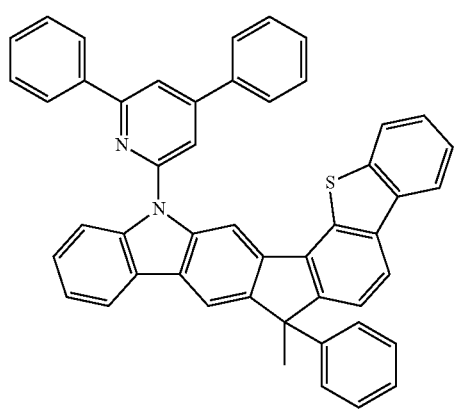
129
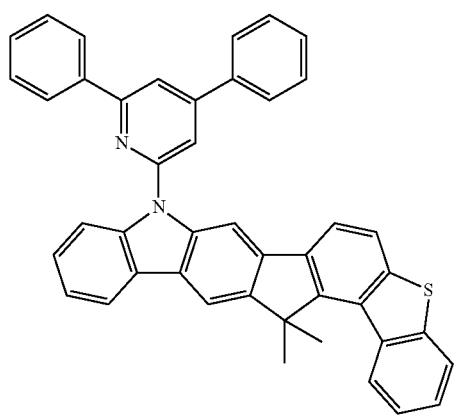
130
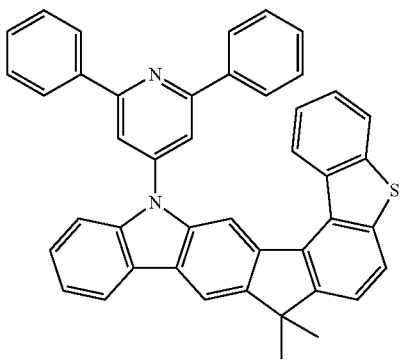
131
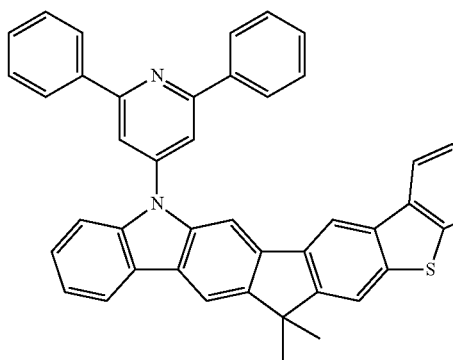
132
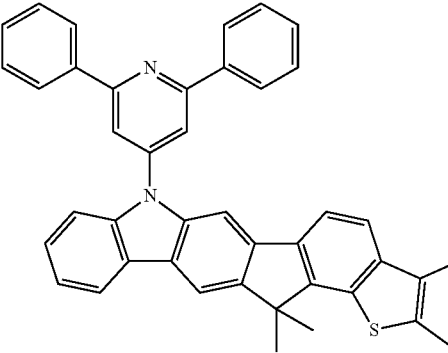
133
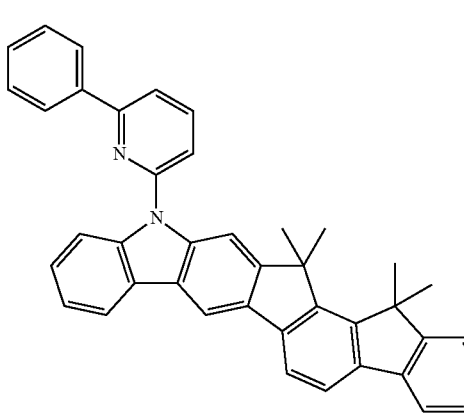

134
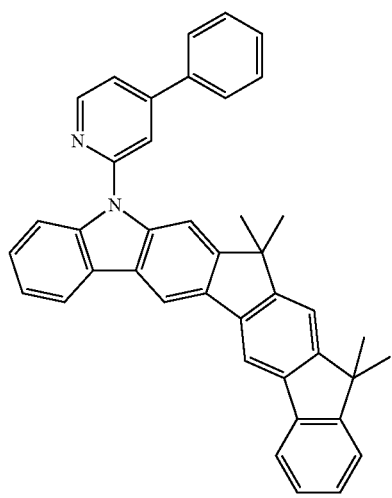
135
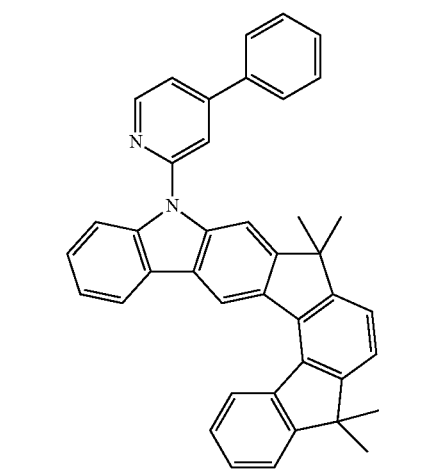
136
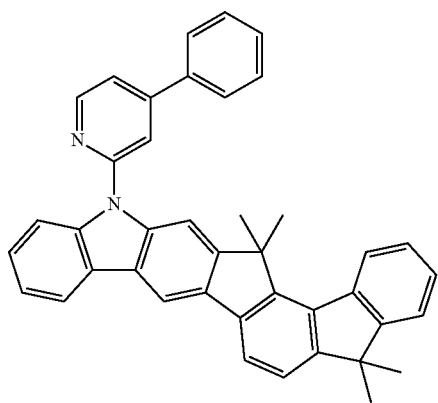
137
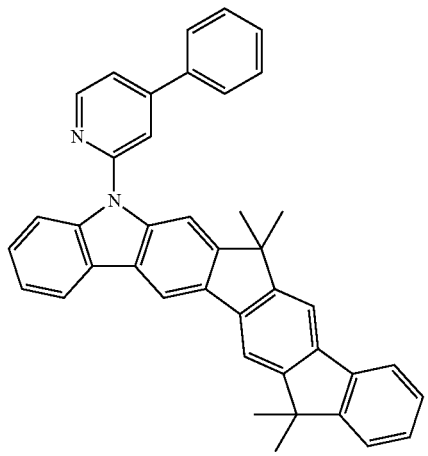
138
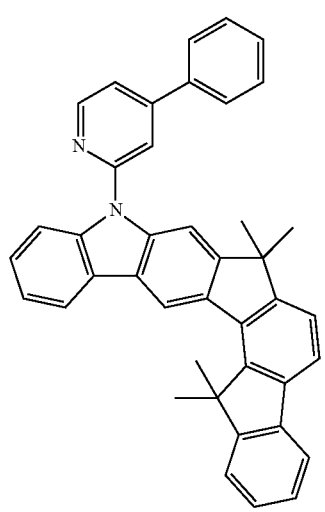
139
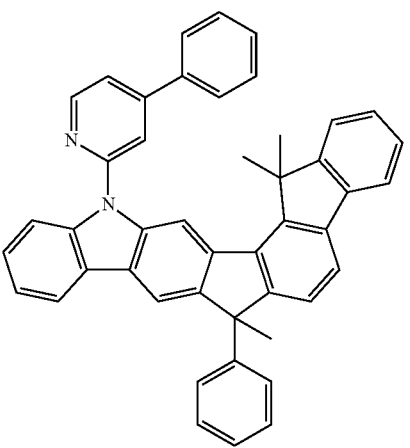

85
-continued
140
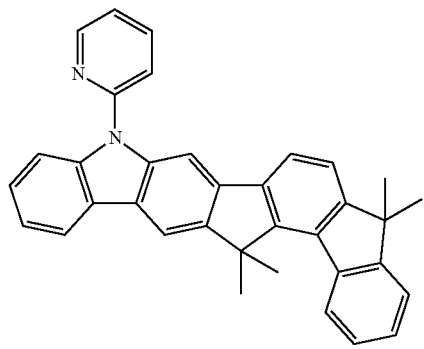
141
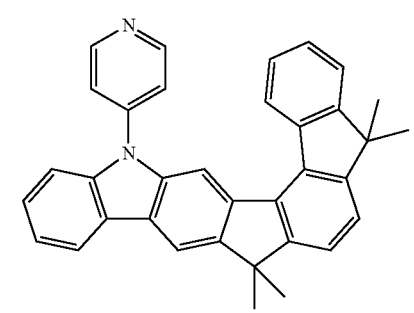
142
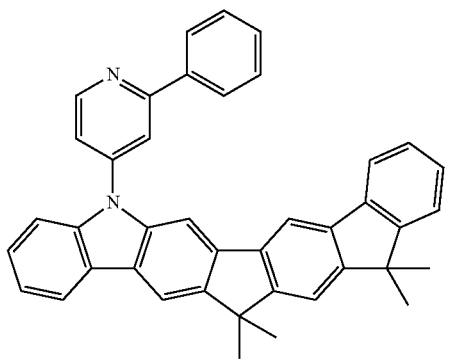
143
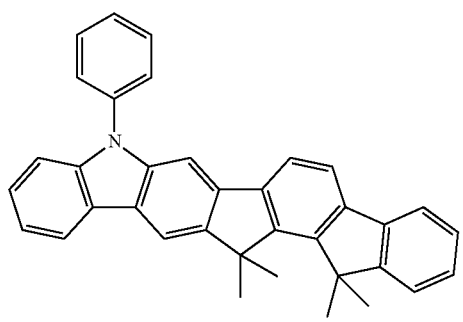
86
-continued
144
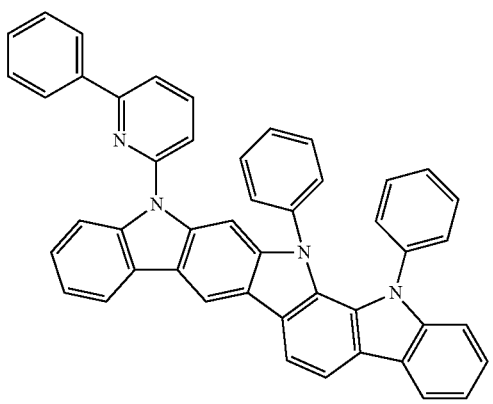
145
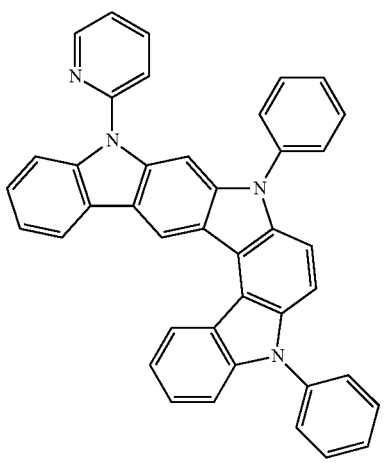
146
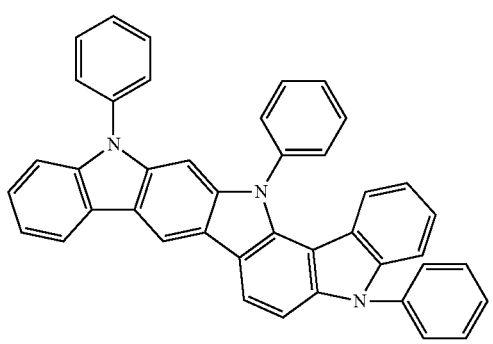

147
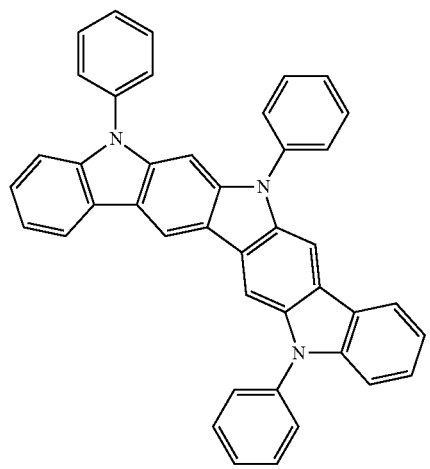
148
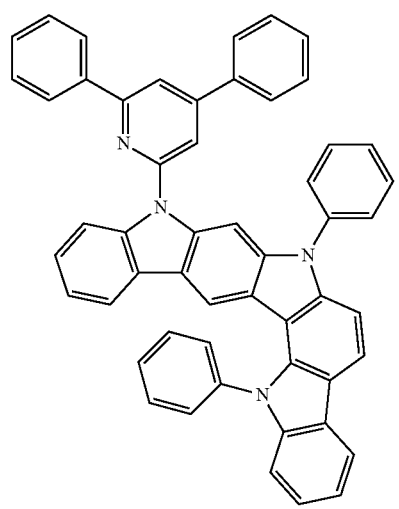
149
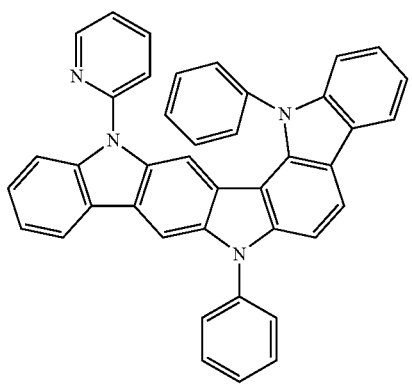
150
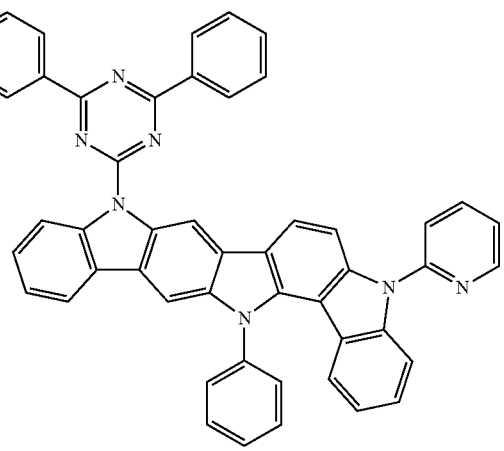
151
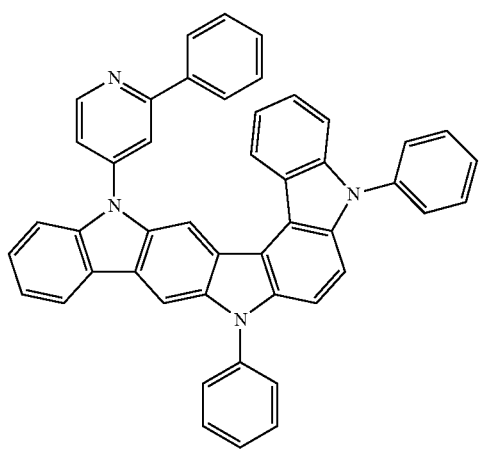
152
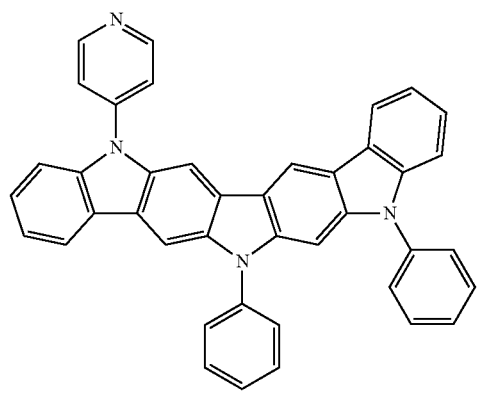

US 10,903,429 B2
89
-continued
153
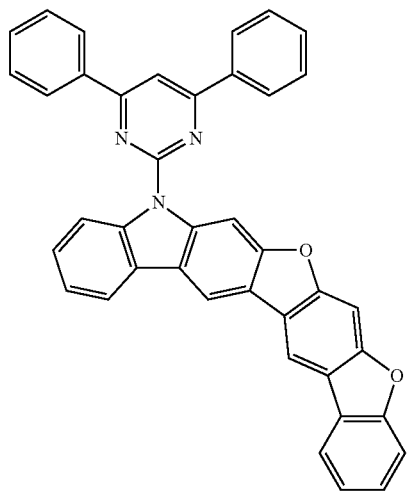
154
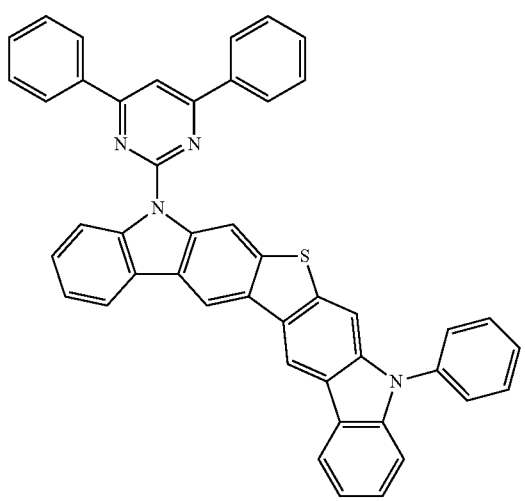
155
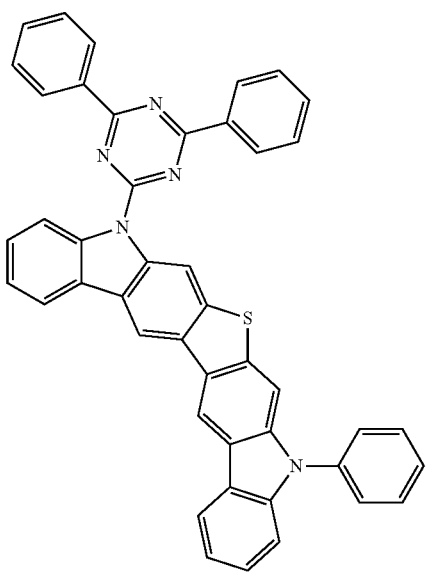
90
-continued
156
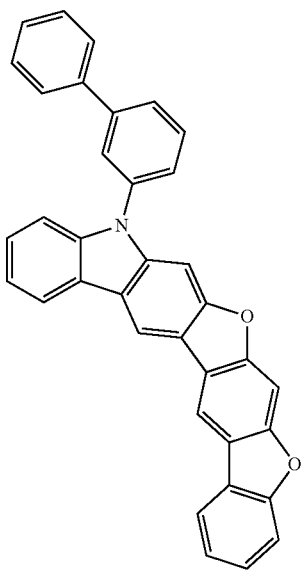
157
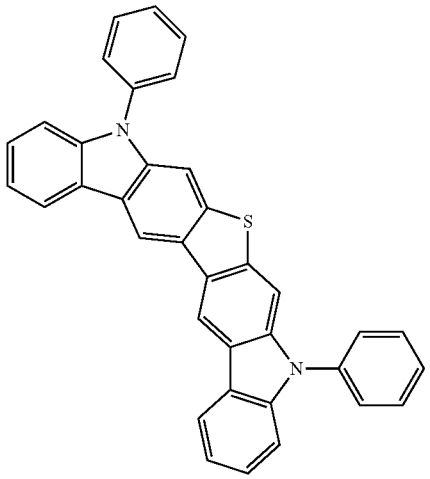
158
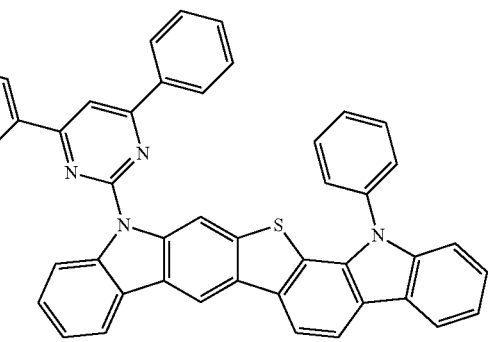

159
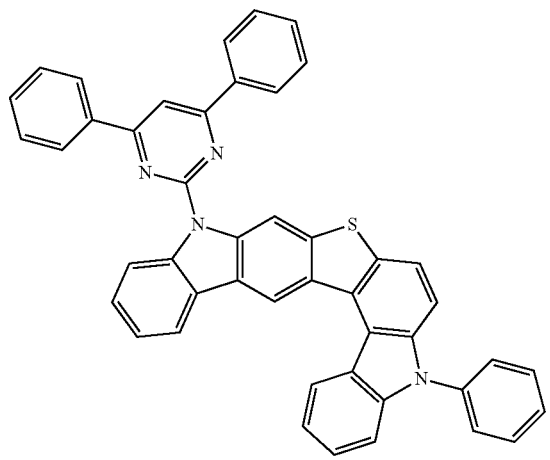
160
161
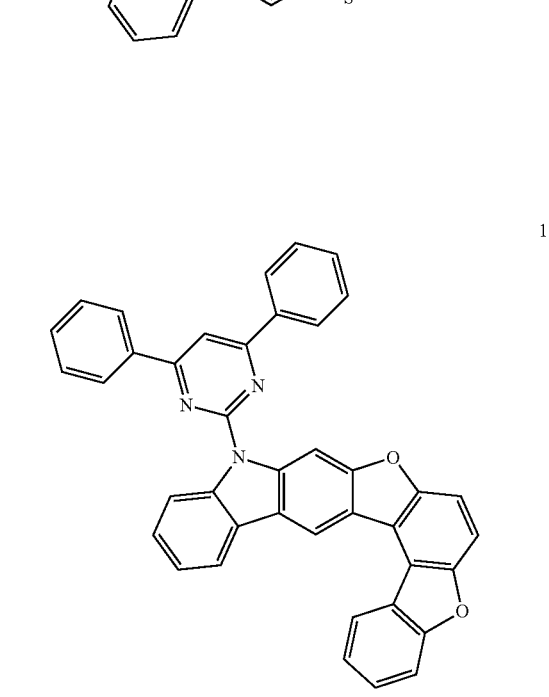
162
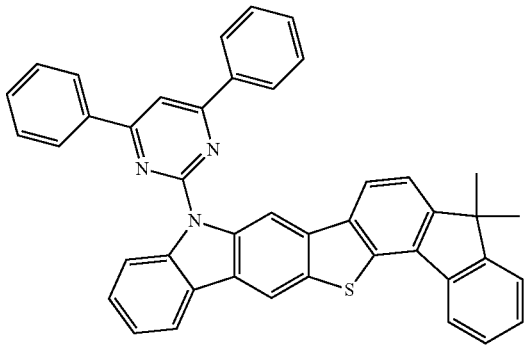
163
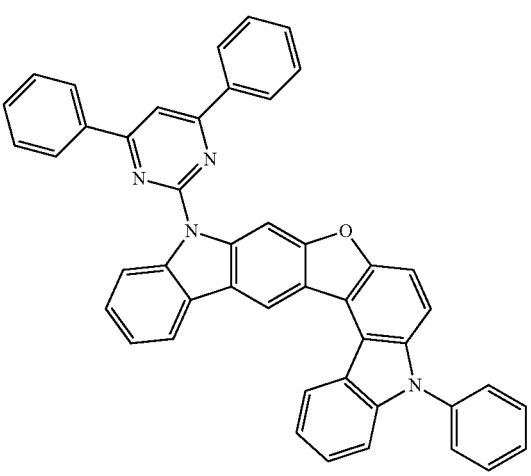
164
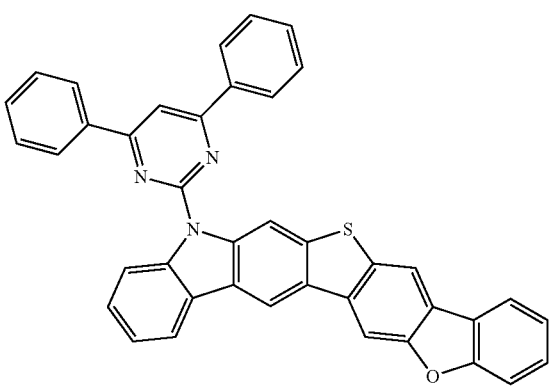
165
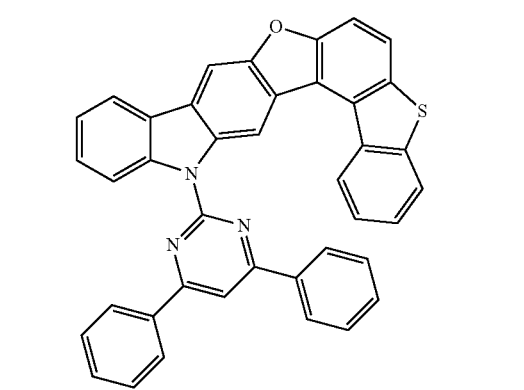

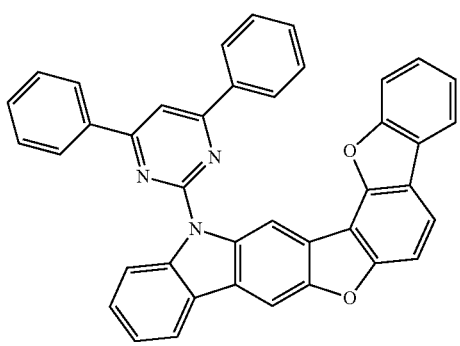

166

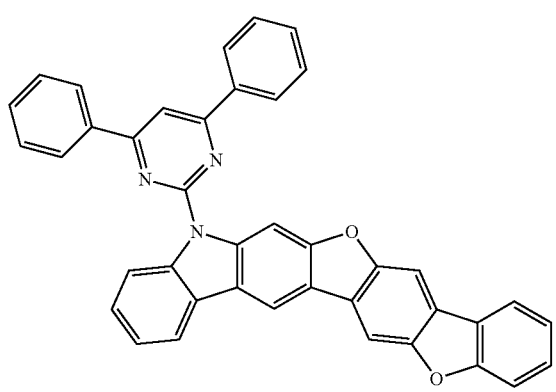

167

The condensed cyclic compound represented by Formula 1 can have relatively high $T_g$ (for example, $T_g$ of 130° C. or more) and relatively low $T_{ev}$ (for example, $T_{ev}$ of 350° C. or less) since the condensed cyclic compound represented by Formula 1 have a rigid core in which plurality of rings are fused each other. Therefore, the condensed cyclic compound represented by Formula 1 can have a good thermal stability.

Furthermore, the condensed cyclic compound represented by Formula 1 can have a bipolar structure in which an electron transporting moiety and a hole transporting moiety are present since $X_{11}$ and $X_{21}$ can be various groups as described in the present disclosure. Due to these characteristics, the condensed cyclic compound can have appropriate HOMO, LUMO and $T_1$ energy levels for use as a material for forming an electric device, for example, an organic light-emitting device (for example, a host for an emission layer or a material for a hole transport layer).

For example, the highest occupied molecular orbital (HOMO), lowest unoccupied molecular orbital (LUMO) and $T_1$ energy level of Compounds 50, 59 to 63, 153, 154, 158 to 166 were simulated by using Gaussian, and simulation evaluation results are shown in Table 2 below.

TABLE 2

| Compound No. | HOMO (eV) | LUMO (eV) | $T_1$ (eV) |
|---|---|---|---|
| 50 | −5.101 | −1.734 | 2.783 |
| 59 | −5.007 | −1.784 | 2.675 |
| 60 | −5.013 | −1.807 | 2.683 |
| 61 | −5.137 | −1.757 | 2.778 |
| 62 | −5.074 | −1.804 | 2.658 |
| 63 | −4.971 | −1.777 | 2.565 |
| 153 | −5.302 | 1.845 | 2.793 |
| 154 | −5.041 | −1.743 | 2.759 |
| 158 | −5.089 | −1.812 | 2.708 |

TABLE 2-continued

| Compound No. | HOMO (eV) | LUMO (eV) | $T_1$ (eV) |
|---|---|---|---|
| 159 | −5.005 | −1.738 | 2.677 |
| 160 | −5.042 | −1.809 | 2.657 |
| 161 | −5.374 | −1.799 | 2.781 |
| 162 | −5.236 | −1.846 | 2.680 |
| 163 | −5.047 | −1.729 | 2.712 |
| 164 | −5.323 | −1.805 | 2.696 |
| 165 | −5.329 | −1.862 | 2.619 |
| 166 | −5.407 | −1.767 | 2.734 |

From Table 2, it is confirmed that the condensed cyclic compound represented by Formula 1 has appropriate HOMO, LUMO and $T_1$ energy levels for use as a material for forming an electric device, for example, an organic light-emitting device (for example, a host for an emission layer or a material for a hole transport layer).

According to an embodiment of the present disclosure, the condensed cyclic compound can be used for a green phosphorescent host or a material of a hole transport layer, but is not limited thereto.

A synthesis method of the condensed cyclic compound represented by Formula 1 may be referred to a synthesis example that will be described in detail for one of ordinary skill in the art to readily understand.

The condensed cyclic compound represented by Formulae 1 may be included in an organic layer of an organic light-emitting device, for example, may be used as a host of an emission layer in the organic layer. According to another aspect, an organic light-emitting device may include a first electrode;

a second electrode; and an organic layer disposed between the first electrode and the second electrode, wherein the organic layer includes an emission layer and at least one of the condensed cyclic compound represented by Formula 1.

The organic light-emitting device includes an organic layer including a condensed cyclic compound represented by Formula 1 and thus may have a low driving voltage, a high efficiency, a high luminance, and a long lifespan.

The condensed cyclic compound represented by Formula 1 may be used between a pair of electrodes of the organic light-emitting device. For example, the condensed cyclic compound may be included in at least one of the emission layer, a hole transport region between the first electrode and the emission layer (e.g., including at least one of a hole injection payer, a hole transport layer, and an electron blocking layer), and an electron transport region (e.g., including at least one of a hole blocking layer, an electron transporting layer, and an electron injection layer) between the emission layer and the second electrode. For example, the condensed cyclic compound represented by Formula 1 may be included in at least one of the emission layer and the hole transport region. Here, when the condensed cyclic compound is included in the emission layer, the emission layer may further include a dopant, and the condensed cyclic compound in the emission layer may serve as a host. The emission layer may be a green emission layer emitting green light, and the dopant may be a phosphorescent dopant.

As used herein, the expression "(an organic layer) includes at least one condensed cyclic compounds" may include a case in which "(an organic layer) includes one condensed cyclic compound of Formula 1 and a case in which two or more different condensed cyclic compounds of Formula 1".

For example, the organic layer may include, as the condensed cyclic compound, only Compound 1. In this regard, Compound 1 may be situated in the emission layer of the organic light-emitting device. In another embodiment, the organic layer may include Compound 1 and Compound 2 as the condensed cyclic compound. In this regard, Compound 1 and Compound 2 may be situated in the same layer (for example, Compound 1 and Compound 2 may all exist in the emission layer), or different layers (for example, Compound 1 may exist in the emission layer while Compound 2 may exist in the hole transport region).

For example,
the first electrode may be an anode,
the second electrode may be a cathode, and
the organic layer may include
i) a hole transport region disposed between the first electrode and the emission layer, wherein the hole transport region includes at least one of a hole injection layer, a hole transport layer, and an electron blocking layer; and
ii) an electron transport region disposed between the emission layer and the second electrode, wherein the hole transport region includes at least one of a hole blocking layer, an electron transporting layer, and an electron injection layer.

As used herein, the term "organic layer" refers to a single layer and/or a plurality of layers disposed between the first electrode and the second electrode of an organic light-emitting device. The "organic layer" may include, in addition to an organic compound, an organometallic complex including a metal.

According to an embodiment of the present disclosure, the organic layer of the organic light-emitting device may include at least one selected from a first compound represented by Formula 41 and a second compound represented by Formula 61, addition to the condensed cyclic compound represented by Formula 1:

Formula 41

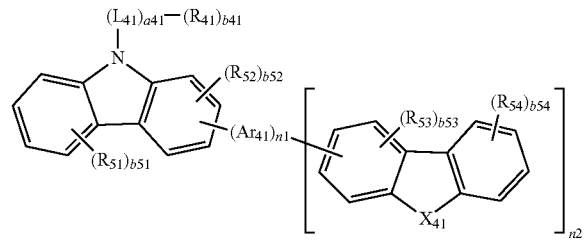

Formula 61

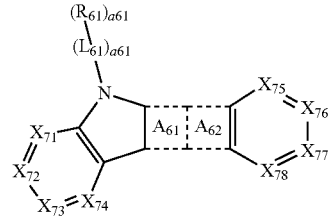

Formula 61A

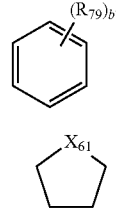

Formula 61B wherein in the formulae above, $X_{41}$ may be $N-[(L_{42})_{a42}-(R_{42})_{b42}]$, S, O, S(=O), S(=O)$_2$, C(=O), C(R$_{43}$)(R$_{44}$), Si(R$_{43}$)(R$_{44}$), P(R$_{43}$), P(=O)(R$_{43}$), or C=N(R$_{43}$);

Ring $A_{61}$ in Formula 61 may be represented by Formula 61A;

Ring $A_{62}$ in Formula 61 may be represented by Formula 61B;

$X_{61}$ may be $N-[(L_{62})_{a62}-(R_{62})_{b62}]$, S, O, S(=O), S(=O)$_2$, C(=O), C(R$_{63}$)(R$_{64}$), Si(R$_{63}$)(R$_{64}$), P(R$_{63}$), P(=O)(R$_{63}$), or C=N(R$_{63}$);

$X_{71}$ may be C(R$_{71}$) or N, $X_{72}$ may be C(R$_{72}$) or N, $X_{73}$ may be C(R$_{73}$) or N, $X_{74}$ may be C(R$_{74}$) or N, $X_{75}$ may be C(R$_{75}$) or N, $X_{76}$ may be C(R$_{76}$) or N, $X_{77}$ may be C(R$_{77}$) or N, $X_{78}$ may be C(R$_{78}$) or N;

Ar$_{41}$, L$_{41}$, L$_{42}$, L$_{61}$, and L$_{62}$ may be each independently selected from a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, and a substituted or unsubstituted divalent non-aromatic condensed hetero-polycyclic group;

n1 and n2 may be each independently an integer selected from 0 to 3;

a41, a42, a61, and a62 may be each independently an integer selected from 0 to 3;

R$_{41}$ to R$_{44}$, R$_{51}$ to R$_{54}$, R$_{61}$ to R$_{64}$, and R$_{71}$ to R$_{79}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed hetero-polycyclic group, —N(Q$_1$)(Q$_2$), —Si(Q$_3$)(Q$_4$)(Q$_5$), and —B(Q$_6$)(Q$_7$);

b41, b42, b51 to b54, b61, b62, and b79 may be each independently an integer selected from 1 to 3;

at least one of substituents of the substituted C$_1$-C$_{60}$ alkylene group, substituted C$_2$-C$_{60}$ alkenylene group, substituted C$_3$-C$_{10}$ cycloalkylene group, substituted C$_1$-C$_{10}$ heterocycloalkylene group, substituted C$_3$-C$_{10}$ cycloalkenylene group, substituted C$_1$-C$_{10}$ heterocycloalkenylene group, substituted C$_6$-C$_{60}$ arylene group, substituted C$_1$-C$_{60}$ heteroarylene group, substituted divalent non-aromatic condensed polycyclic group, substituted divalent non-aromatic condensed hetero-polycyclic group, substituted C$_1$-C$_{60}$ alkyl group, substituted C$_2$-C$_{60}$ alkenyl group, substituted C$_2$-C$_{60}$ alkynyl group, substituted C$_1$-C$_{60}$ alkoxy group, substituted C$_3$-C$_{10}$ cycloalkyl group, substituted C$_1$-C$_{10}$ heterocycloalkyl group, substituted C$_3$-C$_{10}$ cycloalkenyl group, substituted C$_1$-C$_{10}$ heterocycloalkenyl group, substituted C$_6$-C$_{60}$ aryl group, substituted $C_6$-$C_{60}$ aryloxy group, substituted $C_6$-$C_{60}$ arylthio group, substituted $C_1$-$C_{60}$ heteroaryl group, substituted a monovalent non-aromatic condensed polycyclic group, and a substituted a monovalent non-aromatic condensed hetero-polycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed hetero-polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic hetero-condensed polycyclic group.

For example, at least one of i) the condensed cyclic compound represented by Formula 1 and ii) at least one of the first compound represented by Formula 41 and the second compound represented by Formula 61 may be included in the emission layer of the organic light-emitting device.

For example, the emission layer of the organic light-emitting device may include a first host, a second host and a dopant, the first host may include the condensed cyclic compound represented by Formula 1, and the second host may include at least one of the first compound represented by Formula 41 and the second compound represented by Formula 61.

A weight ratio of the first host to the second host in the emission layer may be each independently in a range of 1:99 to 99:1, for example, 10:90 to 90:10. When the weight ratio of the first host and the second host is within these ranges, holes and electrons provided to the emission layer may be effectively controlled.

The ring $A_{61}$ is fused to an adjacent 5-membered ring and the ring $A_{62}$ in Formula 61, with sharing carbons. The ring $A_{62}$ is fused to the ring $A_{61}$ and an adjacent 6-membered ring in Formula 61, with sharing carbons.

According to an embodiment, $X_{41}$ may be N-[($L_{42}$)$_{a42}$-($R_{42}$)$_{b42}$], S or O, but is not limited thereto.

According to other embodiment, $X_{61}$ may be N-[($L_{62}$)$_{a62}$-($R_{62}$)$_{b62}$], S or O, but is not limited thereto.

According to other embodiment, $X_{71}$ may be C($R_{71}$), $X_{72}$ may be C($R_{72}$), $X_{73}$ may be C($R_{73}$), $X_{74}$ may be C($R_{74}$), $X_{75}$ may be C($R_{75}$), $X_{76}$ may be C($R_{76}$), $X_{77}$ may be C($R_{77}$), $X_{78}$ may be C($R_{78}$), but is not limited thereto.

At least two of $R_{71}$ to $R_{74}$ in Formula 61 may be optionally linked to each other to form a saturated or an unsaturated ring (for example, a benzene or a naphthalene).

At least two of $R_{75}$ to $R_{78}$ in Formula 61 may be optionally linked to each other to form a saturated or an unsaturated ring (for example, a benzene or a naphthalene).

Examples of $Ar_{41}$, $L_{41}$, $L_{42}$, $L_{61}$ and $L_{62}$ refer to examples of $L_1$ in the present disclosure.

According to an embodiment, $Ar_{41}$, $L_{41}$, $L_{42}$, $L_{61}$ and $L_{62}$ may be each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group an imidazopyrimidinylene group, and an imidazopyridinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{20}$ aryl group, a $C_1$-$C_{20}$ heteroaryl group, a monovalent non-aromatic condensed polycyclic group, a monovalent non-aromatic condensed heteropolycyclic group, and —Si($Q_{33}$)($Q_{34}$)($Q_{35}$);

wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

According to other embodiment, $Ar_{41}$, $L_{41}$, $L_{42}$, $L_{61}$ and $L_{62}$ may be each independently selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, and a substituted or unsubstituted divalent non-aromatic condensed polycyclic group.

According to other embodiment, $Ar_{41}$, $L_{41}$, $L_{42}$, $L_{61}$ and $L_{62}$ may be each independently selected from a phenylene group, a naphthylene group, a fluorenylene group, a spiro-fluorenylene group, a phenalenylene group, a phenanthrenylene group, an anthracenylene group, a fluoranthenylene group, a triphenylenylene group, a pyrenylene group and a chrysenylene group; and a phenylene group, a naphthylene group, a fluorenylene group, a spiro-fluorenylene group, a phenalenylene group, a phenanthrenylene group, an anthracenylene group, a fluoranthenylene group, a triphenylenylene group, a pyrenylene group and a chrysenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a biphenyl group (phenyl group substituted with a phenyl group), a naphthyl group, a fluorenyl group, a spiro-fluorenyl group, a phenalenyl group, a phenanthrenyl group, an anthracenyl group, a fluoranthenyl group, a triphenylenyl group, a pyrenyl group and a chrysenyl group, but is not limited thereto.

a41 denotes the number of groups $L_{41}$, and a41 may be 0, 1, 2, 3, 4 or 5, for example, 0, 1, or 2. When a41 is 0, *-$(L_4)_{a41}$-*' in Formula 41 is a single bond. When a41 is 2 or higher, groups $L_{41}$ may be identical to or different from each other. The descriptions of a42, a61, and a62 denotes the number of groups $L_{42}$, $L_{61}$ and $L_{62}$, respectively, may be understood from the descriptions of a41.

n1 denotes the number of groups $Ar_{41}$ in Formula 41 and n1 may be 0, 1, 2 or 3, for example, 0 or 1. For example, n1 may be 0, but is limited thereto.

For example, a41, a42, a61 and a62 may be each independently 0 or 1, but is not limited thereto.

Examples of $R_{41}$ to $R_{44}$, $R_{51}$ to $R_{54}$, $R_{61}$ to $R_{64}$, and $R_{71}$ to $R_{79}$ refer to examples of $R_1$ in the present disclosure.

According to an embodiment, $R_{41}$ to $R_{44}$, $R_{51}$ to $R_{54}$, $R_{61}$ to $R_{64}$, and $R_{71}$ to $R_{79}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a pentalenyl group, a naphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a picenyl group, a perylenyl group, a pentaphenyl group, a carbazolyl group, a benzofuranyl group, a benzothiophenyl group, a dibenzofuranyl group, a dibenzothiophenyl group, a benzocarbazolyl group and a dibenzocarbazolyl group; and a phenyl group, a pentalenyl group, a naphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a picenyl group, a perylenyl group, a pentaphenyl group, a carbazolyl group, a benzofuranyl group, a benzothiophenyl group, a dibenzofuranyl group, a dibenzothiophenyl group, a benzocarbazolyl group and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid or a salt thereof, sulfonic acid or a salt thereof, phosphoric acid or a salt thereof, a $C_1$-$C_{20}$ alkyl group, a $C_1$-$C_{20}$ alkoxy group, a phenyl group, a pentalenyl group, a naphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a picenyl group, a perylenyl group, a pentaphenyl group, a carbazolyl group, a benzofuranyl group, a benzothiophenyl group, a dibenzofuranyl group, a dibenzothiophenyl group, a benzocarbazolyl group and a dibenzocarbazolyl group, but are not limited thereto.

According to an embodiment, $R_{51}$, $R_{53}$ and $R_{54}$, in Formula 41 and $R_{71}$ to $R_{79}$ in Formula 61 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_2$-$C_{20}$ alkenyl group, a $C_2$-$C_{20}$ alkynyl group and a $C_1$-$C_{20}$ alkoxy group.

According to other embodiment, $R_{51}$, $R_{53}$ and $R_{54}$, in Formula 41 and $R_{71}$ to $R_{79}$ in Formula 61 may be all hydrogens.

According to other embodiment, $R_{41}$, $R_{42}$ and $R_{52}$ in Formula 41 and $R_{61}$ and $R_{62}$ in Formula 61 may be each independently represented by one of Formulae 4-1 to 4-31.

According to other embodiment, $R_{41}$, $R_{42}$ and $R_{52}$ in Formula 41 and $R_{61}$ and $R_{62}$ in Formula 61 may be each independently represented by one of Formulae 4-1 to 4-5 and 4-26 to 4-31.

For example, the first compound may be represented by one of Formulae 41-1 to 41-12 below, and the second compound may be represented by one of Formulae 61-1 to 61-6:

Formula 41-1

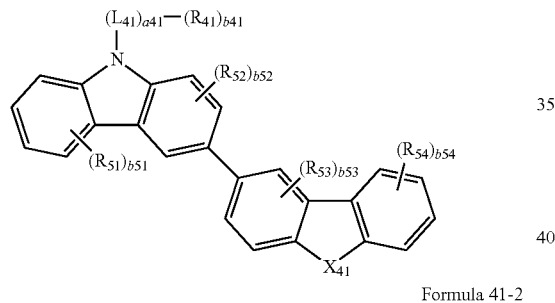

Formula 41-2

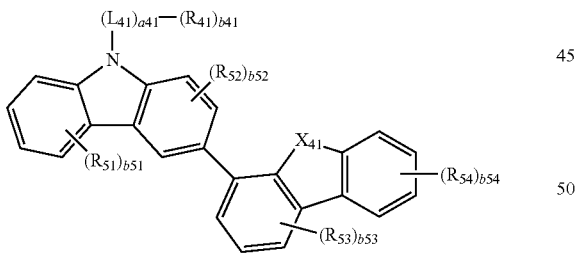

Formula 41-3

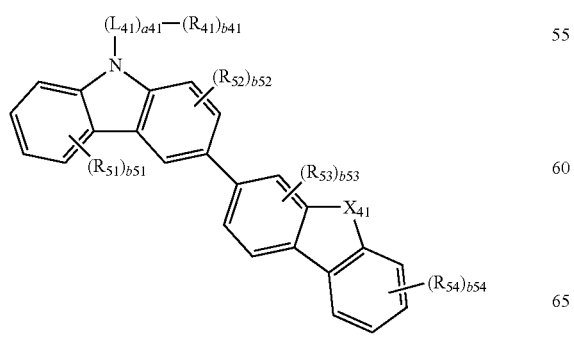

Formula 41-4

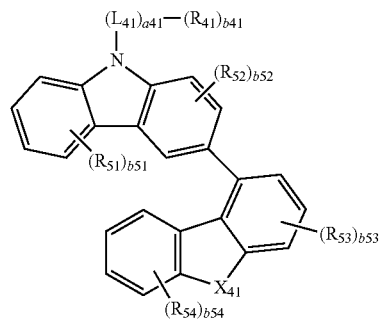

Formula 41-5

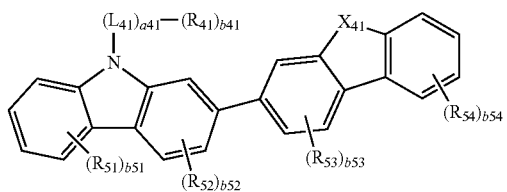

Formula 41-6

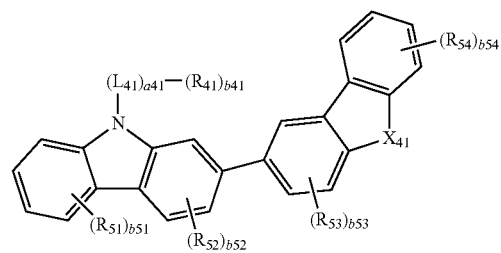

Formula 41-7

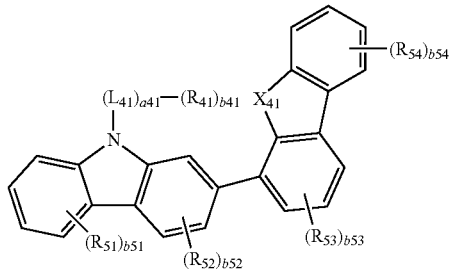

Formula 41-8

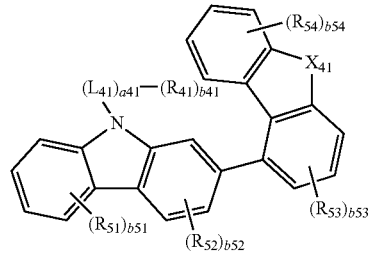

Formula 41-9

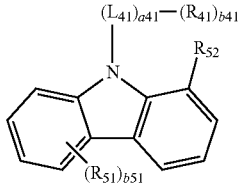

Formula 41-10

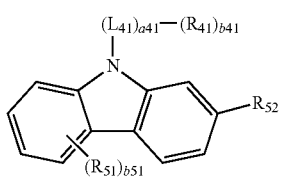

Formula 41-11

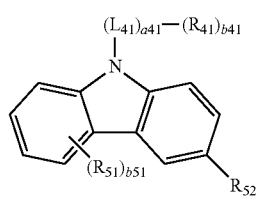

Formula 41-12

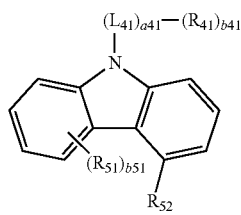

Formula 61-1

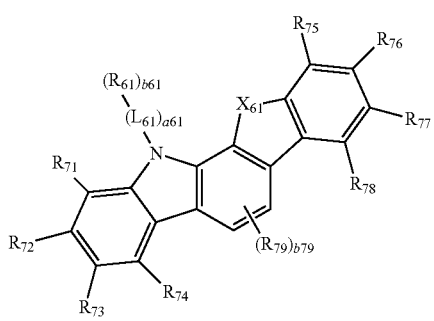

Formula 61-2

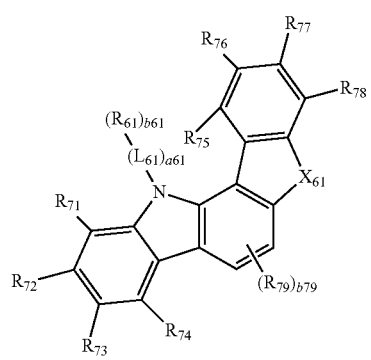

Formula 61-3

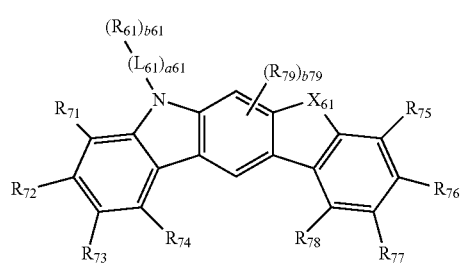

Formula 61-4

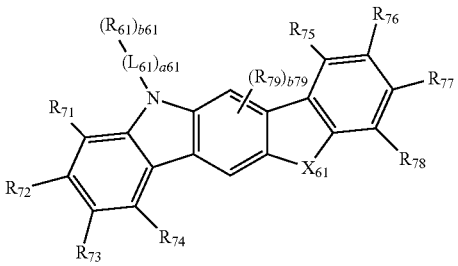

Formula 61-5

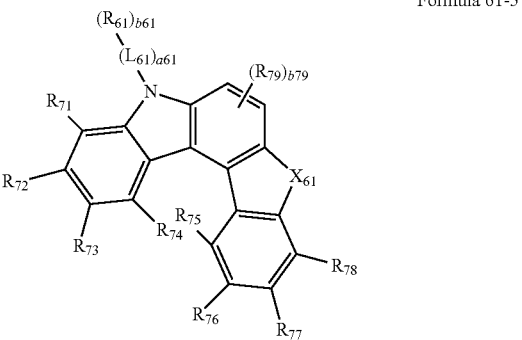

Formula 61-6

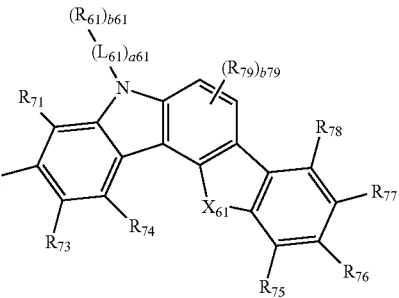

$X_{41}$, $X_{61}$, $L_{41}$, $L_{42}$, a41, a42, $L_{61}$, $L_{62}$, a61, a62, $R_{41}$ to $R_{44}$, b41, b42, $R_{61}$ to $R_{64}$, b61, b62, $R_{71}$ to, $R_{79}$ and b79 in Formulae 41-1 to 41-12 and 61-1 to 61-6 are already described above.

According to an embodiment, the first compound represented by Formula 41 may include one of Compounds A1 to A83 below, and the second compound represented by Formula 61 may include one of Compounds B1 to B20, but they are not limited thereto:

A1

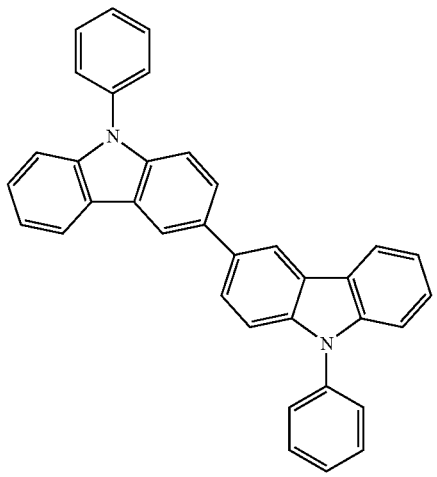

-continued
A2
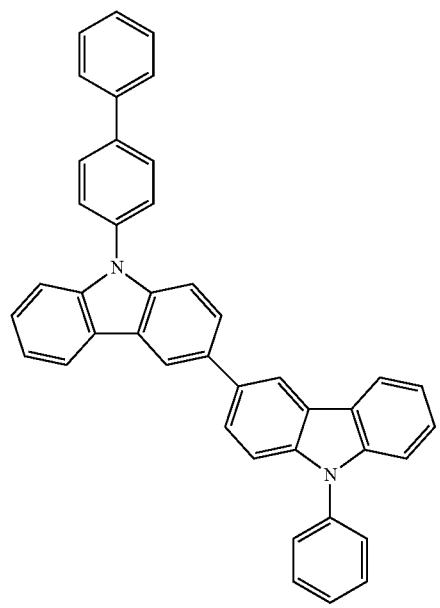
A3
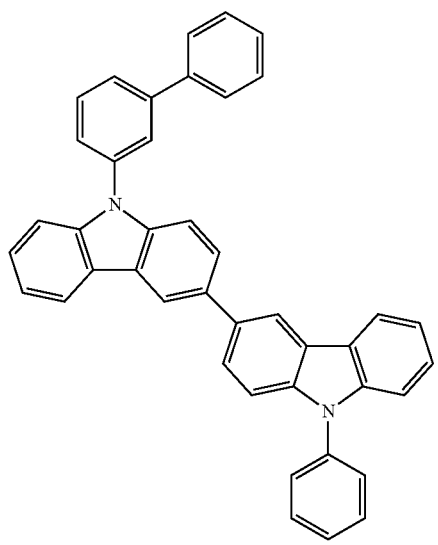
-continued
A4
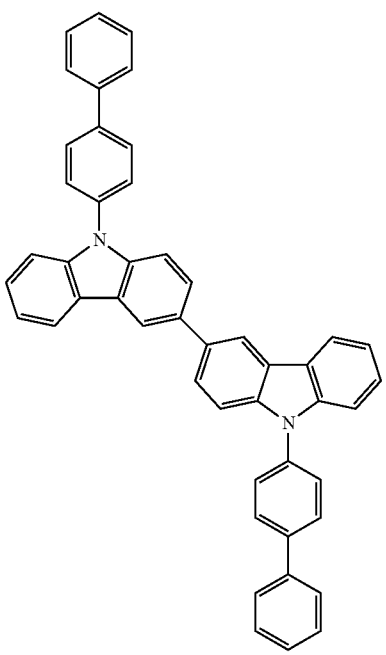
A5
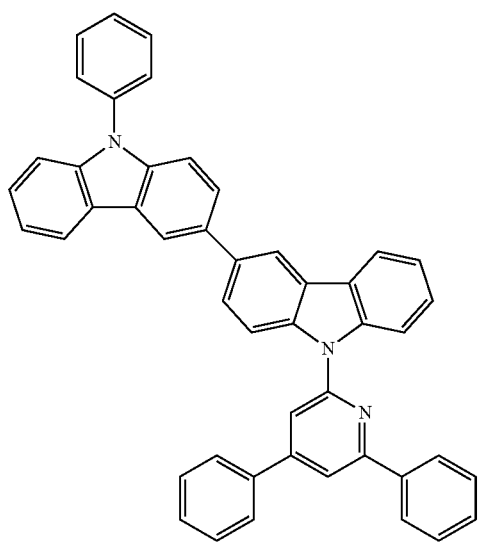

A6
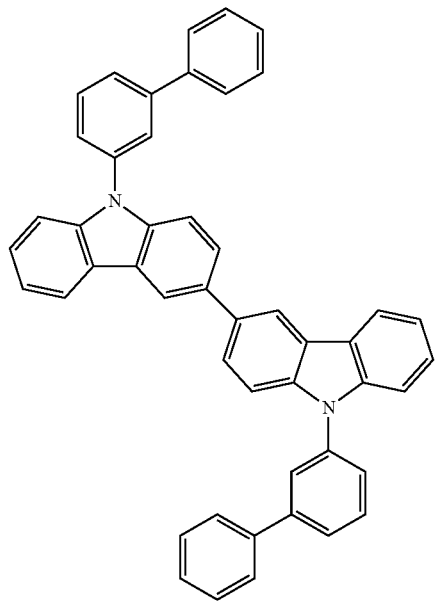
A8
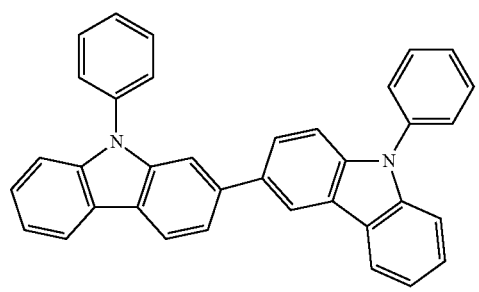
A9
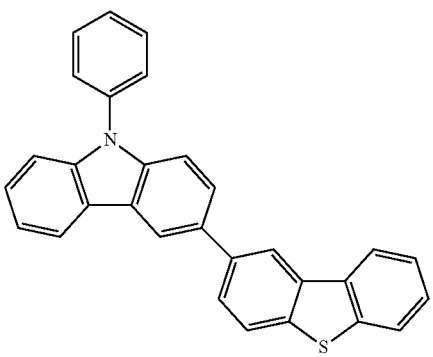
A10
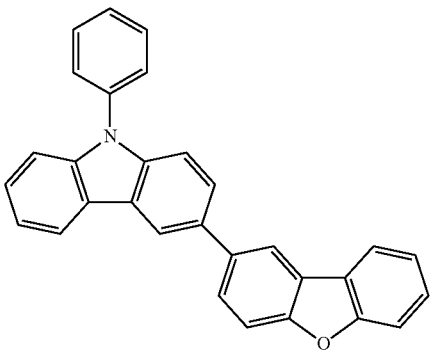
A11

A12 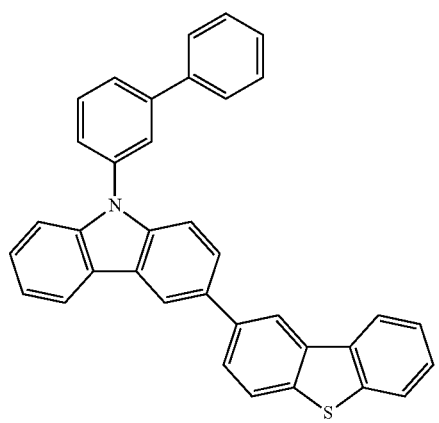
A13 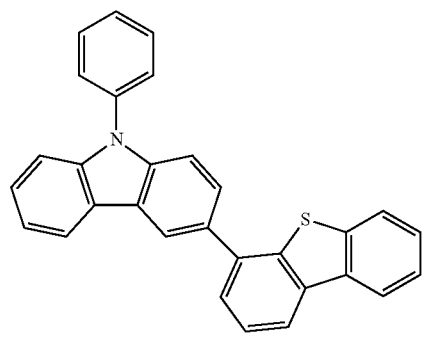
A14 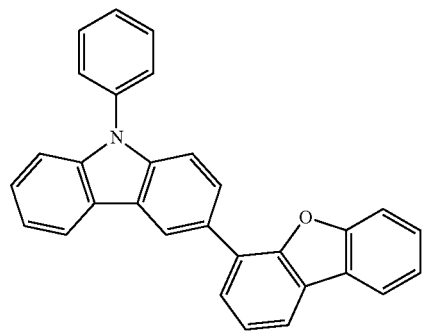
A15 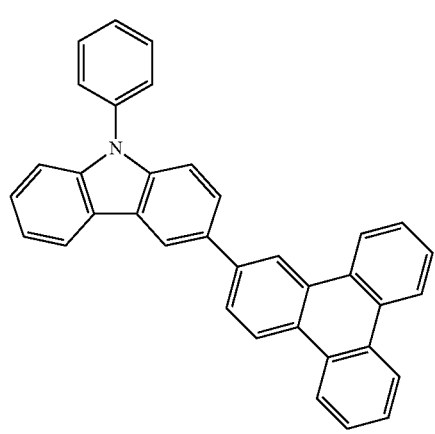
A16 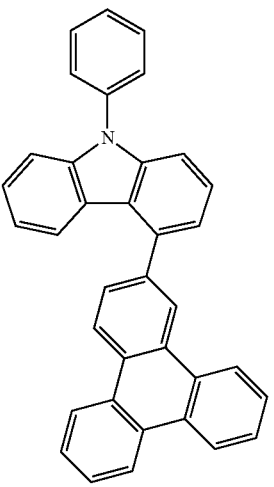
A17 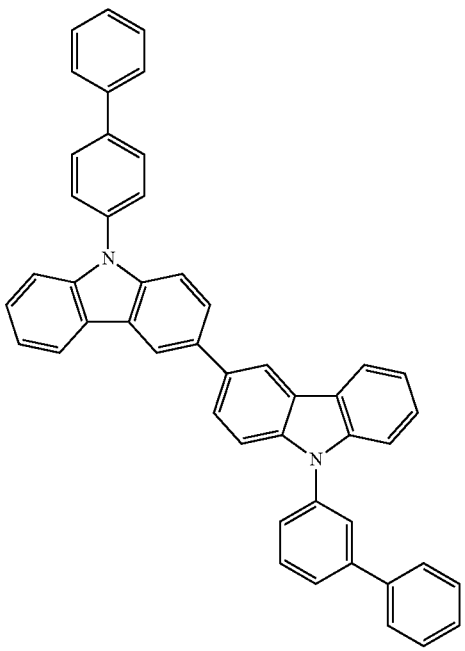
A18 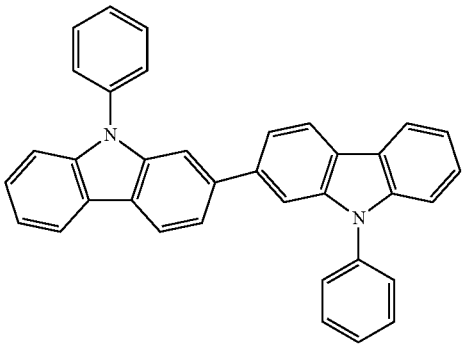

-continued
A19
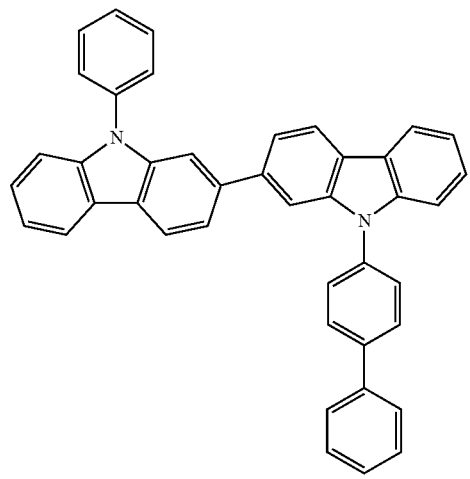
A20
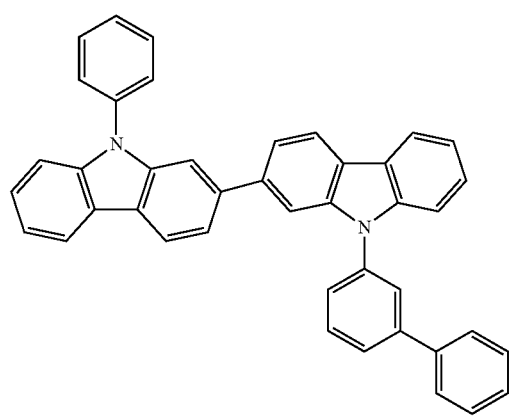
A21
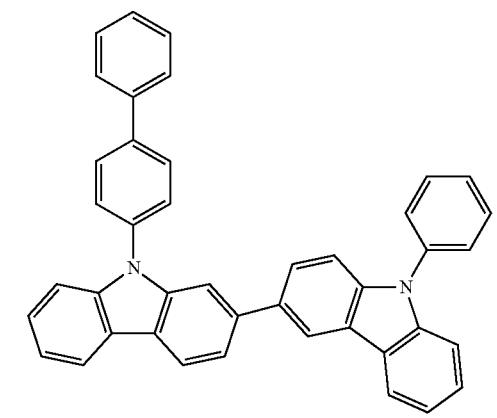
A22
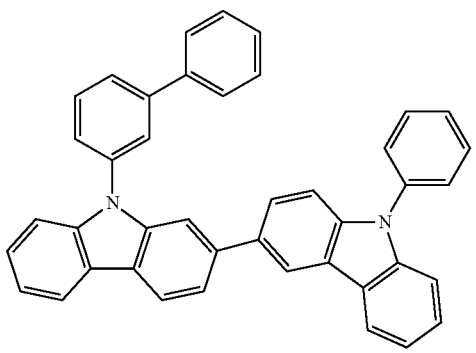
-continued
A23
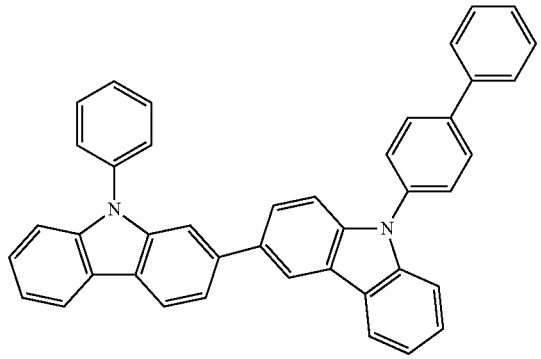
A24
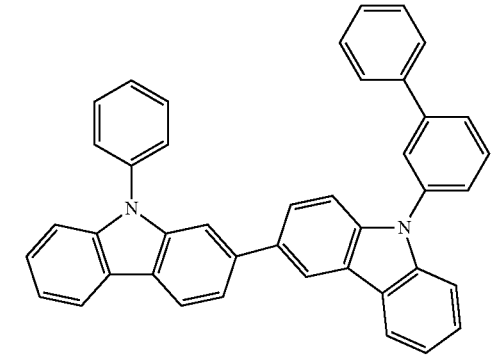
A25
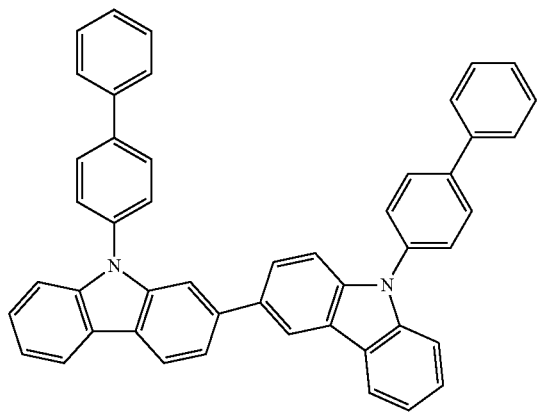
A26
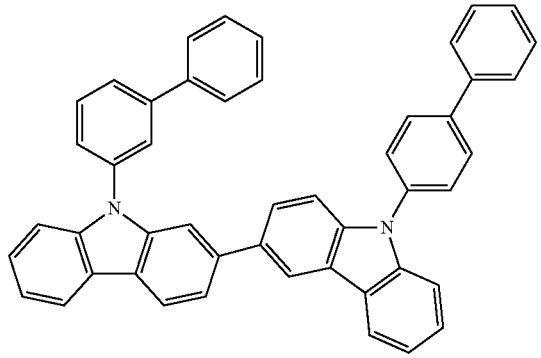

A27
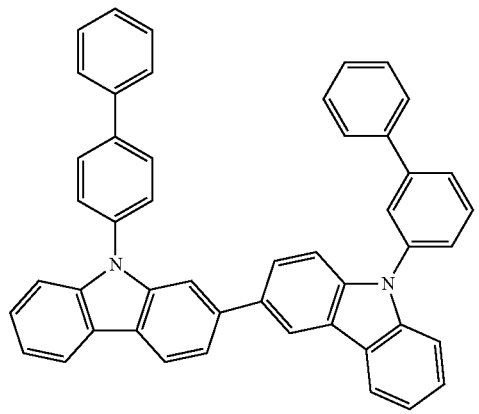
A28
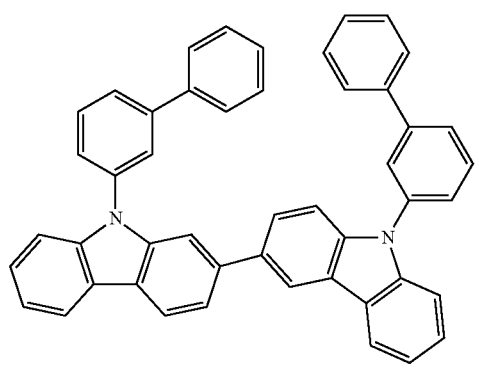
A29
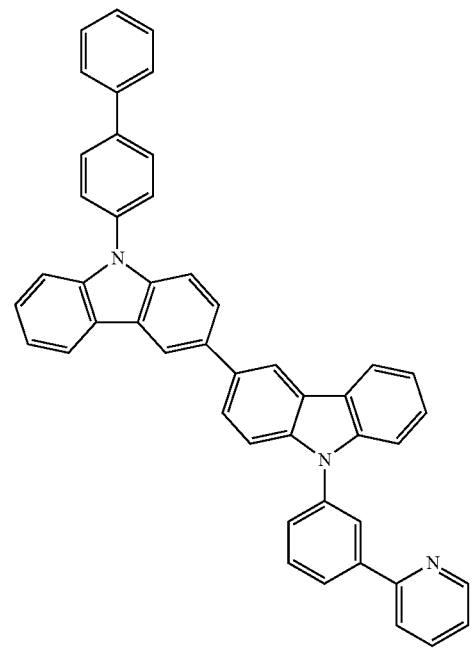
A30
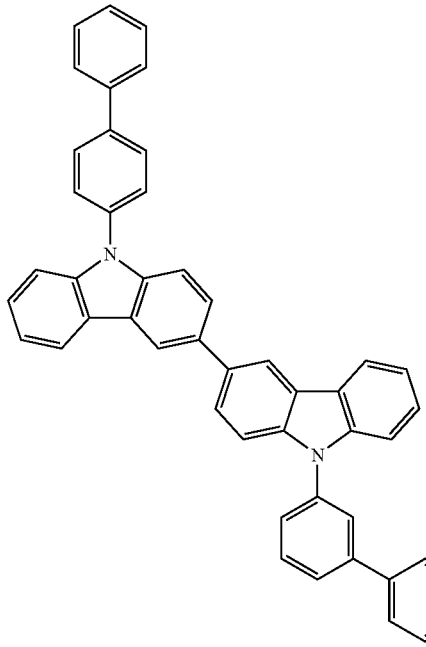
A31
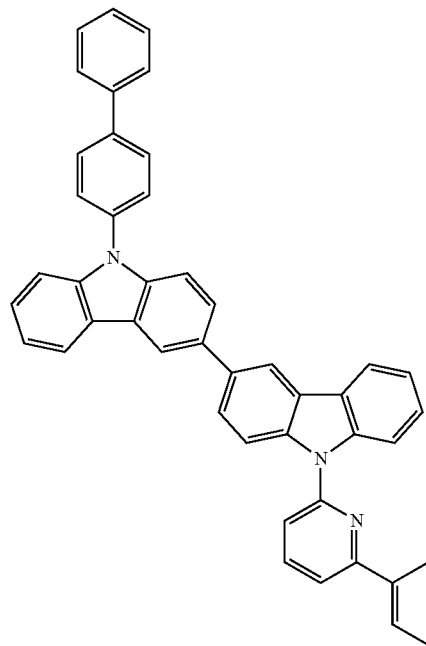

A32
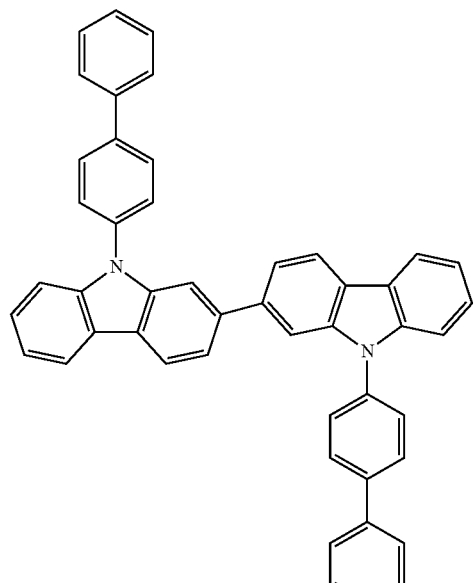
A33
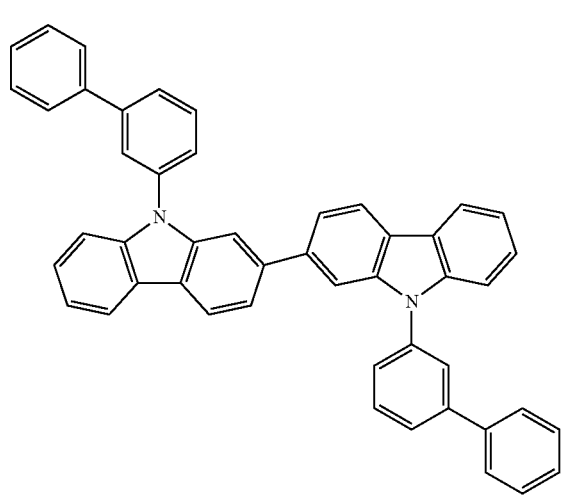
A34
A35
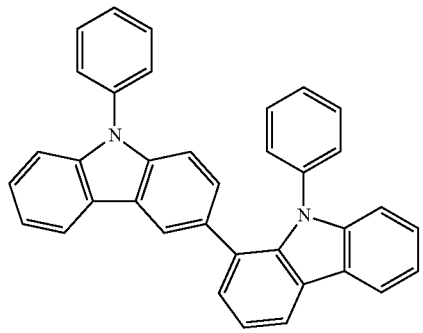
A36
A37
A38
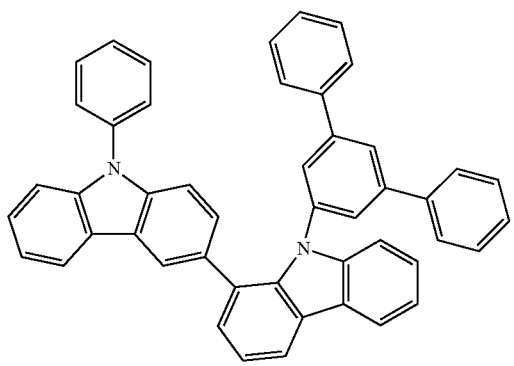

A39
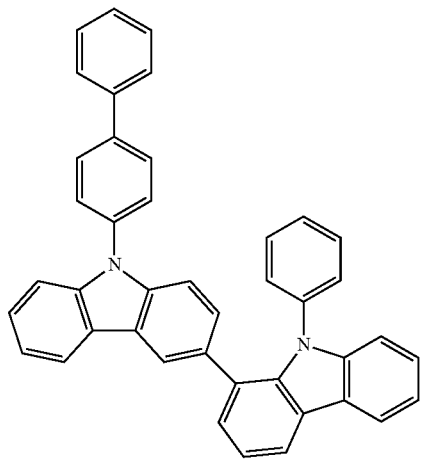
A40
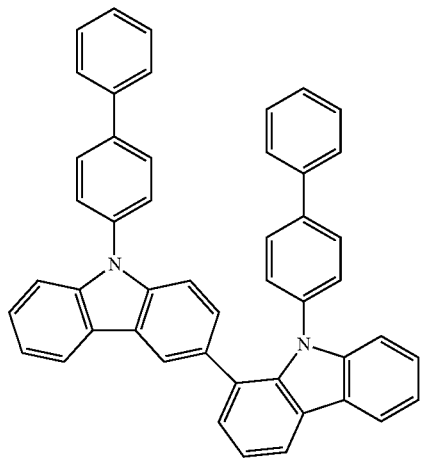
A41
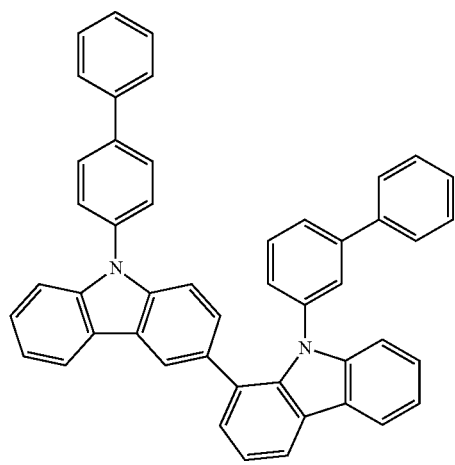
A42
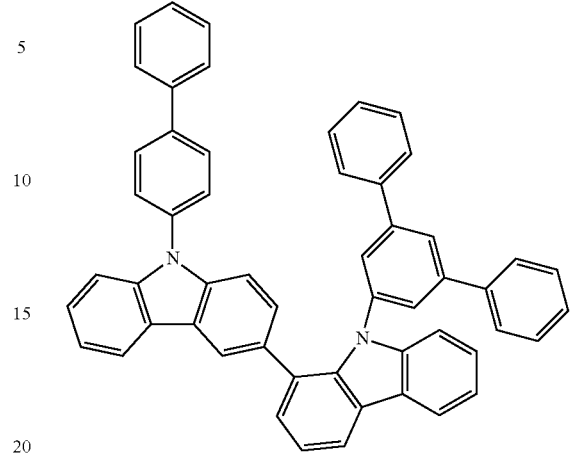
A43
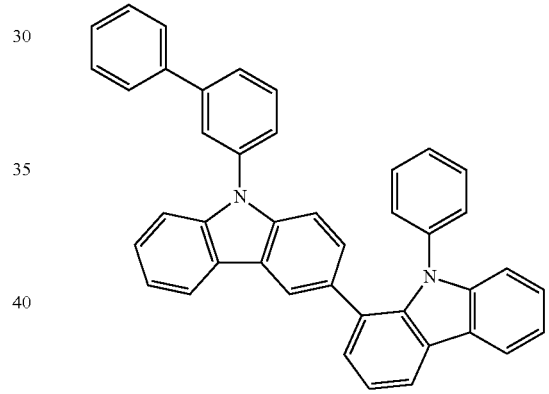
A44
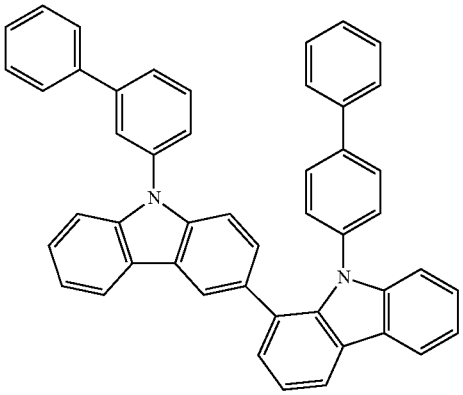

A45
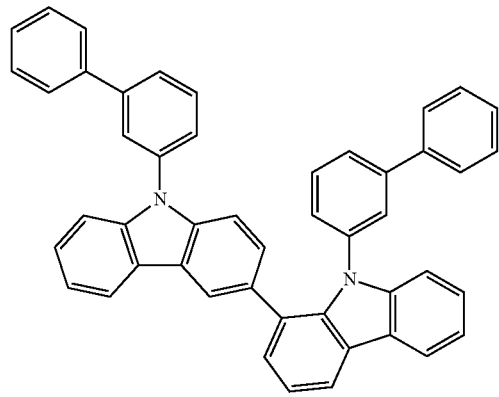
A49
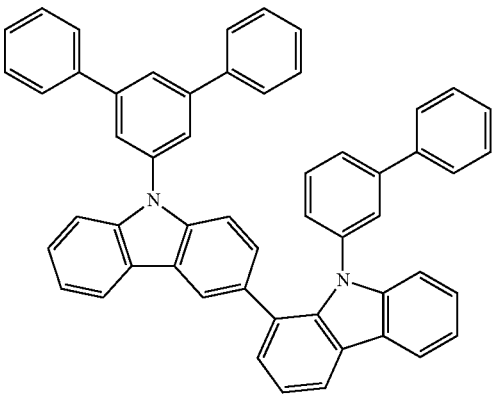
A46
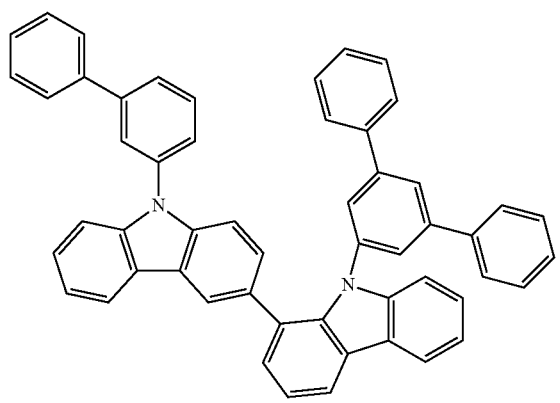
A50
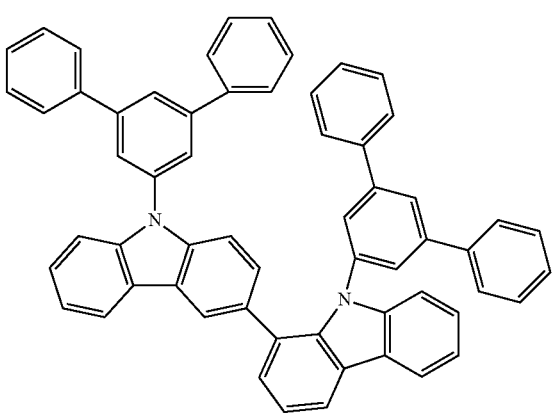
A47
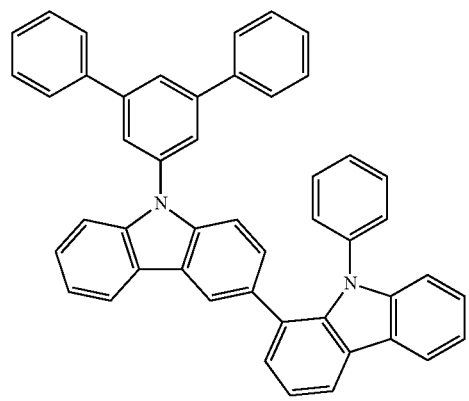
A51
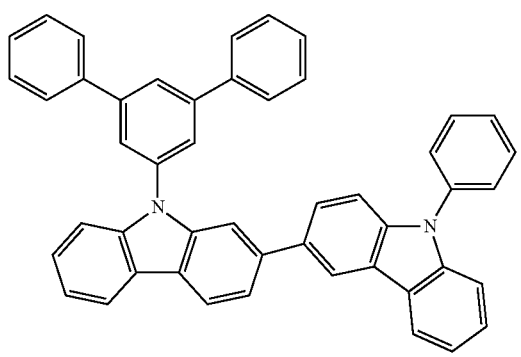
A48
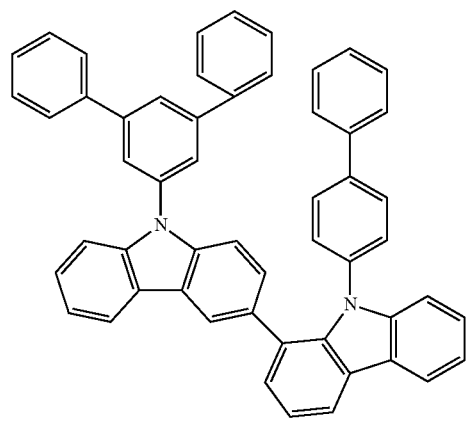
A52
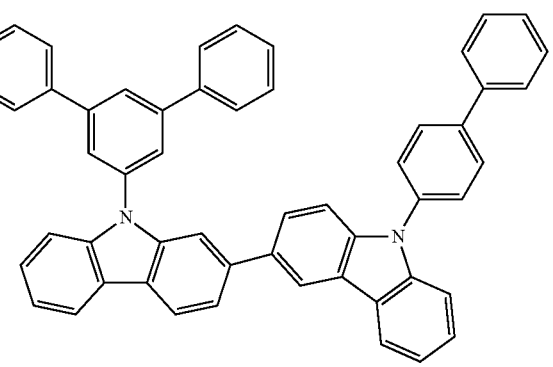

-continued
A53
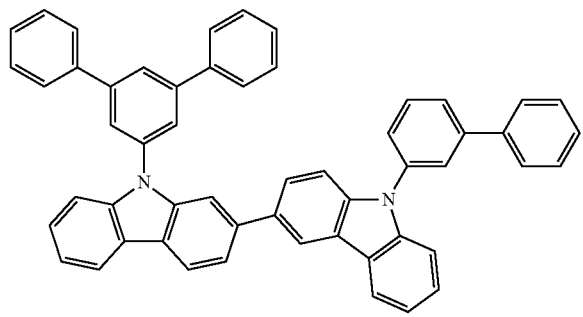
A54
A55
-continued
A56
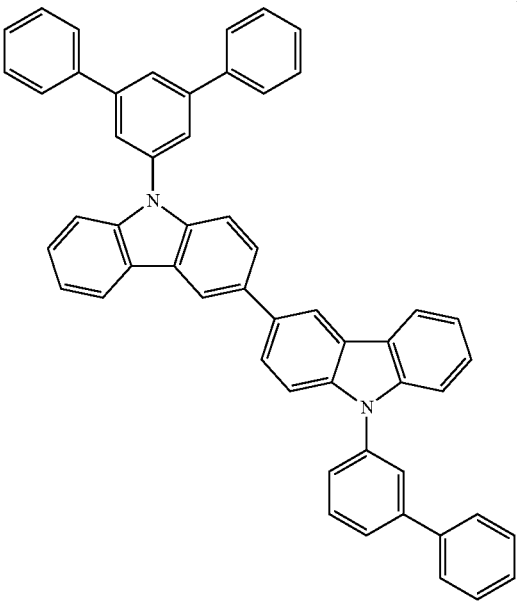
A57
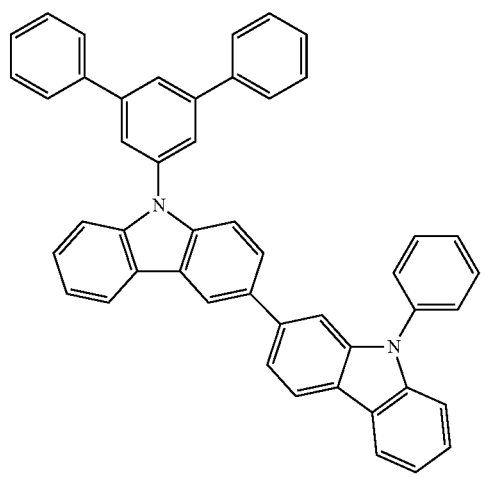
A58
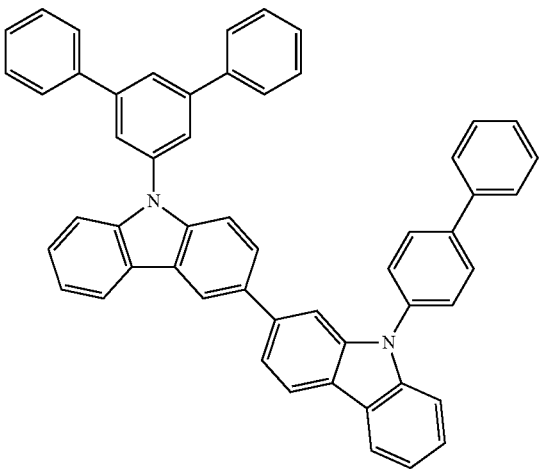

123
-continued
A59
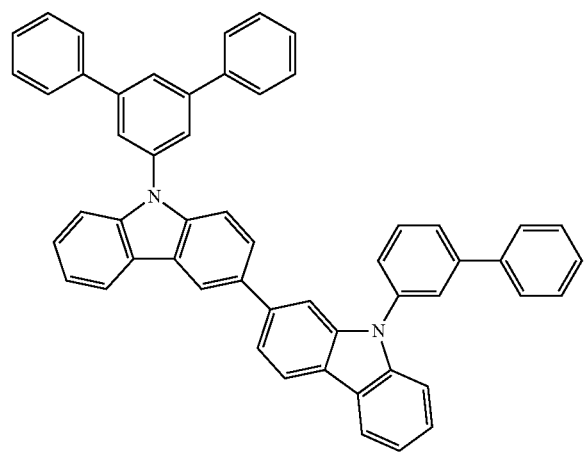
A60
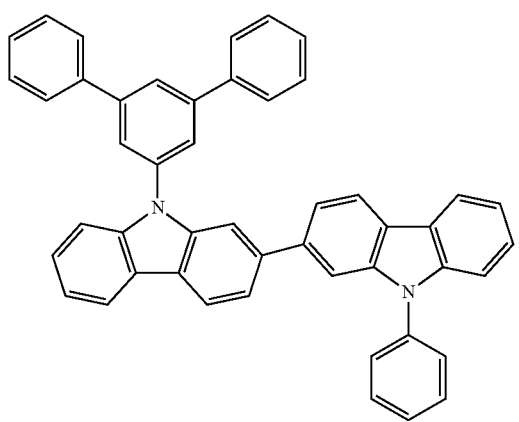
A61
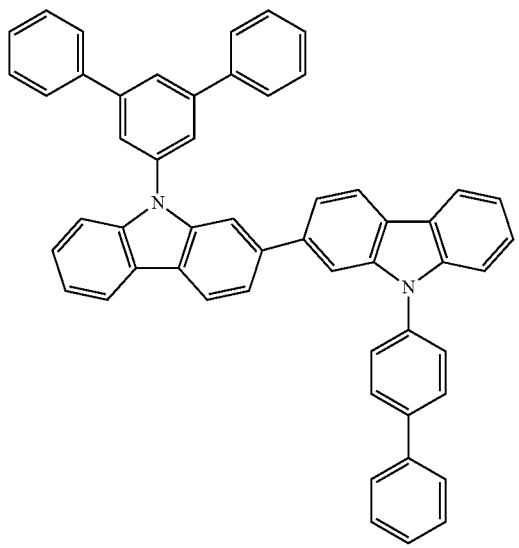
124
-continued
A62
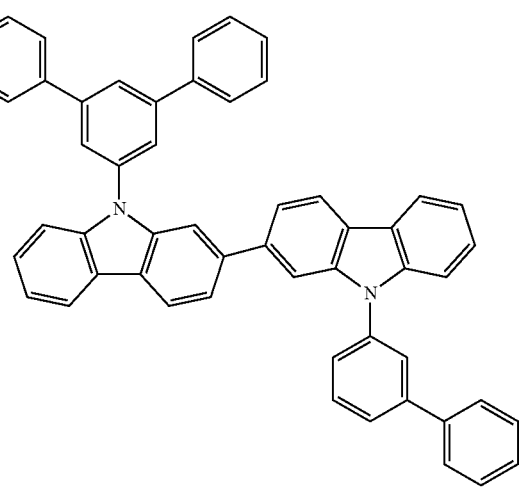
A63
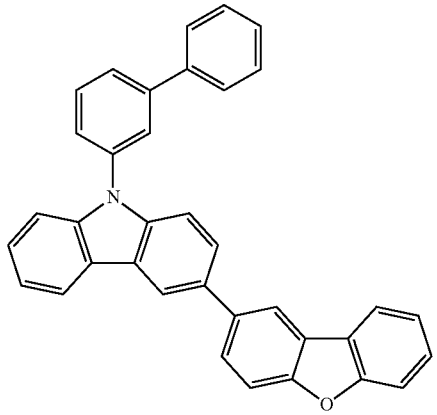
A64
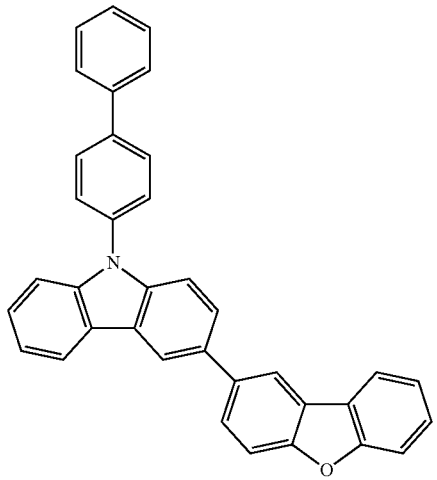

A65
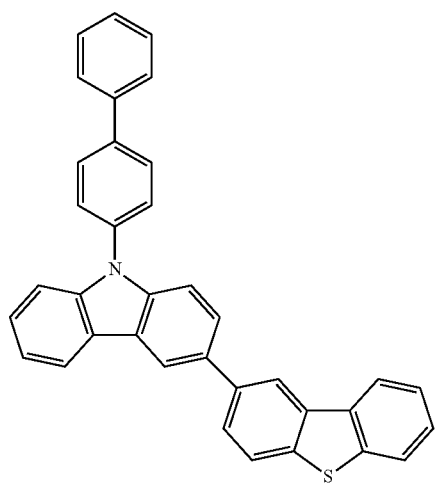
A66
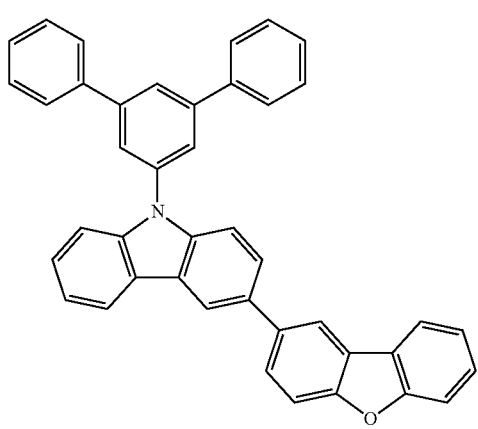
A67
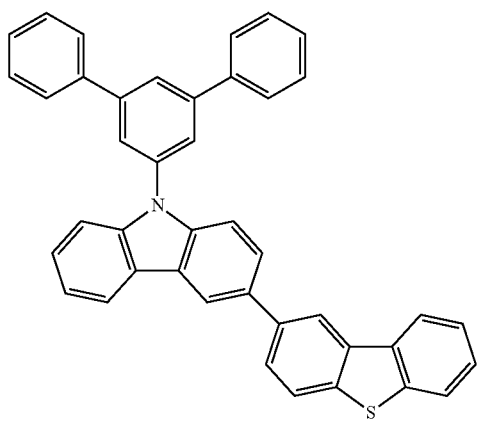
A68
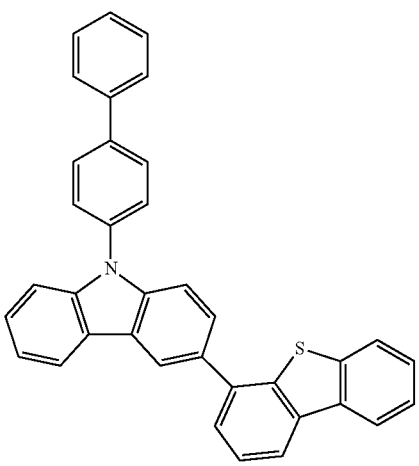
A69
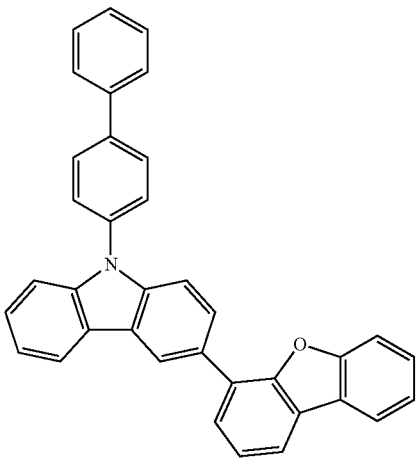
A70
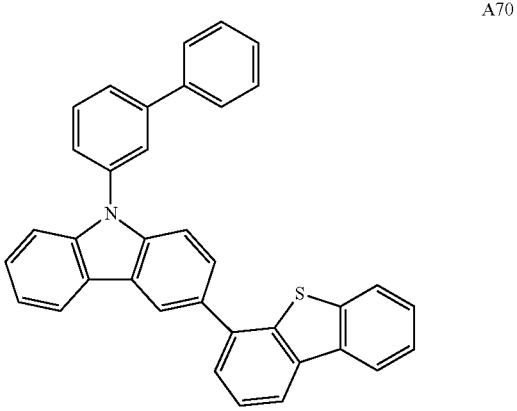

A71
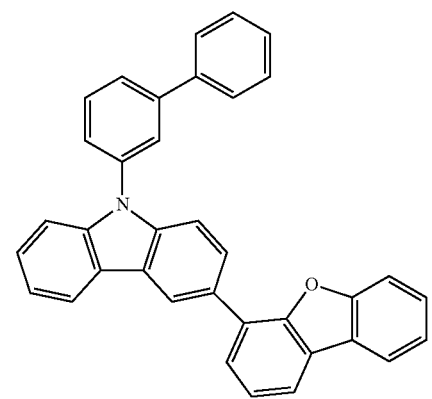
A72
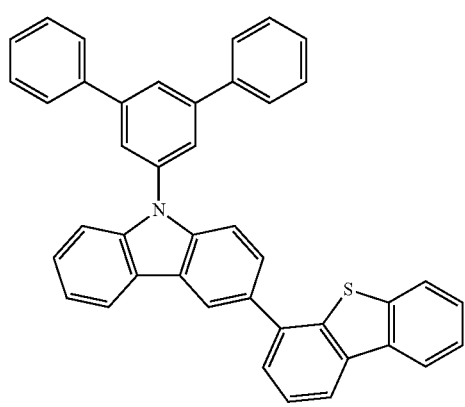
A73
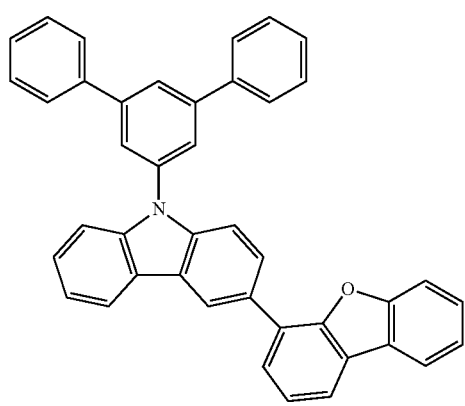
A74
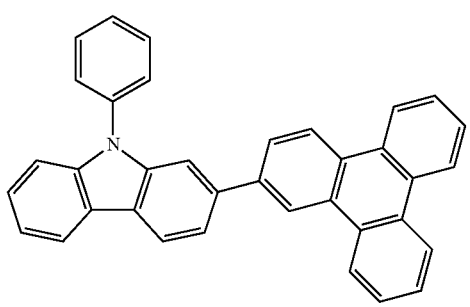
A75
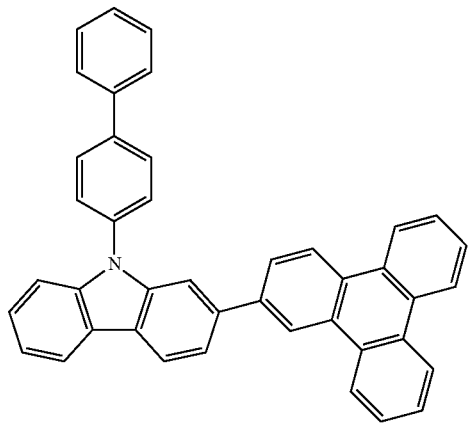
A76
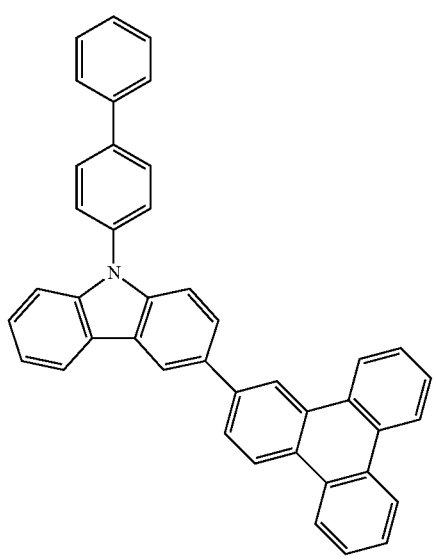
A77
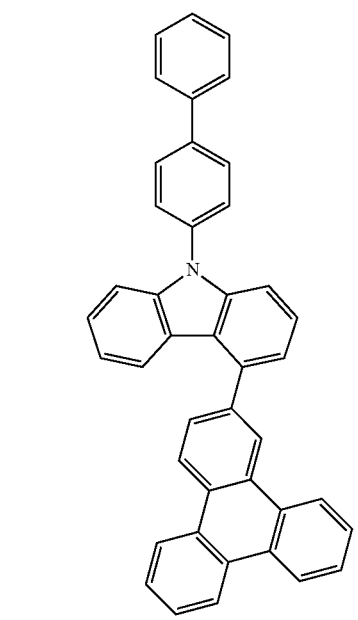

A78
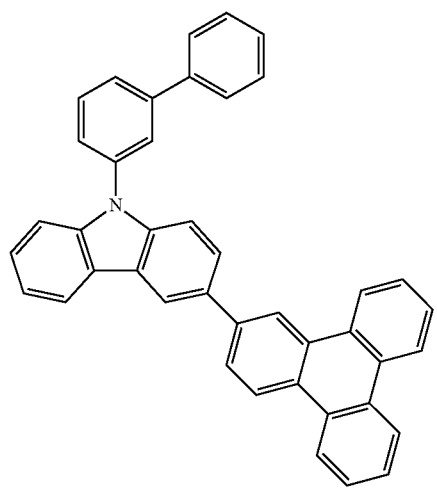
A81
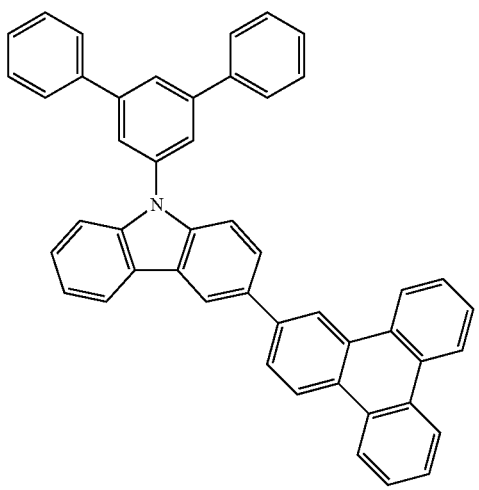
A79
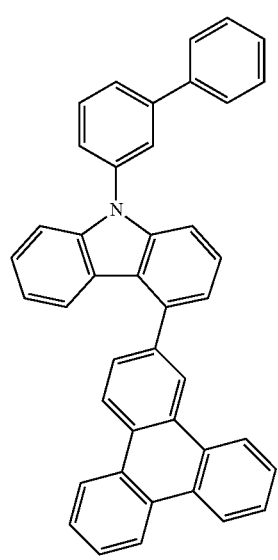
A82
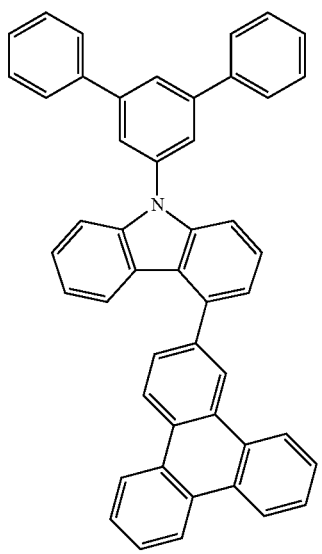
A80
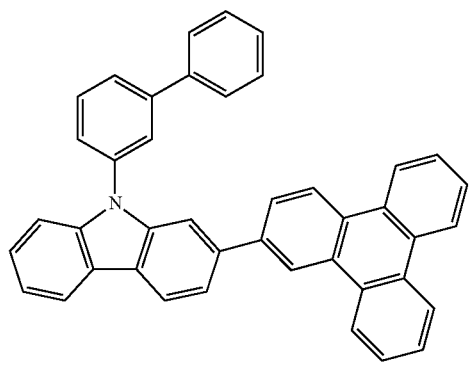
A83
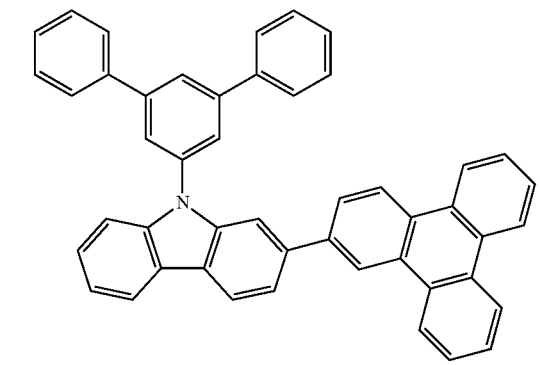

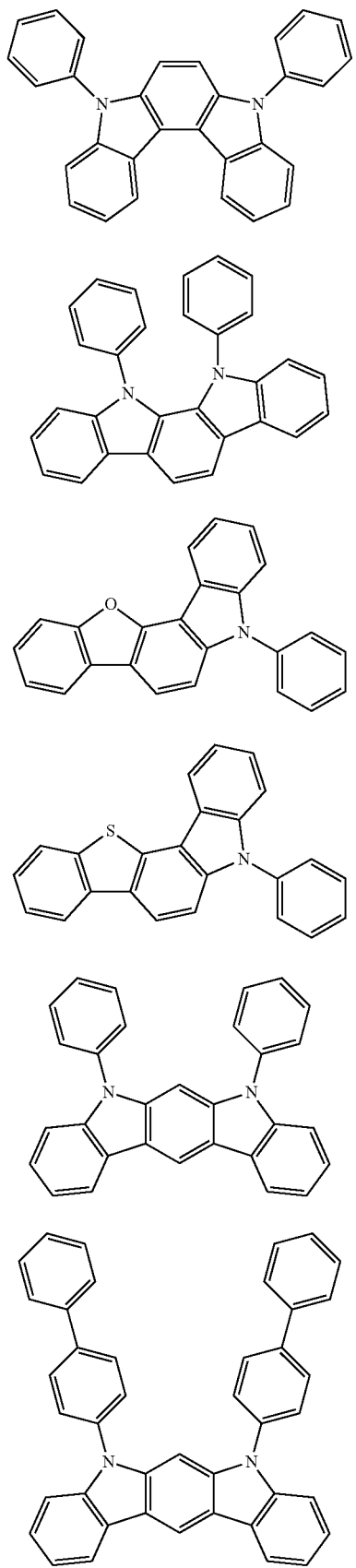
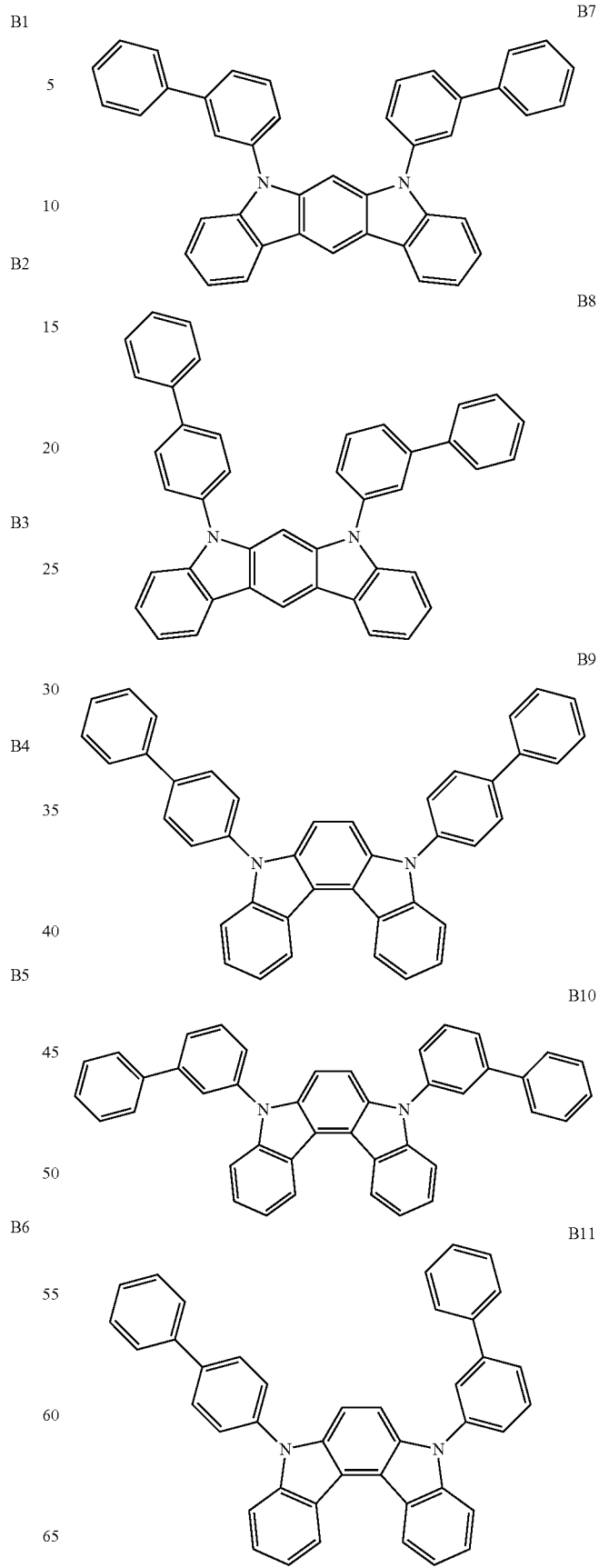

B12
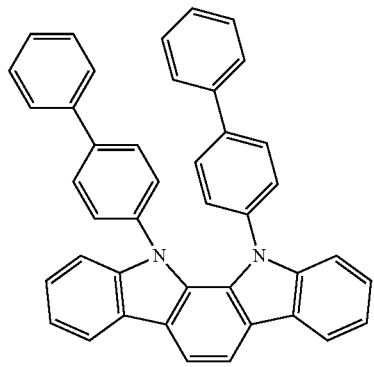

B13
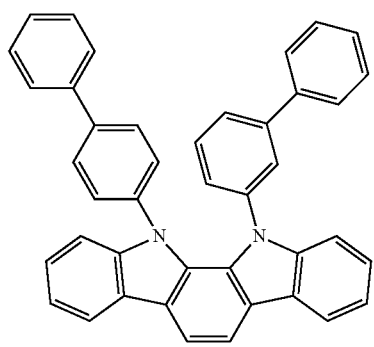

B14
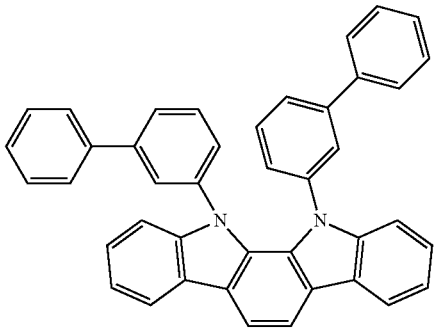

B15
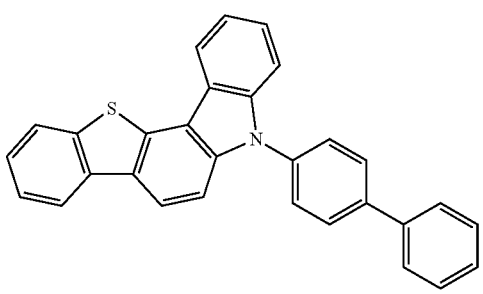

B16
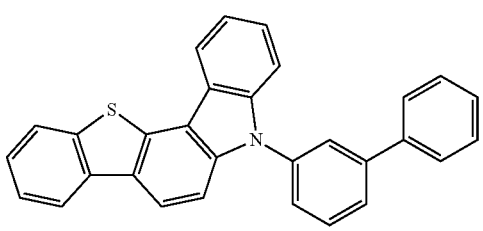

B17
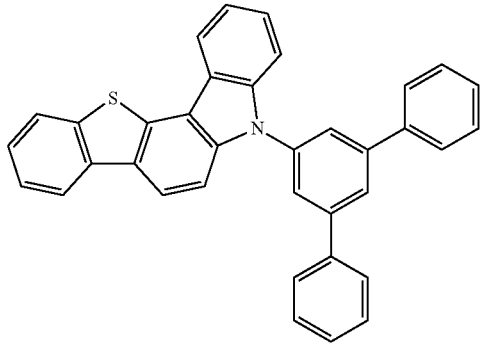

B18
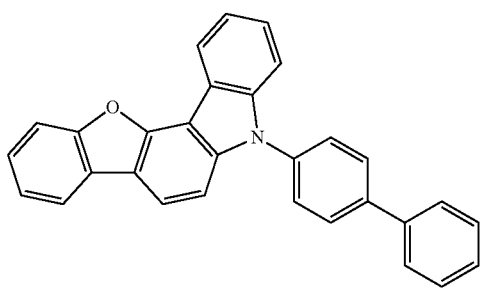

B19
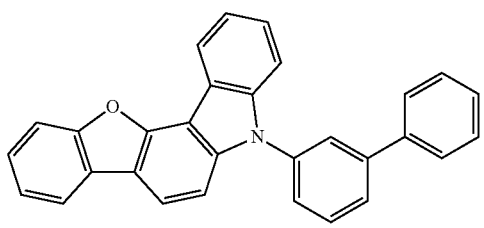

B20
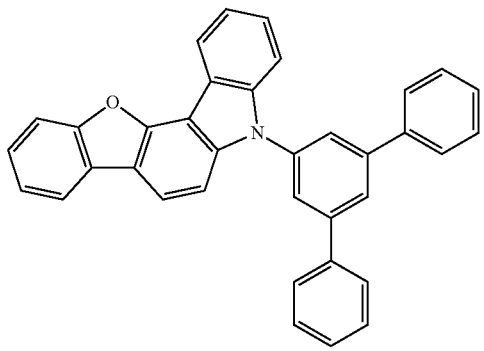

When the organic layer (for example, the emission layer) of the organic light-emitting device includes at least one of the first compound represented by Formula 41 and the second compound represented by Formula 61, in addition to the condensed cyclic compound represented by Formula 1, holes and electrons provided to the emission layer may be effectively controlled. Accordingly, an organic light-emitting device with high luminescent efficiency, high brightness and long lifespan may be obtained.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

A substrate may be additionally disposed under the first electrode 11 or above the second electrode 19. For the substrate, any substrate suitable in a general organic light-emitting device may be used, and the substrate may be a glass substrate or a transparent plastic substrate, each with excellent mechanical strength, thermal stability, transparency, surface smoothness, ease of handling, and waterproofness.

The first electrode 11 may be formed by depositing or sputtering a material for forming the first electrode on the substrate. The first electrode 11 may be an anode. The material for the first electrode 11 may be selected from materials with a high work function so that holes may be easily injected. The first electrode 11 may be a reflective electrode, a semi-transmissive electrode, or a transmissive electrode. The material for the first electrode 11 may be an indium tin oxide (ITO), indium zinc oxide (IZO), tin oxide ($SnO_2$), or zinc oxide (ZnO). In some embodiments, the material for the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layer structure or a multi-layer structure including two or more layers.

An organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one of a hole injection layer, a hole transport layer, an electron blocking layer, and a buffer layer.

The hole transport region may include only either a hole injection layer or a hole transport layer. In some embodiments, the hole transport region may have a structure of hole injection layer/hole transport layer or hole injection layer/hole transport layer/electron blocking layer, which are sequentially stacked on the first electrode 11.

When the hole transport region includes a hole injection layer (HIL), the HIL may be formed on the first electrode 11 by using any one of various methods, for example, vacuum deposition, spin coating, casting, or Langmuir-Blodgett (LB) deposition.

When a HIL is formed by vacuum deposition, the deposition conditions may vary according to a material that is used to form the HIL, and the desired structure and thermal characteristics of the HIL. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (Å/sec). However, the deposition conditions are not limited thereto.

When the HIL is formed using spin coating, coating conditions may vary according to the material used to form the HIL, and the structure and thermal properties of the HIL. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for a hole transport layer (HTL) and an electron blocking layer (EBL) may be referred to conditions for forming the HIL.

The hole transport region may include at least one of the condensed cyclic compounds described above. For example, a HTL included in the hole transport region may include at least one of the condensed cyclic compounds described above.

In an embodiment, the hole transport region (e.g., a HTL in the hole transport region) may include a condensed cyclic compound represented by Formula 1 in which $L_3$ is selected from a substituted or unsubstituted $C_6$-$C_{60}$ arylene group and a substituted or unsubstituted divalent non-aromatic condensed polycyclic group and $R_3$ is selected from a substituted or unsubstituted $C_6$-$C_{60}$ aryl group and a substituted or unsubstituted monovalent non-aromatic condensed polycyclic group, but is not limited thereto.

In another embodiment, the hole transport region (e.g., a HTL in the hole transport region) may include a condensed cyclic compound represented by Formula 1 in which $L_3$ is selected from
a phenylene group, a naphthylene group, and a triphenylene group; and
a phenylene group, a naphthylene group, and a triphenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, and a chrysenyl group, and $R_3$ is selected from Formulae 4-1 to 4-5, but is not limited thereto.

Alternatively, the hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

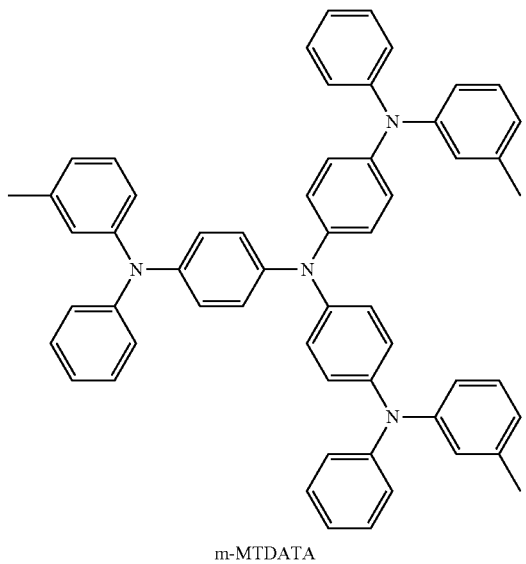

m-MTDATA

-continued
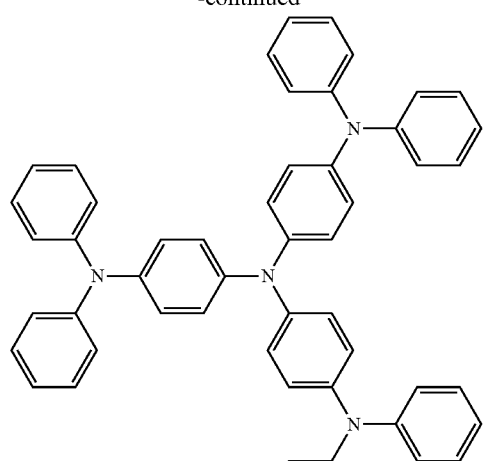
TDATA
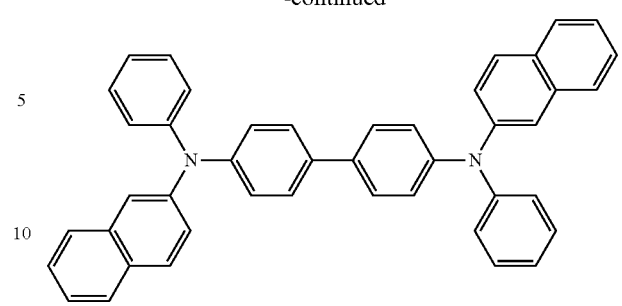
β-NPB
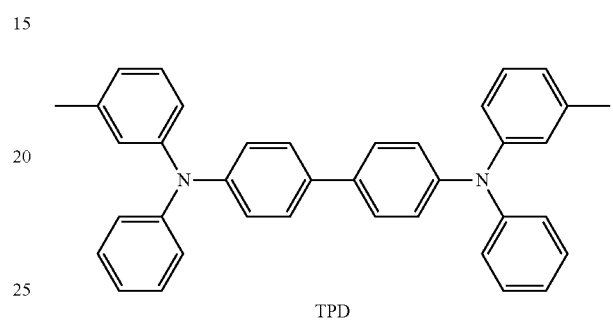
TPD
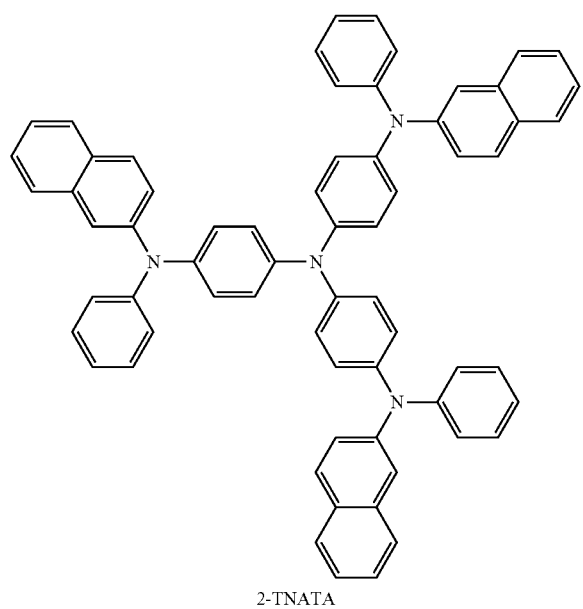
2-TNATA
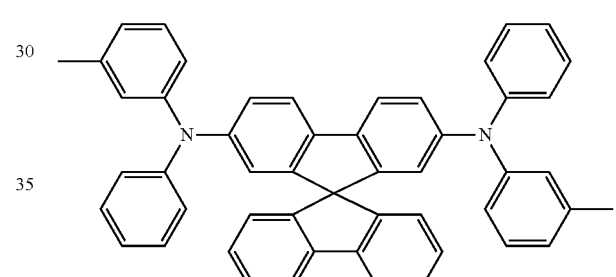
Spiro-TPD
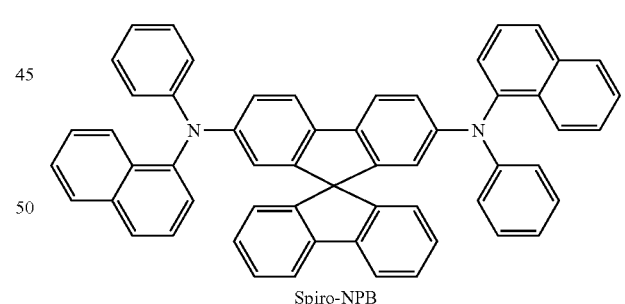
Spiro-NPB
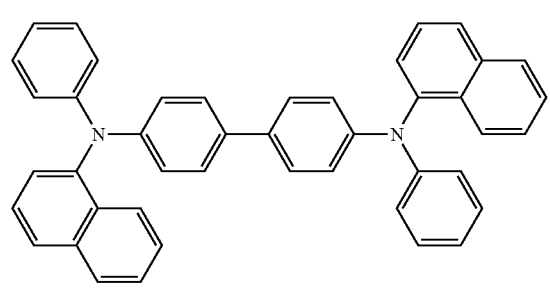
NPB
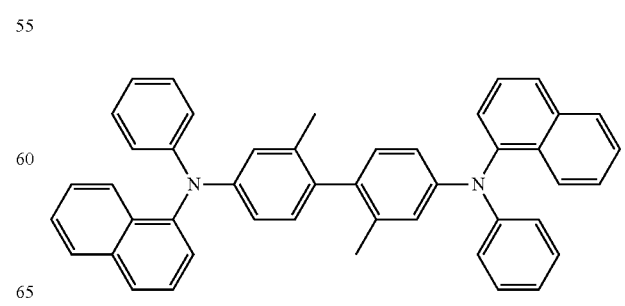
methylated NPB

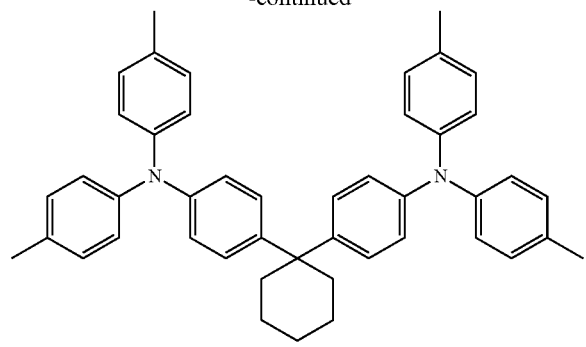

TAPC

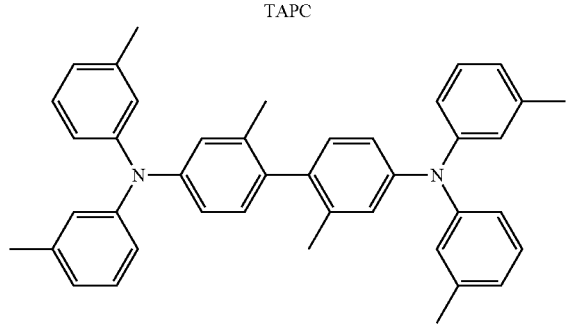

HMTPD

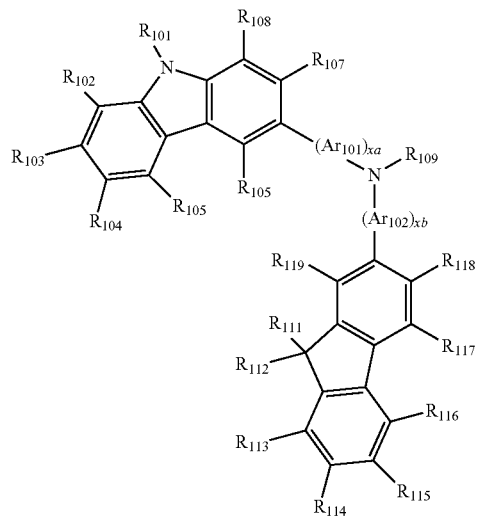

Formula 201

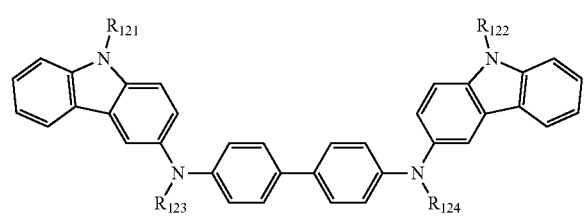

Formula 202

In Formula 201, $Ar_{101}$ to $Ar_{102}$ may be, each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group.

In Formula 201, xa and xb may be, each independently, an integer selected from 0 to 5, for example, 0, 1, or 2. For example, xa may be 1, and xb may be 0, but xa and xb are not limited thereto.

In Formulae 201 and 202, $R_{101}$ to $R_{108}$, $R_{111}$ to $R_{119}$, and $R_{121}$ to $R_{124}$ may be, each independently, but not limited to, selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group (e.g., a methyl group, an ethyl group, a propyl group, a butyl group, a pentyl group, or a hexyl group), and a $C_1$-$C_{10}$ alkoxy group (e.g., a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, an anthracenyl group, a fluorenyl group, and a pyrenyl group; or a phenyl group, a naphthyl group, an anthracenyl group, a fluorenyl group, and a pyrenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group.

In Formula 201, $R_{109}$ may be selected from, a phenyl group, a naphthyl group, an anthracenyl group, and a pyridinyl group; and a phenyl group, a naphthyl group, an anthracenyl group, and a pyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group.

In an embodiment, the compound represented by Formula 201 may be represented by Formula 201A, but is not limited thereto:

Formula 201A

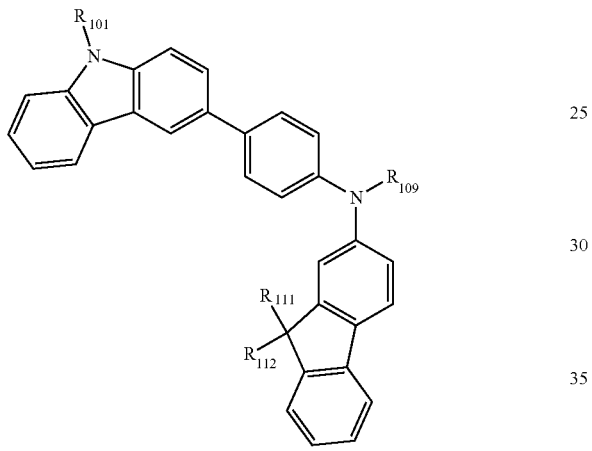

In Formula 201A, the descriptions of $R_{101}$, $R_{111}$, $R_{112}$, and $R_{109}$ are defined above in the present specification.

For example, the compound represented by Formula 201 and the compound represented by Formula 202 may include Compounds HT1 to HT20 below, but are not limited thereto:

HT1

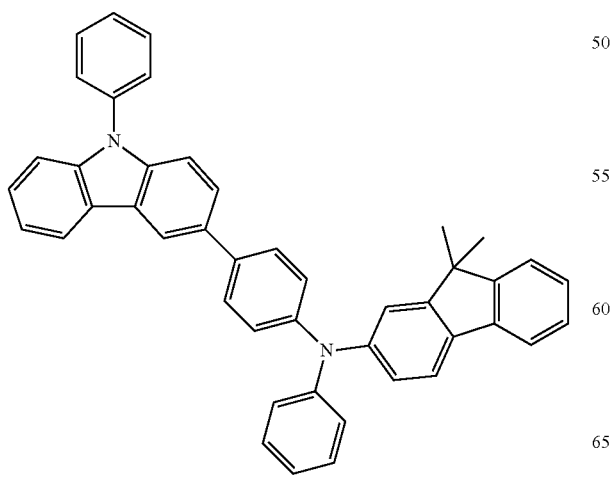

HT2

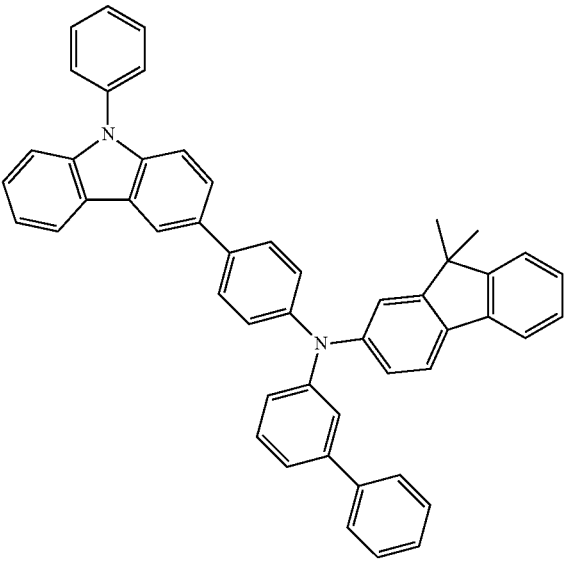

HT3

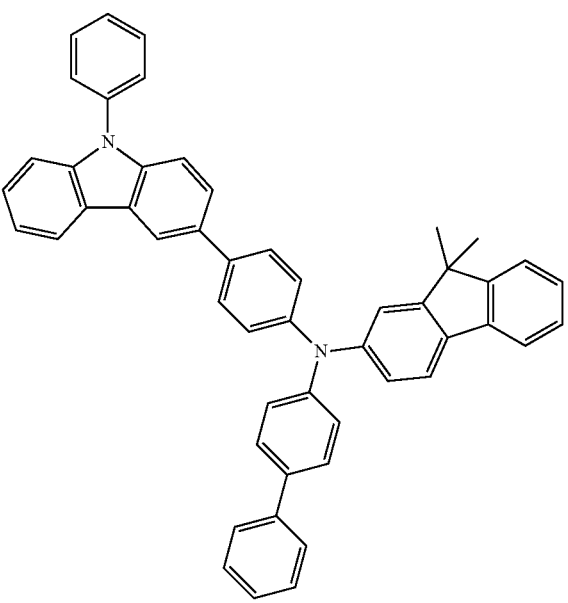

HT4
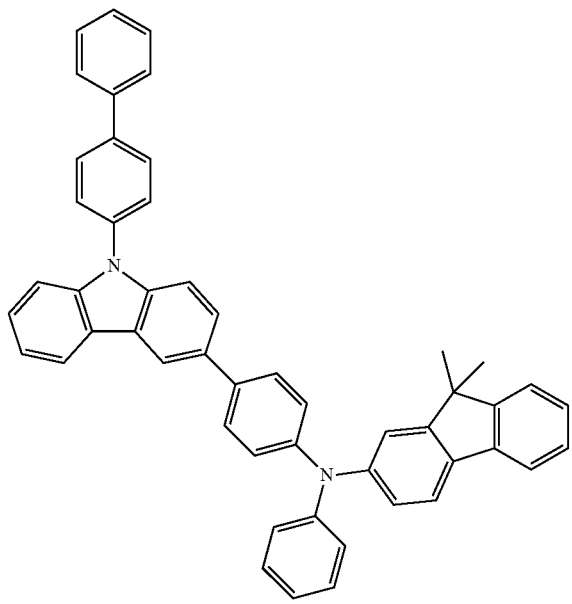
HT5
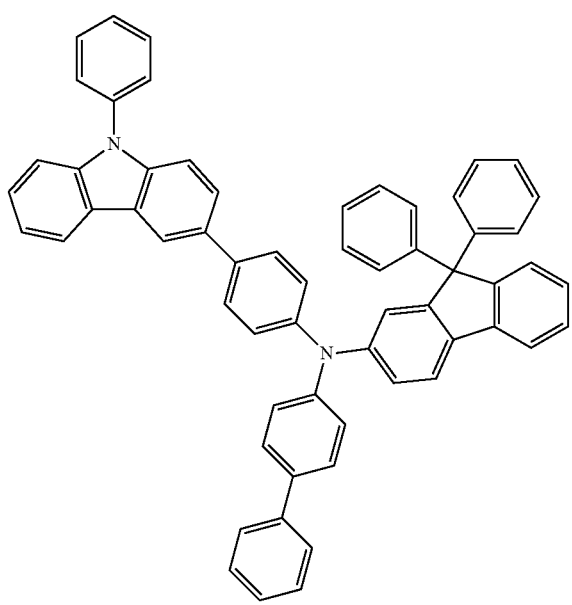
HT6
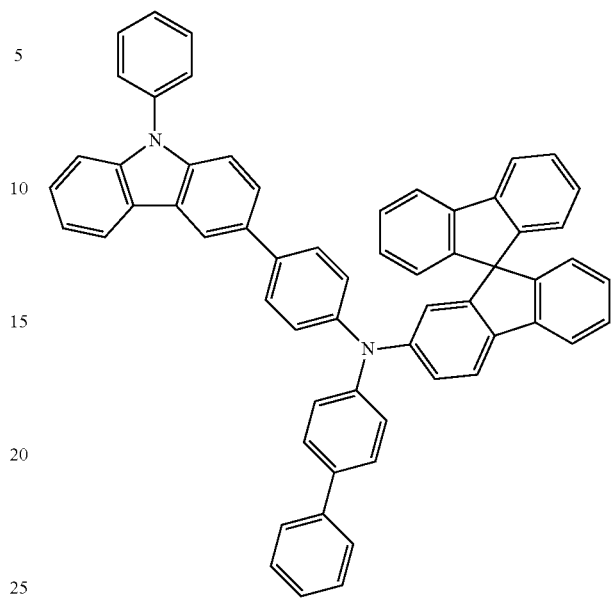
HT7
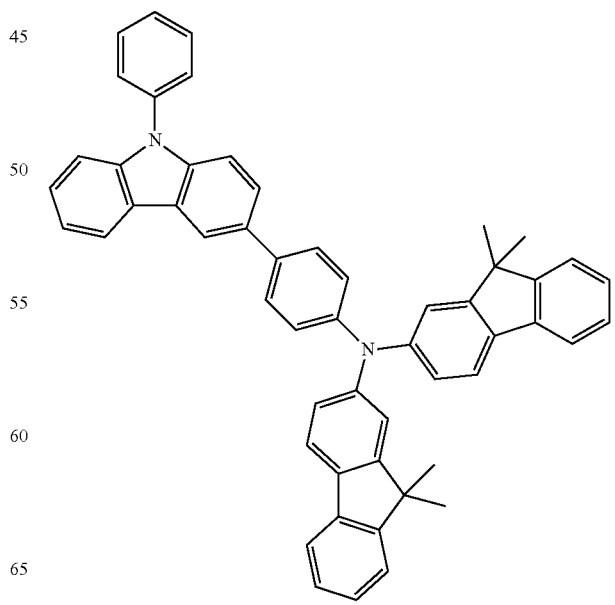

HT8
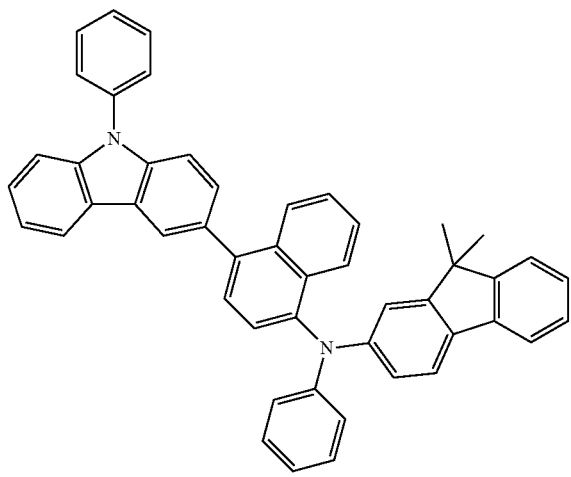
HT9
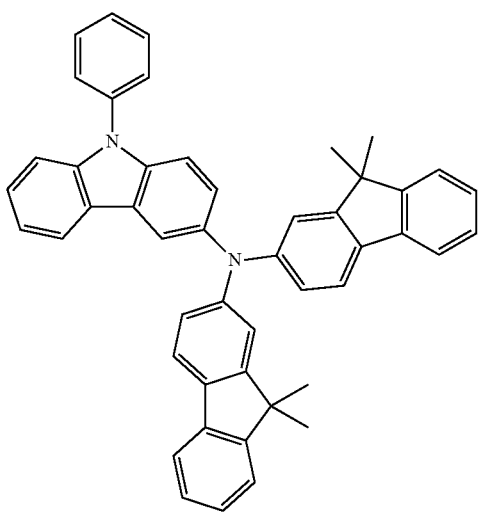
HT10
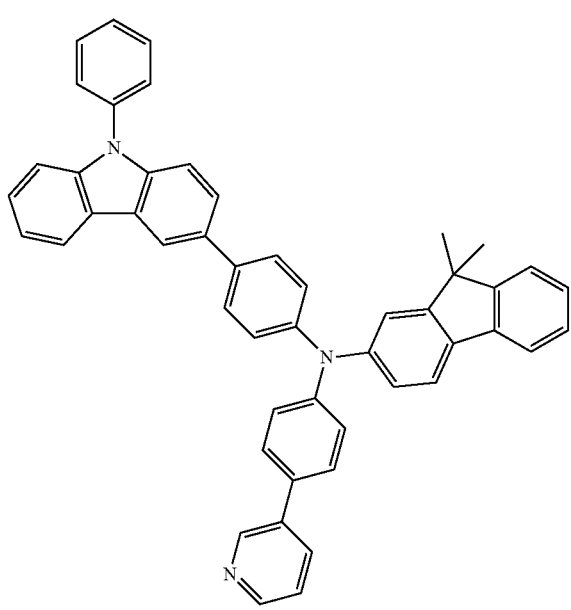
HT11
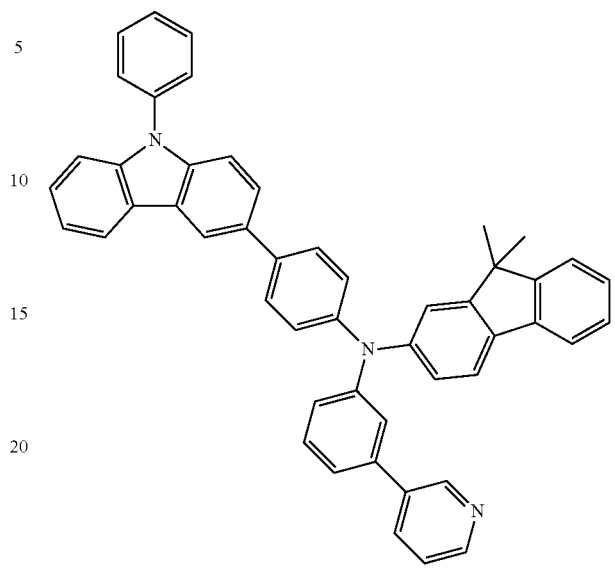
HT12
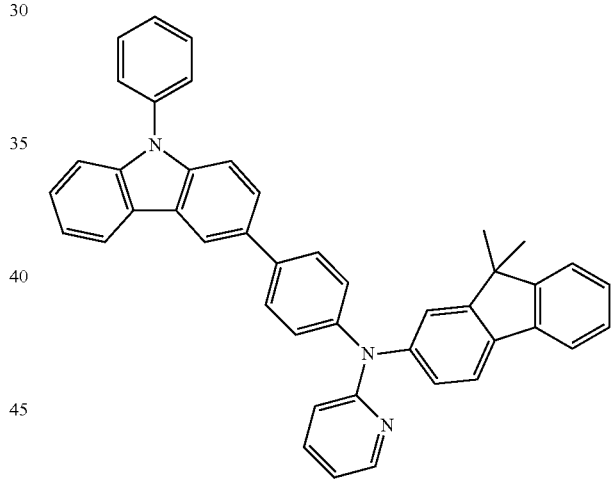
HT13
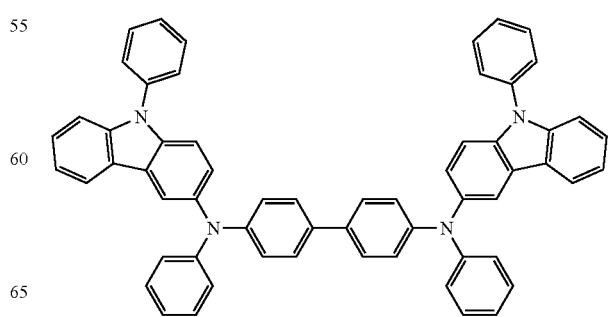

HT14
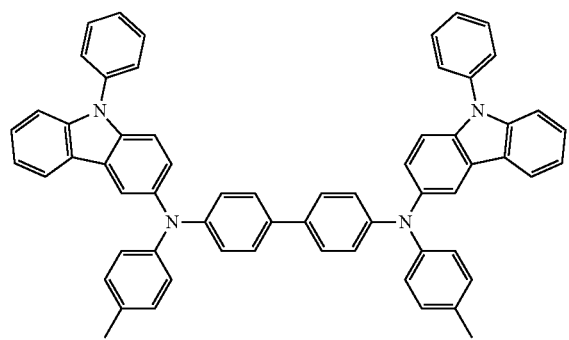

HT15
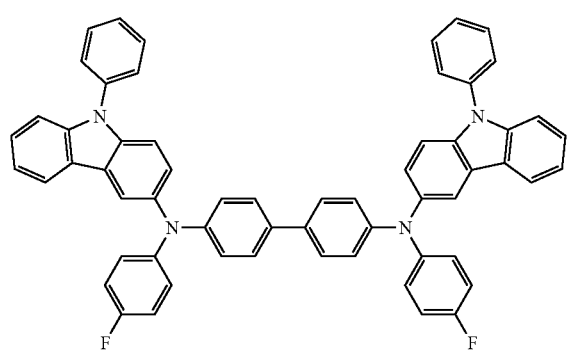

HT16
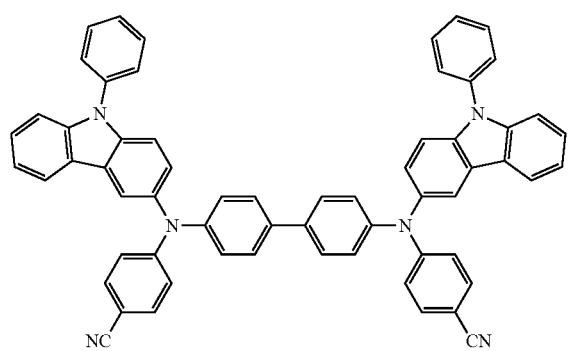

HT17
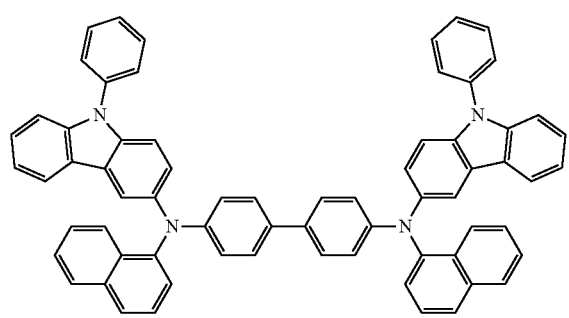

HT18
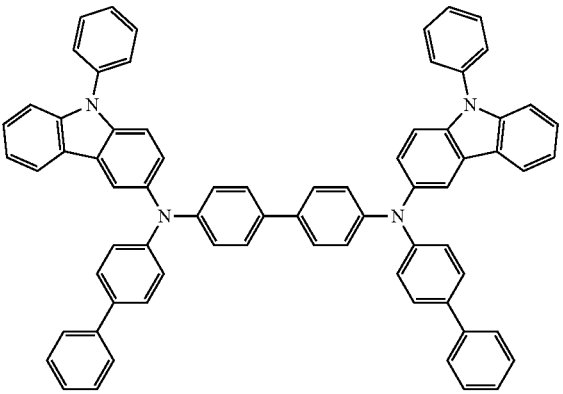

HT19
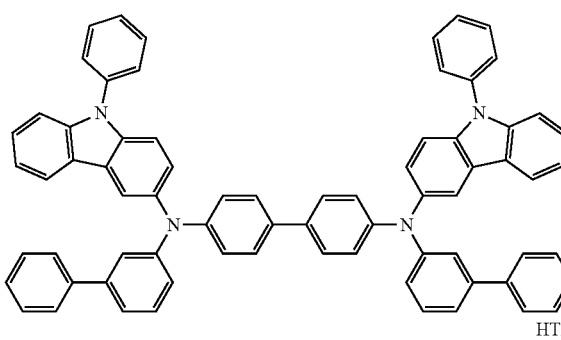

HT20
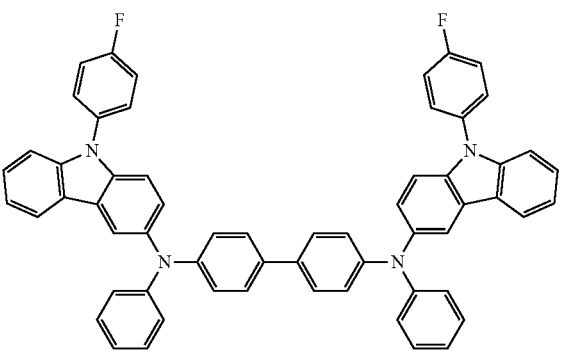

A thickness of the hole transport region may be in a range of about 100 Å to about 10,000 Å, for example, about 100 Å to about 1,000 Å. When the hole transport region includes a HIL and a HTL, a thickness of the HIL may be in a range of about 100 Å to about 10,000 Å, for example, about 100 Å to about 1,000 Å, and a thickness of the HTL may be in a range of about 50 Å to about 2,000 Å, for example, about 100 Å to about 1,500 Å. When the thicknesses of the hole transport region, the HIL, and the HTL are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound, but is not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 below, but are not limited thereto:

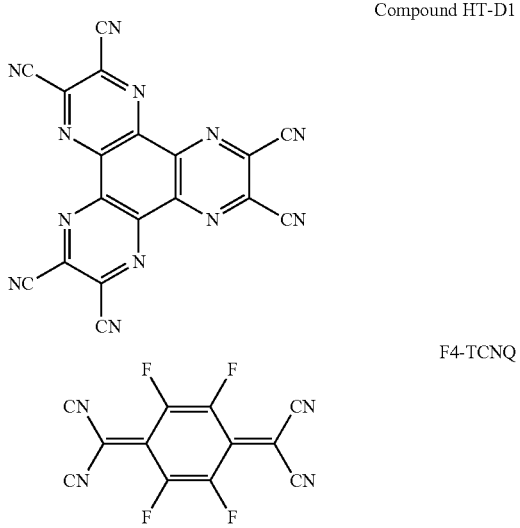

The hole transport region may further include a buffer layer.

The buffer layer compensates an optical resonance distance according to the wavelength of light emitted from an emission layer to increase efficiency.

Then, an emission layer (EML) may be formed on the hole transport region by vacuum deposition, spin coating, casting, LB deposition, or the like. When the EML is formed by vacuum deposition or spin coating, the deposition or coating conditions may be similar to those applied to form the hole injection layer although the deposition or coating conditions may vary according to the compound that is used to form the EML.

The EML may include a host and a dopant. The host may include at least one condensed cyclic compound represented by Formula 1.

For example, the host may include a compound represented by Formula 1 in which $R_3$ is a substituted or unsubstituted $C_1$-$C_{60}$ heteroaryl group or a substituted or unsubstituted monovalent non-aromatic condensed heteropolycyclic group, but the host is not limited thereto.

In an embodiment, the host may include a compound represented by Formula 1 in which $R_3$ is a group represented by one of Formulae 4-6 to 4-25, but the host is not limited thereto.

When the organic light-emitting device is a full color organic light-emitting device, the EML may be patterned into a red EML, a green EML, and a blue EML. In some embodiments, due to a stack structure including a red EML, a green EML, and/or a blue EML, the EML may emit white light. A host in the red EML, the green EML, and the blue EML may include at least one of the condensed cyclic compound represented by Formula 1. In an embodiment, the host in the green EML may include at least one of the condensed cyclic compounds represented by Formula 1.

According to an embodiment, the host in the emission layer may include a first host and a second host, the first host may include the at least one of the condensed cyclic compound represented by Formula 1, and the second host may include at least one of the first compound represented by Formula 41 and the second compound represented by Formula 61.

A dopant in the EML may be a fluorescent dopant that emits light according to a fluorescent emission mechanism or a phosphorescent dopant that emits light according to a phosphorescent emission mechanism.

In an embodiment, the EML may include a host including at least one condensed cyclic compounds represented by Formula 1 and a phosphorescent dopant.

The phosphorescent dopant may include an organic metal compound represented by Formula 81 below:

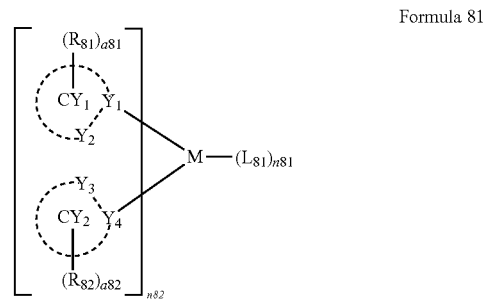

Formula 81

In Formula 81,

M may be selected from iridium (Ir), platinum (Pt), osmium (Os), titanium (Ti), zirconium (Zr), hafnium (Hf), europium (Eu), terbium (Tb), and thulium (Tm);

$Y_1$ to $Y_4$ may be each independently carbon (C) or nitrogen (N);

$Y_1$ and $Y_2$ are linked via a single bond or a double bond, and $Y_3$ and $Y_4$ are linked via a single bond or a double bond;

$CY_1$ and $CY_2$ are each independently selected from a benzene, a naphthalene, a fluorene, a spiro-fluorene, an indene, a pyrrole, a thiophene, a furan, an imidazole, a pyrazole, a thiazole, an isothiazole, an oxazole, an isooxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzooxazole, an isobenzooxazole, a triazole, a tetrazole, an oxadiazole, a triazine, a dibenzofuran, or a dibenzothiophene, and $CY_1$ and $CY_2$ are optionally linked to each other via a single bond or an organic linking group;

$R_{81}$ to $R_{82}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), or —B($Q_6$)($Q_7$);

a81 and a82 are each independently an integer selected from 1 to 5;

n81 is an integer selected from 0 to 4;

n82 is 1, 2, or 3; and $L_{81}$ is selected from a monovalent organic ligand, a divalent organic ligand, and a trivalent organic ligand.

The descriptions of $R_{81}$ and $R_{82}$ are the same as the description of $R_{11}$ in the present specification.

The phosphorescent dopant may include at least one of Compounds PD1 to PD74, but is not limited thereto (where, Compound PD1 is Ir(ppy)$_3$):

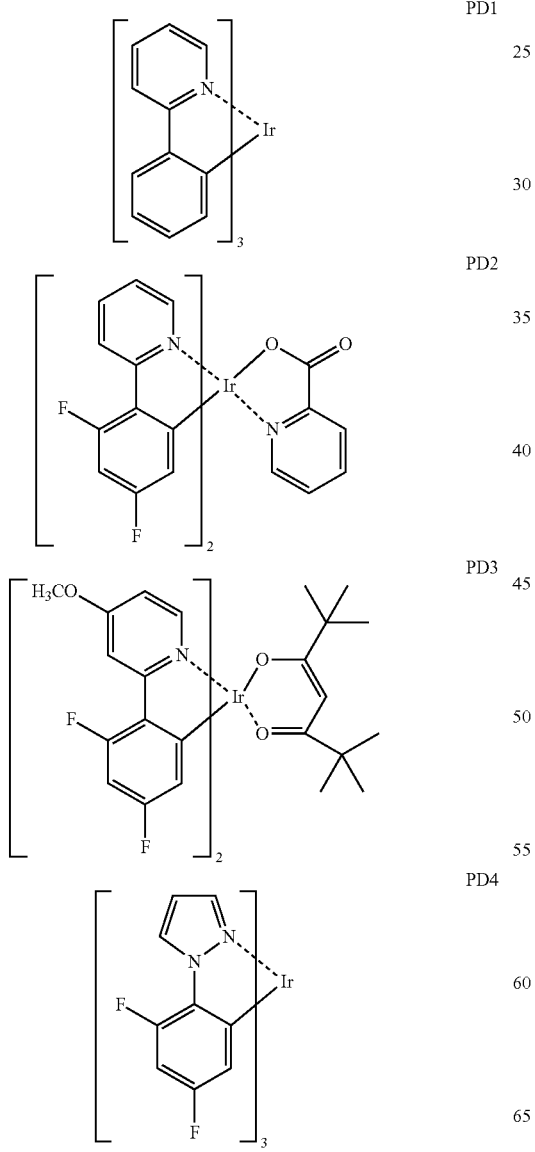

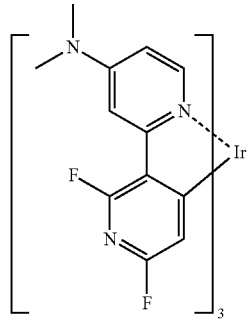

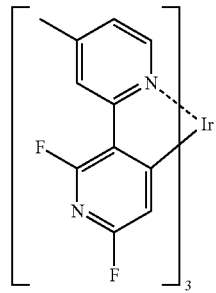

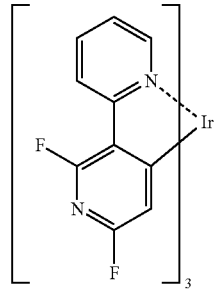

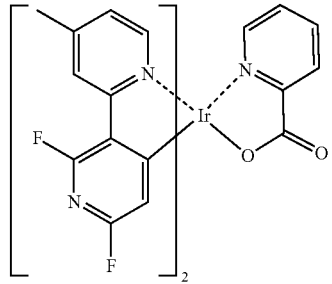

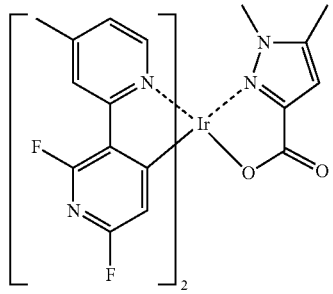

PD10 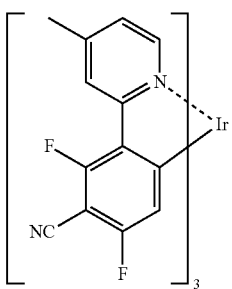
PD11 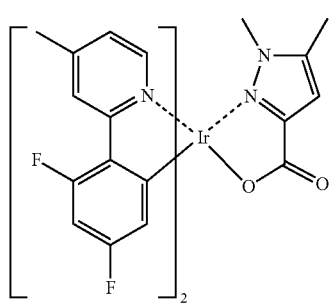
PD12 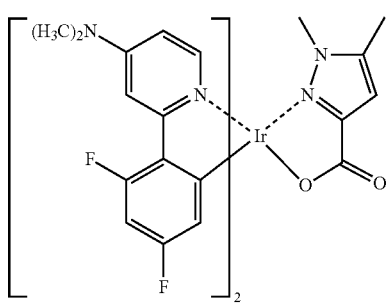
PD13 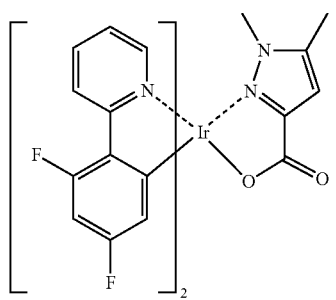
PD14 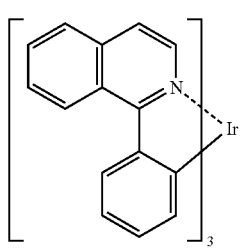
PD15 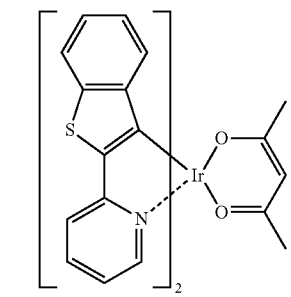
PD16 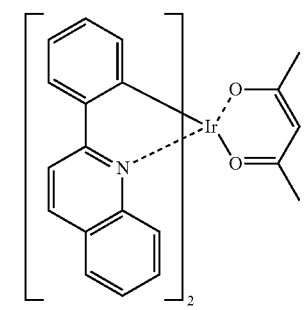
PD17 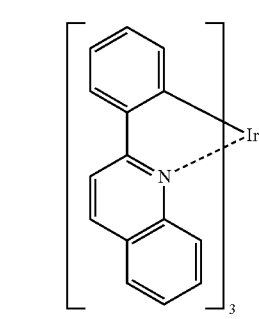
PD18 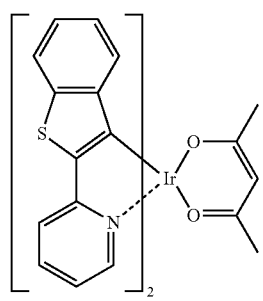
PD19

PD20 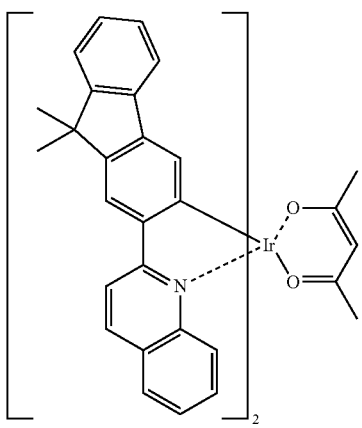
PD21 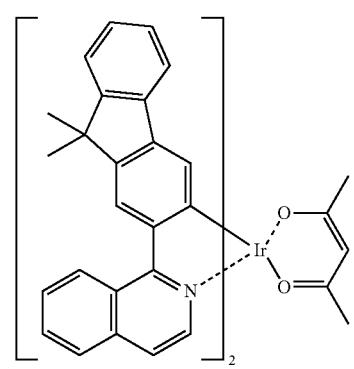
PD22 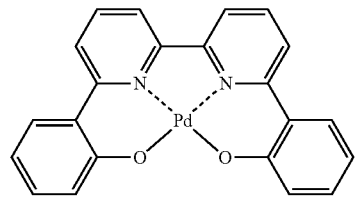
PD23 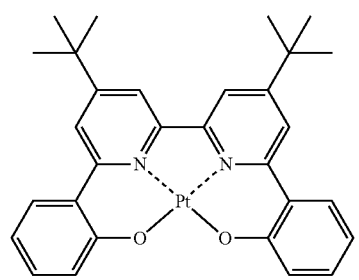
PD24 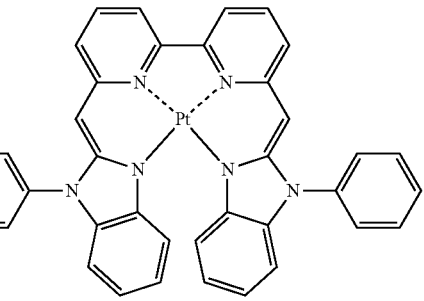
PD25 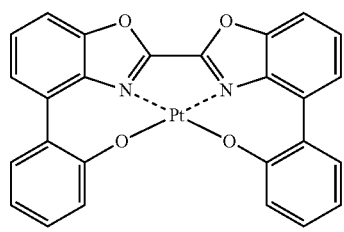
PD26 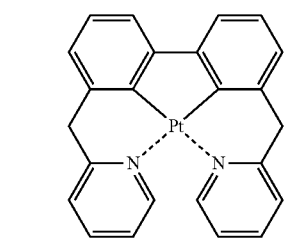
PD27 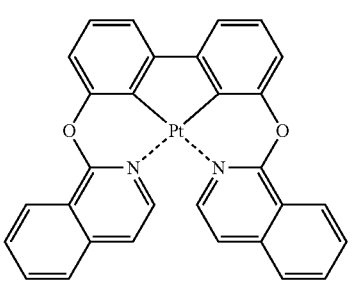
PD34 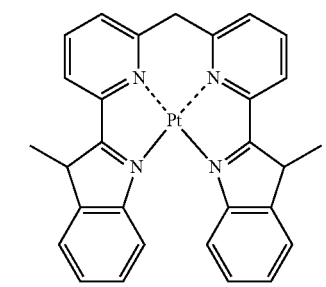
PD35 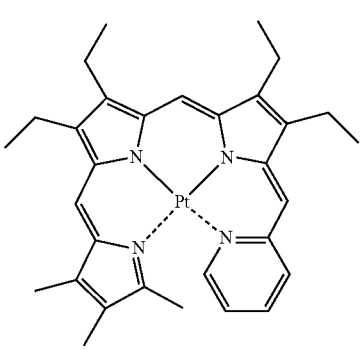
PD36 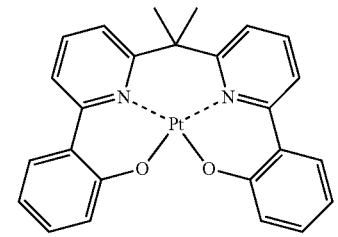

-continued
PD37
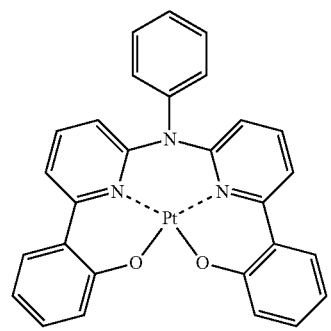
PD38
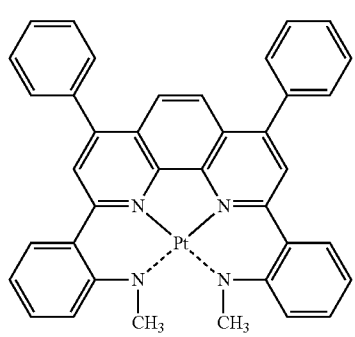
PD39
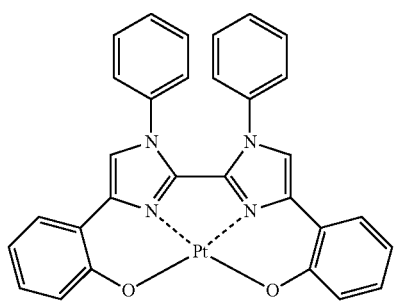
PD40
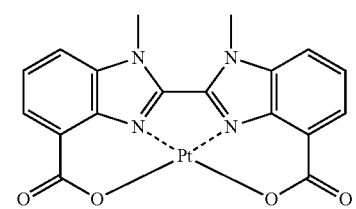
PD41
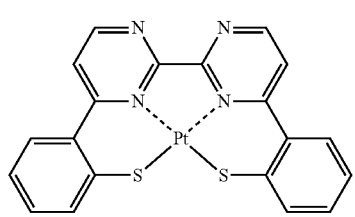
-continued
PD42
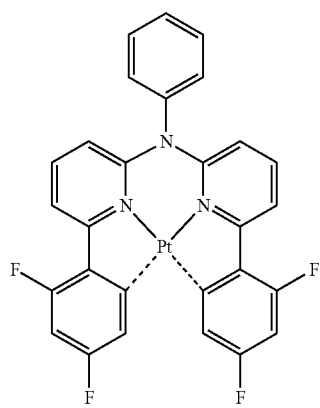
PD43
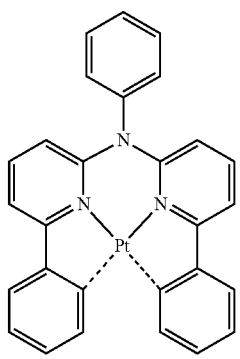
PD44
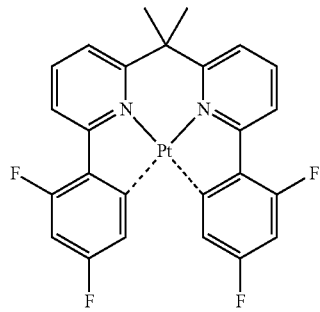
PD45
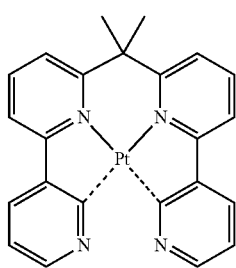
PD46
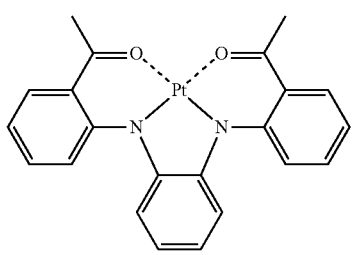

PD47
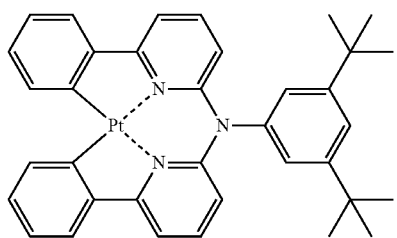
PD48
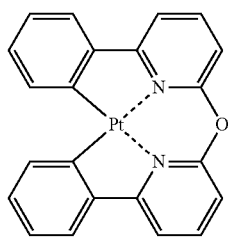
PD49
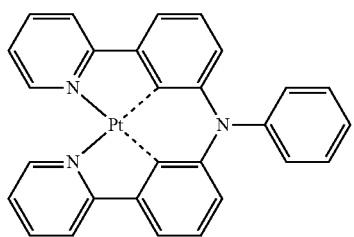
PD50
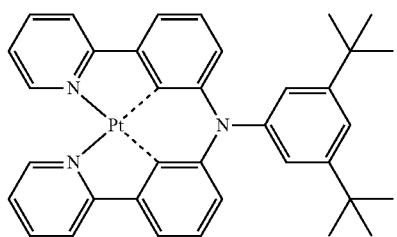
PD51
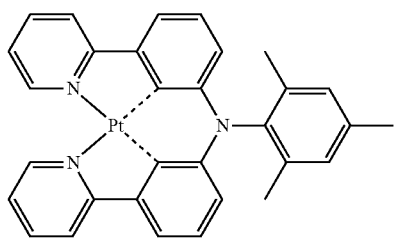
PD52
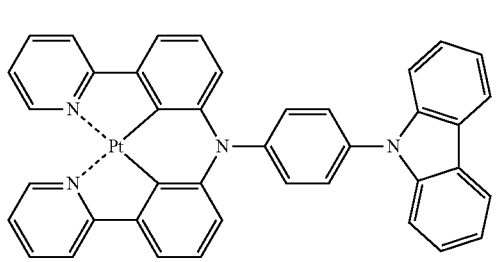
PD53
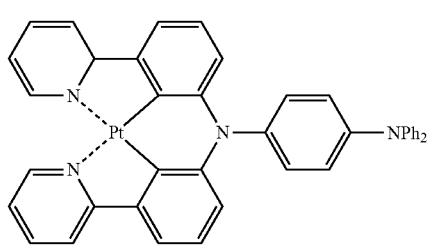
PD54
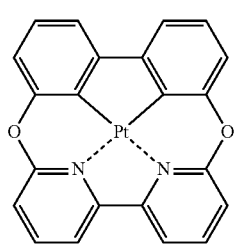
PD55
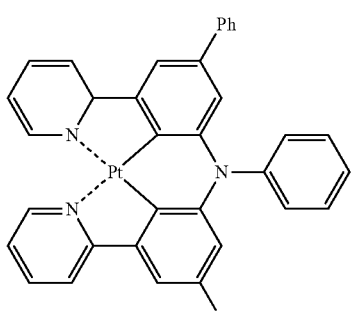
PD56
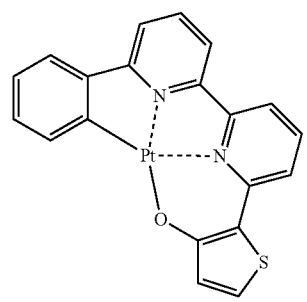
PD57
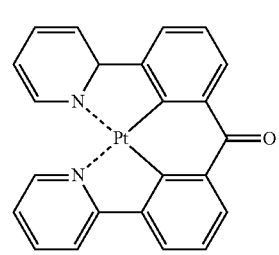

-continued
PD58
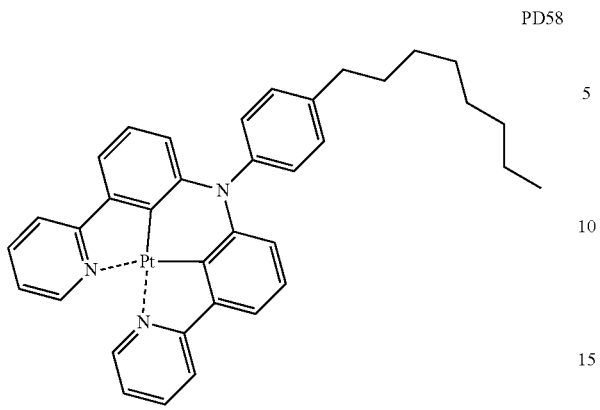
PD59
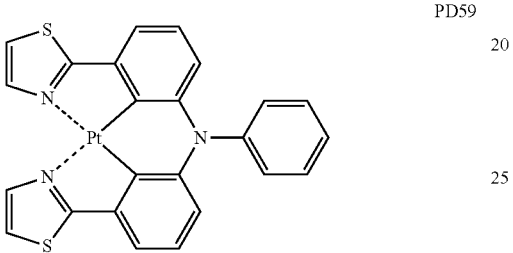
PD60
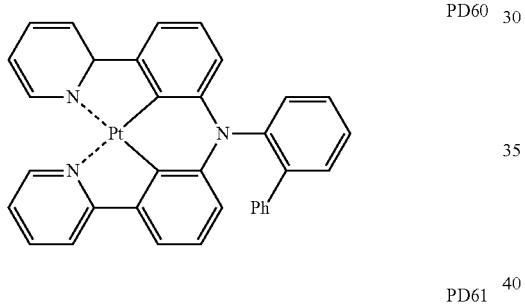
PD61
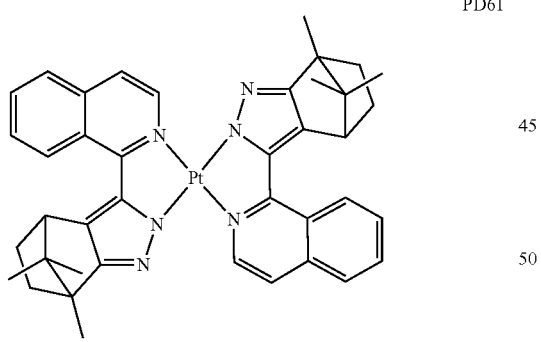
PD62
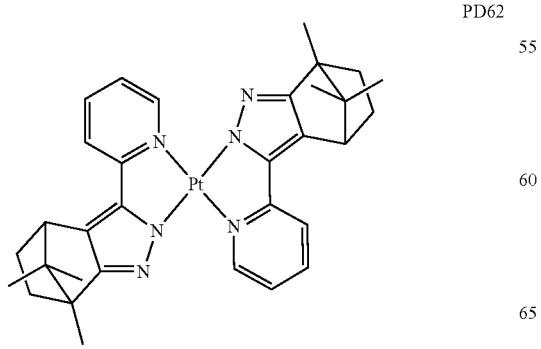
-continued
PD63
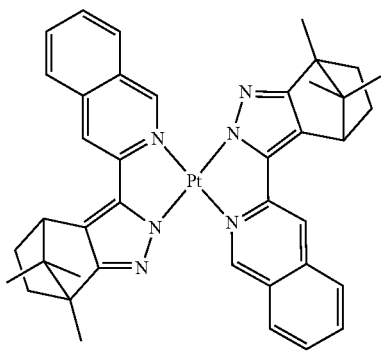
PD64
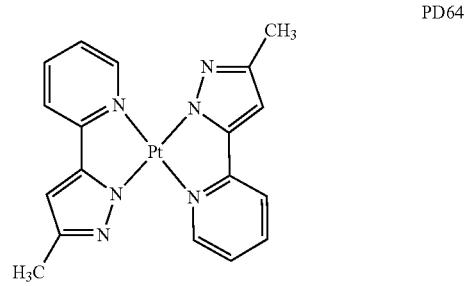
PD65
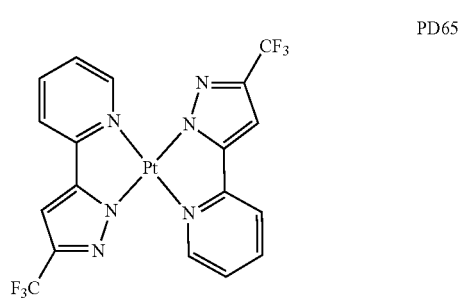
PD66
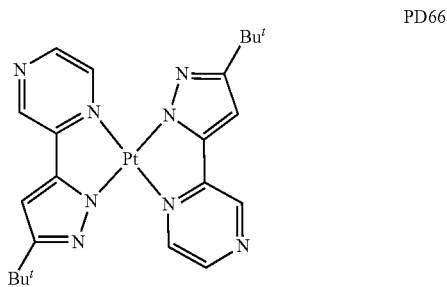
PD67
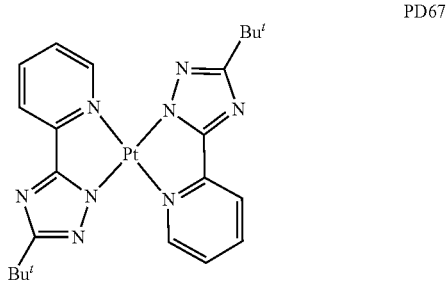

PD68
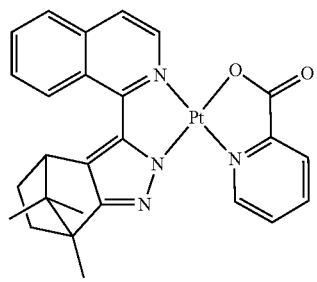
PD69
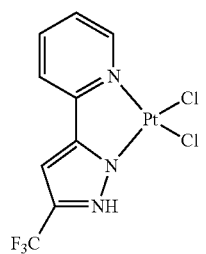
PD70
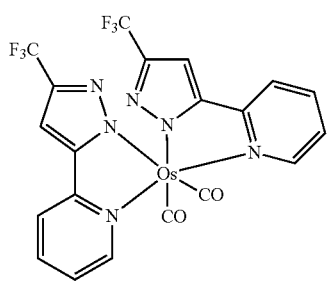
PD71
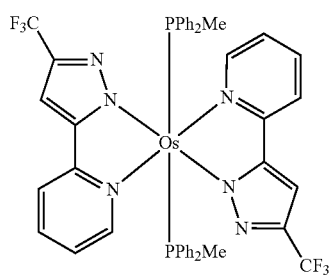
PD72
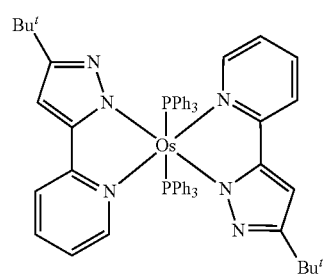
PD73
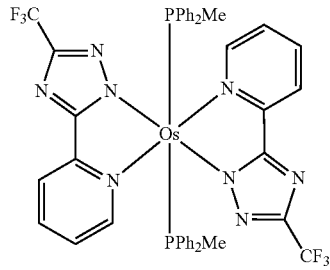
PD74
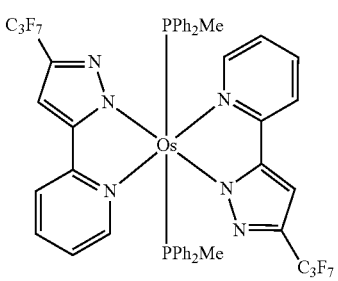
In some embodiments, the phosphorescent dopant may include PtOEP or Compound PhGD illustrated below:
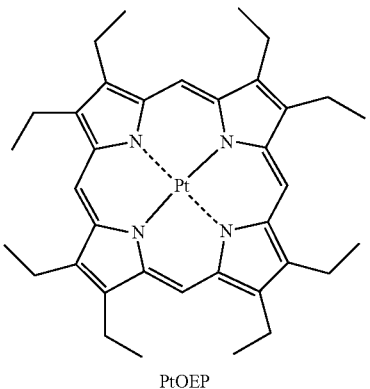
PtOEP
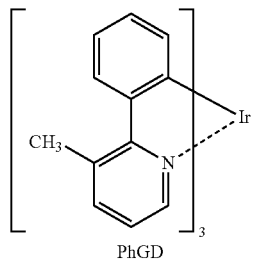
PhGD
The fluorescent dopant may include at least one selected from DPVBi, DPAVBi, TBPe, DCM, DCJTB, Coumarin 6, and C545T:

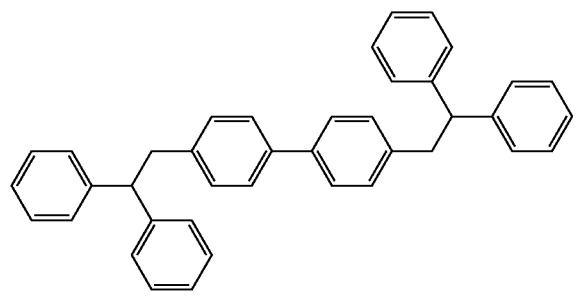
DPVBi
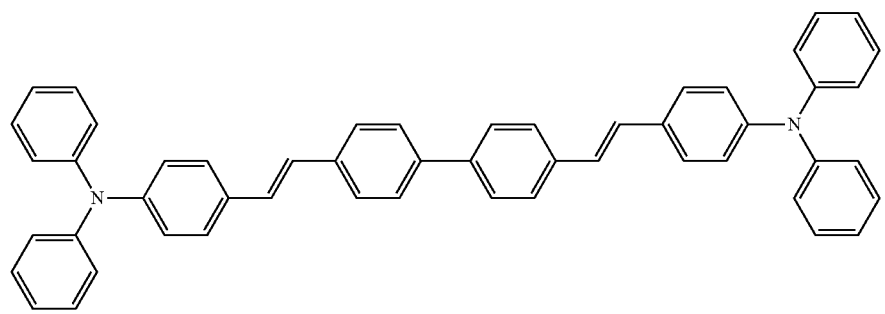
DPAVBi
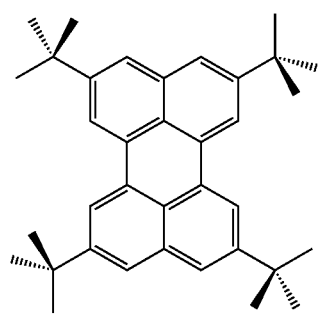
TBPe
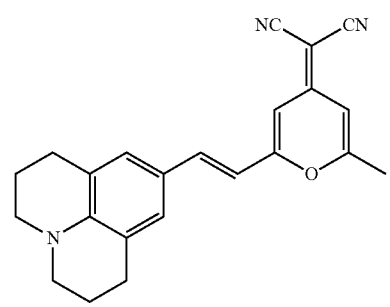
DCM
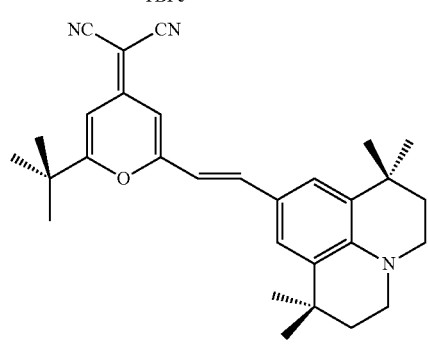
DCJTB
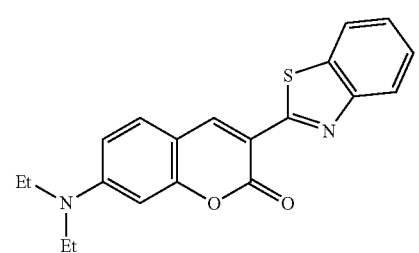
Coumarin 6
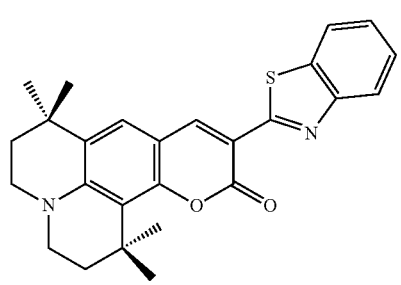
C545T When the EML includes a host and a dopant, an amount of the dopant may be in a range of about 0.01 part to about 20 parts by weight based on 100 parts by weight of the host, but is not limited thereto.

A thickness of the EML may be in a range of about 100 Å to about 1,000 Å, for example, about 200 Å to about 600 Å. When the thickness of the EML is within these ranges, excellent light-emission characteristics may be obtained without a substantial increase in driving voltage.

Then, an electron transport region may be disposed on the EML.

The electron transport region may include at least one of a hole blocking layer, an electron transport layer, and an electron injection layer.

For example, the electron transport region may have a structure of electron transport layer, hole blocking layer/electron transport layer/electron injection layer or electron transport layer/electron injection layer, but is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and Bphen, but is not limited thereto:

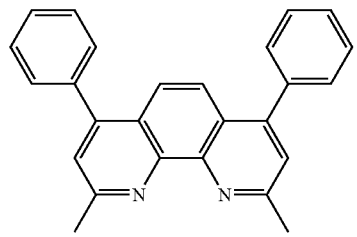

BCP

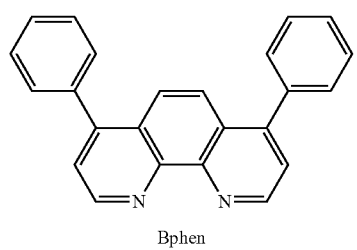

Bphen

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include, in addition to the condensed cyclic compound represented by Formula 1, at least one selected from BCP, Bphen, $Alq_3$, Balq, TAZ, and NTAZ:

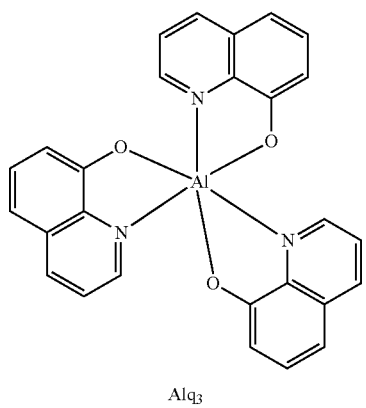

$Alq_3$

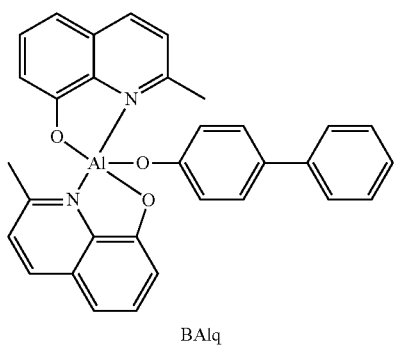

BAlq

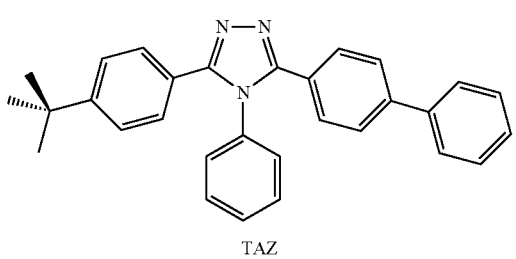

TAZ

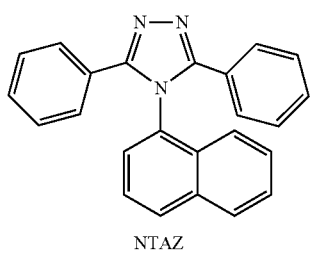

NTAZ

In some embodiments, the electron transport layer may include at least one of Compounds ET1 and ET2, but are not limited thereto:

ET1

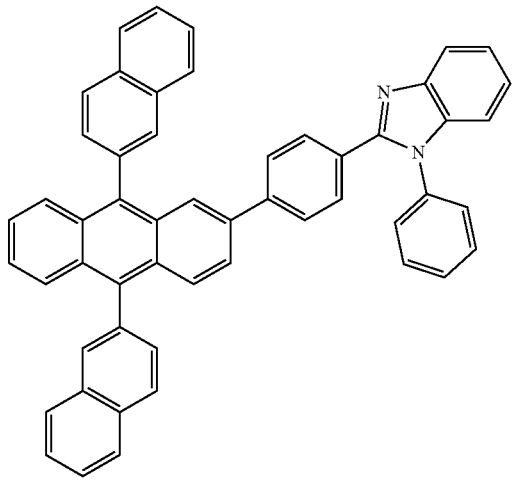

ET2

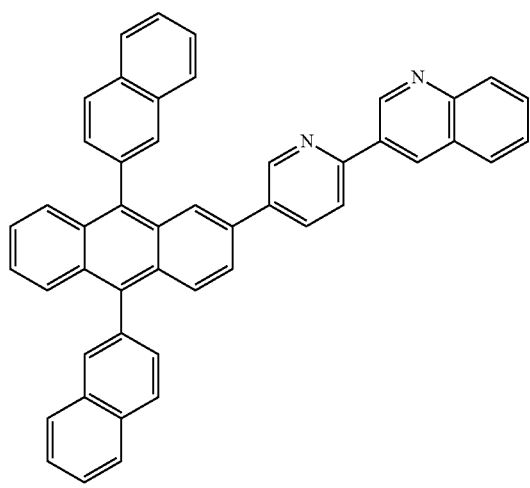

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

The electron transport layer may further include, in addition to the materials described above, a metal-containing material.

The metal-containing material may include a Li complex. The Li complex may include, for example, Compound ET-D1 (lithium quinolate, LiQ) or ET-D2:

ET-D1

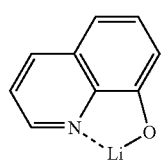

ET-D2

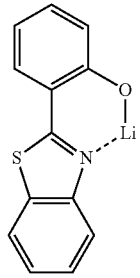

Also, the electron transport region may include an electron injection layer (EIL) that allows electrons to be easily provided from the second electrode 19.

The EIL may include at least one selected from, LiF, NaCl, CsF, $Li_2O$, and BaO.

A thickness of the EIL may be in a range of about 1 Å to about 100 Å, for example, about 3 Å to about 90 Å. When the thickness of the EIL is within the range described above, the EIL may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. In some embodiments, a transmissive electrode formed using ITO or IZO may be used as the second electrode 19 to manufacture a top emission type light-emitting device.

Hereinbefore, the organic light-emitting device 10 has been described with reference to FIG. 1, but is not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (where, $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a hydrocarbon group formed by substituting at least one carbon double bond in the middle or at the end of the $C_2$-$C_{60}$ alkyl group. Detailed examples thereof are an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by substituting at least one carbon triple bond in the middle or at the end of the $C_2$-$C_{60}$ alkyl group. Detailed examples thereof are an ethynyl group and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent monocyclic group having at least one hetero atom selected from N, O, P, and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof and is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one hetero atom selected from N, O, P, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system that has at least one hetero atom selected from N, O, P, and S as a ring-forming atom, and 1 to 60 carbon atoms. A $C_1$-$C_{60}$ heteroarylene group used herein refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —$OA_{102}$ (where, $A_{102}$ is the $C_6$-$C_{60}$ aryl group), a $C_6$-$C_{60}$ arylthio group indicates —$SA_{103}$ (where, $A_{103}$ is the $C_6$-$C_{60}$ aryl group), and a $C_7$-$C_{60}$ arylalkyl indicates -$A_{104}A_{105}$ (wherein $A_{104}$ is the $C_6$-$C_{60}$ aryl group and $A_{105}$ is the $C_1$-$C_{60}$ alkyl group).

A $C_1$-$C_{60}$ heteroaryloxy used herein indicates —$OA_{106}$ (wherein $A_{106}$ is the $C_1$-$C_{60}$ heteroaryl group), a $C_1$-$C_{60}$ heteroarylthio indicates —$SA_{107}$ (wherein $A_{107}$ is the $C_1$-$C_{60}$ heteroaryl group), and a $C_2$-$C_{60}$ heteroarylalkyl indicates -$A_{108}A_{109}$ (wherein $A_{108}$ is the $C_1$-$C_{60}$ heteroaryl group and $A_{109}$ is the $C_1$-$C_{60}$ alkyl group).

A monovalent non-aromatic condensed polycyclic group as used herein refers to a monovalent group that has two or more rings condensed to each other, only carbon atoms (for example, the number of carbon atoms may be in a range of 8 to 60) as a ring forming atom, wherein the entire molecular structure is non-aromatic. An example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group that has two or more rings condensed to each other, has a heteroatom selected from N, O, P, and S, other than carbon atoms (for example, the number of carbon atoms may be in a range of 1 to 60), as a ring forming atom, and is non-aromatic in the entire molecular structure. An example of the monovalent non-aromatic condensed heteropolycyclic group is a carbazolyl group. A divalent non-aromatic condensed heteropolycyclic group as used herein refers to a divalent group having the same structure as the monovalent non-aromatic condensed heteropolycyclic group.

At least one of substituents of the substituted $C_1$-$C_{60}$ alkylene group, substituted $C_2$-$C_{60}$ alkenylene group, substituted $C_2$-$C_{60}$ alkynylene group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_1$-$C_{60}$ heteroaryloxy group, substituted $C_1$-$C_{60}$ heteroarylthio group, substituted $C_2$-$C_{60}$ heteroarylalkyl group, substituted monovalent non-aromatic condensed polycyclic group, and substituted monovalent non-aromatic condensed heteropolycyclic group may be a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, or a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); or —N($Q_{31}$)($Q_{32}$), —Si($Q_{33}$)($Q_{34}$)($Q_{35}$), or —B($Q_{36}$)($Q_{37}$).

Also, $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one substituent of the substituted $C_1$-$C_{60}$ alkylene group, substituted $C_1$-$C_{60}$ alkenylene group, substituted $C_1$-$C_{60}$ alkynylene group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_1$-$C_{60}$ heteroaryloxy group, substituted $C_1$-$C_{60}$ heteroarylthio group, substituted $C_2$-$C_{60}$ heteroarylalkyl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_2$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isooxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isooxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$); and $Q_1$ to $Q_7$, $Q_{11}$ to $Q_{17}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

As used herein, the term "a biphenyl group" denotes "a phenyl group substituted with a phenyl group".

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that a molar equivalent of A was identical to a molar equivalent of B.

EXAMPLE

Synthesis Example 1

Synthesis of Compound 153

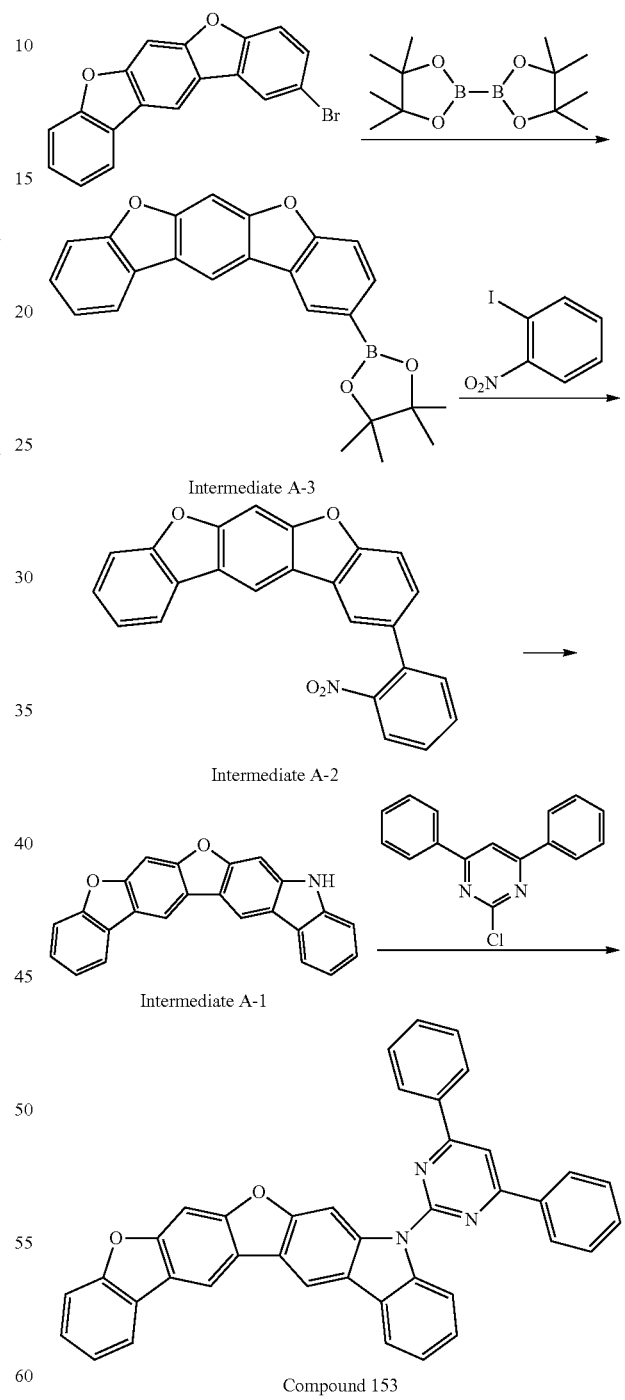

Synthesis of Intermediate A-3

114 g of 2-bromo-benzo[1,2-b:5,4-b]bisbenzofuran, 11.3 g of 4,4,4',4',5,5,5',5'-octamethyl-2,2'-bi(1,3,2-dioxaborolane), 0.5 g of PdCl$_2$(dppf), and 8.8 g of KOAc were added to a flask, a nitrogen atmosphere was formed after forming a vacuum condition, 150 mL of DMF was added thereto, and then heat-stirred at a temperature of 100° C. for 8 hours. The resultant obtained therefrom was crystallized by being poured into a 1000 ml of MeOH, stirred and filtered, and then the solid obtained therefrom was dissolved in 500 ml of toluene by heating the solution. The resultant obtained therefrom was filtered by using silica, the solvent was removed therefrom so that a volume of the remaining solution was 100 ml, crystallized by being poured into 1 L of MeOH and dried, and thus 79.4 g of Intermediate A-3 was obtained.

Synthesis of Intermediate A-2

1 g of Intermediate A-3, 0.8 g of 1-iodo-2-nitrobenzene, 0.3 g of Pd(PPh$_3$)$_4$, and 1 g of K$_2$CO$_3$ were added to 20 ml of THF/H$_2$O (at a volume ratio of 1:1) and heat-stirred at a temperature of 90° C. for 8 hours. The resultant obtained therefrom was extracted twice by using 20 ml of methylene chloride, the solvent in the obtained extract was removed by adding 2 g of MgSO$_4$ to the extract, and then the extract was purified by using a silica-gel column chromatography to obtain 0.85 g of Intermediate A-2.

Synthesis of Intermediate A-1

1 g of Intermediate A-2 and 2.1 g of PPh$_3$ were added to 15 ml of 1,2-dichlorobenzene, heat-stirred for 22 hours, and the residue obtained after removing the solvent by distillation in the solution was purified by using a silica-gel column chromatography to obtain 0.59 g of Intermediate A-1.

Synthesis of Compound 153

1 g of Intermediate A-1, 0.95 g of 2-chloro-4,6-diphenylpyrimidine, 0.1 g of Pd$_2$(dba)$_3$, 0.6 g of NaOtBu were added to a flask, a nitrogen atmosphere was formed after forming a vacuum condition, 0.1 g of tri(tert-butyl)phosphine and 15 mL of toluene were added thereto, and then heat-stirred at a temperature of 110° C. for 8 hours. The solvent in the resultant obtained therefrom was removed under vacuum and then purified by using a silica-gel column chromatography to obtain 1.41 g of Compound 153. The obtained compound was confirmed by LC-MS.

C$_{40}$H$_{23}$N$_3$O$_2$: M$^+$ 577.19

$^1$H NMR (500 MHz, CDCl$_3$): δ, ppm 8.59 (d, 1H), 8.25~8.22 (m, 2H), 8.17 (d, 1H), 8.04~8.02 (m, 4H), 7.74~7.73 (m, 2H), 7.53~7.50 (m, 1H), 7.45~7.35 (m, 9H), 7.32~7.28 (m, 1H), 7.16~7.13 (m, 1H), 7.00 (s, 1H)

Synthesis Example 2

Synthesis of Compound 154

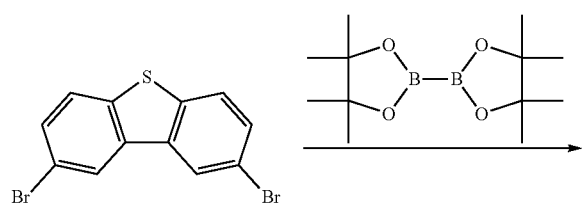

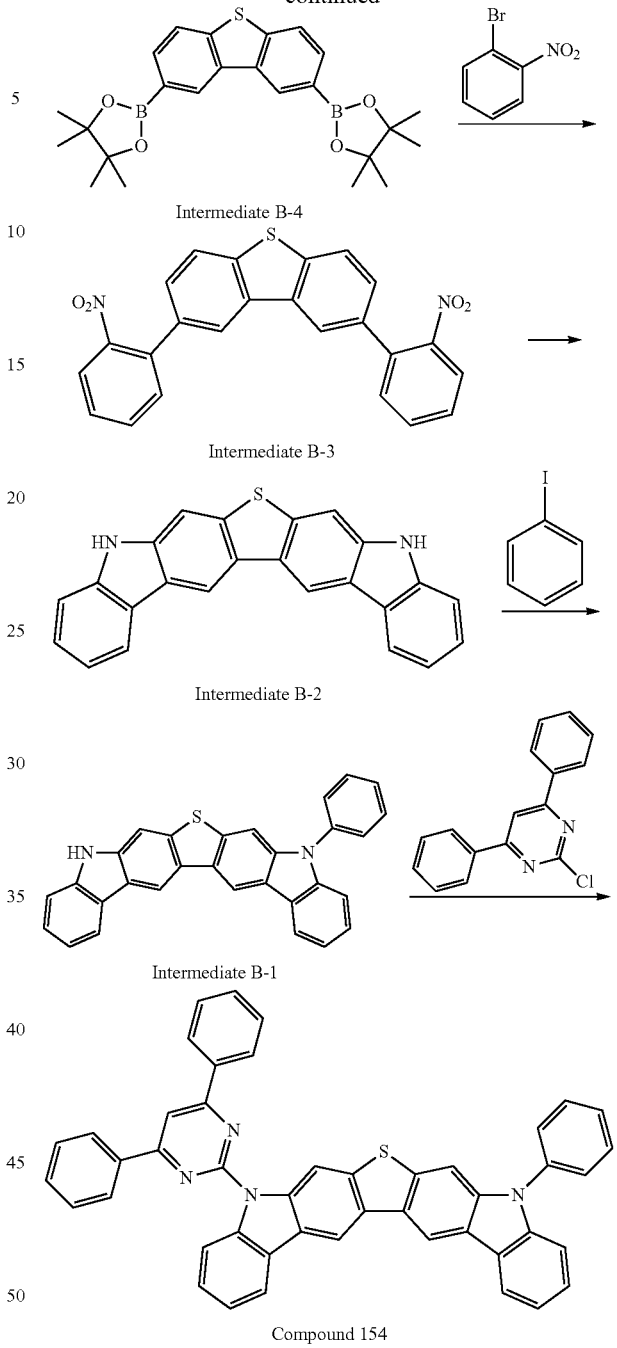

Synthesis of Intermediate B-4

1.0 g of 2,8-dibromodibenzo[b,d]thiophene, 2.2 g of 4,4',4',5,5,5',5'-octamethyl-2,2'-bi(1,3,2-dioxaborolane), 0.2 g of PdCl$_2$(dppf), and 1.7 g of KOAc were added to a flask, a nitrogen atmosphere was formed after forming a vacuum condition, 15.0 mL of DMF was added thereto, and then heat-stirred at a temperature of 80° C. for 18 hours. 10.0 mL of H$_2$O was then added to the obtained resultant, stirred and filtered, and the solid obtained therefrom was washed with 50 ml of MeOH. Then, the remaining solid was purified by using a silica-gel column chromatography to obtain 1.1 g of Intermediate B-4.

Synthesis of Intermediate B-3

1 g of Intermediate B-4, 1.2 g of 1-iodo-2-nitrobenzene, 0.3 g of Pd(PPh$_3$)$_4$, and 1.9 g of K$_2$CO$_3$ were added to 30 ml of THF and H$_2$O (at a volume ratio of 1:1) and then heat-stirred at a temperature of 80° C. for 10 hours. The resultant obtained therefrom was extracted by using methylene chloride and MgSO$_4$ is added to the extract to remove water to obtain a concentrate. The concentrate was purified by using a silica-gel column chromatography to obtain 0.81 g of Intermediate B-3.

Synthesis of Intermediate B-2

1 g of Intermediate B-3 and 3.1 g of PPh$_3$ were added to 12 ml of 1,2-dichlorobenzene and heat-stirred for 24 hours, the solvent therefrom was removed, and the residue obtained therefrom was purified by using a silica-gel column chromatography to obtain 0.31 g of Intermediate B-2.

Synthesis of Intermediate B-1

1 g of Intermediate B-2, 0.6 g of iodobenzene, 0.2 g of Pd$_2$(dba)$_3$, and 0.6 g of NaOtBu were added into a flask, and then a nitrogen atmosphere was formed after forming a vacuum condition in the flask. 0.1 g of tri(tert-butyl)phosphine and 15 ml of toluene were added thereto and heat-stirred at a temperature of 110° C. for 8 hours, and a solvent in the resultant was removed under vacuum condition. Then, the resultant was purified by using a silica-gel column chromatography to obtain 0.8 g of Intermediate B-1.

Synthesis of Compound 154

1 g of Intermediate B-1, 1.1 g of 2-chloro-4,6-diphenylpyrimidine, 0.2 g of Pd$_2$(dba)$_3$, and 0.5 g of NaOtBu were added into a flask, and then a nitrogen atmosphere was formed after forming a vacuum condition in the flask. 0.1 g of tri(tert-butyl)phosphine and 15 ml of toluene were added thereto and heat-stirred at a temperature of 110° C. for 8 hours, and a solvent in the resultant was removed under vacuum condition. Then, the resultant was purified by using a silica-gel column chromatography to obtain 0.95 g of Compound 154. The obtained compound was confirmed by LC-MS.

C$_{46}$H$_{28}$N$_4$S: M$^+$ 668.31

$^1$H NMR (300 MHz, CDCl$_3$): δ, ppm 8.90 (d, 1H), 8.04 (d, 1H), 7.93 (d, 1H), 7.85 (d, 1H), 7.74 (d, 1H), 7.60 (s, 2H), 7.47 (td, 2H), 7.35~7.11 (m, 15H), 7.06~7.00 (m, 1H), 6.80 (t, 2H), 6.58 (t, 1H).

Synthesis Example 3

Synthesis of Compound 155

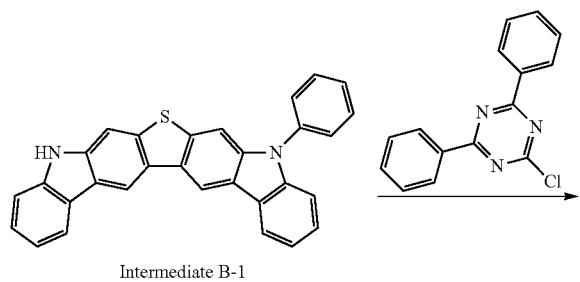

Intermediate B-1

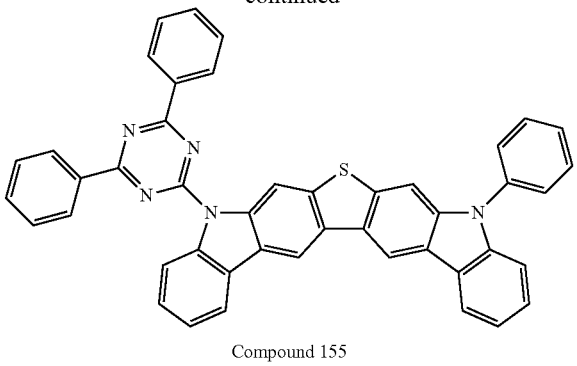

Compound 155

1 g of Intermediate B-1 was added to 11 ml of DMF, 0.2 g of NaH was added thereto and stirred at room temperature for 30 minutes, and 0.9 g of 2-chloro-4,6-diphenyl-1,3,5-triazine was added thereto and stirred at room temperature for 8 hours. Methylene chloride was added to the resultant to dissolve the solid therein, washed with H$_2$O, and then MgSO$_4$ was used to remove water and concentrate the resultant. The concentrate obtained therefrom was purified by using a silica-gel column chromatography to obtain 1.38 g of Compound 155. The compound was confirmed by LC-MS.

C$_{45}$H$_{27}$N$_5$S: M$^+$ 669.24

$^1$H NMR (300 MHz, CDCl$_3$): δ, ppm 8.93 (d, 1H), 8.03 (d, 1H), 7.92 (d, 2H), 7.69 (q, 4H), 7.51 (td, 2H), 7.40~7.08 (m, 13H), 7.06~7.00 (m, 1H), 6.83 (t, 2H), 6.58 (t, 1H).

Synthesis Example 4

Synthesis of Compound 156

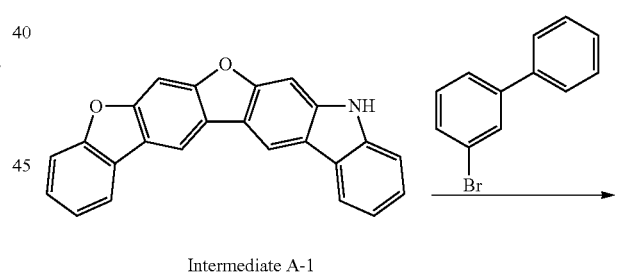

Intermediate A-1

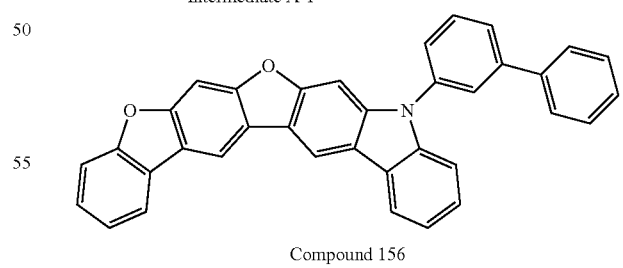

Compound 156

1 g Intermediate A-1, 0.81 g of 3-bromo-1,1'-biphenyl, 0.1 g of Pd$_2$(dba)$_3$, and 0.6 g of NaOtBu were added to a flask, and then a nitrogen atmosphere was formed after forming a vacuum condition in the flask. 0.1 g of tri(tert-butyl)phosphine and 15 ml of toluene were added thereto and heat-stirred at a temperature of 110° C. for 12 hours, and a solvent in the resultant was removed under vacuum condition. Then, the resultant was purified by using a silica-gel column chromatography to obtain 1.18 g of Compound 156. The obtained compound was confirmed by LC-MS.

$C_{36}H_{21}NO_2$: M+499.18

$^1$H NMR (500 MHz, DMSO): δ, ppm 9.33 (s, 1H), 8.30 (d, 1H), 8.23 (d, 1H) 8.17~8.15 (m, 2H) 7.78 (d, 1H), 7.72 (d, 1H), 7.64~7.36 (m, 13H), 7.29~7.26 (m, 1H)

Synthesis Example 5

Synthesis of Compound 157

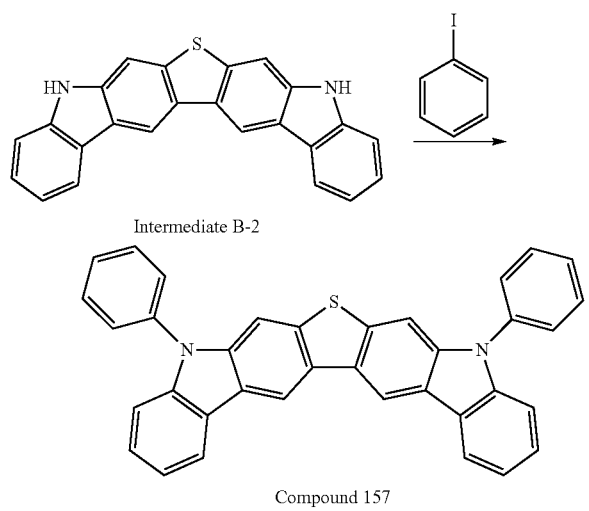

Intermediate B-2

Compound 157

1 g of Intermediate B-2, 1.6 g of iodobenzene, 0.2 g of Pd$_2$(dba)$_3$, and 1.01 g of NaOtBu were added to a flask, and then a nitrogen atmosphere was formed after forming a vacuum condition in the flask. 0.1 g of tri(tert-butyl)phosphine and 15 ml of toluene were added thereto and heat-stirred at a temperature of 110° C. for 8 hours, and a solvent in the resultant was removed under vacuum condition. Then, the resultant was purified by using a silica-gel column chromatography to obtain 0.4 g of Compound 157. The obtained compound was confirmed by LC-MS.

$C_{36}H_{22}N_2S$: M$^+$ 514.54

$^1$H NMR (300 MHz, CDCl$_3$): δ, ppm 8.20~8.15 (m, 2H), 8.01 (d, 1H), 7.96~7.92 (m, 2H), 7.87 (d, 1H), 7.63 (d, 1H), 7.51~7.28 (m, 10H), 7.20~7.14 (m, 2H), 7.10~7.04 (m, 2H), 6.82~6.76 (m, 1H)

Example 1

As an anode, a glass substrate having ITO/Ag/ITO deposited thereon at 70/1,000/70 Å was cut to a size of 50 mm×50 mm×0.5 mm and then, sonicated in isopropyl alcohol and pure water, each for 5 minutes, washed by exposure to UV ozone for 30 minutes, and then the anode was mounted in a vacuum depositor.

Then, 2-TNATA was vacuum deposited on the anode on the glass substrate to form a hole injection layer having a thickness of 600 Å, and then 4,4'-bis[N-(1-naphthyl)-N-phenylamino]biphenyl (NPB) was vacuum deposited on the hole injection layer to form a hole transport layer at a thickness of 1,000 Å.

Compound 153 (a host) and Ir(ppy)$_3$ (a dopant) were co-deposited on the hole transport layer at a weight ratio of 90:10 to form an emission layer at a thickness of 250 Å.

BCP was vacuum deposited on the emission layer to form a hole blocking layer at a thickness of 50 Å, Alq$_3$ was deposited on the hole blocking layer to form an electron transport layer having a thickness of 350 Å, LiF was deposited on the electron transport layer to form an electron injection layer having a thickness of 10 Å, and then, Mg and Ag were vacuum deposited on the electron injection layer at a weight ratio of 90:10 to form a cathode having a thickness of 120 Å, thereby completing manufacturing of an organic light-emitting device.

Examples 2 and 3 and Comparative Example 1

An organic light-emitting device was manufactured in the same manner as in Example 1, except that compounds described in Table 3 were used instead of Compound 153 as a host in forming the emission layer.

Evaluation Example 1

Driving voltages, current densities, efficiencies, and luminances of the organic light-emitting devices prepared in Examples 1 to 3 and Comparative Example 1 were evaluated by using a luminance meter PR650 Spectoscan Source Measurement Unit (PhotoResearch) by applying power from a current-voltmeter (Keithley SMU 236), and the results are shown in Table 3.

TABLE 3

| | Host | Driving voltage (V) | Current density (mA/cm$^2$) | Luminance (cd/m$^2$) | Efficiency (cd/A) |
|---|---|---|---|---|---|
| Example 1 | Compound 153 | 4.1 | 10 | 5,332 | 54.3 |
| Example 2 | Compound 154 | 3.7 | 10 | 4,960 | 43.1 |
| Example 3 | Compound 155 | 3.5 | 10 | 4813 | 48.3 |
| Comparative Example 1 | CBP | 6.8 | 10 | 4,766 | 47.7 |

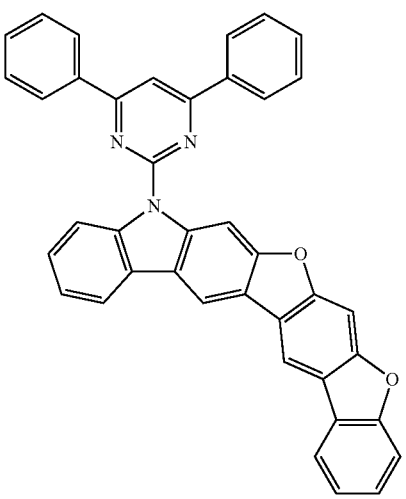

153

-continued

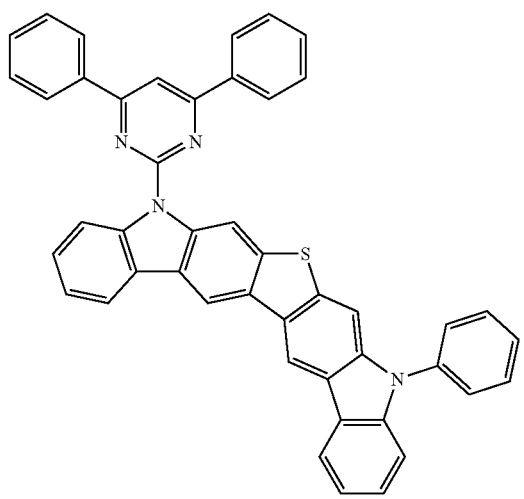
154

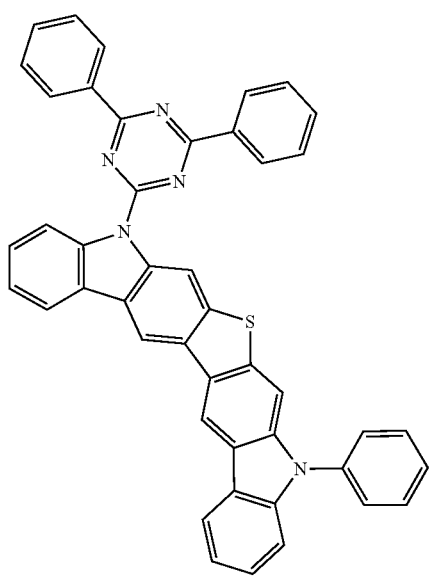
155

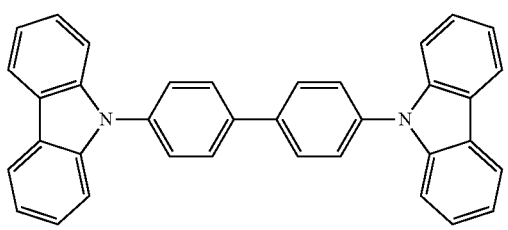
CBP

Referring to Table 3, it is confirmed that the organic light-emitting devices prepared in Examples 1 to 3 have lower driving voltages, higher efficiency, and higher luminances than those of the organic light-emitting device prepared in Comparative Example 1.

Example 4

An organic light-emitting device was manufactured in the same manner as in Example 1, except that Compound 156 was used instead of NPB in forming the hole transport layer, and CBP was used instead of Compound 153 as a host in forming the emission layer.

Example 5

An organic light-emitting device was manufactured in the same manner as in Example 4, except that Compound 157 was used instead of Compound 156 in forming the hole transport layer.

Evaluation Example 2

Driving voltages of the organic light-emitting devices prepared in Examples 4 and 5 and Comparative Example 1 were evaluated by applying power from a current voltmeter (Keithley SMU 236), and the results are shown in Table 4.

TABLE 4

|  | Hole transparent layer | Driving voltage (V) | Current density (mA/cm$^2$) |
| --- | --- | --- | --- |
| Example 4 | Compound 156 | 6.1 | 10 |
| Example 5 | Compound 157 | 6.6 | 10 |
| Comparative Example 1 | NPB | 6.8 | 10 |

Referring to Table 4, it was confirmed that the organic light-emitting devices prepared in Examples 4 and 5 have lower driving voltages compared to that of the organic light-emitting device prepared in Comparative Example 1.

Example 6

An organic light-emitting device was manufactured in the same manner as in Example 1, except that Compound 155 (a host) and Ir(ppy)$_3$ (a dopant) were co-deposited on the hole transport layer at a weight ratio of 85:15 to form an emission layer.

Example 7

An organic light-emitting device was manufactured in the same manner as in Example 1, except that Compound 155 (a first host), Compound A2 (a second host) and Ir(ppy)$_3$ (a dopant) were co-deposited on the hole transport layer at a weight ratio of 45:45:10 to form an emission layer.

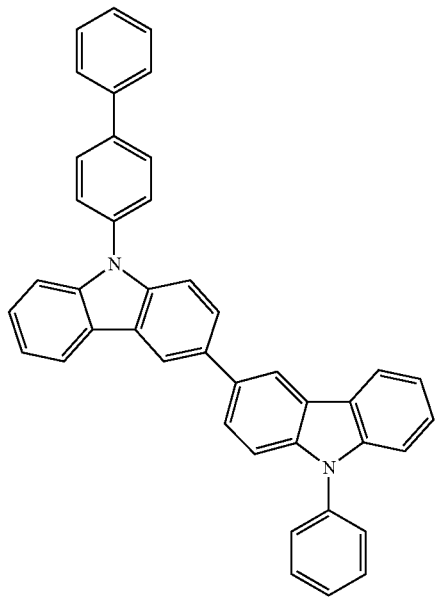

A2

Evaluation Example 3

Driving voltages, current densities, efficiencies, and luminances of the organic light-emitting devices prepared in Examples 6 and 7 were evaluated by using a luminance meter PR650 Spectoscan Source Measurement Unit (PhotoResearch) by applying power from a current-voltmeter (Keithley SMU 236), and the results are shown in Table 5. For comparison, data for Comparative Example 1 were shown in Table 5.

TABLE 5

| | Host | Driving voltage (V) | Current density (mA/cm$^2$) | Luminance (cd/m$^2$) | Efficiency (cd/A) |
|---|---|---|---|---|---|
| Example 1 | Compound 155 (host:dopant = 85:15) | 3.9 | 10 | 6,884 | 50.9 |
| Example 2 | Compound 155 and Compound A2 (weight ratio of 1:1) | 3.8 | 10 | 5,662 | 56.7 |
| Comparative Example 1 | CBP | 6.8 | 10 | 4,766 | 47.7 |

Referring to Table 5, it is confirmed that the organic light-emitting devices prepared in Examples 6 to 7 have lower driving voltages, higher efficiency, and higher luminances than those of the organic light-emitting device prepared in Comparative Example 1.

As described above, according to the one or more of the above embodiments, a condensed cyclic compound has excellent electrical characteristics and thermal stability, and thus an organic light-emitting device including the condensed cyclic compound may have a low driving voltage, a high efficiency and a high luminance characteristics.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A condensed cyclic compound represented by one of Formulae 1-1 to 1-12:

Formula 1-1

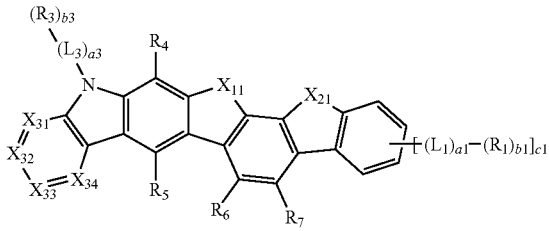

Formula 1-2

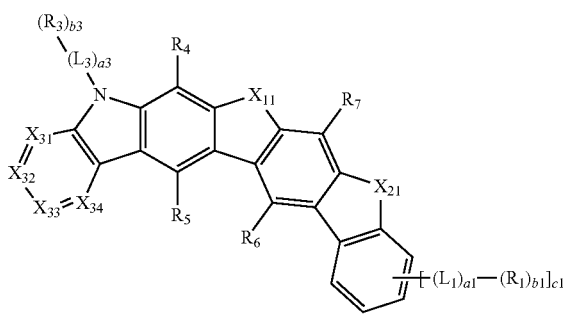

Formula 1-3

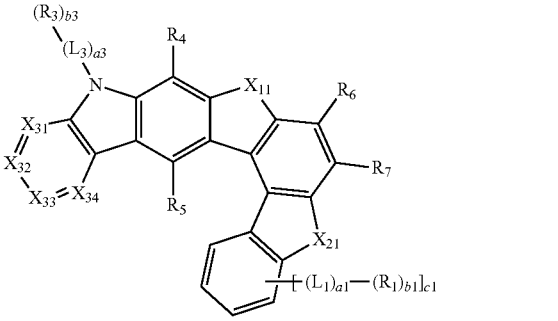

Formula 1-4

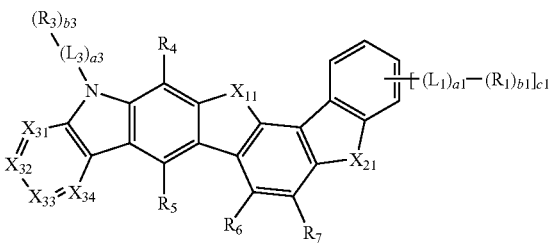

Formula 1-5

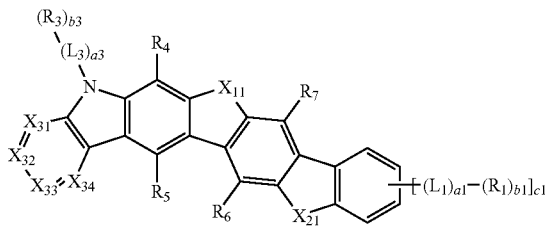

Formula 1-6

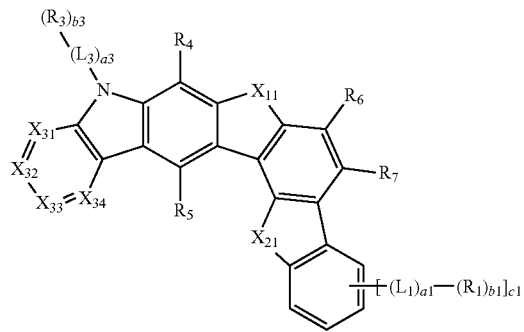

Formula 1-7

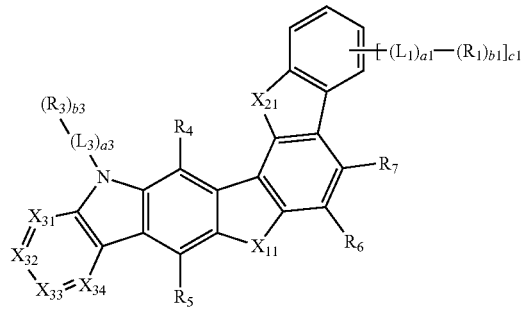

Formula 1-8

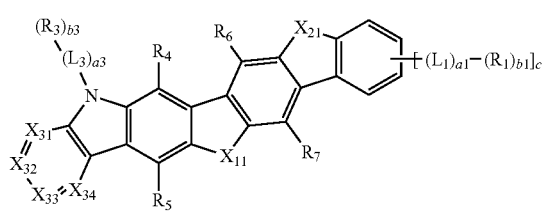

Formula 1-9

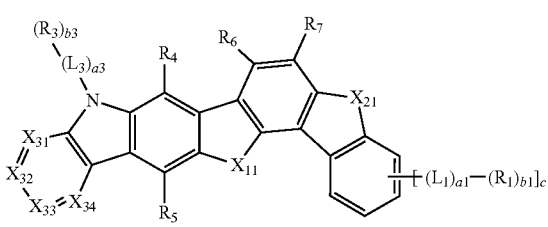

Formula 1-10

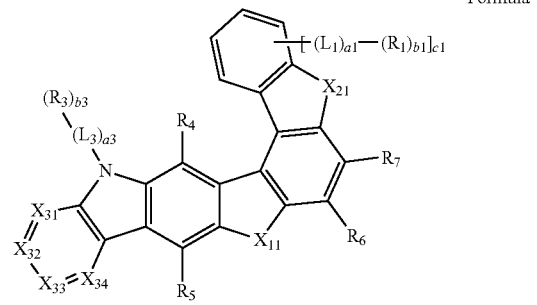

Formula 1-11

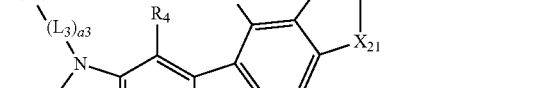

Formula 1-12

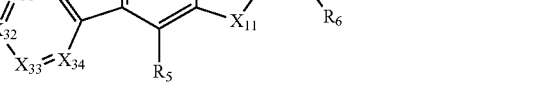

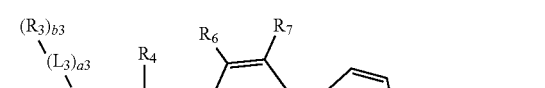

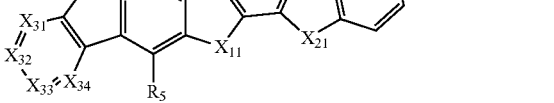

wherein, in Formulae 1-1 to 1-12, $X_{11}$ is N-[$(L_{11})_{a11}$-$(R_{11})_{b11}$], S, O, C(=O), C($R_{12}$)($R_{13}$), Si($R_{12}$)($R_{13}$), P($R_{12}$), or P(=O)($R_{12}$);

$X_{21}$ is N-[$(L_{21})_{a21}$-$(R_{21})_{b21}$], S, O, S(=O), S(=O)$_2$, C(=O), Si($R_{22}$)($R_{23}$), P($R_{22}$), or P(=O)($R_{22}$);

provided that when $X_{11}$ is C($R_{12}$)($R_{13}$), then $X_{21}$ is S, O, S(=O), S(=O)$_2$, C(=O), Si($R_{22}$)($R_{23}$), P($R_{22}$), or P(=O)($R_{22}$);

provided that when $X_{21}$ is N-[$(L_{21})_{a21}$-$(R_{21})_{b21}$], then $X_{11}$ is N-[$(L_{11})_{a11}$-$(R_{11})_{b11}$], S, O, C(=O), Si($R_{12}$)($R_{13}$), P($R_{12}$), or P(=O)($R_{12}$); $X_{31}$ to $X_{34}$ are each independently N or C-[$(L_2)_{a2}$-$(R_2)_{b2}$];

provided that conditions i) to iv) are met:

i) in Formulae 1-1 to 1-12, when $X_{11}$ is N-[$(L_{11})_{a11}$-$(R_{11})_{b11}$], $X_{21}$ is not N-[$(L_{21})_{a21}$-$(R_{21})_{b21}$], ii) in Formula 1-8, when $X_{11}$ is S, $X_{21}$ is not N-[$(L_{21})_{a21}$-$(R_{21})_{b21}$], iii) in Formula 1-8, when $X_{11}$ is Si($R_{12}$)($R_{13}$), $X_{21}$ is not N-[$(L_{21})_{a21}$-$(R_{21})_{b21}$], iv) in Formulae 1-1 to 1-12, when $X_{21}$ is N-[$(L_{21})_{a21}$-$(R_{21})_{b21}$], $X_{11}$ is not N-[$(L_{11})_{a11}$-$(R_{11})_{b11}$];

$L_1$ to $L_3$, $L_{11}$, and $L_{21}$ are each independently selected from the group consisting of a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a3, a11, and a21 are each independently an integer selected from 0 to 5;

$R_1$ to $R_7$, $R_{11}$ to $R_{13}$, and $R_{21}$ to $R_{23}$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

b1 to b3, b11, and b21 are each independently an integer selected from 1 to 5;

c1 is an integer selected from 1 to 4;

provided that:

i) in Formulae 1-1 and 1-3 to 1-12, when $X_{11}$ is not N-[($L_{11}$)$_{a11}$-($R_{11}$)$_{b11}$], a3 is an integer selected from 1 to 5 and $L_3$ is a substituted or unsubstituted $C_1$-$C_{10}$ heterocycloalkylene group, a substituted or unsubstituted $C_1$-$C_{10}$ heterocycloalkenylene group, a substituted or unsubstituted $C_1$-$C_{60}$ heteroarylene group, or a substituted or unsubstituted divalent non-aromatic condensed heteropolycyclic group;

ii) in Formula 1-2, when $X_{11}$ is not N-[($L_{11}$)$_{a11}$-($R_{11}$)$_{b11}$], a3 is an integer selected from 1 to 5 and $L_3$ is selected from Formulae 2-9 to 2-23:

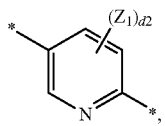
Formula 2-9

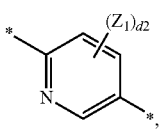
Formula 2-10

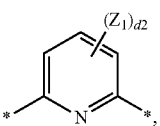
Formula 2-11

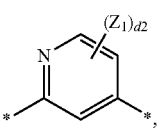
Formula 2-12

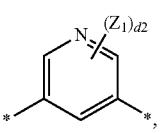
Formula 2-13

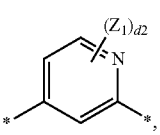
Formula 2-14

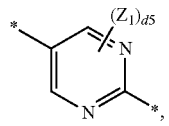
Formula 2-15

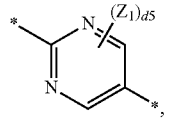
Formula 2-16

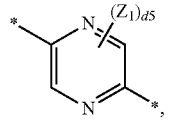
Formual 2-17

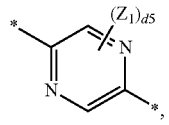
Formula 2-18

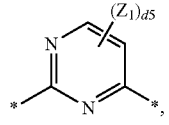
Formula 2-19

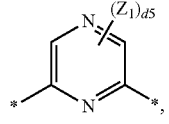
Formula 2-20

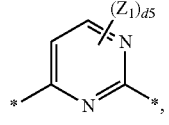
Formula 2-21

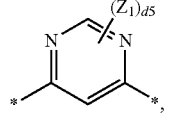
Formula 2-22

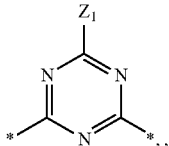
Formula 2-23 wherein, in Formulae 2-9 to 2-23

$Z_1$ is selected from the group consisting of a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and a biphenyl group, d2 is an integer selected from 1 to 3, and d5 is an integer of 1 or 2; and iii) in Formulae 1-1 to 1-12, when $X_{11}$ is N-[($L_{11}$)$_{a11}$-($R_{11}$)$_{b11}$], a11 is an integer selected from 1 to 5 and $L_{11}$ is a substituted or unsubstituted $C_1$-$C_{10}$ heterocycloalkylene group, a substituted or unsubstituted $C_1$-$C_{10}$ heterocycloalkenylene group, a substituted or unsubstituted $C_1$-$C_{60}$ heteroarylene group, or a substituted or unsubstituted divalent non-aromatic condensed heteropolycyclic group;

at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, or the substituted monovalent non-aromatic condensed heteropolycyclic group is selected from the group consisting of:

a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group.

2. The condensed cyclic compound of claim 1, wherein the compound is represented by one of Formulae 1A-1 to 1A-12:

Formula 1A-1

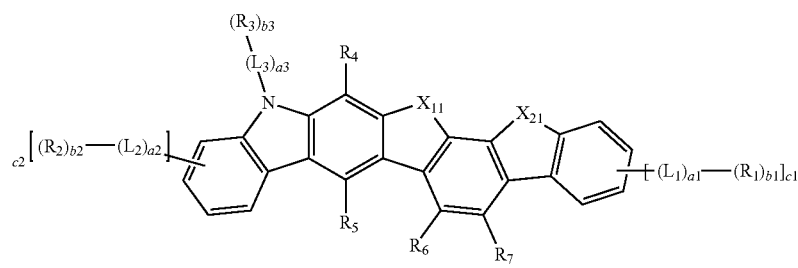

-continued
Formula 1A-2
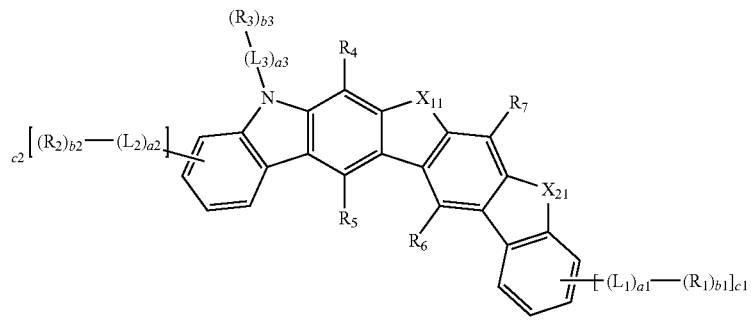
Formula 1A-3
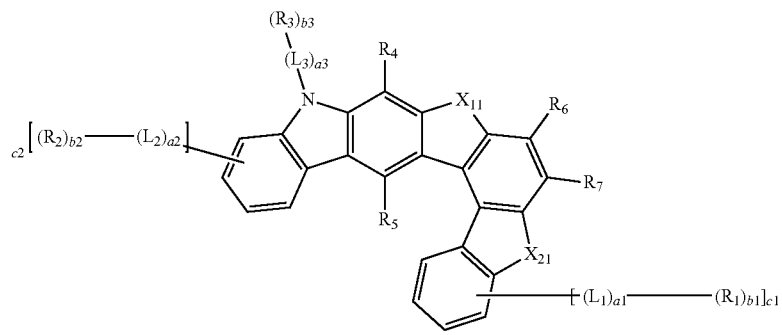
Formula 1A-4
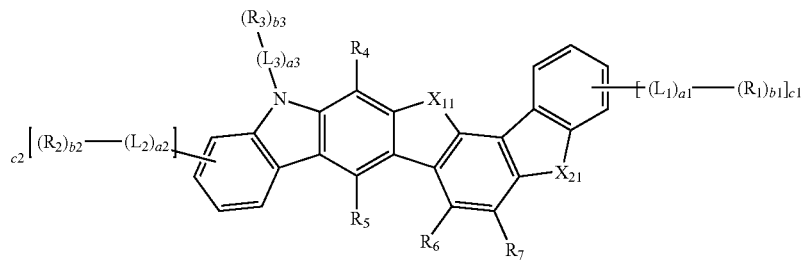
Formula 1A-5
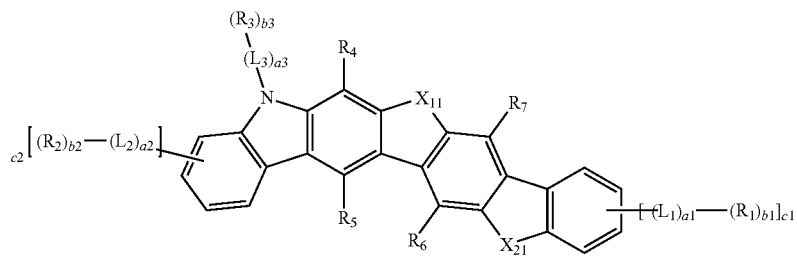
Formula 1A-6
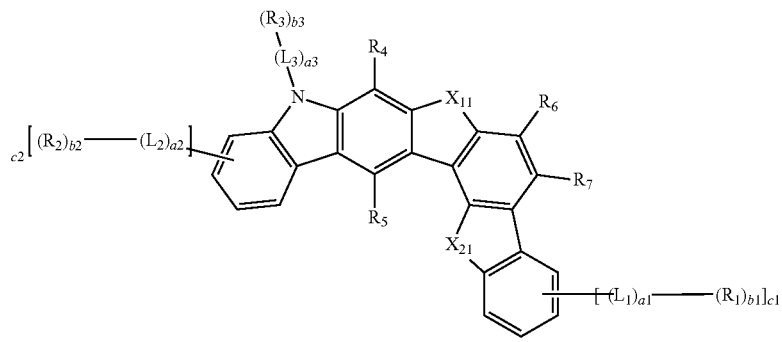

-continued
Formula 1A-7
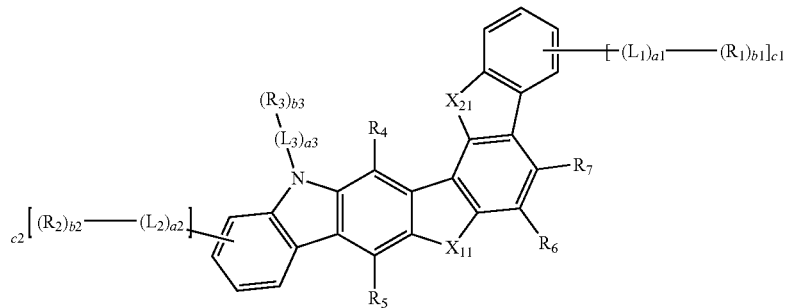
Formula 1A-8
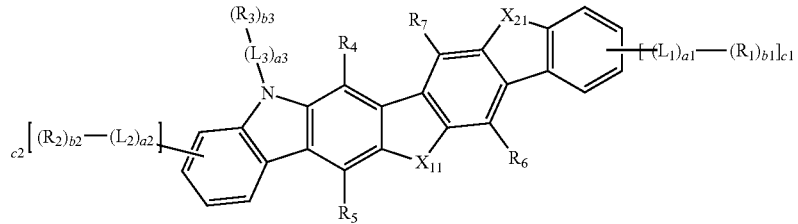
Formula 1A-9
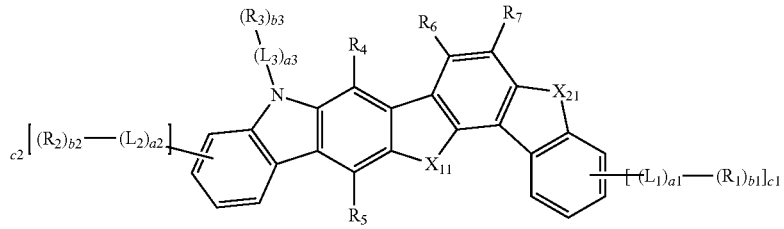
Formula 1A-10
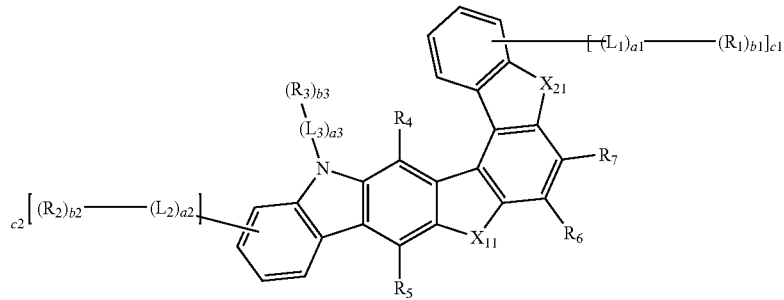
Formula 1A-11
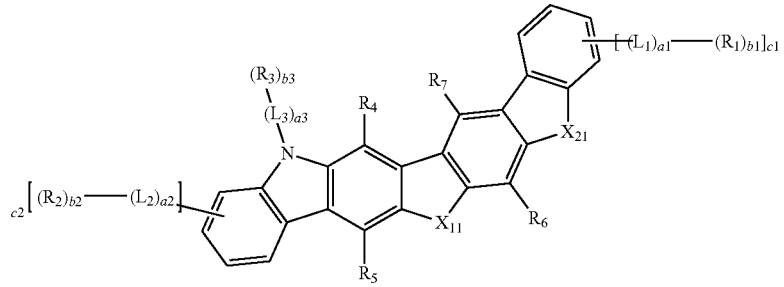
Formula 1A-12
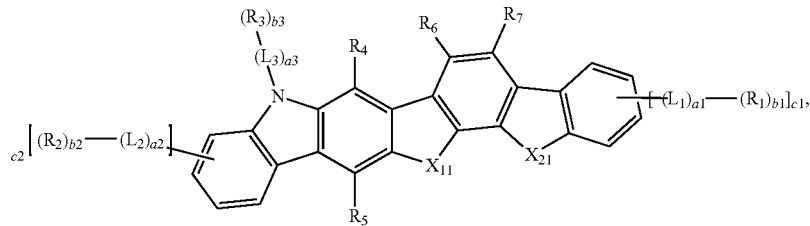

wherein, in Formulae 1A-1 to 1A-12, c2 is an integer selected from 1 to 4.

3. The condensed cyclic compound of claim 2, wherein
when the condensed cyclic compound is represented by Formula 1-2, the compound is represented by one of Formulae 1A-2-2 to 1A-2-7, 1A-2-9 to 1A-2-12, 1A-2-14 to 1A-2-17 or 1A-2-19 to 1A-2-22,
when the condensed cyclic compound is represented by Formula 1-4, the compound is represented by one of Formulae 1A-4-2 to 1A-4-4, 1A-4-7 to 1A-4-9, 1A-4-11 to 1A-4-14, 1A-4-16 to 1A-4-19 or 1A-4-21 to 1A-4-24,
when the condensed cyclic compound is represented by Formula 1-8, the compound is represented by one of Formulae 1A-8-1 to 1A-8-3, 1A-8-5 to 1A-8-7, 1A-8-9 to 1A-8-12, 1A-8-14 to 1A-8-16 or 1A-8-18 to 1A-8-20, and
when the condensed cyclic compound is represented by Formula 1-11, the compound is represented by one of Formulae 1A-11-3 to 1A-11-5, 1A-11-7 to 1A-11-9, 1A-11-11 to 1A-11-14, 1A-11-16 to 1A-11-19 or 1A-11-21 to 1A-11-24:

| Formula No. | Backbone of corresponding Formula | $X_{11}$ in a backbone of corresponding Formula | $X_{12}$ in a backbone of corresponding Formula |
|---|---|---|---|
| 1A-2-2 | 1A-2 | $C(R_{12})(R_{13})$ | O |
| 1A-2-3 | 1A-2 | $C(R_{12})(R_{13})$ | S |
| 1A-2-4 | 1A-2 | $C(R_{12})(R_{13})$ | $Si(R_{22})(R_{23})$ |
| 1A-2-5 | 1A-2 | $N-[(L_{11})_{a11}-(R_{11})_{b11}]$ | O |
| 1A-2-6 | 1A-2 | $N-[(L_{11})_{a11}-(R_{11})_{b11}]$ | S |
| 1A-2-7 | 1A-2 | $N-[(L_{11})_{a11}-(R_{11})_{b11}]$ | $Si(R_{22})(R_{23})$ |
| 1A-2-9 | 1A-2 | O | $N-[(L_{21})_{a21}-(R_{21})_{b21}]$ |
| 1A-2-10 | 1A-2 | O | O |
| 1A-2-11 | 1A-2 | O | S |
| 1A-2-12 | 1A-2 | O | $Si(R_{22})(R_{23})$ |
| 1A-2-14 | 1A-2 | S | $N-[(L_{21})_{a21}-(R_{21})_{b21}]$ |
| 1A-2-15 | 1A-2 | S | O |
| 1A-2-16 | 1A-2 | S | S |
| 1A-2-17 | 1A-2 | S | $Si(R_{22})(R_{23})$ |
| 1A-2-19 | 1A-2 | $Si(R_{12})(R_{13})$ | $N-[(L_{21})_{a21}-(R_{21})_{b21}]$ |
| 1A-2-20 | 1A-2 | $Si(R_{12})(R_{13})$ | O |
| 1A-2-21 | 1A-2 | $Si(R_{12})(R_{13})$ | S |
| 1A-2-22 | 1A-2 | $Si(R_{12})(R_{13})$ | $Si(R_{22})(R_{23})$ |
| 1A-4-2 | 1A-4 | $C(R_{12})(R_{13})$ | O |
| 1A-4-3 | 1A-4 | $C(R_{12})(R_{13})$ | S |
| 1A-4-4 | 1A-4 | $C(R_{12})(R_{13})$ | $Si(R_{22})(R_{23})$ |
| 1A-4-7 | 1A-4 | $N-[(L_{11})_{a11}-(R_{11})_{b11}]$ | O |
| 1A-4-8 | 1A-4 | $N-[(L_{11})_{a11}-(R_{11})_{b11}]$ | S |
| 1A-4-9 | 1A-4 | $N-[(L_{11})_{a11}-(R_{11})_{b11}]$ | $Si(R_{22})(R_{23})$ |
| 1A-4-11 | 1A-4 | O | $N-[(L_{21})_{a21}-(R_{21})_{b21}]$ |
| 1A-4-12 | 1A-4 | O | O |
| 1A-4-13 | 1A-4 | O | S |
| 1A-4-14 | 1A-4 | O | $Si(R_{22})(R_{23})$ |
| 1A-4-16 | 1A-4 | S | $N-[(L_{21})_{a21}-(R_{21})_{b21}]$ |
| 1A-4-17 | 1A-4 | S | O |
| 1A-4-18 | 1A-4 | S | S |
| 1A-4-19 | 1A-4 | S | $Si(R_{22})(R_{23})$ |
| 1A-4-21 | 1A-4 | $Si(R_{12})(R_{13})$ | $N-[(L_{21})_{a21}-(R_{21})_{b21}]$ |
| 1A-4-22 | 1A-4 | $Si(R_{12})(R_{13})$ | O |
| 1A-4-23 | 1A-4 | $Si(R_{12})(R_{13})$ | S |
| 1A-4-24 | 1A-4 | $Si(R_{12})(R_{13})$ | $Si(R_{22})(R_{23})$ |
| 1A-8-1 | 1A-8 | $Si(R_{12})(R_{13})$ | O |
| 1A-8-2 | 1A-8 | $C(R_{12})(R_{13})$ | S |
| 1A-8-3 | 1A-8 | $C(R_{12})(R_{13})$ | $Si(R_{22})(R_{23})$ |
| 1A-8-5 | 1A-8 | $N-[(L_{11})_{a11}-(R_{11})_{b11}]$ | O |
| 1A-8-6 | 1A-8 | $N-[(L_{11})_{a11}-(R_{11})_{b11}]$ | S |
| 1A-8-7 | 1A-8 | $N-[(L_{11})_{a11}-(R_{11})_{b11}]$ | $Si(R_{22})(R_{23})$ |
| 1A-8-9 | 1A-8 | O | $N-[(L_{21})_{a21}-(R_{21})_{b21}]$ |
| 1A-8-10 | 1A-8 | O | O |
| 1A-8-11 | 1A-8 | O | S |
| 1A-8-12 | 1A-8 | O | $Si(R_{22})(R_{23})$ |
| 1A-8-14 | 1A-8 | S | O |
| 1A-8-15 | 1A-8 | S | S |
| 1A-8-16 | 1A-8 | S | $Si(R_{22})(R_{23})$ |
| 1A-8-18 | 1A-8 | $Si(R_{12})(R_{13})$ | O |
| 1A-8-19 | 1A-8 | $Si(R_{12})(R_{13})$ | S |
| 1A-8-20 | 1A-8 | $Si(R_{12})(R_{13})$ | $Si(R_{22})(R_{23})$ |
| 1A-11-3 | 1A-11 | $C(R_{12})(R_{13})$ | O |
| 1A-11-4 | 1A-11 | $C(R_{12})(R_{13})$ | S |
| 1A-11-5 | 1A-11 | $C(R_{12})(R_{13})$ | $Si(R_{22})(R_{23})$ |
| 1A-11-7 | 1A-11 | $N-[(L_{11})_{a11}-(R_{11})_{b11}]$ | O |
| 1A-11-8 | 1A-11 | $N-[(L_{11})_{a11}-(R_{11})_{b11}]$ | S |
| 1A-11-9 | 1A-11 | $N-[(L_{11})_{a11}-(R_{11})_{b11}]$ | $Si(R_{22})(R_{23})$ |
| 1A-11-11 | 1A-11 | O | $N-[(L_{21})_{a21}-(R_{21})_{b21}]$ |
| 1A-11-12 | 1A-11 | O | O |
| 1A-11-13 | 1A-11 | O | S |
| 1A-11-14 | 1A-11 | O | $Si(R_{22})(R_{23})$ |
| 1A-11-16 | 1A-11 | S | $N-[(L_{21})_{a21}-(R_{21})_{b21}]$ |
| 1A-11-17 | 1A-11 | S | O |
| 1A-11-18 | 1A-11 | S | S |
| 1A-11-19 | 1A-11 | S | $Si(R_{22})(R_{23})$ |
| 1A-11-21 | 1A-11 | $Si(R_{12})(R_{13})$ | $N-[(L_{21})_{a21}-(R_{21})_{b21}]$ |
| 1A-11-22 | 1A-11 | $Si(R_{12})(R_{13})$ | O |
| 1A-11-23 | 1A-11 | $Si(R_{12})(R_{13})$ | S |
| 1A-11-24 | 1A-11 | $Si(R_{12})(R_{13})$ | $Si(R_{22})(R_{23})$. |

4. The condensed cyclic compound of claim 1, wherein the compound is represented by one of Formulae 1-1 to 1-7 or 1-9 to 1-12,
wherein, in Formulae 1-1 to 1-7 and 1-9 to 1-12,
$X_{11}$ and $X_{21}$ are each independently O or S;
$X_{11}$ is O or S, and $X_{21}$ is $N-[(L_{21})_{a21}-(R_{21})_{b21}]$; or
$X_{11}$ is $N-[(L_{11})_{a11}-(R_{11})_{b11}]$, and $X_{21}$ is O or S;
$X_{11}$ is $C(R_{12})(R_{13})$, and $X_{21}$ is O.

5. The condensed cyclic compound of claim 1, wherein the compound is represented by Formula 1-2, wherein, in Formula 1-2, $X_{11}$ is O or S, and $X_{21}$ is O, S, or N-$[(L_{21})_{a21}-(R_{21})_{b21}]$.

6. The condensed cyclic compound of claim 1, wherein $L_1$ to $L_3$, $L_{11}$, and $L_{21}$ are each independently selected from the group consisting of:
a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group an imidazopyrimidinylene group, and an imidazopyridinylene group, each substituted with at least one selected from the group consisting of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{20}$ aryl group, a $C_1$-$C_{20}$ heteroaryl group, a monovalent non-aromatic condensed polycyclic group, a monovalent non-aromatic condensed heteropolycyclic group, and —Si($Q_{33}$)($Q_{34}$)($Q_{35}$), wherein $Q_{33}$ to $Q_{35}$ are each independently selected from the group consisting of a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

7. The condensed cyclic compound of claim 1, wherein $L_1$ to $L_3$, $L_{11}$, and $L_{21}$ are each independently one of Formulae 2-1 to 2-34:

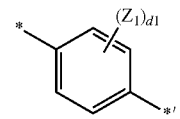
Formula 2-1

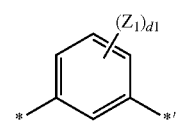
Formula 2-2

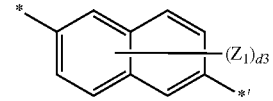
Formula 2-3

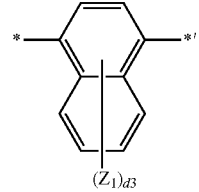
Formula 2-4

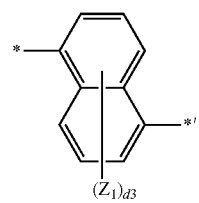
Formula 2-5

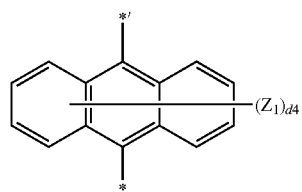
Formula 2-6

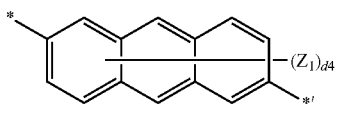
Formula 2-7

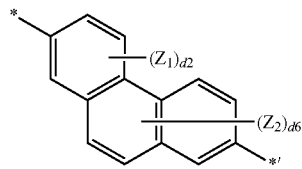
Formula 2-8

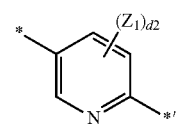
Formula 2-9

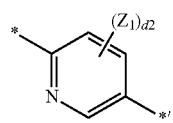
Formula 2-10

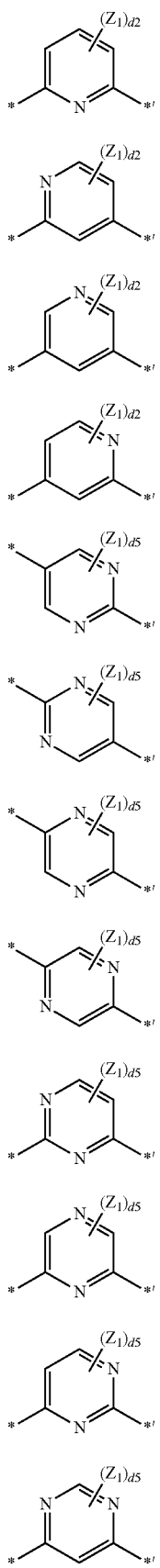
Formula 2-11
Formula 2-12
Formula 2-13
Formula 2-14
Formula 2-15
Formula 2-16
Formula 2-17
Formula 2-18
Formula 2-19
Formula 2-20
Formula 2-21
Formula 2-22
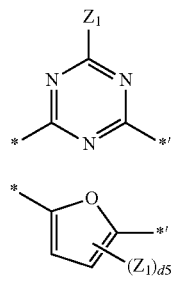
Formula 2-23
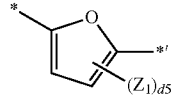
Formula 2-24
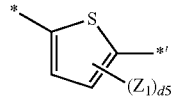
Formula 2-25
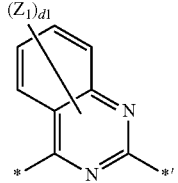
Formula 2-26
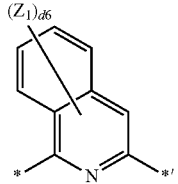
Formula 2-27
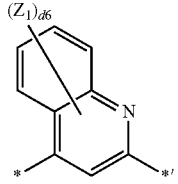
Formula 2-28
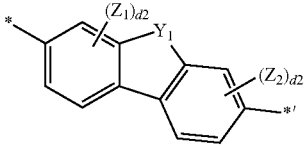
Formula 2-29
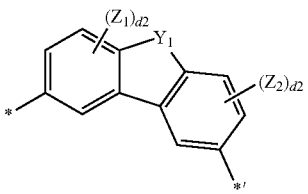
Formula 2-30
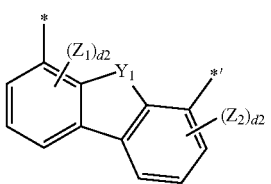
Formula 2-31

Formula 2-32

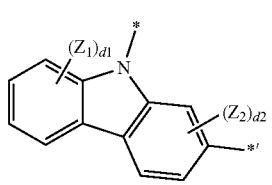

Formula 2-33

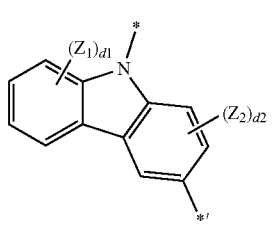

Formula 2-34

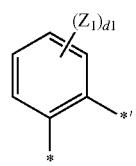

Formula 3-1

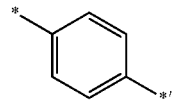

Formula 3-2

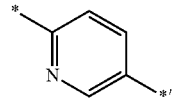

Formula 3-3

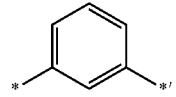

Formula 3-4

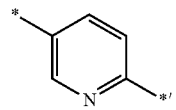

Formula 3-5

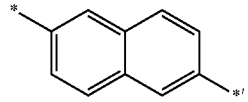

Formula 3-6

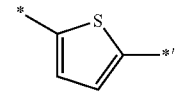

Formula 3-7

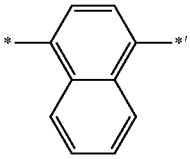

Formula 3-8

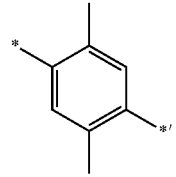

Formula 3-9

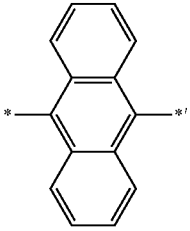

Formula 3-10

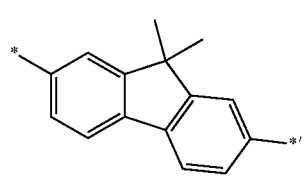

wherein, in Formulae 2-1 to 2-34, $Y_1$ is O, S, S(=O), S(=O)$_2$, C($Z_3$)($Z_4$), N($Z_5$), or Si($Z_6$)($Z_7$);

$Z_1$ to $Z_7$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —Si($Q_{33}$)($Q_{34}$)($Q_{35}$), wherein $Q_{33}$ to $Q_{35}$ are each independently selected from the group consisting of a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

d1 is an integer selected from 1 to 4;
d2 is an integer selected from 1 to 3;
d3 is an integer selected from 1 to 6;
d4 is an integer selected from 1 to 8;
d5 is an integer of 1 or 2;
d6 is an integer selected from 1 to 5; and
* and *' each indicates a binding site to a neighboring atom.

8. The condensed cyclic compound of claim 1, wherein $L_1$ to $L_3$, $L_{11}$, and $L_{21}$ are each independently one of Formulae 3-1 to 3-21:

205
-continued

Formula 3-11
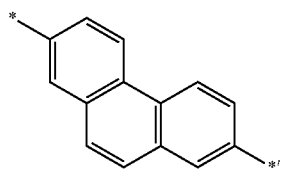

Formula 3-12
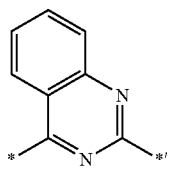

Formula 3-13
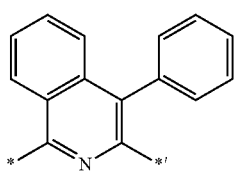

Formula 3-14
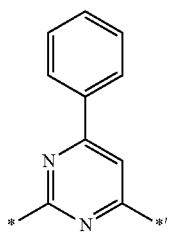

Formula 3-15
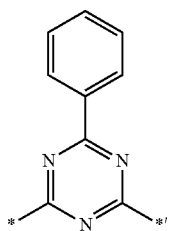

Formula 3-16
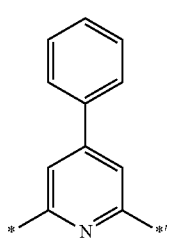

Formula 3-17
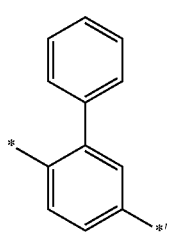

206
-continued

Formula 3-18
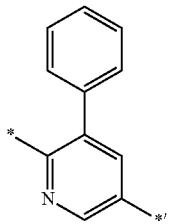

Formula 3-19
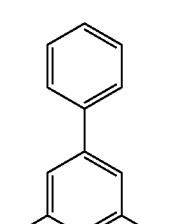

Formula 3-20
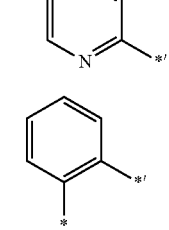

Formula 3-21 wherein * and *' each indicates a binding site to a neighboring atom.

9. The condensed cyclic compound of claim 1, wherein $R_1$ to $R_7$, $R_{11}$ to $R_{13}$, and $R_{21}$ to $R_{23}$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, a substituted or unsubstituted monovalent non-aromatic condensed heteropolycyclic group, and —Si($Q_3$)($Q_4$)($Q_5$).

10. The condensed cyclic compound of claim 1, wherein conditions i) and ii) are met:
    i) when $X_{11}$ is N-[($L_{11}$)$_{a11}$-($R_{11}$)$_{b11}$], at least one of $R_3$ or $R_{11}$, and
    ii) when $X_{21}$ is N-[($L_{21}$)$_{a11}$-($R_{21}$)$_{b11}$], at least one of $R_3$ or $R_{21}$, are each independently selected from the group consisting of a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group.

11. The condensed cyclic compound of claim 1, wherein $R_1$ to $R_7$, $R_{11}$ to $R_{13}$, and $R_{21}$ to $R_{23}$ are each independently selected from the group consisting of:

a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, or a phosphoric acid or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, or —Si($Q_{33}$)($Q_{34}$)($Q_{35}$); and —Si($Q_3$)($Q_4$)($Q_5$), wherein $Q_3$ to $Q_5$ and $Q_{33}$ to $Q_{35}$ are each independently selected from the group consisting of a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

12. The condensed cyclic compound of claim 1, wherein $R_1$ to $R_7$, $R_{11}$ to $R_{13}$, and $R_{21}$ to $R_{23}$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, one of Formulae 4-1 to 4-31, and —Si($Q_3$)($Q_4$)($Q_5$), wherein $Q_3$ to $Q_5$ are each independently selected from the group consisting of a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group:

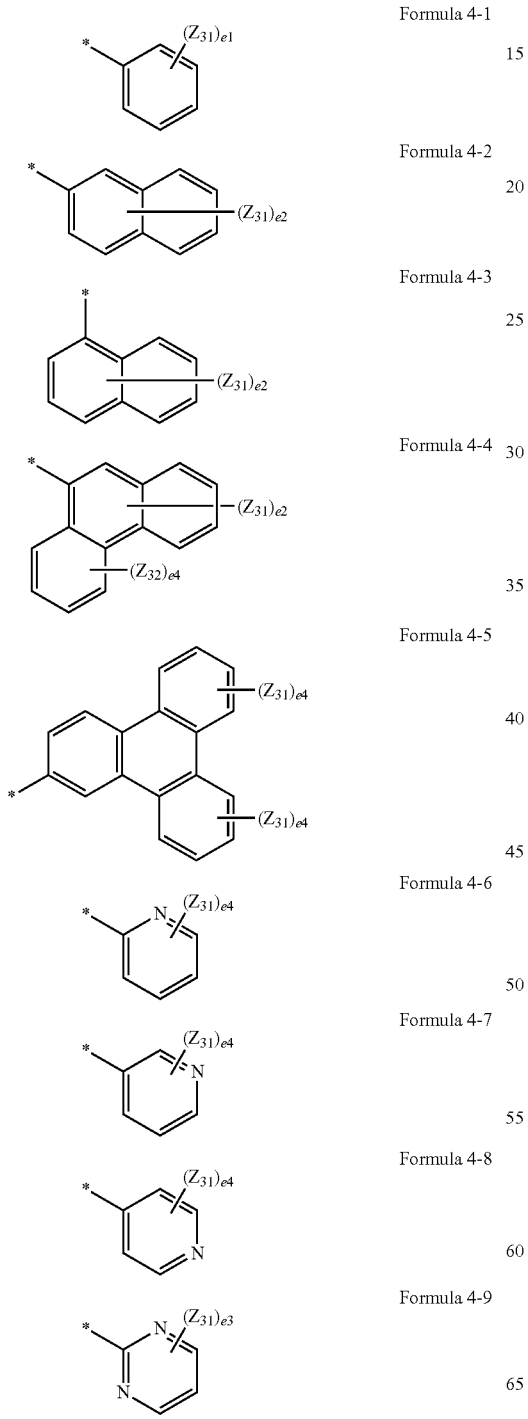

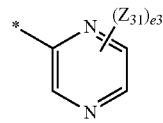 Formula 4-10

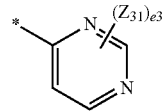 Formula 4-11

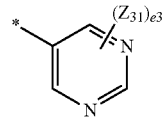 Formula 4-12

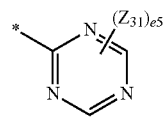 Formula 4-13

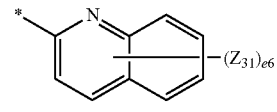 Formula 4-14

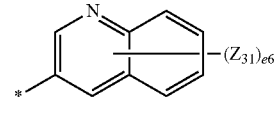 Formula 4-15

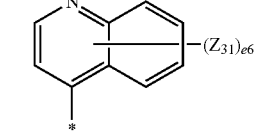 Formula 4-16

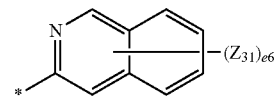 Formula 4-17

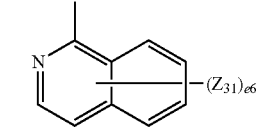 Formula 4-18

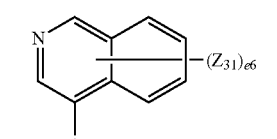 Formula 4-19

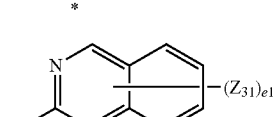 Formula 4-20

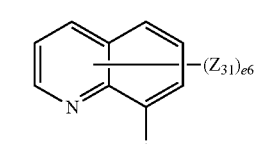 Formula 4-21

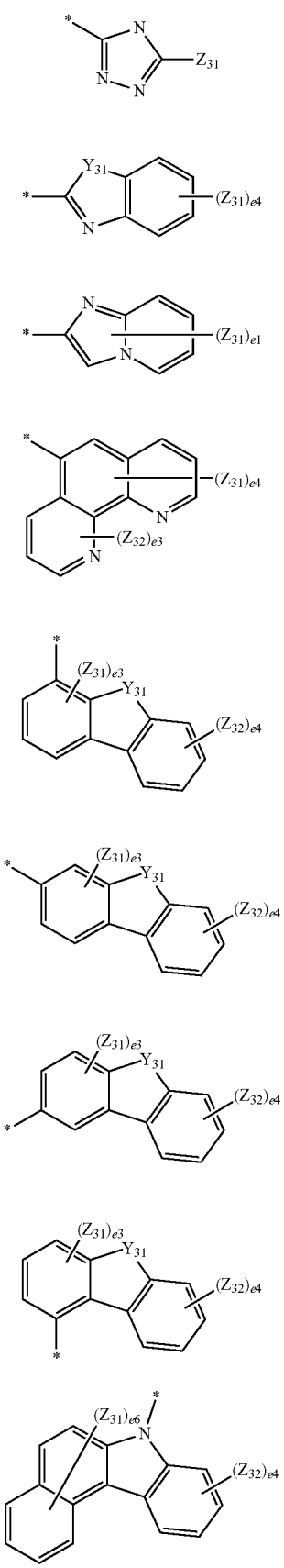

Formula 4-22
Formula 4-23
Formula 4-24
Formula 4-25
Formula 4-26
Formula 4-27
Formula 4-28
Formula 4-29
Formula 4-30

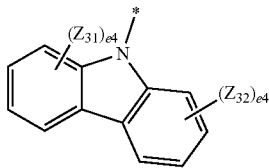

Formula 4-31 wherein, in Formulae 4-1 to 4-31, $Y_{31}$ is O, S, $C(Z_{33})(Z_{34})$, $N(Z_{35})$, or $Si(Z_{36})(Z_{37})$;

$Z_{31}$ to $Z_{37}$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and —$Si(Q_{33})(Q_{34})(Q_{35})$, wherein $Q_{33}$ to $Q_{35}$ are each independently selected from the group consisting of a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

e1 is an integer selected from 1 to 5, e2 is an integer selected from 1 to 7, e3 is an integer selected from 1 to 3, e4 is an integer selected from 1 to 4, e5 is an integer selected from 1 or 2, e6 is an integer selected from 1 to 6, and

* indicates a binding site to a neighboring atom.

13. The condensed cyclic compound of claim 1, wherein $R_1$ to $R_7$, $R_{11}$ to $R_{13}$, and $R_{21}$ to $R_{23}$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, one of Formulae 5-1 to 5-55, and —$Si(Q_3)(Q_4)(Q_5)$, wherein $Q_3$ to $Q_5$ are each independently selected from the group consisting of a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group:

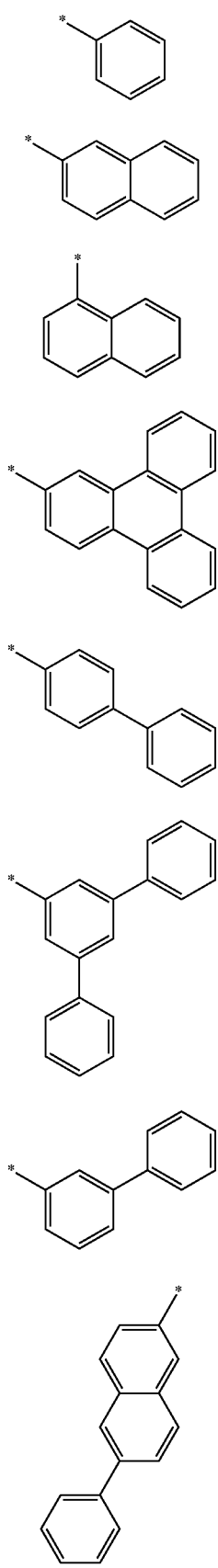
Formula 5-1
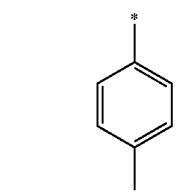
Formula 5-9
Formula 5-2
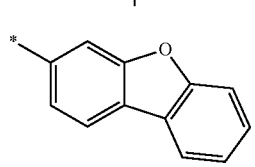
Formula 5-10
Formula 5-3
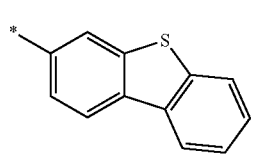
Formula 5-11
Formula 5-4
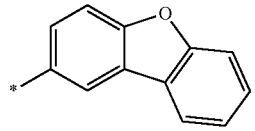
Formula 5-12
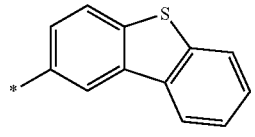
Formula 5-13
Formula 5-5
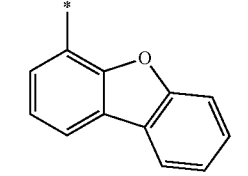
Formula 5-14
Formula 5-6
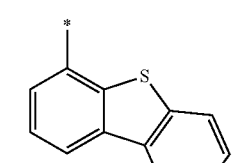
Formula 5-15
Formula 5-7
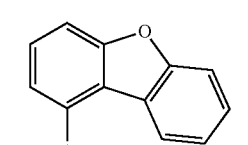
Formula 5-16
Formula 5-8
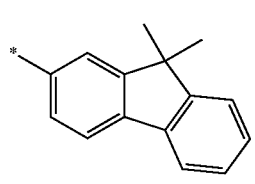
Formula 5-17
Formula 5-18

Formula 5-19
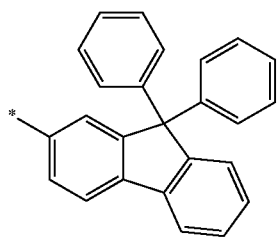
Formula 5-20
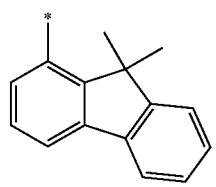
Formula 5-21
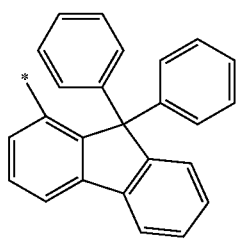
Formula 5-22
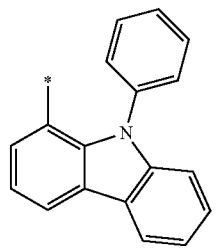
Formula 5-23
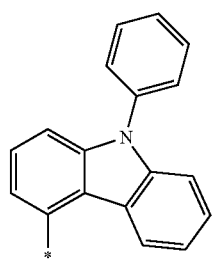
Formula 5-24
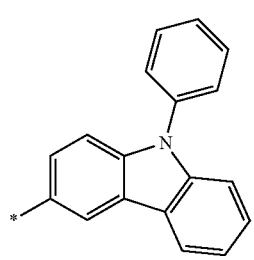
Formula 5-25
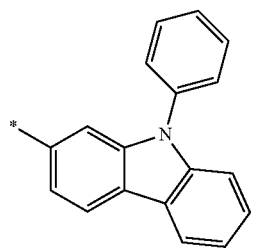
Formula 5-26
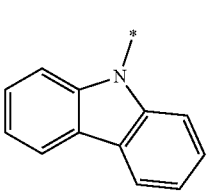
Formula 5-27
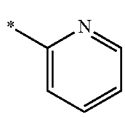
Formula 5-28
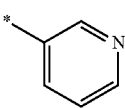
Formula 5-29
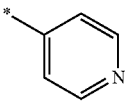
Formula 5-30
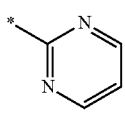
Formula 5-31
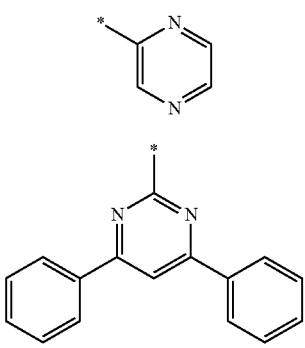
Formula 5-32
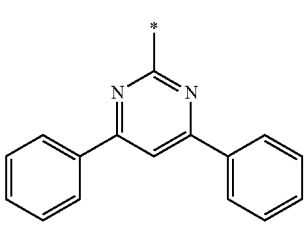
Formula 5-33
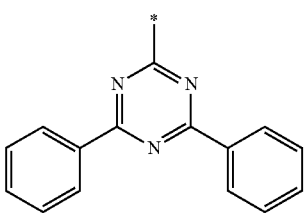

-continued
Formula 5-34
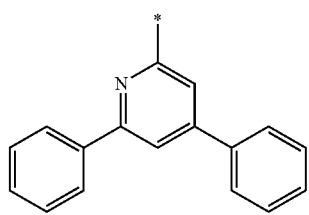
Formula 5-35
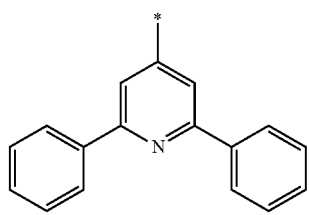
Formula 5-36
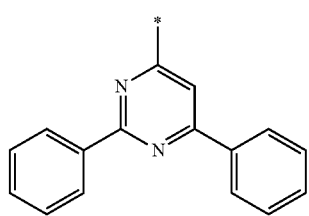
Formula 5-37
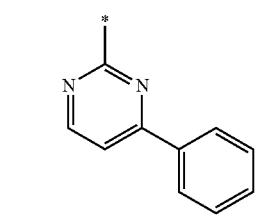
Formula 5-38
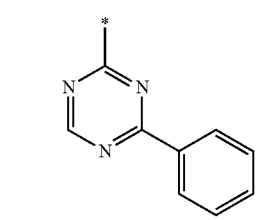
Formula 5-39
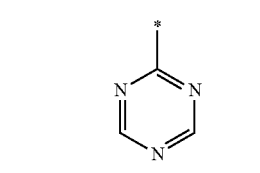
Formula 5-40
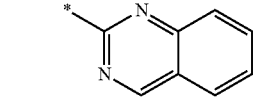
Formula 5-41
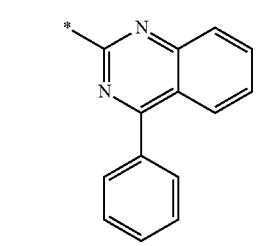
-continued
Formula 5-42
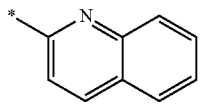
Formula 5-43
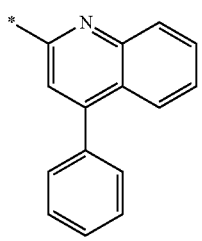
Formula 5-44
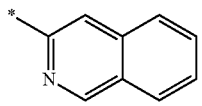
Formula 5-45
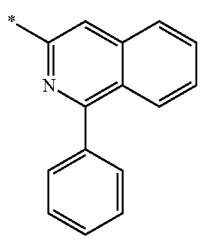
Formula 5-46
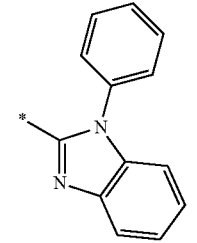
Formula 5-47
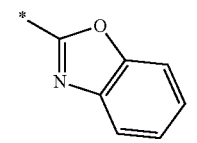
Formula 5-48
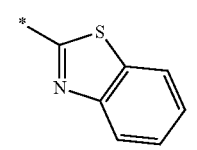
Formula 5-49
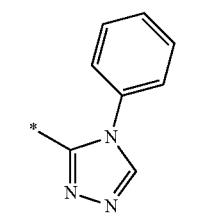

-continued

Formula 5-50

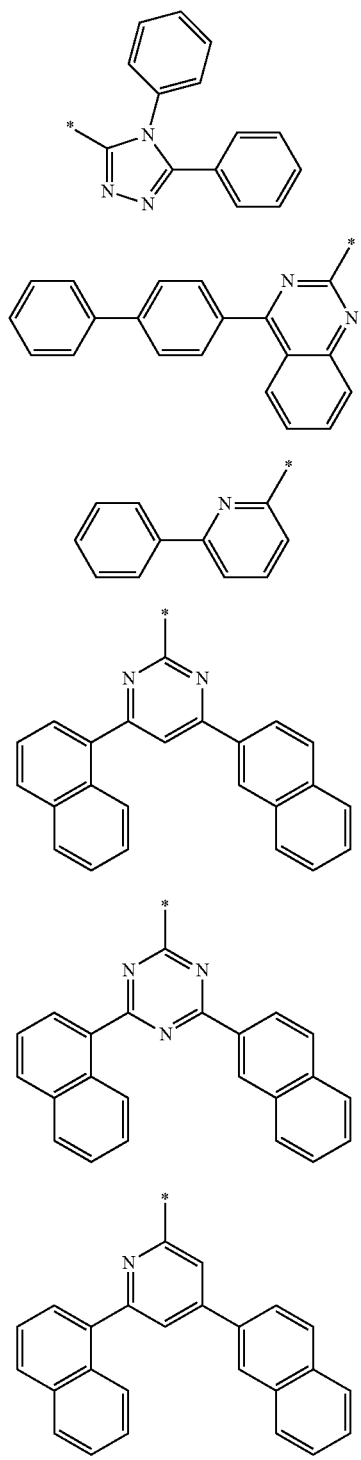

Formula 5-51

Formula 5-52

Formula 5-53

Formula 5-54

Formula 5-55

* indicates a binding site to a neighboring atom.

14. An organic light-emitting device comprising:
a first electrode;
a second electrode; and
an organic layer disposed between the first electrode and the second electrode,
wherein the organic layer comprises an emission layer and at least one of the condensed cyclic compound of claim 1.

15. A condensed cyclic compound represented by one of Formulae 1-1 to 1-12:

Formula 1-1

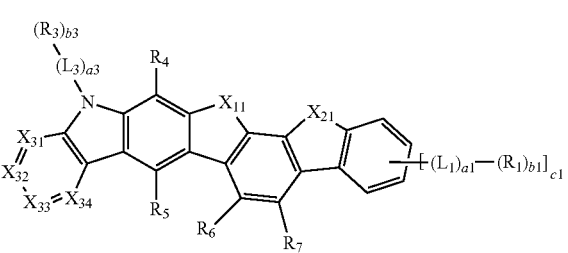

Formula 1-2

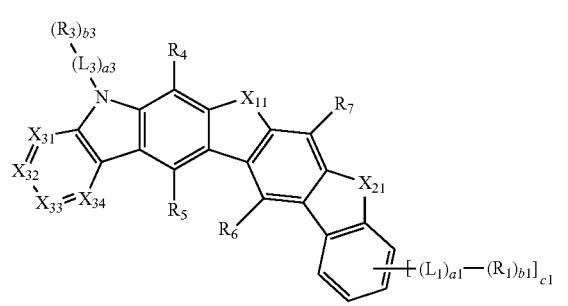

Formula 1-3

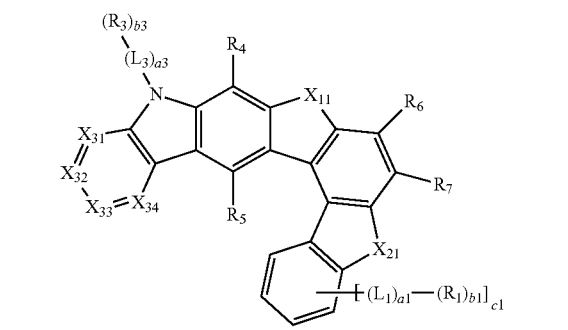

Formula 1-4

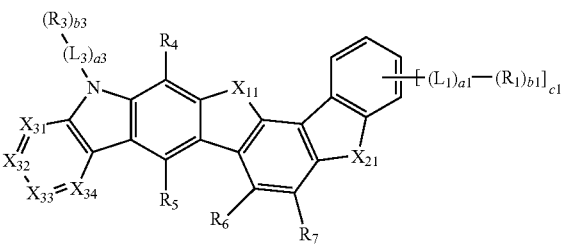

Formula 1-5

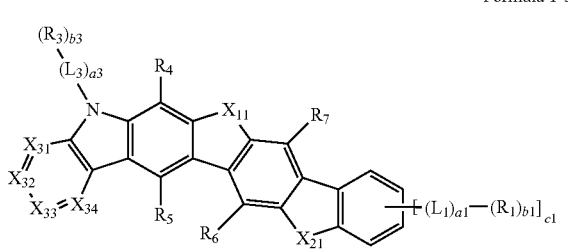

-continued

Formula 1-6

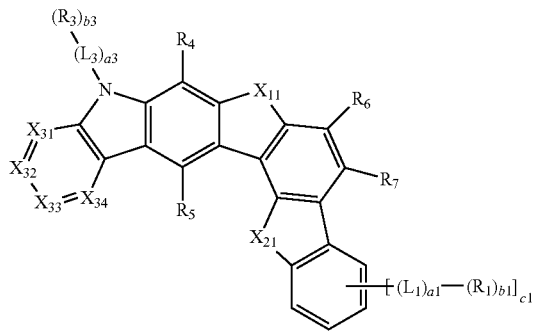

Formula 1-7

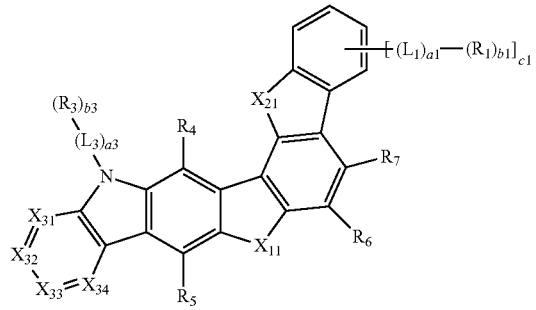

Formula 1-8

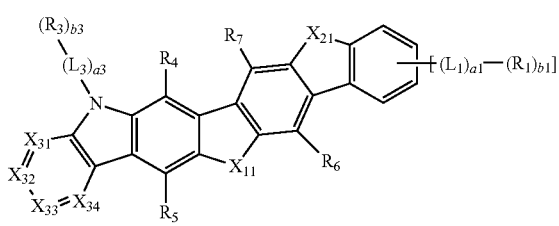

Formula 1-9

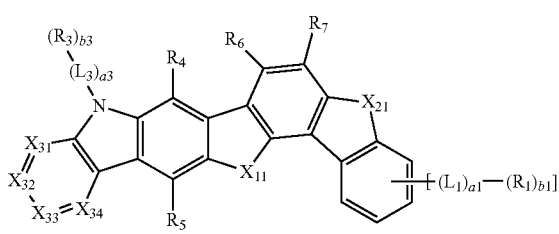

Formula 1-10

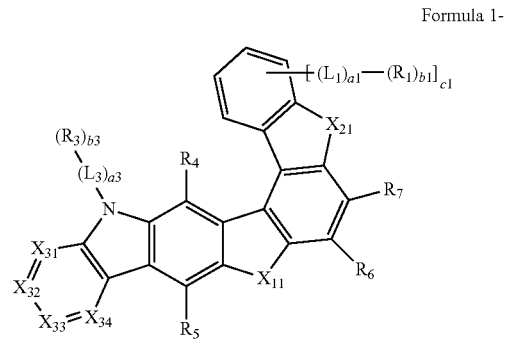

-continued

Formula 1-11

Formula 1-12

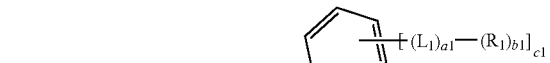

wherein, in Formulae 1-1 to 1-12, $X_{11}$ is N-[$(L_{11})_{a11}$-$(R_{11})_{b11}$], S, O, C(=O), C($R_{12}$)($R_{13}$), Si($R_{12}$)($R_{13}$), P($R_{12}$), or P(=O)($R_{12}$);

$X_{21}$ is N-[$(L_{21})_{a21}$-$(R_{21})_{b21}$], S, O, S(=O), S(=O)$_2$, C(=O), Si($R_{22}$)($R_{23}$), P($R_{22}$), or P(=O)($R_{22}$);

provided that when $X_{11}$ is C($R_{12}$)($R_{13}$), then $X_{21}$ is S, O, S(=O), S(=O)$_2$, C(=O), Si($R_{22}$)($R_{23}$), P($R_{22}$), or P(=O)($R_{22}$);

provided that when $X_{21}$ is N-[$(L_{21})_{a21}$-$(R_{21})_{b21}$], then $X_{11}$ is N-[$(L_{11})_{a11}$-$(R_{11})_{b11}$], S, O, C(=O), Si($R_{12}$)($R_{13}$), P($R_{12}$), or P(=O)($R_{12}$);

$X_{31}$ to $X_{34}$ are each independently N or C-[$(L_2)_{a2}$-$(R_2)_{b2}$];

provided that conditions i) to iv) are met:
i) in Formulae 1-1 to 1-12, when $X_{11}$ is N-[$(L_{11})_{a11}$-$(R_{11})_{b11}$], $X_{21}$ is not N-[$(L_{21})_{a21}$-$(R_{21})_{b21}$],
ii) in Formula 1-8, when $X_{11}$ is S, $X_{21}$ is not N-[$(L_{21})_{a21}$-$(R_{21})_{b21}$],
iii) in Formula 1-8, when $X_{11}$ is Si($R_{12}$)($R_{13}$), $X_{21}$ is not N-[$(L_{21})_{a21}$-$(R_{21})_{b21}$],
iv) in Formulae 1-1 to 1-12, when $X_{21}$ is N-[$(L_{21})_{a21}$-$(R_{21})_{b21}$], $X_{11}$ is not N-[$(L_{11})_{a11}$-$(R_{11})_{b11}$];

$L_1$ to $L_3$, $L_{11}$, and $L_{21}$ are each independently selected the group consisting of from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a3, a11, and a21 are each independently an integer selected from 0 to 5;

$R_1$ to $R_7$, $R_{11}$ to $R_{13}$, and $R_{21}$ to $R_{23}$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

provided that:
i) in Formulae 1-1 to 1-12, $R_3$ is selected from the group consisting of:

a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, and —Si($Q_{33}$)($Q_{34}$)($Q_{35}$), ii) in Formula 1-2, when $X_{11}$ is not N-[($L_{11})_{a11}$-($R_{11})_{b11}$], a3 is an integer selected from 1 to 5 and $L_3$ is selected from the group consisting of a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group selected from the group consisting of Formulae 2-9 to 2-23, a substituted or unsubstituted divalent non-aromatic condensed polycyclic group, and a substituted or unsubstituted divalent non-aromatic condensed heteropolycyclic group:

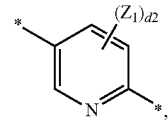

Formula 2-9

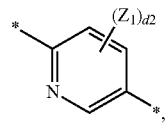

Formula 2-10

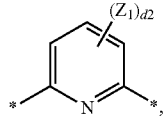

Formula 2-11

-continued

Formula 2-12
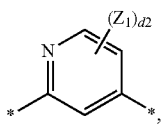

Formula 2-13
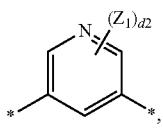

Formula 2-14
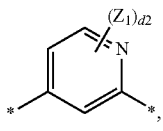

Formula 2-15
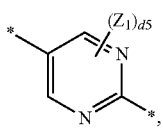

Formula 2-16
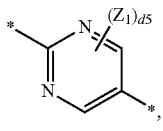

Formual 2-17
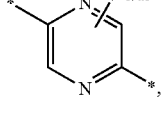

Formula 2-18
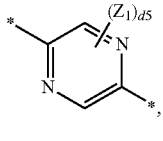

Formula 2-19
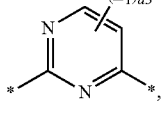

Formula 2-20
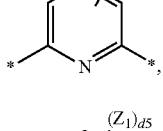

Formula 2-21
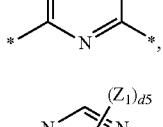

Formula 2-22
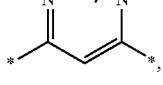

-continued

Formula 2-23
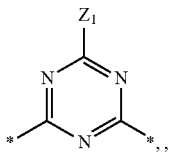

wherein, in Formulae 2-9 to 2-23,
$Z_1$ is selected from the group consisting of a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, and a biphenyl group,
d2 is an integer selected from 1 to 3, and
d5 is an integer of 1 or 2; and
iii) in Formulae 1-1 to 1-12, when $X_{11}$ is N-[$(L_{11})_{a11}$-$(R_{11})_{b11}$], $R_{11}$ is selected from the group consisting of:
a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and
a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, or —Si($Q_{33}$)($Q_{34}$)($Q_{35}$), wherein $Q_{33}$ to $Q_{35}$ are each independently selected from the group consisting of a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

b1 to b3, b11, and b21 are each independently an integer selected from 1 to 5;

c1 is an integer selected from 1 to 4;

at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, substituted $C_6$-$C_{60}$ aryloxy group, substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, or the substituted monovalent non-aromatic condensed heteropolycyclic group is selected from the group consisting of:

a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$); wherein $Q_1$ to $Q_7$, $Q_{11}$ to $Q_{17}$, $Q_{21}$ to $Q_{27}$, and $Q_{31}$ to $Q_{37}$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group.

16. A condensed cyclic compound represented by one of Compounds 1 to 155 and 158 to 167:

1

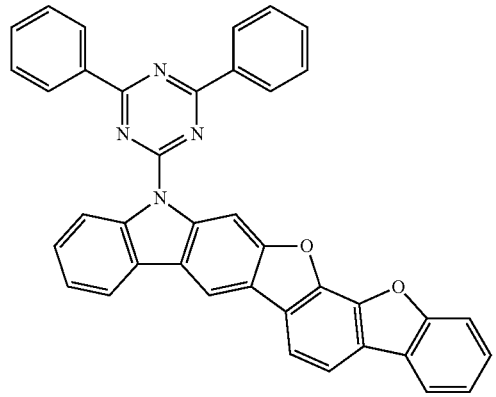

2

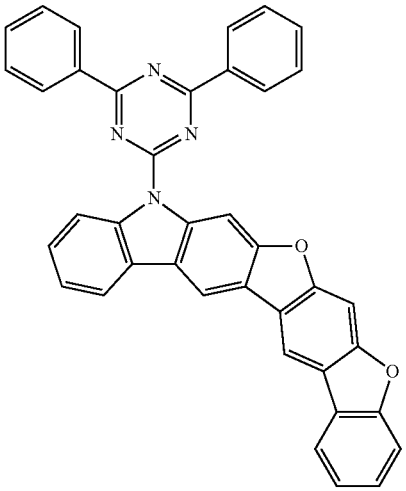

3

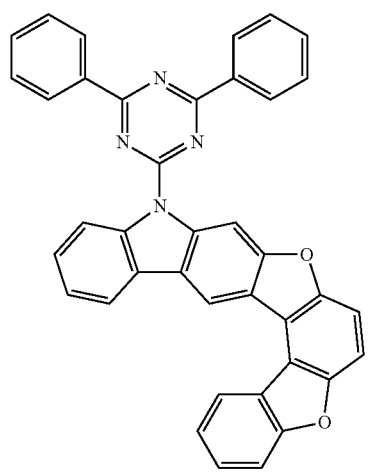

4

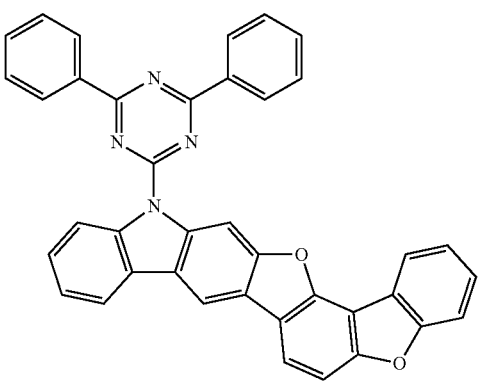

5

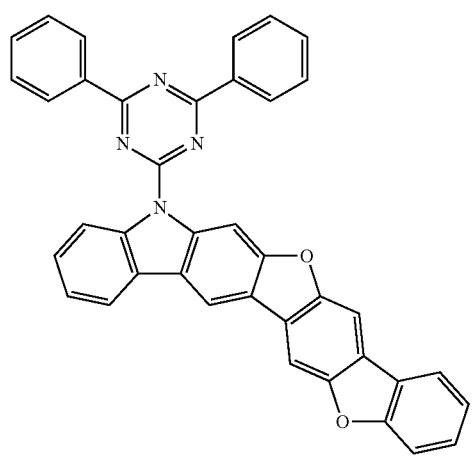

6

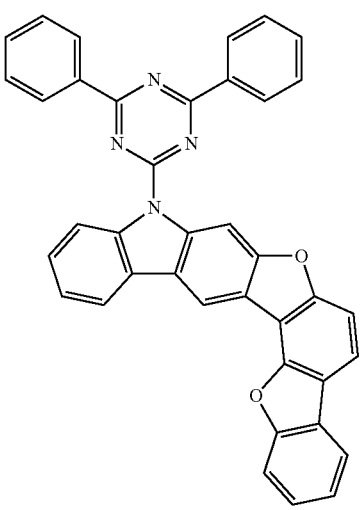

-continued
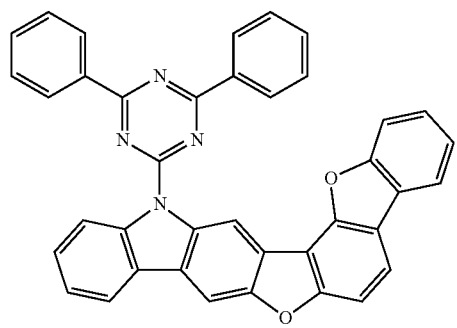
7
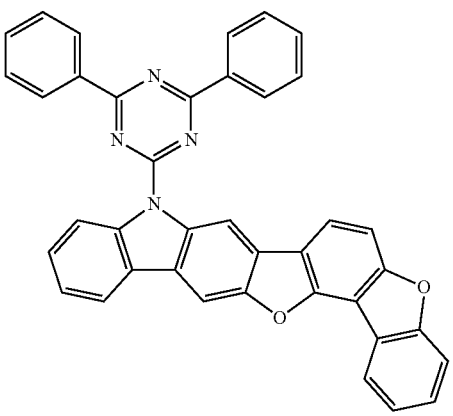
8
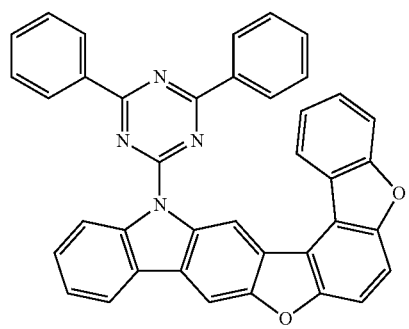
9
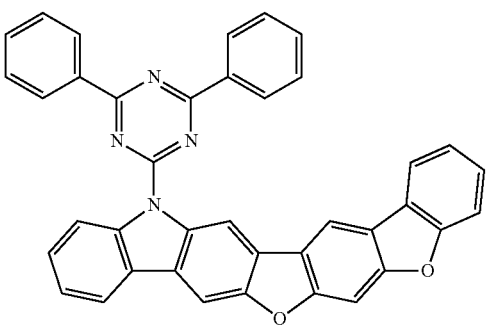
10
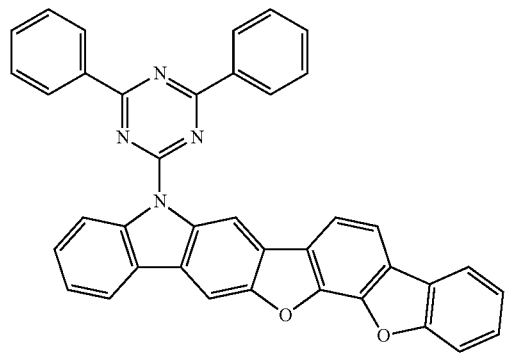
11
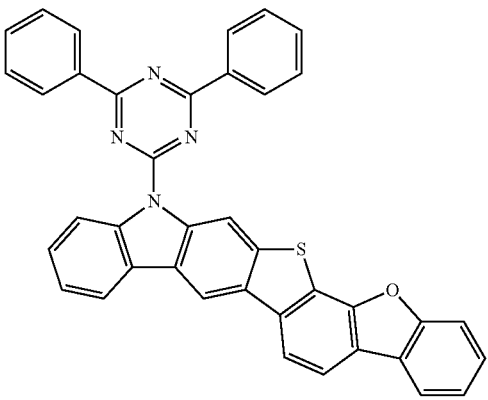
12
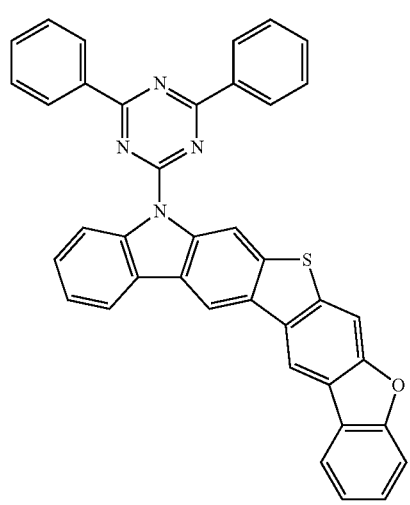
13
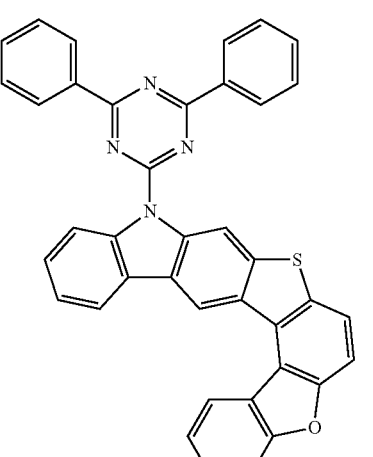
14

-continued
15
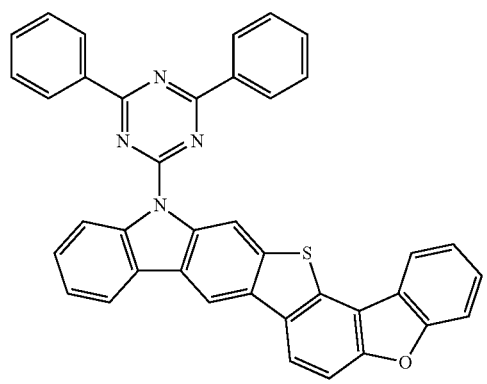
16
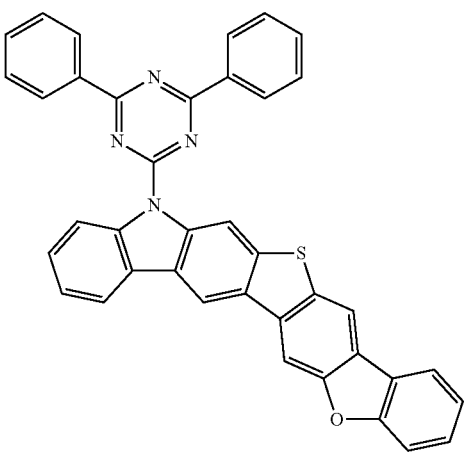
17
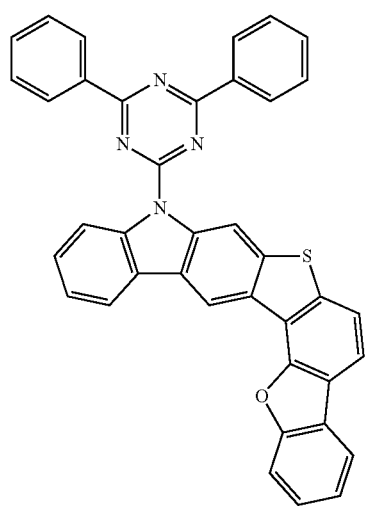
18
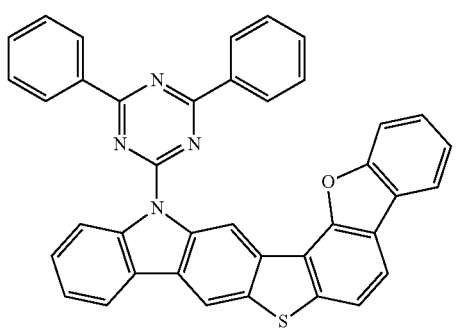
19
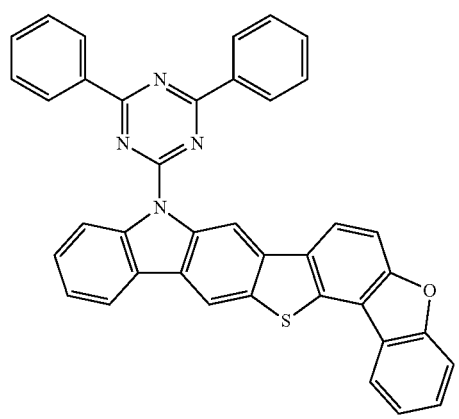
20
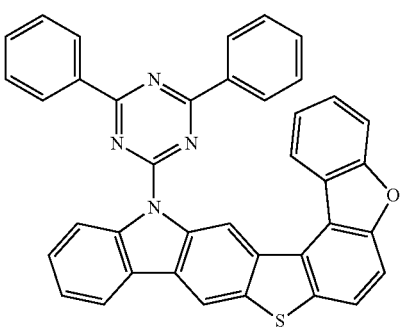

-continued
21
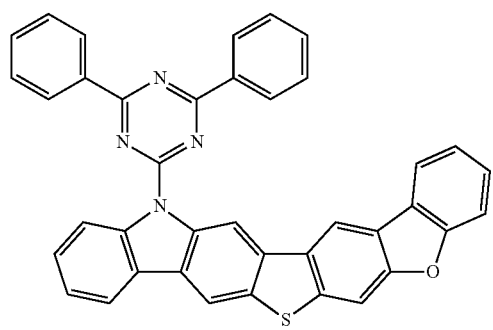
22
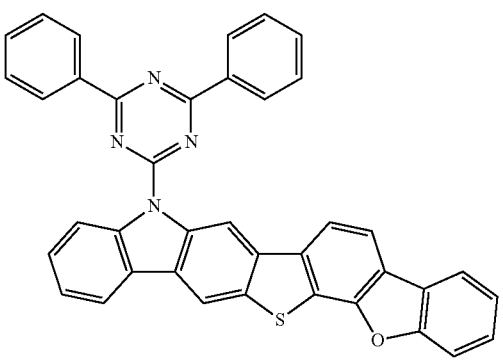
23
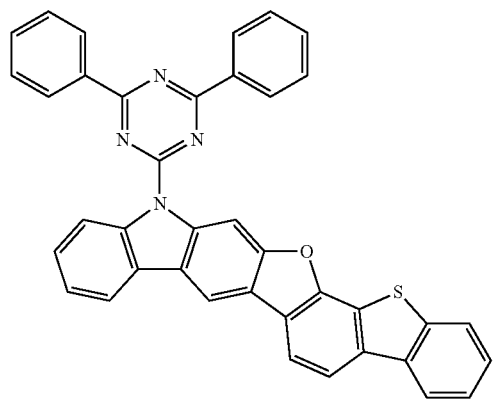
24
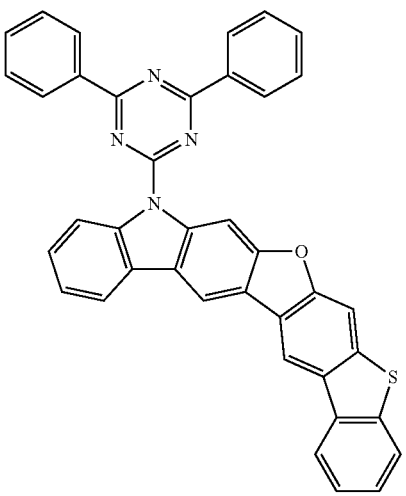
25
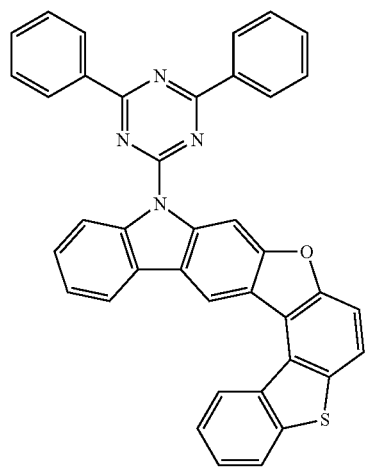
26
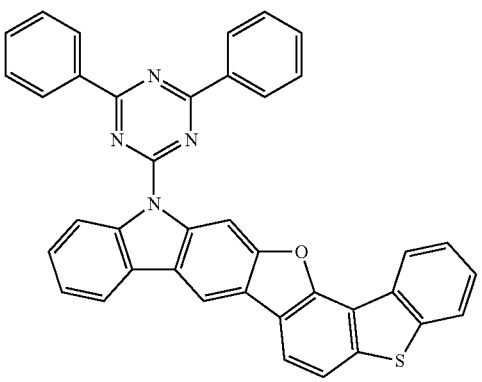

-continued
27
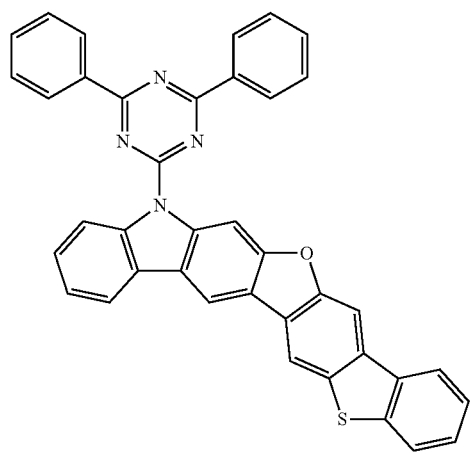
28
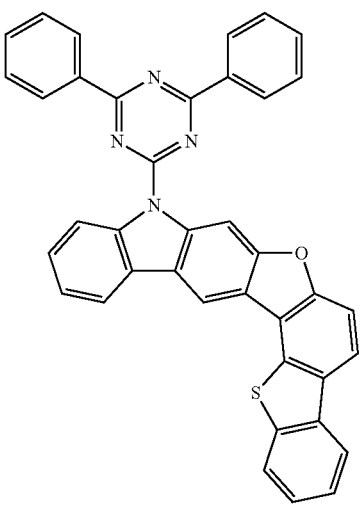
29
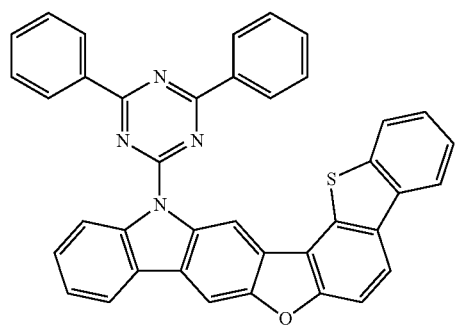
30
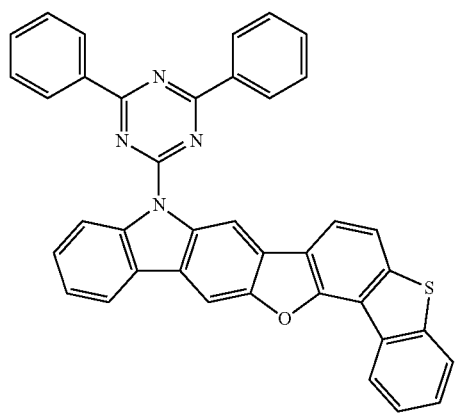
31
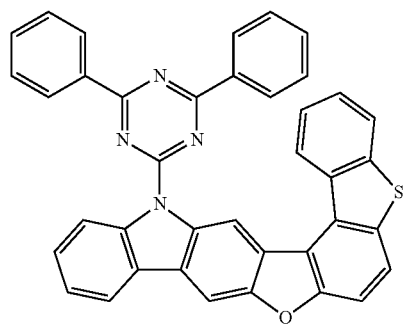
32
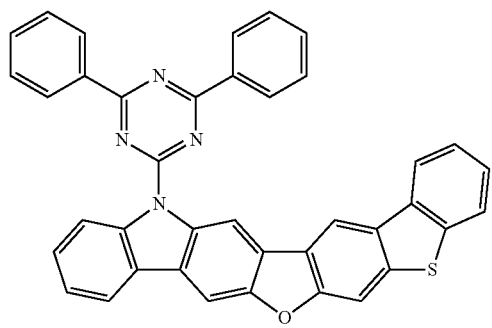
33
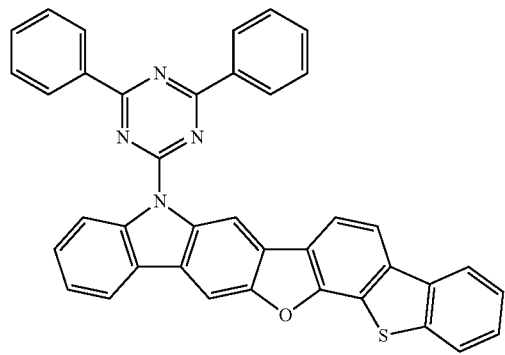
34
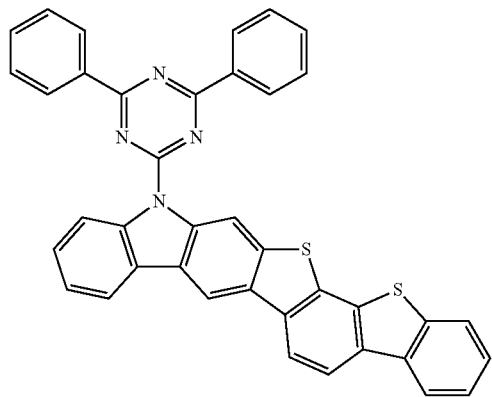

-continued
35 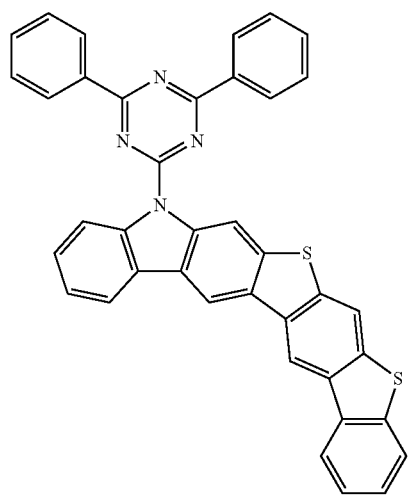 36 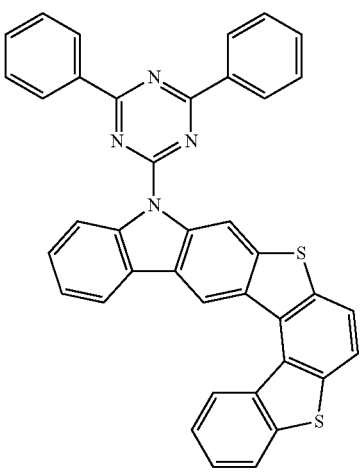
37 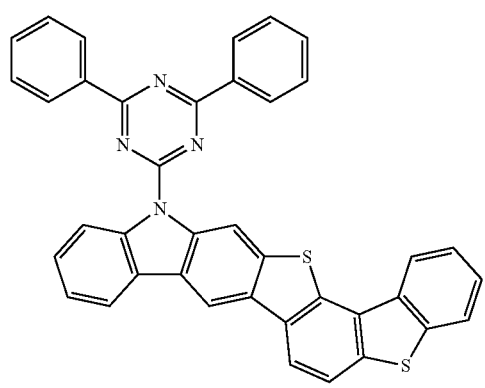 38 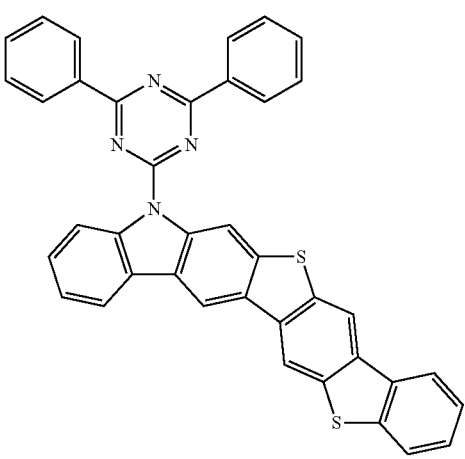
39 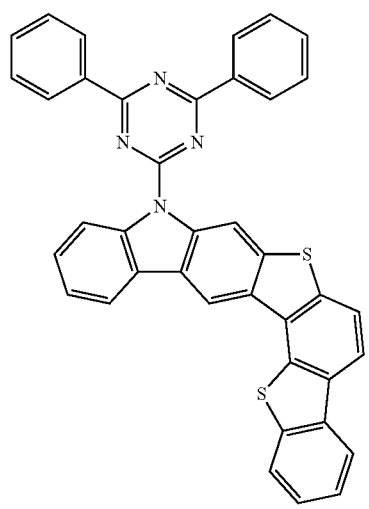 40 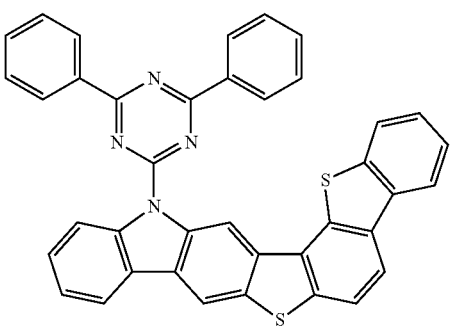

-continued
41
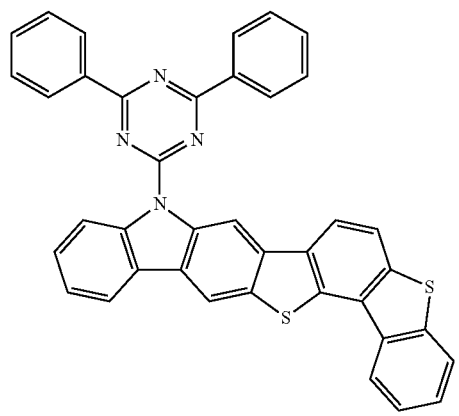
42
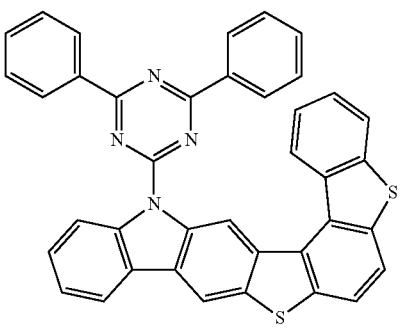
43
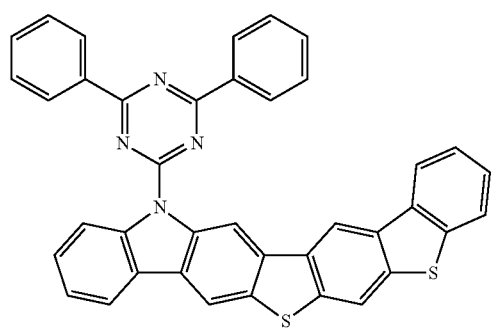
44
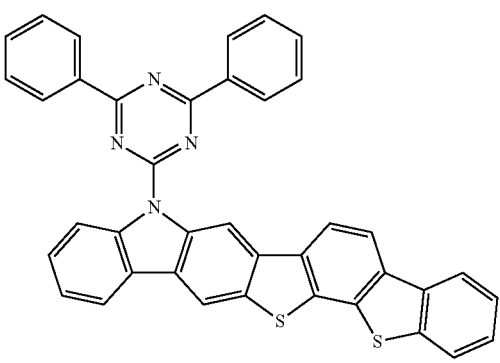
45
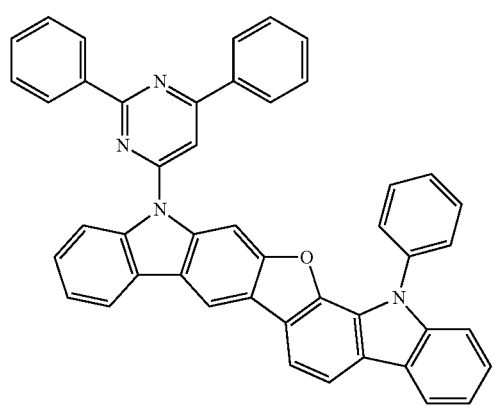
46
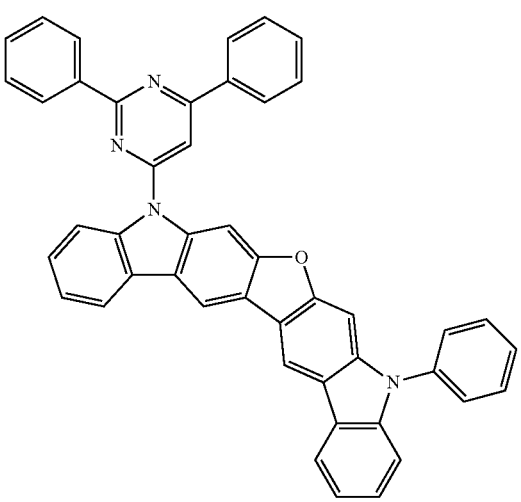

-continued
47
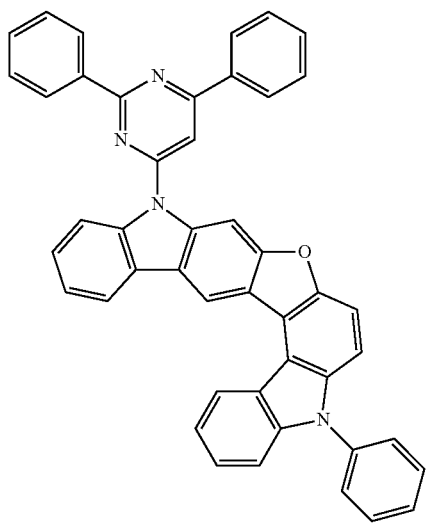
48
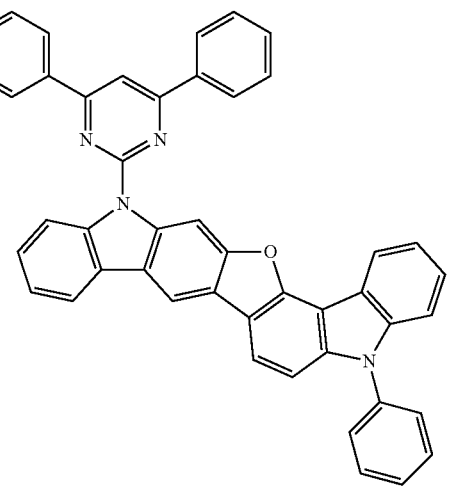
49
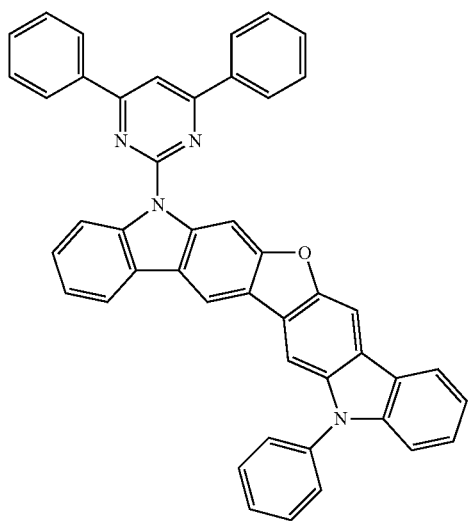
50
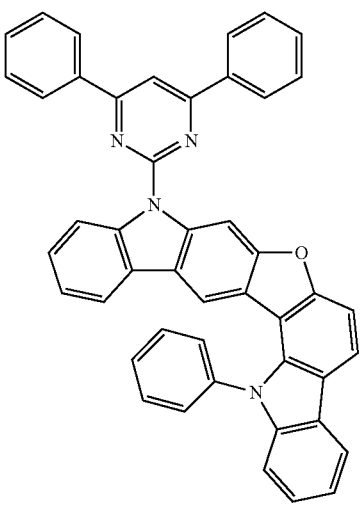
51
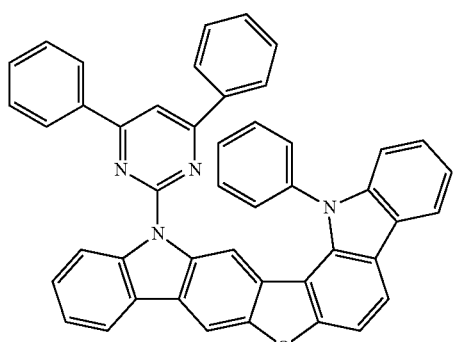
52
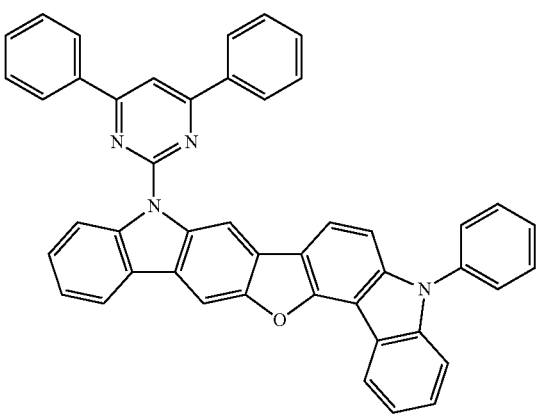

-continued
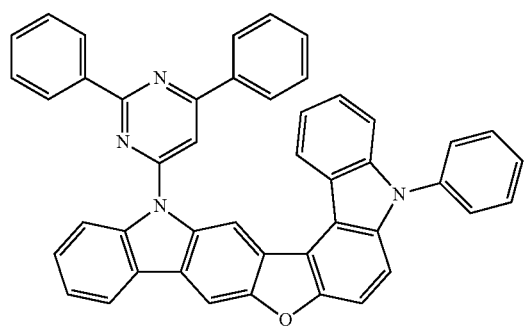
53
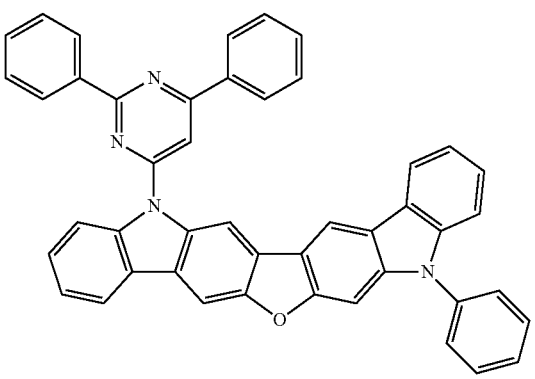
54
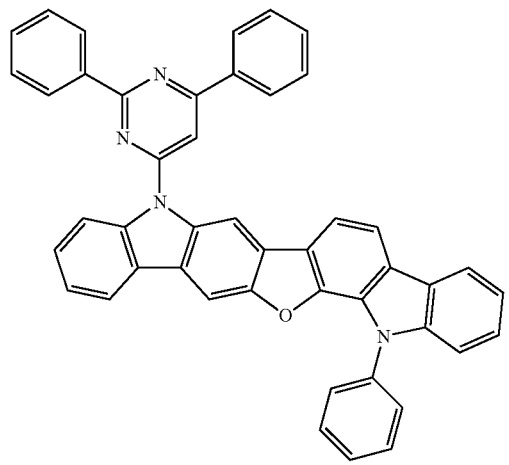
55
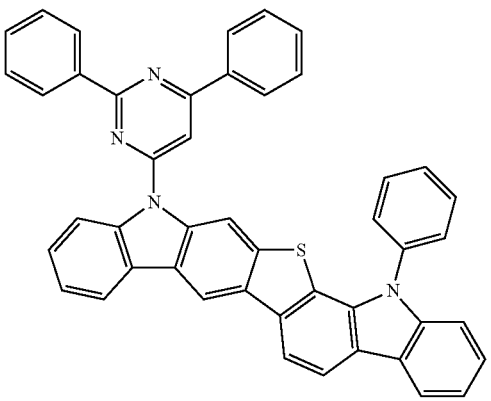
56
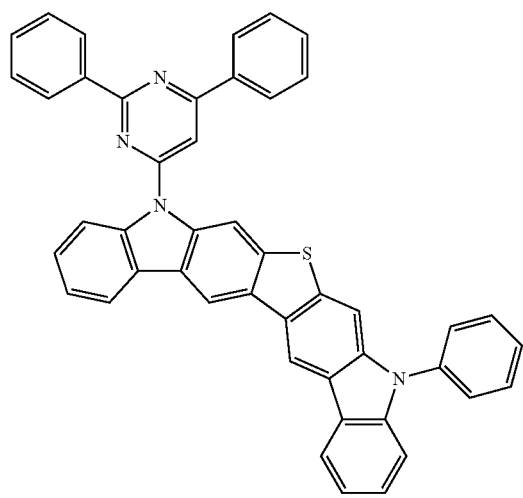
57
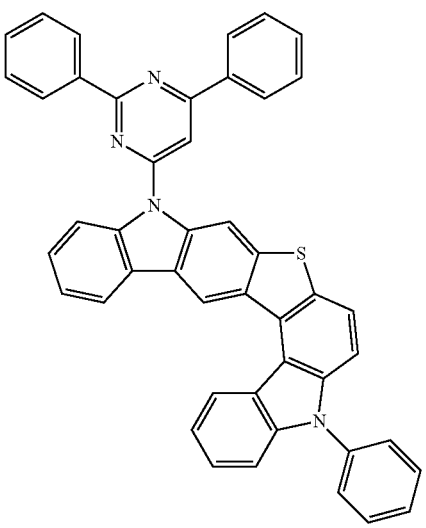
58

59
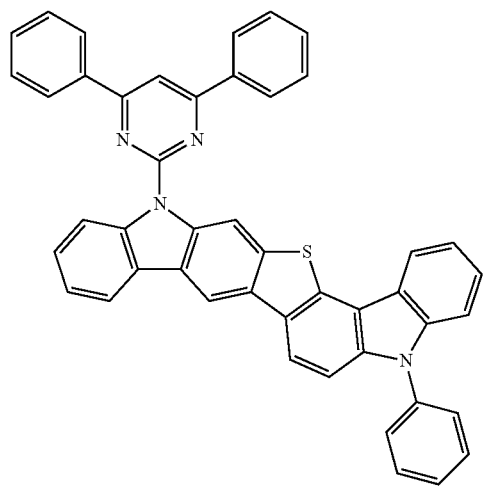
60
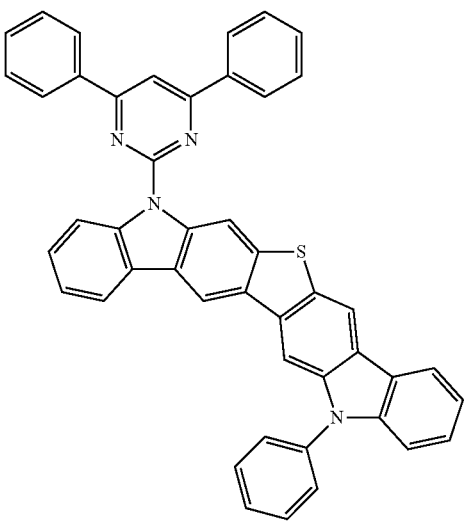
61
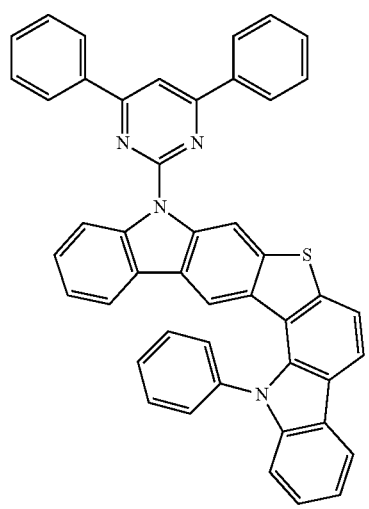
62
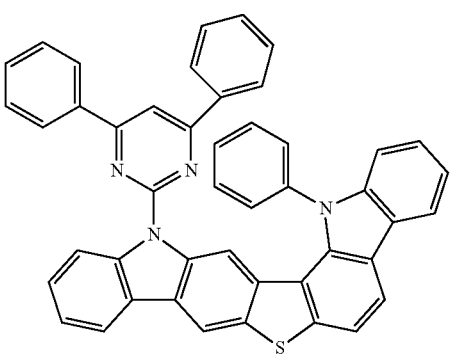
63
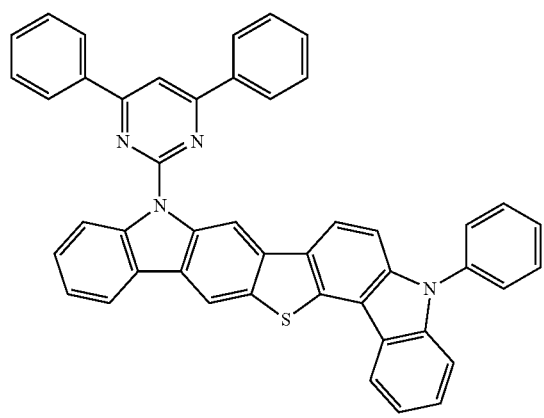
64
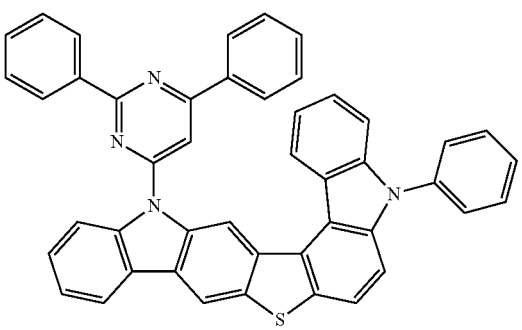

-continued
65
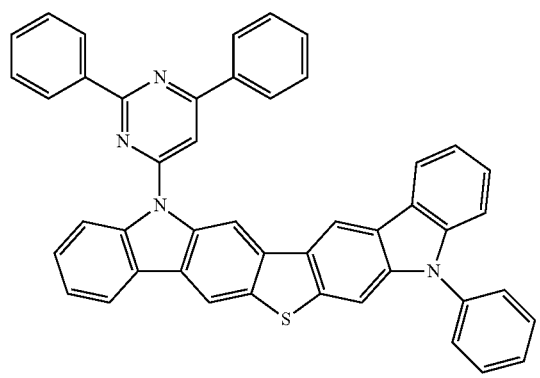
66
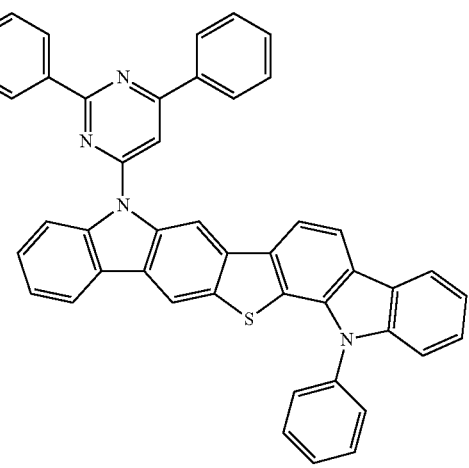
67
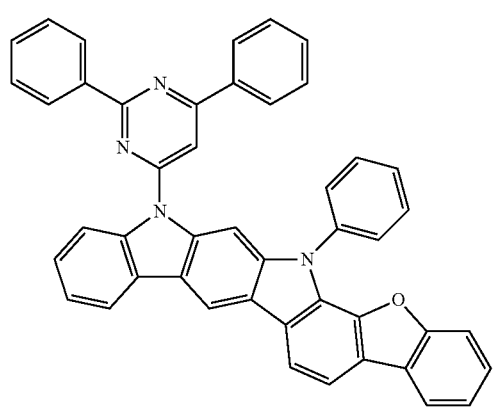
68
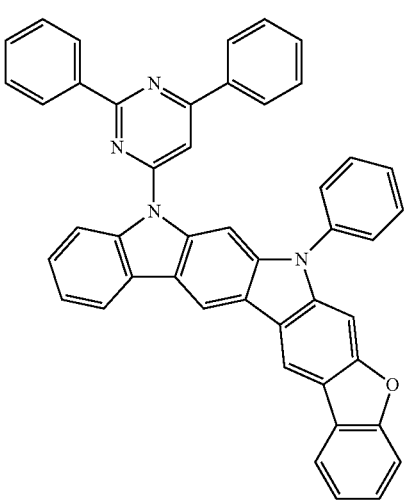
69
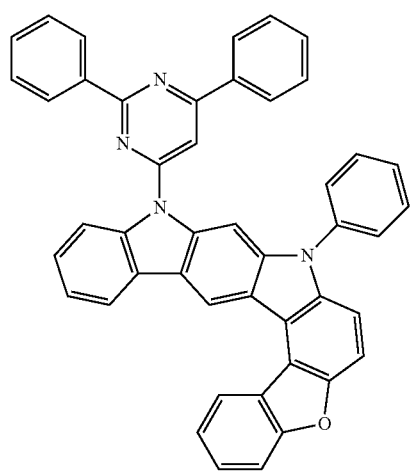
70
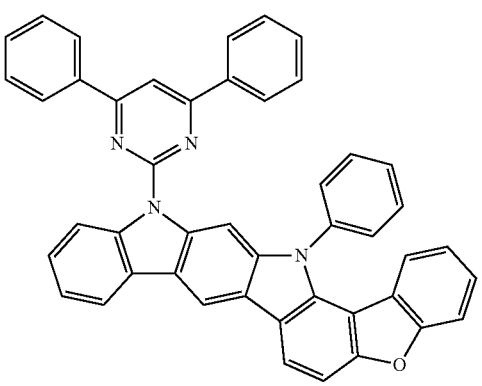

-continued
71
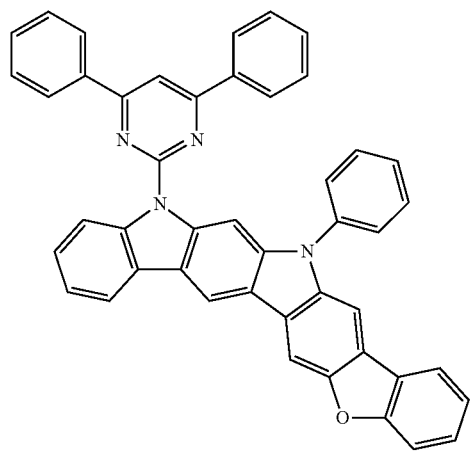
72
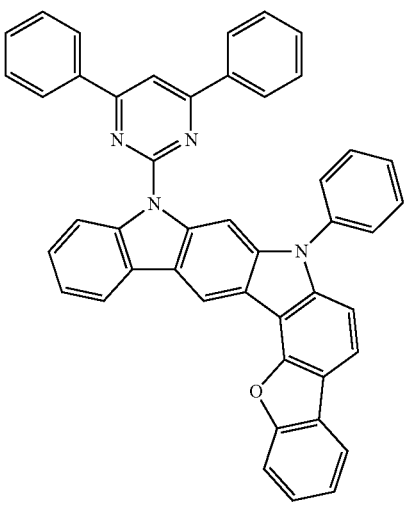
73
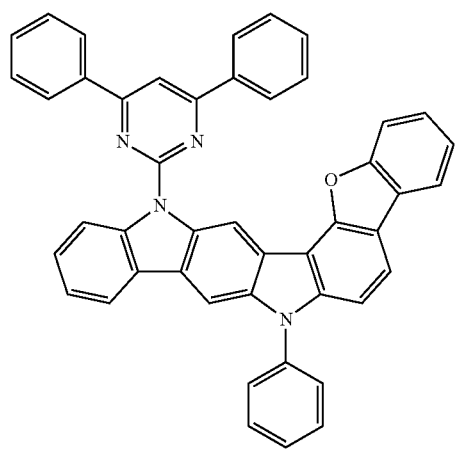
74
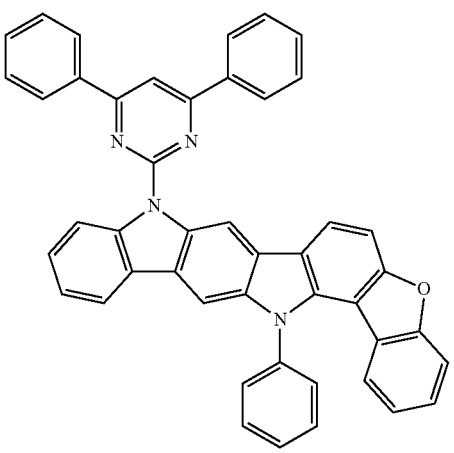
75
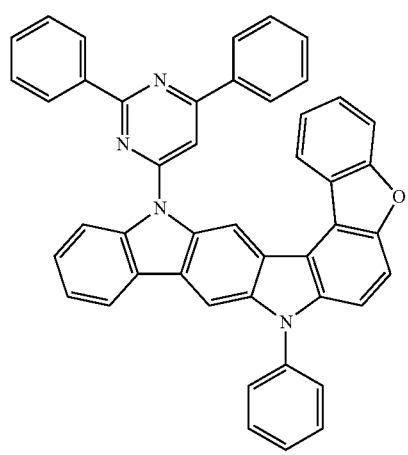
76
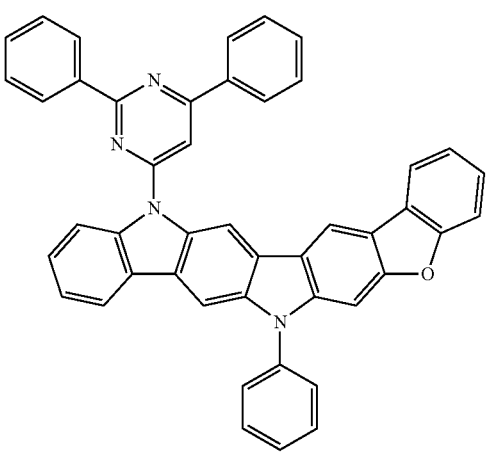

-continued
77
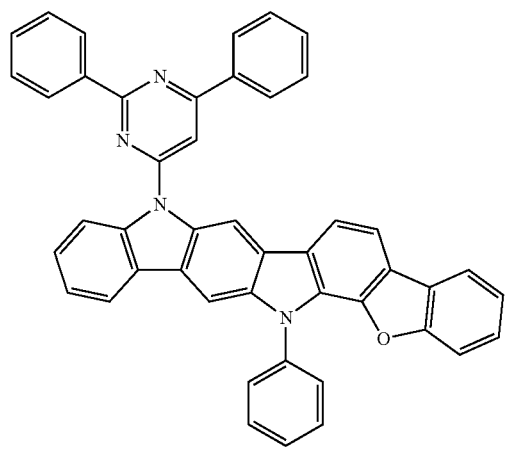
78
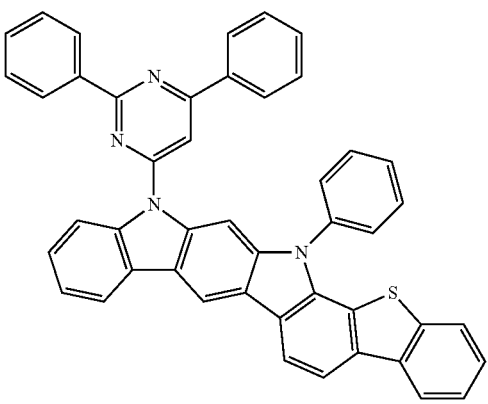
79
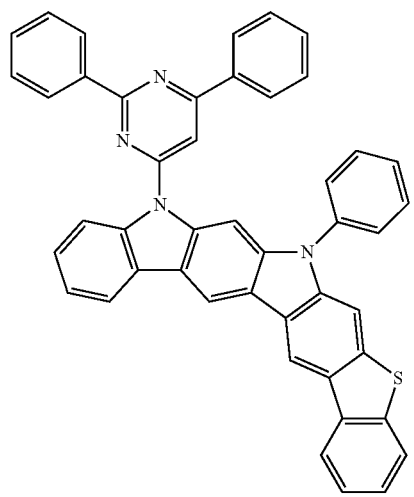
80
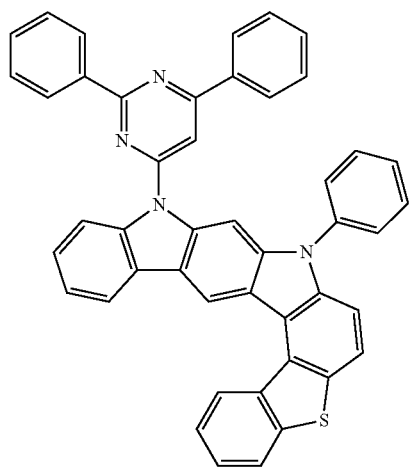
81
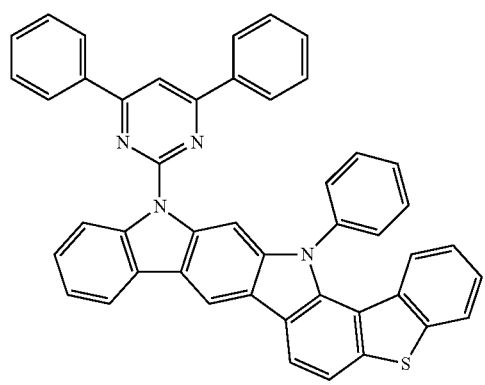
82
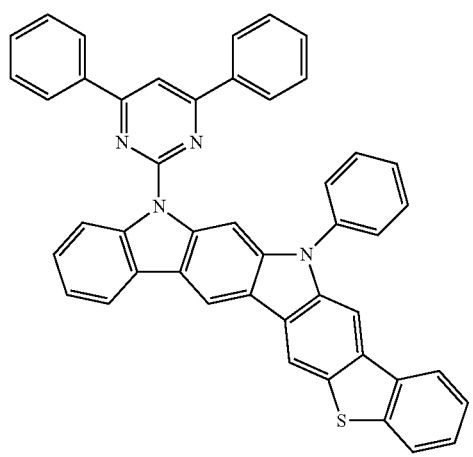

-continued
83
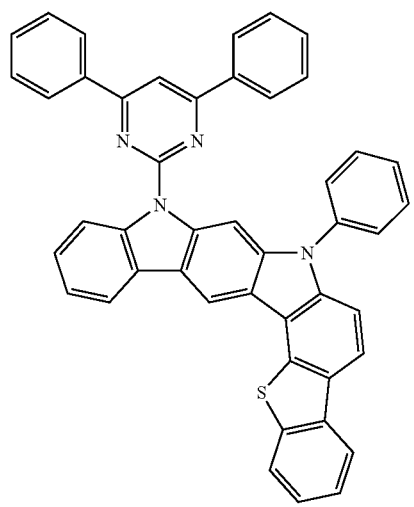
84
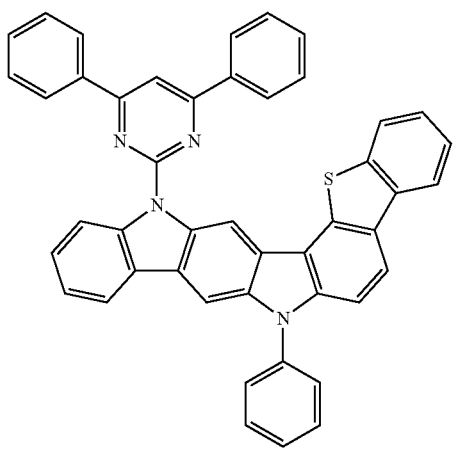
85
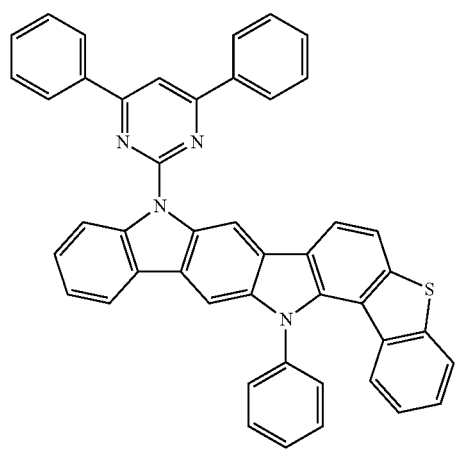
86
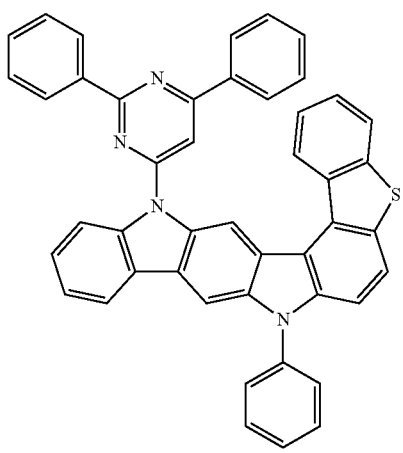
87
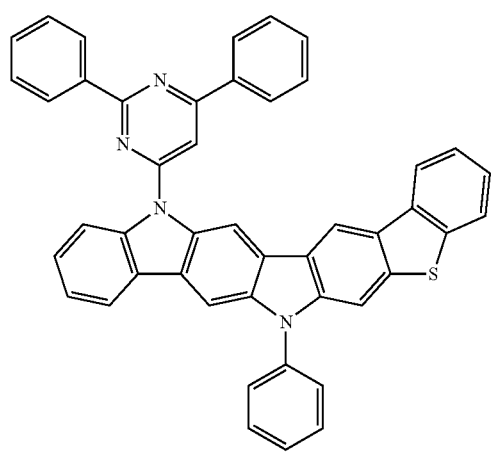
88
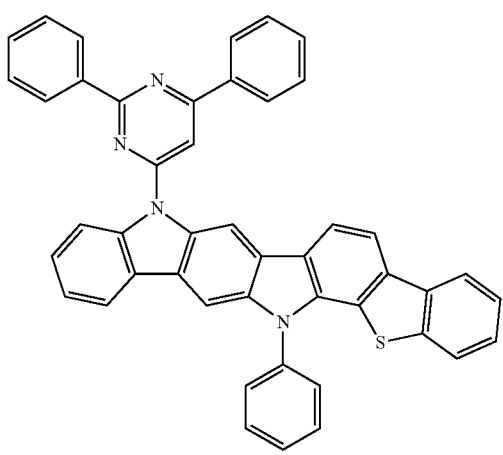

-continued
89
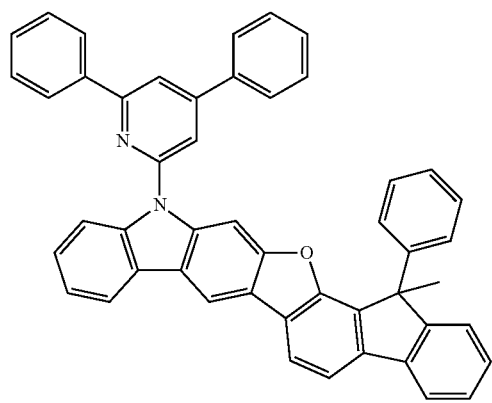
90
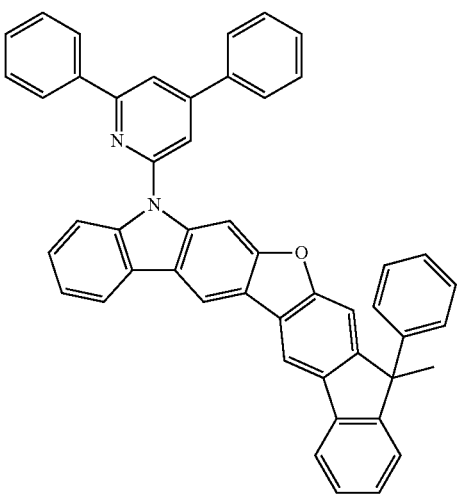
91
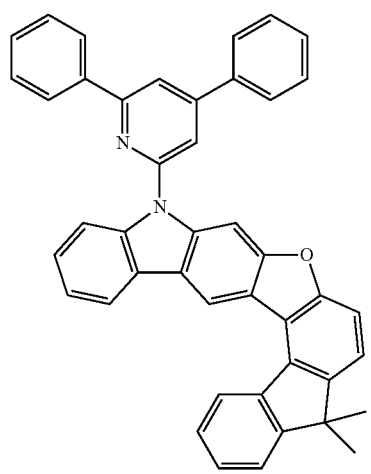
92
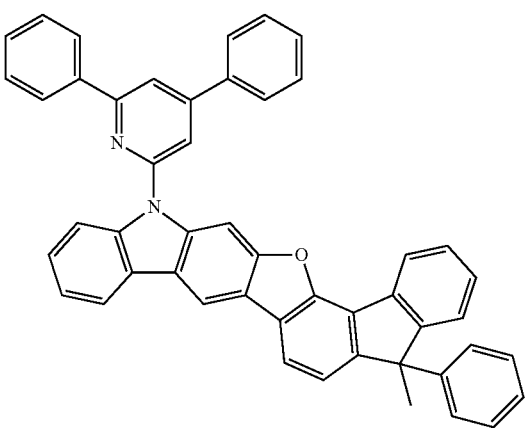
93
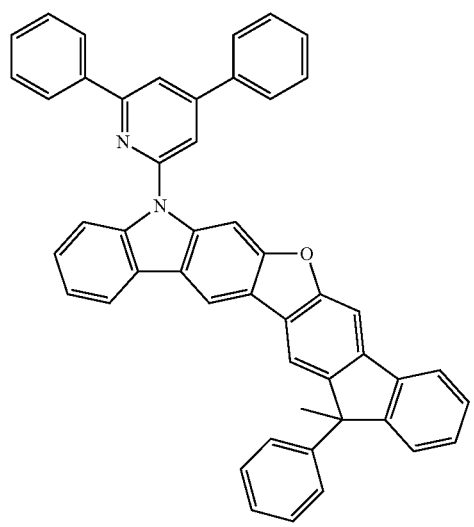
94
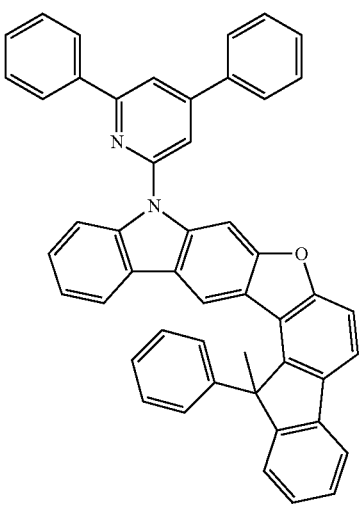

-continued
95
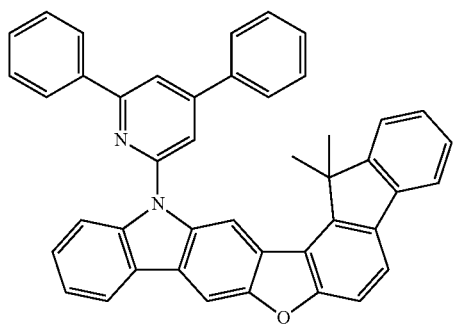
96
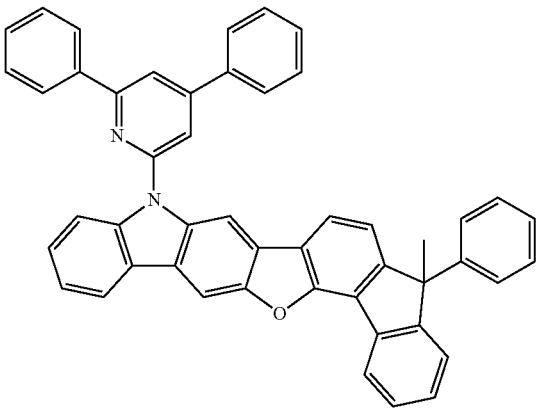
97
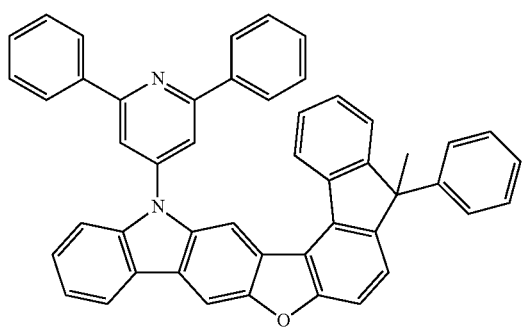
98
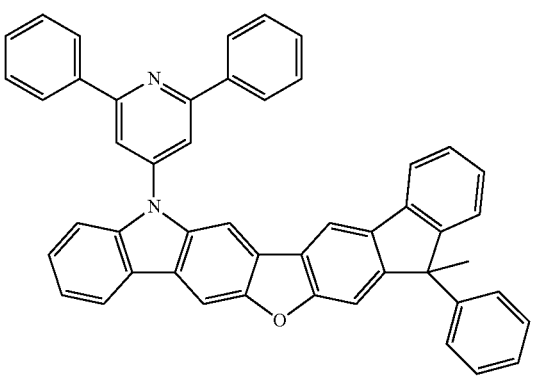
99
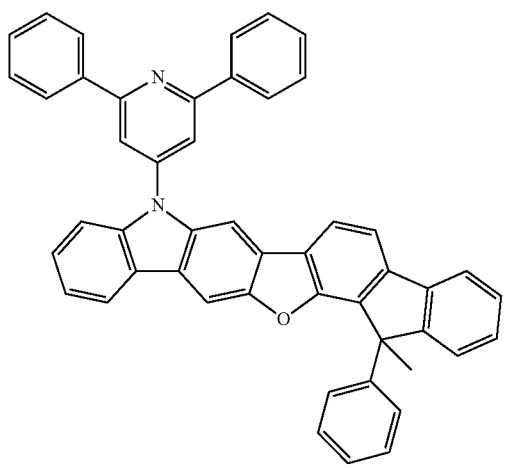
100
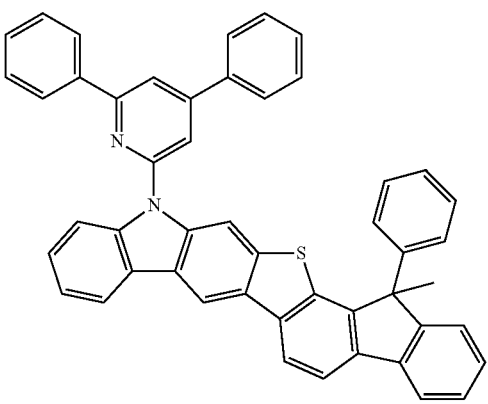

-continued
101
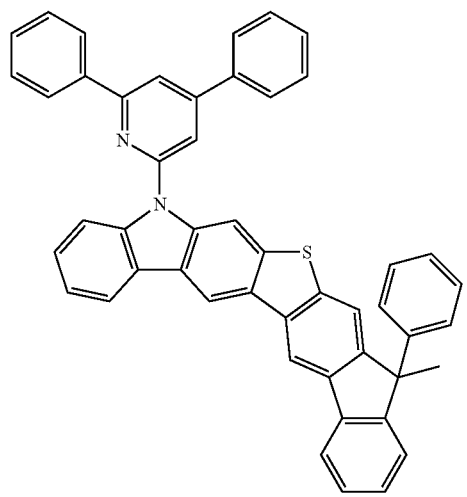
102
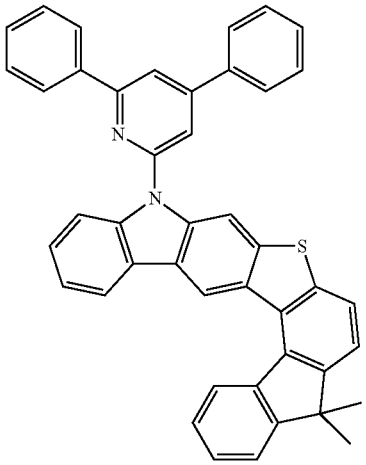
103
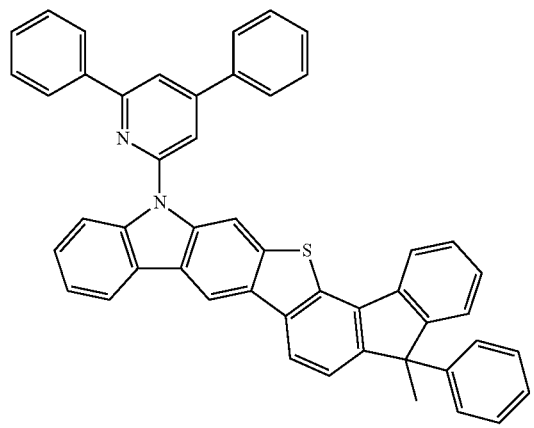
104
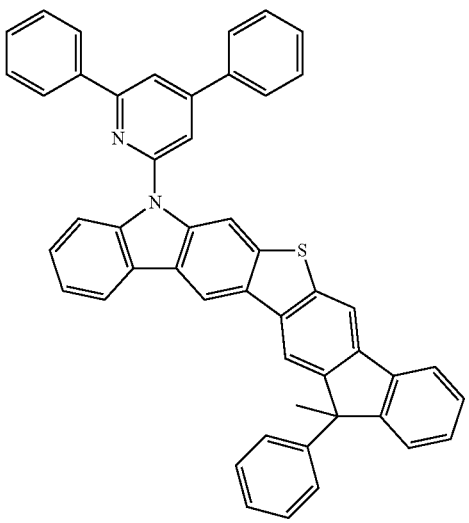
105
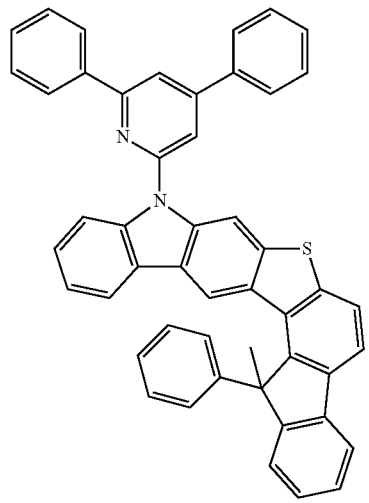
106
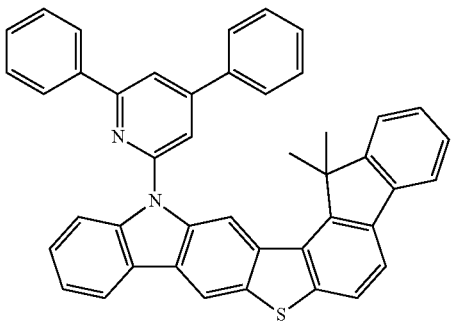

-continued
107
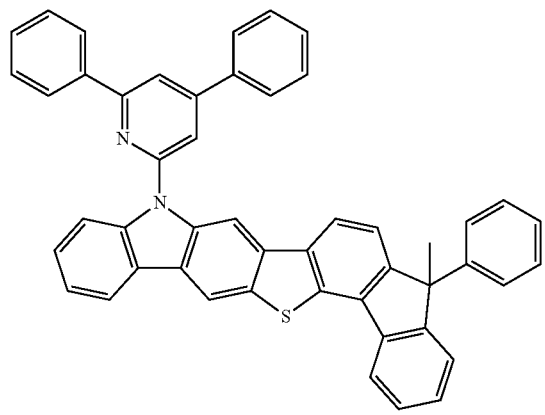
108
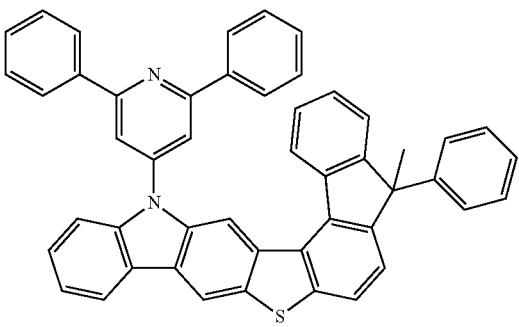
109
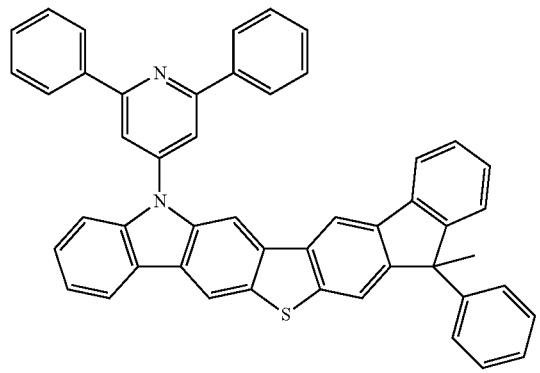
110
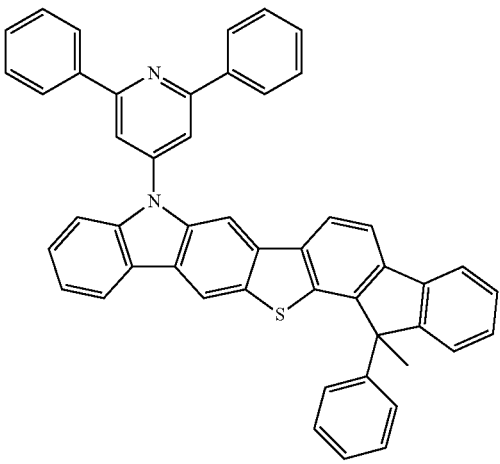
111
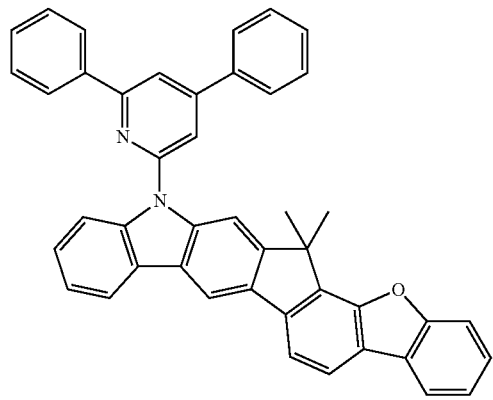
112
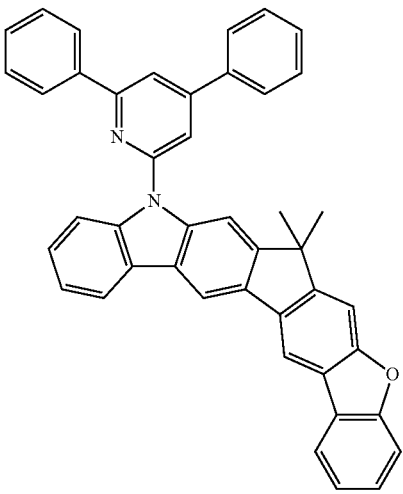

-continued
113 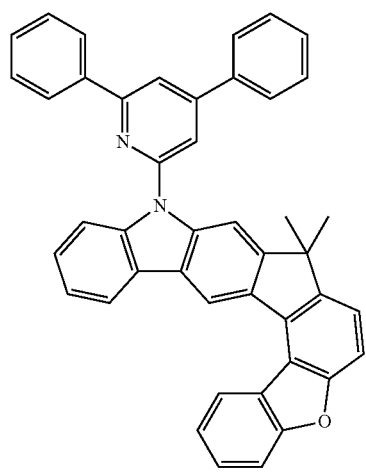
114 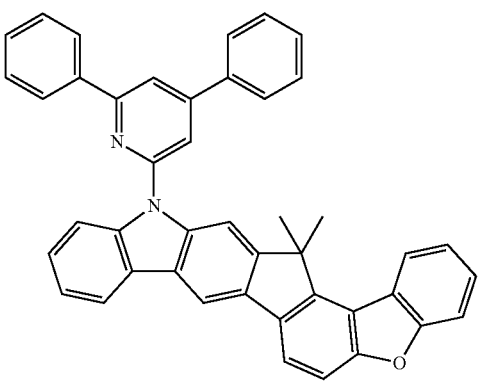
115 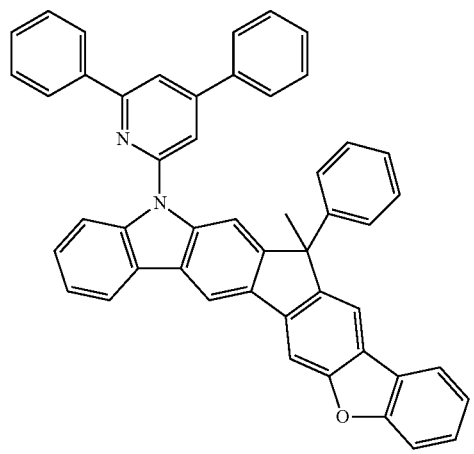
116 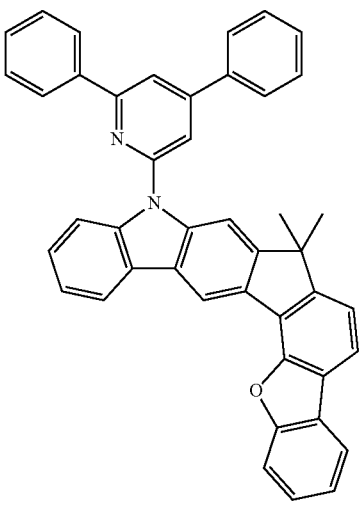
117 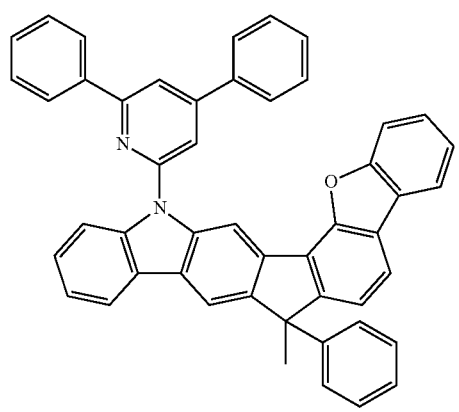
118 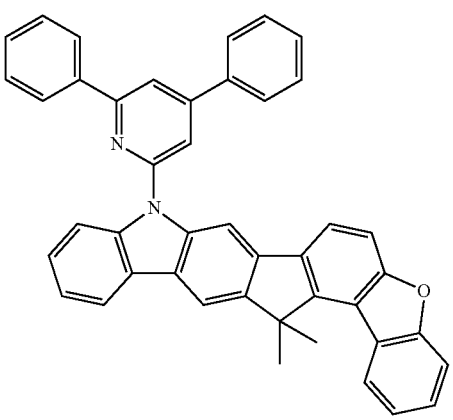

-continued
119
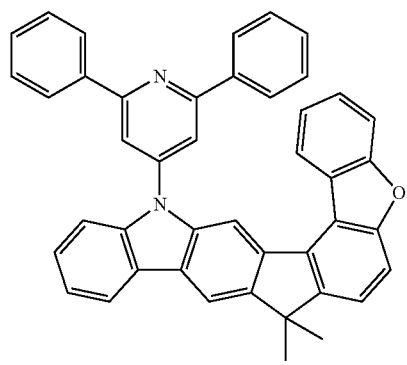
120
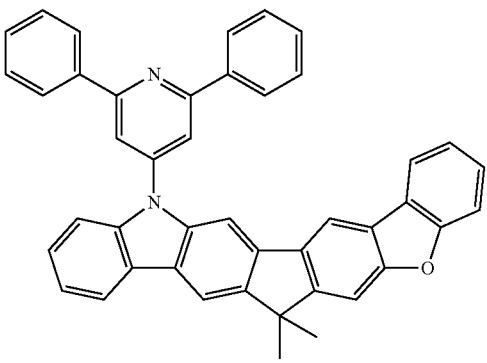
121
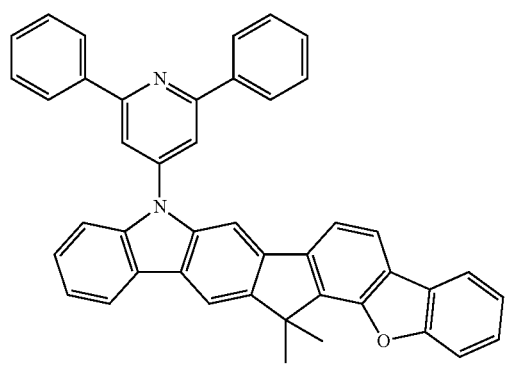
122
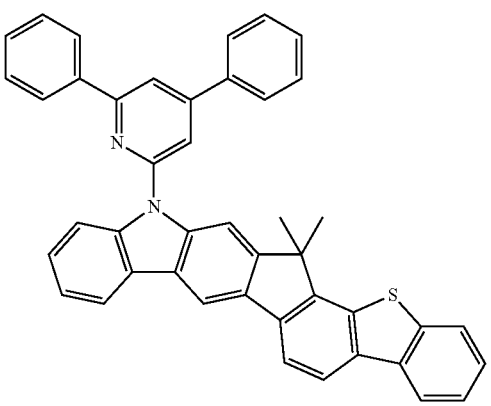
123
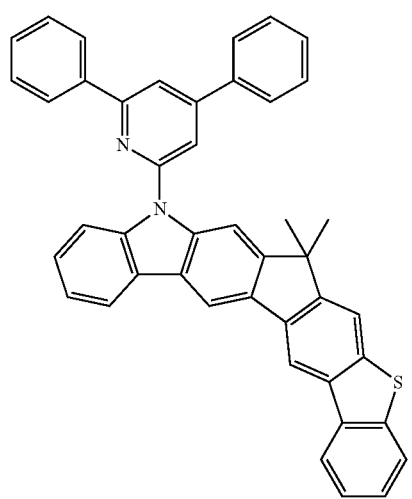
124
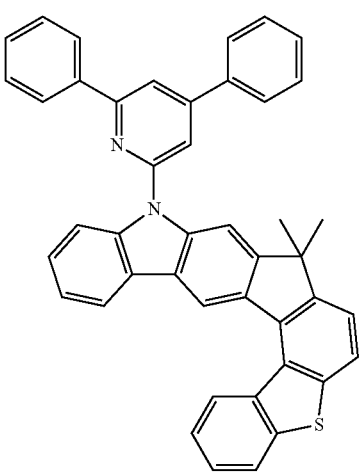

-continued
125
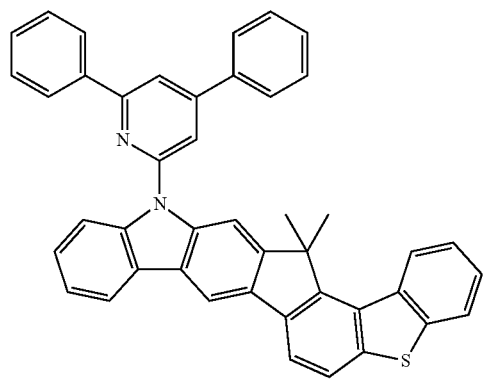
126
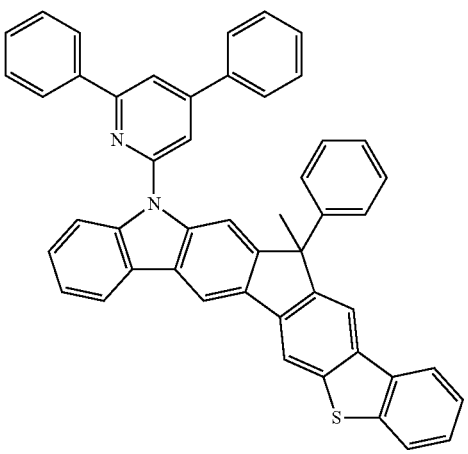
127
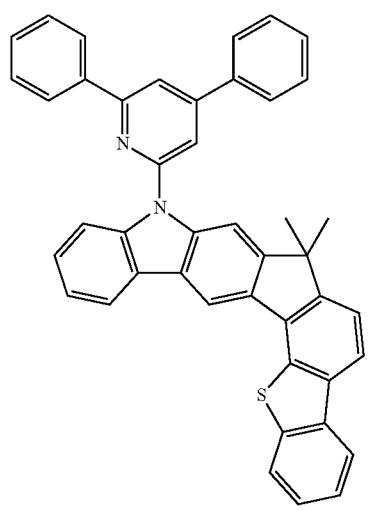
128
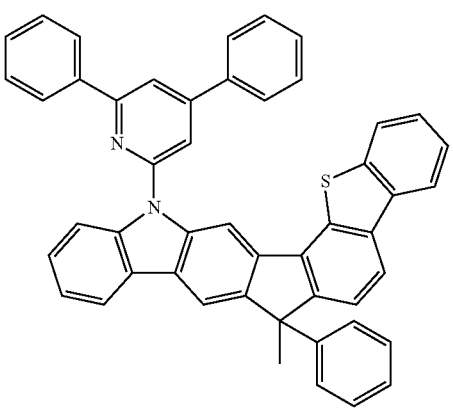
129
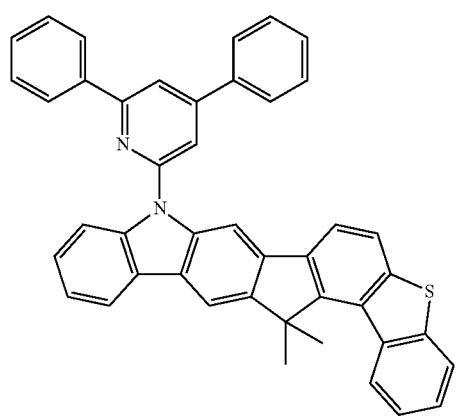
130
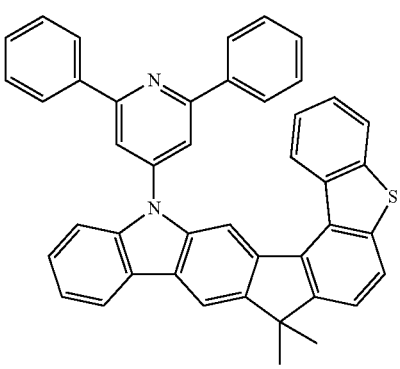

-continued
131
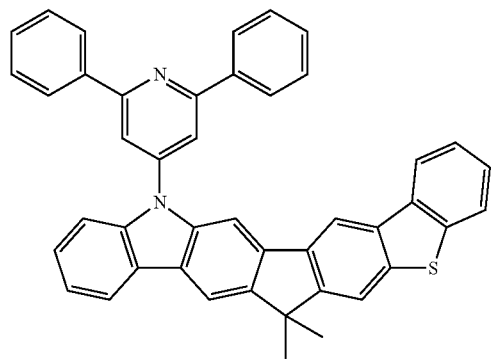
132
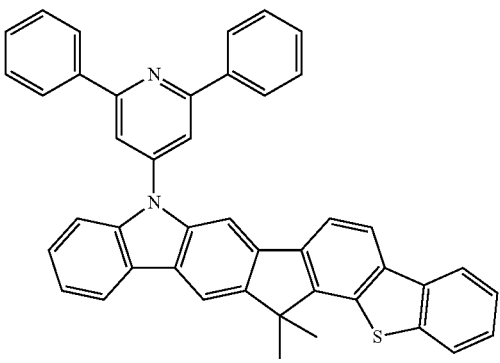
133
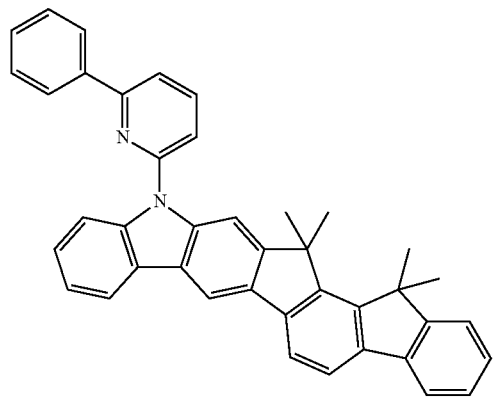
134
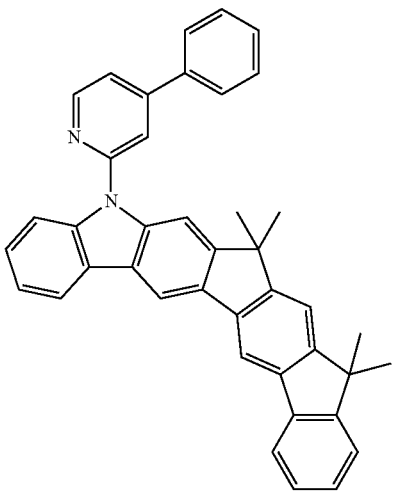
135
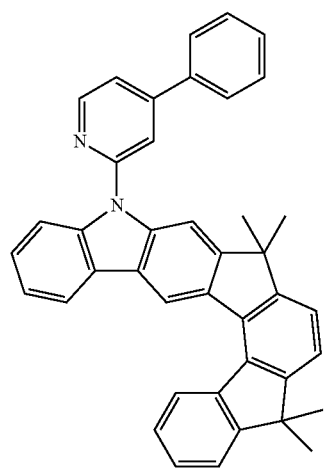
136
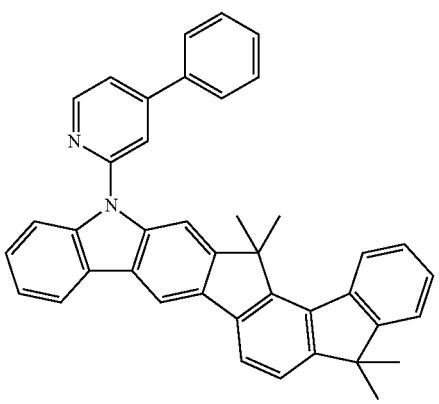

137
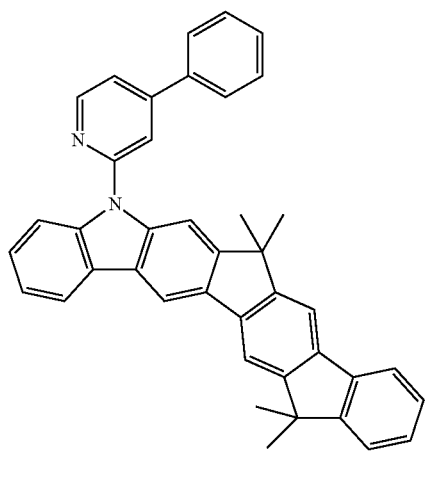
138
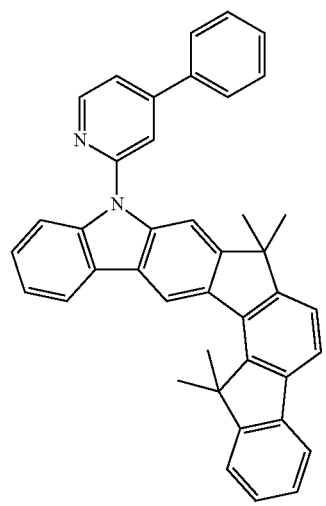
139
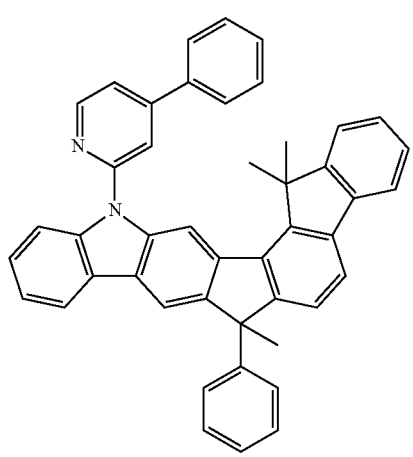
140
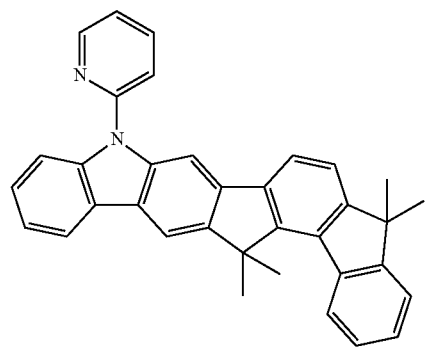
141
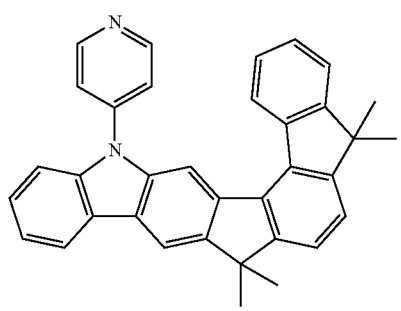
142
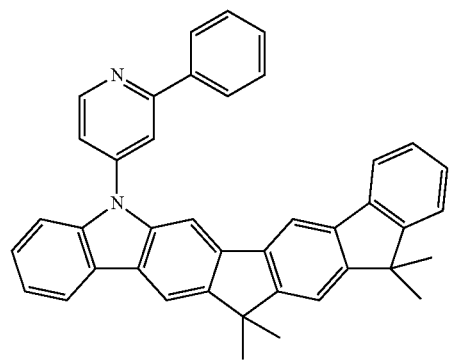

-continued
143
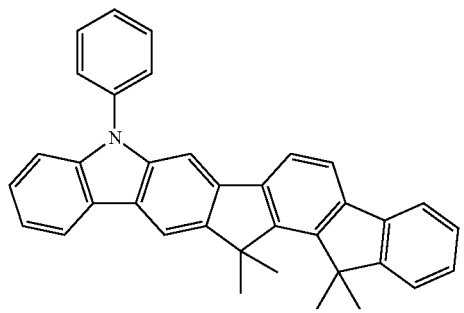
144
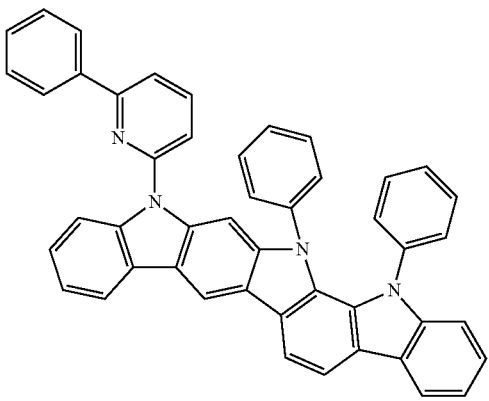
145
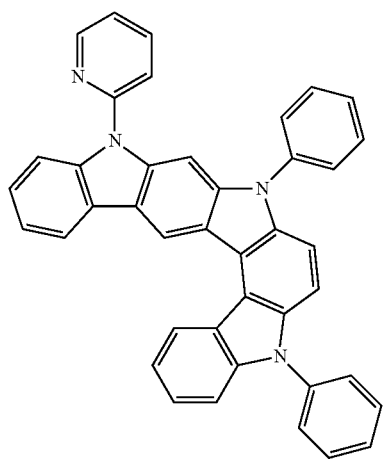
146
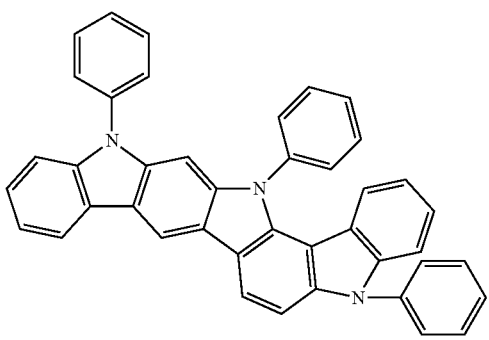
147
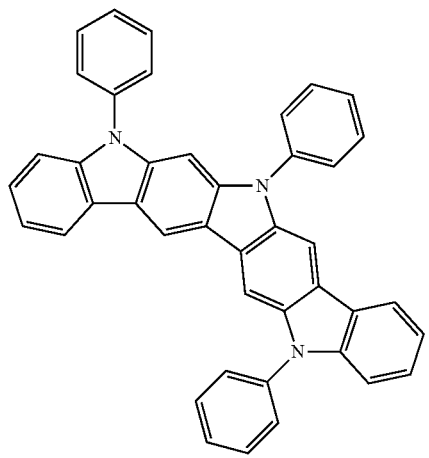
148
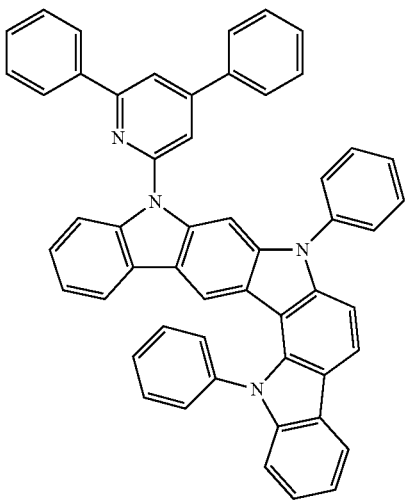

-continued
149
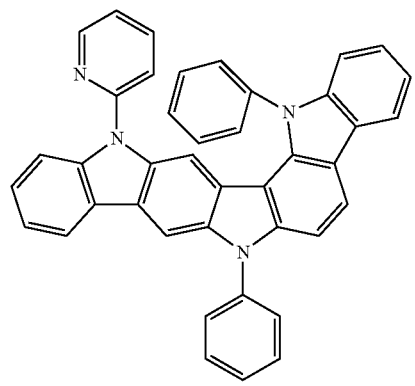
150
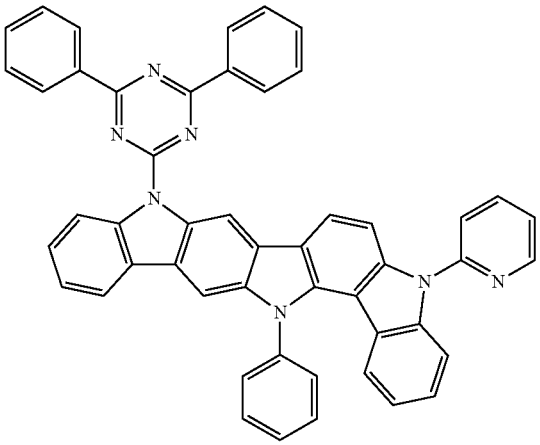
151
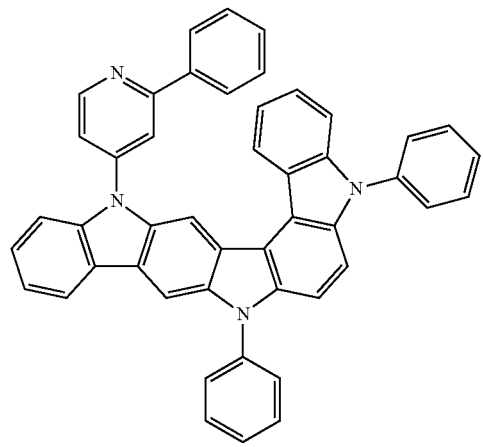
152
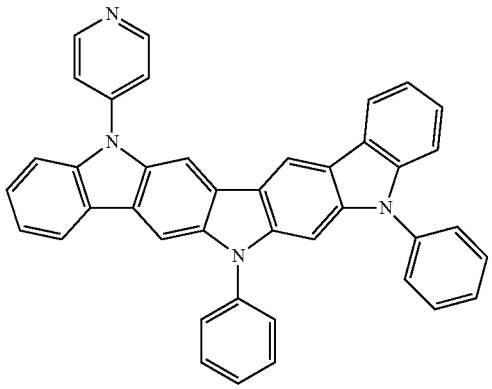
153
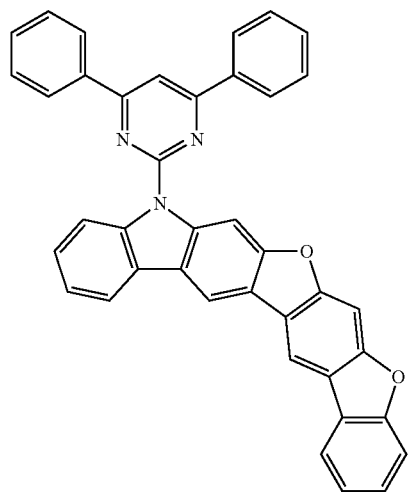
154
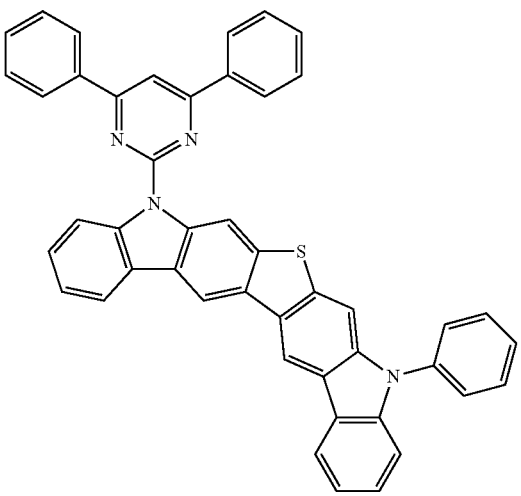

-continued
155
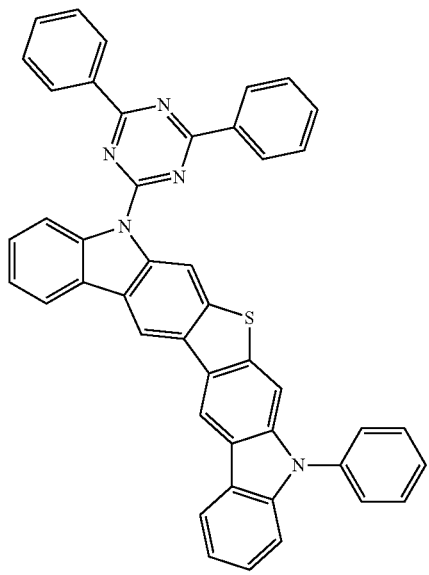
158
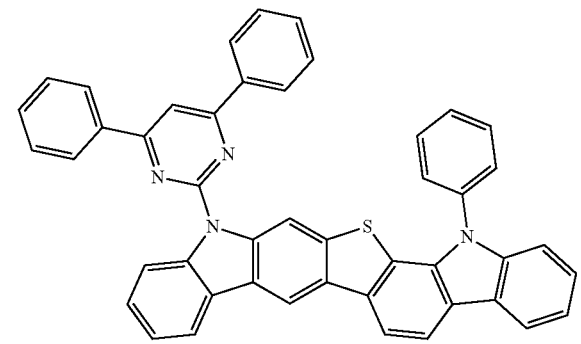
159
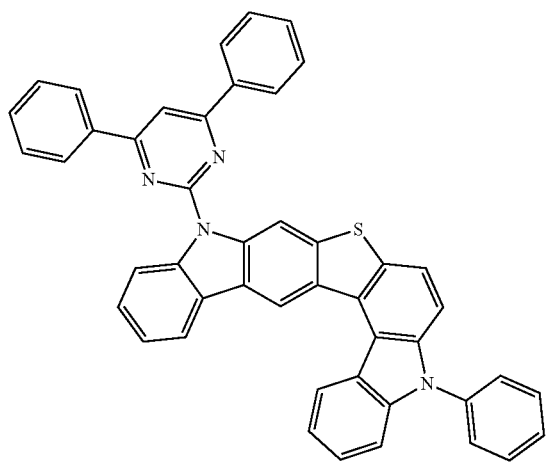
160
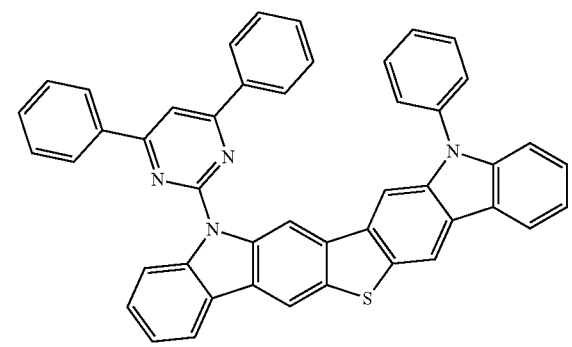
161
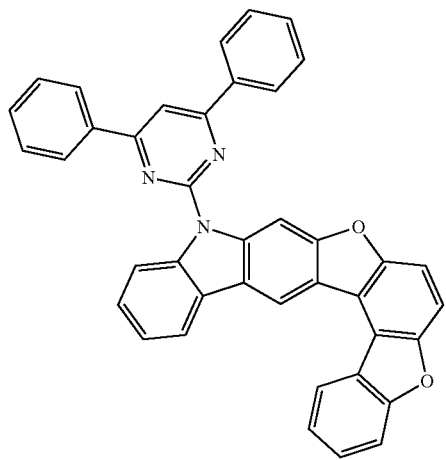
162
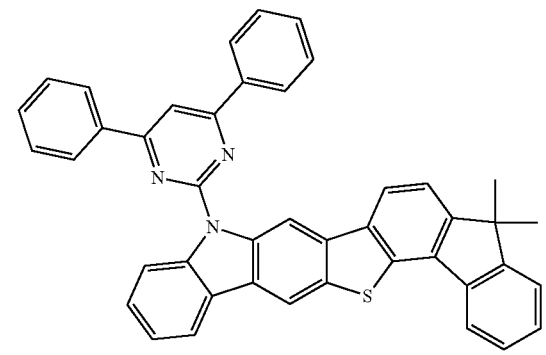

-continued
163
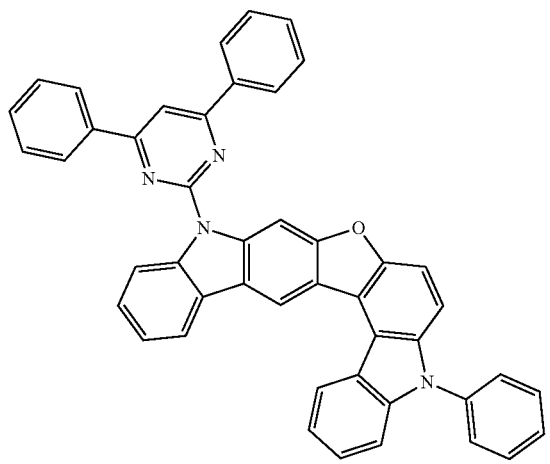
164
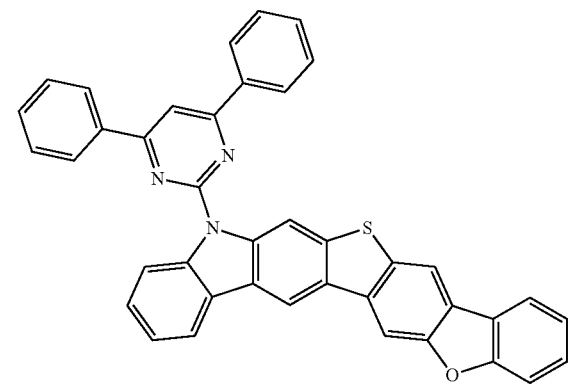
165
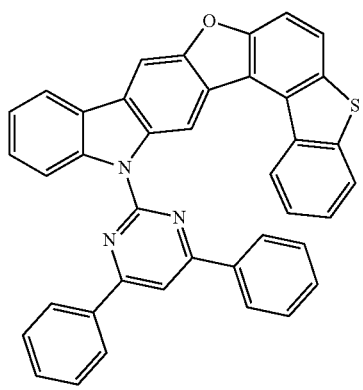
166
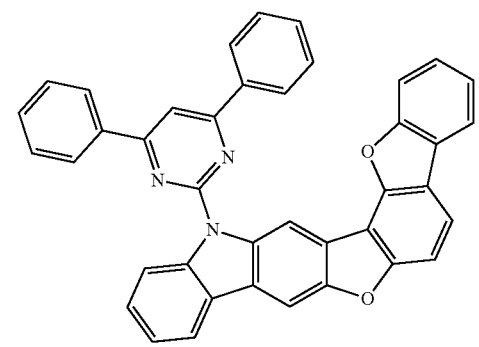
167
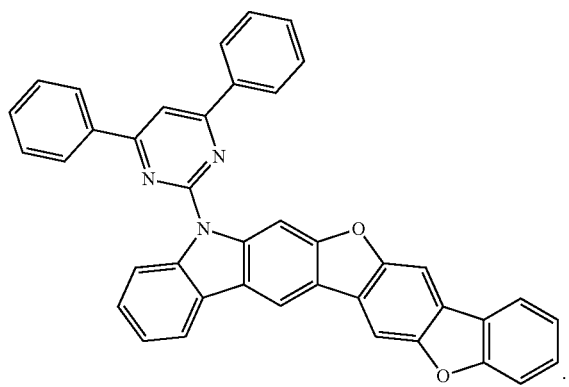
17. An organic light-emitting device comprising:
a first electrode;
a second electrode; and
an organic layer disposed between the first electrode and the second electrode,
wherein the organic layer comprises an emission layer and at least one condensed cyclic compound represented by one of Formulae 1-1 to 1-12:
Formula 1-1
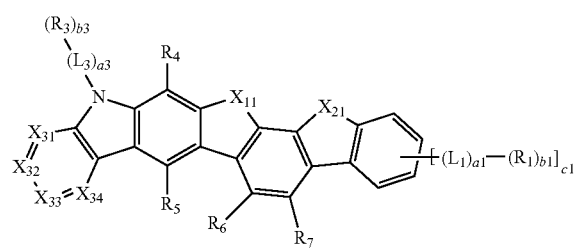

-continued
Formula 1-2
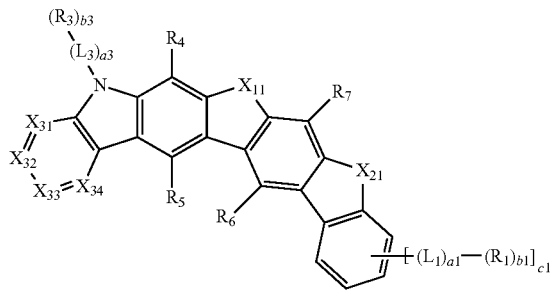
Formula 1-3
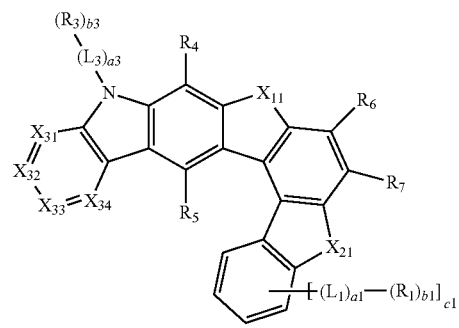
Formula 1-4
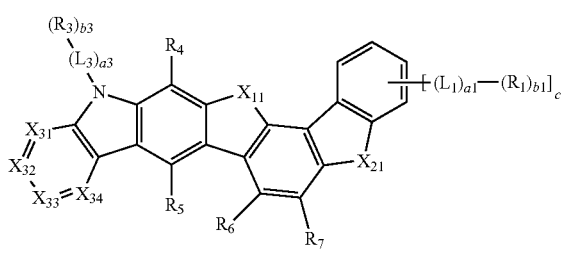
Formula 1-5
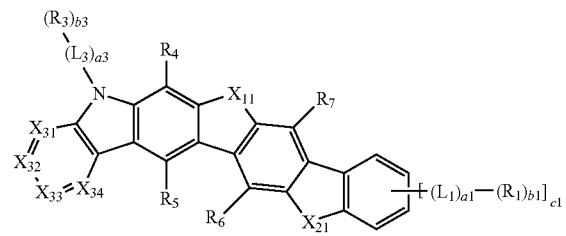
Formula 1-6
Formula 1-7
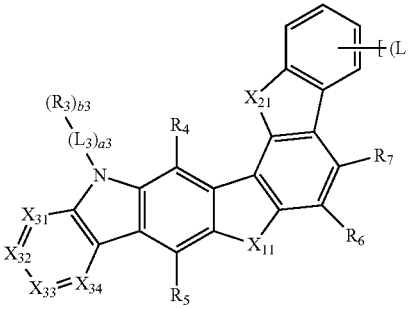
Formula 1-8
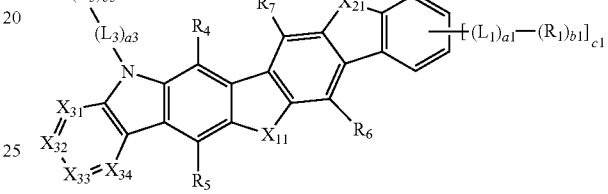
Formula 1-9
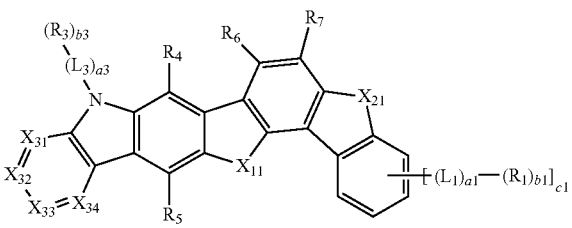
Formula 1-10
Formula 1-11

-continued

Formula 1-12

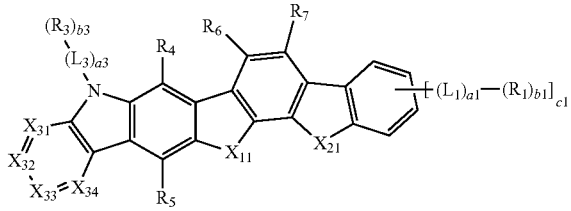

wherein, in Formulae 1-1 to 1-12, $X_{11}$ is N-[$(L_{11})_{a11}$-$(R_{11})_{b11}$], S, O, S(=O), S(=O)$_2$, C(=O), C($R_{12}$)($R_{13}$), Si($R_{12}$)($R_{13}$), P($R_{12}$), or P(=O)($R_{12}$);

$X_{21}$ is N-[$(L_{21})_{a21}$-$(R_{21})_{b21}$], S, O, S(=O), S(=O)$_2$, C(=O), C($R_{22}$)($R_{23}$), Si($R_{22}$)($R_{23}$), P($R_{22}$), or P(=O)($R_{22}$);

provided that when $X_{11}$ is C($R_{12}$)($R_{13}$), then $X_{21}$ is S, O, S(=O), S(=O)$_2$, C(=O), C($R_{22}$)($R_{23}$), Si($R_{22}$)($R_{23}$), P($R_{22}$), or P(=O)($R_{22}$);

provided that when $X_{21}$ is N-[$(L_{21})_{a21}$-$(R_{21})_{b21}$], then $X_{11}$ is N-[$(L_{11})_{a11}$-$(R_{11})_{b11}$], S, O, S(=O), S(=O)$_2$, C(=O), Si($R_{12}$)($R_{13}$), P($R_{12}$), or P(=O)($R_{12}$);

$X_{31}$ to $X_{34}$ are each independently N or C-[$(L_2)_{a2}$-$(R_2)_{b2}$], provided that, in Formula 1-2, at least one selected from $X_{31}$ to $X_{34}$ is N;

provided that conditions i) to vii) are met:

i) in Formula 1-2, when $X_{11}$ is N-[$(L_{11})_{a11}$-$(R_{11})_{b11}$], $X_{21}$ is not N-[$(L_{21})_{a21}$-$(R_{21})_{b21}$] or C($R_{22}$)($R_{23}$), ii) in Formula 1-8, when $X_{11}$ is C($R_{12}$)($R_{13}$), $X_{21}$ is not C($R_{22}$)($R_{23}$), iii) in Formula 1-8, when $X_{11}$ is S, $X_{21}$ is not N-[$(L_{21})_{a21}$-$(R_{21})_{b21}$], iv) in Formula 1-8, when $X_{11}$ is Si($R_{12}$)($R_{13}$), $X_{21}$ is not N-[$(L_{21})_{a21}$-$(R_{21})_{b21}$], v) in Formula 1-11, when $X_{11}$ is N-[$(L_{11})_{a11}$-$(R_{11})_{b11}$], $X_{21}$ is not C($R_{22}$)($R_{23}$)

vi) in Formulae 1-1 to 1-12, when $X_{11}$ is N-[$(L_{11})_{a11}$-$(R_{11})_{b11}$], $X_{21}$ is not N-[$(L_{21})_{a21}$-$(R_{21})_{b21}$], vii) in Formulae 1-1 to 1-12, when $X_{21}$ is N-[$(L_{21})_{a21}$-$(R_{21})_{b21}$], $X_{11}$ is not N-[$(L_{11})_{a11}$-$(R_{11})_{b11}$];

$L_1$ to $L_3$, $L_{11}$, and $L_{21}$ are each independently selected from the group consisting of a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a3, a11, and a21 are each independently an integer selected from 0 to 5;

$R_1$ to $R_7$, $R_{11}$ to $R_{13}$, and $R_{21}$ to $R_{23}$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), provided that:

i) in Formulae 1-1 to 1-12, $R_3$ is selected from the group consisting of:

a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, or —Si($Q_{33}$)($Q_{34}$)($Q_{35}$), and ii) in Formulae 1-1 to 1-12, when $X_{11}$ is N-[($L_{11})_{a11}$-($R_{11})_{b11}$], $R_{11}$ is selected from the group consisting of:

a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, or —Si($Q_{33}$)($Q_{34}$)($Q_{35}$), wherein $Q_{33}$ to $Q_{35}$ are each independently selected from the group consisting of a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

b1 to b3, b11, and b21 are each independently an integer selected from 1 to 5;

c1 is an integer selected from 1 to 4;

at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, or the substituted monovalent non-aromatic condensed heteropolycyclic group is selected from the group consisting of:

a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), or —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group.

18. The organic light-emitting device of claim 17, wherein the first electrode is an anode, the second electrode is a cathode, and the organic layer comprises i) a hole transport region disposed between the first electrode and the emission layer and comprising at least one of a hole injection layer, a hole transport layer, or an electron blocking layer; and ii) an electron transport region disposed between the emission layer and the second electrode and comprising at least one of a hole blocking layer, an electron transport layer, or an electron injection layer.

19. The organic light-emitting device of claim 18, wherein at least one of the emission layer or the hole transport region comprises the condensed cyclic compound.

20. The organic light-emitting device of claim 17, wherein the emission layer comprises the condensed cyclic compound and the emission layer further comprises at least one of a first compound represented by Formula 41 or a second compound represented by Formula 61:

Formula 41

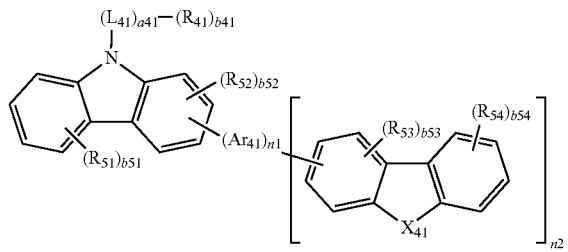

-continued

Formula 61

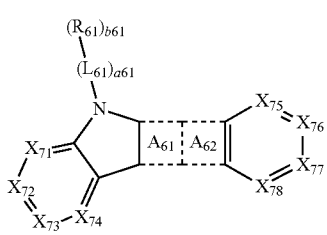

Formula 61A

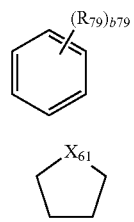

Formula 61B

wherein in the formulae above, $X_{41}$ is $N-[(L_{42})_{a42}-(R_{42})_{b42}]$, S, O, S(=O), S(=O)$_2$, C(=O), C(R$_{43}$)(R$_{44}$), Si(R$_{43}$)(R$_{44}$), P(R$_{43}$), P(=O)(R$_{43}$), or C=N(R$_{43}$);

Ring $A_{61}$ in Formula 61 is represented by Formula 61A;

Ring $A_{62}$ in Formula 61 is represented by Formula 61B;

$X_{61}$ is $N-[(L_{62})_{a62}-(R_{62})_{b62}]$, S, O, S(=O), S(=O)$_2$, C(=O), C(R$_{63}$)(R$_{64}$), Si(R$_{63}$)(R$_{64}$), P(R$_{63}$), P(=O)(R$_{63}$), or C=N(R$_{63}$);

$X_{71}$ is C(R$_{71}$) or N, $X_{72}$ is C(R$_{72}$) or N, $X_{73}$ is C(R$_{73}$) or N, $X_{74}$ is C(R$_{74}$) or N, $X_{75}$ is C(R$_{75}$) or N, $X_{76}$ is C(R$_{76}$) or N, $X_{77}$ is C(R$_{77}$) or N, $X_{78}$ is C(R$_{78}$) or N;

$Ar_{41}$, $L_{41}$, $L_{42}$, $L_{61}$, and $L_{62}$ are each independently selected from the group consisting of a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed hetero-polycyclic group;

n1 is an integer selected from 0 to 3;

n2 is an integer selected from 1 to 3 a41, a42, a61, and a62 are each independently an integer selected from 0 to 3;

$R_{41}$ to $R_{44}$, $R_{51}$ to $R_{54}$, $R_{61}$ to $R_{64}$, and $R_{71}$ to $R_{79}$ are each independently selected from the group consisting of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed hetero-polycyclic group, —N(Q$_1$)(Q$_2$), —Si(Q$_3$)(Q$_4$)(Q$_5$), and —B(Q$_6$)(Q$_7$);

b41, b42, b51 to b54, b61, b62, and b79 are each independently an integer selected from 1 to 3;

at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed hetero-polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted a monovalent non-aromatic condensed polycyclic group, or a substituted monovalent non-aromatic condensed hetero-polycyclic group may be selected from the group consisting of:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed hetero-polycyclic group, —N(Q$_{11}$)(Q$_{12}$), —Si(Q$_{13}$)(Q$_{14}$)(Q$_{15}$), or —B(Q$_{16}$)(Q$_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), or —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from the group consisting of a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed hetero-polycyclic group.

* * * * *